US009650447B2

(12) United States Patent
Kovacs et al.

(10) Patent No.: US 9,650,447 B2
(45) Date of Patent: May 16, 2017

(54) COMPLEMENT RECEPTOR 2 (CR2) TARGETING GROUPS

(75) Inventors: James M. Kovacs, Monument, CO (US); Jonathan P. Hannan, Arvada, CO (US); V. Michael Holers, Denver, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 1075 days.

(21) Appl. No.: 13/697,693

(22) PCT Filed: May 13, 2011

(86) PCT No.: PCT/US2011/036552
§ 371 (c)(1),
(2), (4) Date: Jan. 31, 2013

(87) PCT Pub. No.: WO2011/143637
PCT Pub. Date: Nov. 17, 2011

(65) Prior Publication Data
US 2013/0190477 A1    Jul. 25, 2013

Related U.S. Application Data

(60) Provisional application No. 61/345,035, filed on May 14, 2010.

(51) Int. Cl.
C07K 19/00    (2006.01)
C07K 14/47    (2006.01)

(52) U.S. Cl.
CPC ............ *C07K 19/00* (2013.01); *C07K 14/472* (2013.01)

(58) Field of Classification Search
None
See application file for complete search history.

(56) References Cited

U.S. PATENT DOCUMENTS

| | | | |
|---|---|---|---|
| 4,883,784 A | 11/1989 | Kaneko | |
| 5,212,071 A | 5/1993 | Fearon et al. | |
| 5,260,203 A | 11/1993 | Ladner et al. | |
| 5,310,729 A | 5/1994 | Lernhardt | |
| 5,328,470 A | 7/1994 | Nabel et al. | |
| 5,331,090 A | 7/1994 | Lernhardt | |
| 5,472,939 A | 12/1995 | Fearon et al. | |
| 5,679,345 A | 10/1997 | Sanfilippo et al. | |
| 5,679,546 A | 10/1997 | Ko et al. | |
| 5,851,528 A | 12/1998 | Ko et al. | |
| 5,981,481 A | 11/1999 | Fearon et al. | |
| 6,140,472 A | 10/2000 | Rosengard et al. | |
| 6,214,966 B1 | 4/2001 | Harris | |
| 6,224,866 B1 | 5/2001 | Barbera-Guillem | |
| 6,248,365 B1 | 6/2001 | Romisch et al. | |
| 6,291,239 B1 | 9/2001 | Prodinger et al. | |
| 6,355,245 B1 | 3/2002 | Evans et al. | |
| 6,368,596 B1 | 4/2002 | Ghetie et al. | |
| 6,432,679 B1 | 8/2002 | Mond et al. | |
| 6,458,360 B1 | 10/2002 | Fearon et al. | |
| 6,503,947 B1 | 1/2003 | Lipton et al. | |
| 6,521,450 B1 | 2/2003 | Atkinson et al. | |
| 6,572,856 B1 | 6/2003 | Taylor et al. | |
| 6,820,011 B2 | 11/2004 | Chen et al. | |
| 6,897,290 B1 | 5/2005 | Atkinson et al. | |
| 6,962,903 B2 | 11/2005 | Allison | |
| 7,407,475 B2 | 8/2008 | Allison | |
| 7,423,128 B2 | 9/2008 | Gazit-Bornstein et al. | |
| 7,439,331 B2 | 10/2008 | Fung et al. | |
| 7,576,182 B1 | 8/2009 | Goddard et al. | |
| 7,635,676 B2 | 12/2009 | Allison | |
| 7,635,678 B2 | 12/2009 | Allison | |
| 7,635,679 B2 | 12/2009 | Fumero et al. | |
| 7,635,680 B2 | 12/2009 | Allison | |
| 7,645,739 B2 | 1/2010 | Allison | |
| 7,759,304 B2 | 7/2010 | Gilkeson et al. | |
| 7,964,705 B2 | 6/2011 | Emlen et al. | |
| 7,999,082 B2 | 8/2011 | Holers et al. | |
| 8,007,804 B2 | 8/2011 | Tomlinson et al. | |
| 2002/0103346 A1 | 8/2002 | Vogel et al. | |
| 2003/0077273 A1 | 4/2003 | Linnik et al. | |
| 2003/0165509 A1 | 9/2003 | Ghetie et al. | |

(Continued)

FOREIGN PATENT DOCUMENTS

EP    0358130 A2    3/1990
EP    0402226 A1    12/1990
(Continued)

OTHER PUBLICATIONS

Attwood, Science 290:471-473, 2000.*
Skolnick et al., Trends in Biotech. 18: 34-39, 2000.*
He et al., "A complement-dependent balance between hepatic ischemia/reperfusion injury and liver regeneration in mice," J Clin Invest. 119(8):2304-16 (2009).
Notice of Reasons for Rejection for Japanese Application No. 2013-510357, mailed Jan. 27, 2015 (9 pages).
Qin et al.,"The complement system in liver diseases," Cell Mol Immunol. 3(5):333-340 (2006).
Tang et al, "Exogenous biliverdin ameliorates ischemia-reperfusion injury in small-for-size rat liver grafts," Transplant Proc. 39(5):1338-44 (2007).

(Continued)

*Primary Examiner* — Phillip Gambel
(74) *Attorney, Agent, or Firm* — Clark & Elbing LLP

(57) ABSTRACT

Provided herein are compositions and methods directed to soluble proteins which can selectively deliver modulators of complement activity. Targeted delivery of these modulators is accomplished by selectively mutating particular amino acids in a targeting protein portion of the composition corresponding to at least the first two N-terminal SCR domains of CR2. Depending on the particular combination of mutations introduced into the targeting portion, a complement activity modulator can be selectively delivered to particular ligands of CR2 at sites where complement system activation or suppression is desired.

28 Claims, 5 Drawing Sheets

(56) References Cited

U.S. PATENT DOCUMENTS

| | | |
|---|---|---|
| 2003/0180292 A1 | 9/2003 | Hanna et al. |
| 2004/0005538 A1 | 1/2004 | Chen et al. |
| 2004/0191252 A1 | 9/2004 | Taylor et al. |
| 2004/0219156 A1 | 11/2004 | Goldenberg et al. |
| 2004/0229827 A1 | 11/2004 | Steward et al. |
| 2005/0002128 A1 | 1/2005 | Ito et al. |
| 2005/0032128 A1 | 2/2005 | Halperin |
| 2005/0232920 A1 | 10/2005 | Fung et al. |
| 2005/0260198 A1 | 11/2005 | Holers et al. |
| 2005/0265995 A1 | 12/2005 | Tomlinson et al. |
| 2006/0002944 A1 | 1/2006 | Ashkenazi et al. |
| 2006/0014681 A1 | 1/2006 | Chen et al. |
| 2006/0178308 A1 | 8/2006 | Schwaeble et al. |
| 2006/0263819 A1 | 11/2006 | Hageman et al. |
| 2006/0276388 A1 | 12/2006 | Christa et al. |
| 2006/0292141 A1 | 12/2006 | Holers et al. |
| 2007/0003544 A1 | 1/2007 | Hanna |
| 2007/0020647 A1 | 1/2007 | Hageman et al. |
| 2007/0134260 A1 | 6/2007 | Feger et al. |
| 2007/0172483 A1 | 7/2007 | Schwaeble et al. |
| 2007/0224197 A1 | 9/2007 | Chen et al. |
| 2008/0029911 A1 | 2/2008 | Jeon et al. |
| 2008/0118506 A1 | 5/2008 | An et al. |
| 2008/0221011 A1 | 9/2008 | Gilkeson et al. |
| 2008/0267980 A1 | 10/2008 | Tomlinson et al. |
| 2008/0299114 A1 | 12/2008 | Emlen et al. |
| 2009/0081211 A1 | 3/2009 | Campagne |
| 2009/0087907 A1 | 4/2009 | Pebay et al. |
| 2009/0175875 A1 | 7/2009 | Etemad-Gilbertson et al. |
| 2009/0304706 A1 | 12/2009 | Lu et al. |
| 2011/0014614 A1 | 1/2011 | Liew |
| 2011/0015127 A1 | 1/2011 | Gilkeson et al. |
| 2011/0286938 A1 | 11/2011 | Thurman et al. |
| 2011/0293605 A1 | 12/2011 | Sathish et al. |
| 2012/0014952 A1 | 1/2012 | Tomlinson et al. |
| 2012/0015871 A1 | 1/2012 | Tomlinson et al. |
| 2012/0015872 A1 | 1/2012 | Tomlinson et al. |
| 2012/0135430 A1 | 5/2012 | Zhang et al. |
| 2012/0171206 A1 | 7/2012 | Tomlinson et al. |
| 2013/0029912 A1 | 1/2013 | Holers et al. |
| 2013/0129728 A1 | 5/2013 | Holers et al. |
| 2013/0190477 A1 | 7/2013 | Kovacs et al. |

FOREIGN PATENT DOCUMENTS

| | | |
|---|---|---|
| EP | 0402266 A2 | 12/1990 |
| EP | 1336618 A1 | 8/2003 |
| JP | 05507197 A | 10/1993 |
| JP | 09502985 A | 3/1997 |
| JP | 2002534959 A | 10/2002 |
| JP | 2006-512325 A | 4/2006 |
| JP | 2009-540831 A | 11/2009 |
| WO | WO-91/16437 A1 | 10/1991 |
| WO | WO-96/12742 A1 | 5/1996 |
| WO | WO-98/07835 A2 | 2/1998 |
| WO | WO-99/44625 A1 | 9/1999 |
| WO | WO-00/34317 A2 | 6/2000 |
| WO | WO-00/34317 A3 | 8/2000 |
| WO | WO-00/67796 A1 | 11/2000 |
| WO | WO-02/068579 A2 | 9/2002 |
| WO | WO-2004/045520 A2 | 6/2004 |
| WO | WO-2004/103288 A2 | 12/2004 |
| WO | WO-2005/014618 A2 | 2/2005 |
| WO | WO-2005/044998 A2 | 5/2005 |
| WO | WO-2005/072479 A2 | 8/2005 |
| WO | WO-2005/077417 A1 | 8/2005 |
| WO | WO-2006/030220 A1 | 3/2006 |
| WO | WO-2006/062716 A2 | 6/2006 |
| WO | WO-2006/083533 A2 | 8/2006 |
| WO | WO-2006/088950 A2 | 8/2006 |
| WO | WO-2006/128006 A1 | 11/2006 |
| WO | WO-2007/029008 A2 | 3/2007 |
| WO | WO-2007/035857 A2 | 3/2007 |
| WO | WO-2007/056227 A2 | 5/2007 |
| WO | WO-2007/112403 A2 | 10/2007 |
| WO | WO-2007/129895 A2 | 11/2007 |
| WO | WO-2007/149567 A2 | 12/2007 |
| WO | WO-2008/154251 A2 | 12/2008 |
| WO | WO-2009/029669 A1 | 3/2009 |
| WO | WO-2009/056631 A2 | 5/2009 |
| WO | WO-2009/110918 A1 | 9/2009 |
| WO | WO-2010/015608 A1 | 2/2010 |
| WO | WO-2010/091183 A2 | 8/2010 |
| WO | WO-2010/136311 A2 | 12/2010 |
| WO | WO-2011/057158 A1 | 5/2011 |
| WO | WO-2011/143637 A1 | 11/2011 |
| WO | WO-2011/163412 A1 | 12/2011 |
| WO | WO-2013/117035 A1 | 8/2013 |
| WO | WO-2013/177035 A2 | 11/2013 |

OTHER PUBLICATIONS

Yang et al., "The role of complement C3 in intracerebral hemorrhage-induced brain injury," J Cereb Blood Flow Metab. 26(12):1490-5 (2006).

Atkinson et al., "A role for complement in the enhanced susceptibility of steatotic livers to ischemia and reperfusion injury," Mol Immunol. 44:151-2 (2007).

Marshall et al., "Dissecting the complement pathway in hepatic injury and regeneration with a novel protective strategy," J Exp Med. 211(9):1793-805 (2014).

International Preliminary Report on Patentability and Written Opinion for International Application No. PCT/US2011/041517, dated Dec. 28, 2012 (11 pages).

International Preliminary Report on Patentability and Written Opinion of the International Searching Authority for International Application No. PCT/US2010/040973, dated Jan. 4, 2012 (8 pages).

International Preliminary Report on Patentability and Written Opinion of the International Searching Authority for International Application No. PCT/US2007/014602, dated Dec. 22, 2008 (6 pages).

International Preliminary Report on Patentability and Written Opinion of the International Searching Authority for International Application No. PCT/US2011/036552, dated Nov. 20, 2012 (9 pages).

International Preliminary Report on Patentability and Written Opinion of the International Searching Authority for International Application No. PCT/US2010/055745, dated May 8, 2012 (6 pages).

International Search Report for International Application No. PCT/US2011/041517, completed Oct. 11, 2011 (8 pages).

Supplementary European Search Report for European Application No. 10794833.3, completed Nov. 28, 2013 (8 pages).

Weaver, "Animal studies paint misleading picture," <http://www.nature.com/news/2010/100330/full/news.2010.158.html>, retrieved on Sep. 14, 2014 (3 pages) (2010).

Leu et al., "Triggering of interferon gamma-primed macrophages by various known complement activators for nonspecific tumor cytotoxicity," Cell Immunol. 106(1):114-121 (1987).

Kawasaki, "Structure and function of serum mannan-binding protein," Jpn J Med Mycol. 33(2):105-12 (1992).

"Monoclonal antibody to human C3(C3d), Catalog No. A207," Quidel Corporation Product Catalog, <http://www.quidel.com/products/product_detail.php?prod=73&group=2>, retrieved on Apr. 25, 2013 (2 pages).

"Monoclonal antibody to human C3d (neo), Catalog No. A250," Quidel Corporation Product Catalog, <http://www.quidel.com/products/product_detail.php?prod=160&group=2>, retrieved on Dec. 26, 2013 (2 pages).

Abrahmsen et al., "Engineering subtilisin and its substrates for efficient ligation of peptide bonds in aqueous solution," Biochemistry. 30:4151-4159 (1991).

Aguado et al., "Monoclonal antibodies against complement 3 neoantigens for detection of immune complexes and complement activation. Relationship between immune complex levels, state of C3, and numbers of receptors for C3b," J Clin Invest. 76:1418-26 (1985).

Ahearn et al., "Disruption of the Cr2 locus results in a reduction in B-1a cells and in an imparied B cell response to T-dependent antigen," Immunity. 4(3):251-262 (1996).

(56) References Cited

OTHER PUBLICATIONS

Ahearn et al., "Epstein-Barr virus (EBV) infection of murine L cells expressing recombinant human EBV/C3d receptor," Proc Natl Aced Sci USA. 85:9307-11 (1988).
Ahearn et al., "Structure and function of the complement receptors, CR1 (CD35) and CR2 (CD21)," Adv Immunol. 46:183-219 (1989).
Amsterdam et al., "Limitation of reperfusion injury by a monoclonal antibody to C5a during myocardial infarction in pigs," Am J Physiol. 268(1):H448-57 (1995).
Andrews et al., "Spontaneous murine Lupus-like syndromes. Clinical and immunopathological manifestations in several strains," J Exp Med. 148:1198-215 (1978).
Arumugam et al., "Complement mediators in ischemia-reperfusion injury," Clin Chim Acta. 374:33-45 (2006).
Arumugam et al., "Protective effect of a human C5a receptor antagonist against hepatic ischaemia-reperfusion injury to rats," J Hepatol. 40:934-41 (2004).
Aslam et al., "Folded-back solution structure of monomeric factor H of human complement by synchrotron X-ray and neutron scattering, analytical ultracentrifugation and constrained molecular modelling," J Mol Biol. 309(5):1117-1138 (2001).
Asokan et al., "Characterization of human complement receptor type 2 (CR2/CD21) as a receptor for IFN-alpha: a potential role in systemic lupus erythematosus," J Immunol. 177:383-94 (2006).
Atkinson et al., "Complement-dependent P-selectin expression and injury following ischemic stroke," J Immunol. 177:7266-74 (2006).
Atkinson et al., "Targeted complement inhibition by C3d recognition ameliorates tissue injury without apparent increase in susceptibility to infection," J Clin Invest. 115(9):2444-53 (2005).
Atkinson et al., "Targeted complement inhibitors protect against posttransplant cardiac ischemia and reperfusion injury and reveal an important role for the alternative pathway of complement activation," J Immunol. 185:7007-13 (2010).
Atkinson et al., "Targeted inhibition of the alternative complement pathway delays the onset of antibody-mediated rejection in a mouse heterotopic heart transplant model," Mol Immunol. 44:3944, Abstract No. P24 (2007).
Aubry et al., "CD21 is a ligand for CD23 and regulates IgE production," Nature. 358(6386):505-507 (1992).
Aubry et al., "CD23 interacts with a new functional extracytoplasmic domain involving N-linked oligosaccharides on CD21," J Immunol. 152:5806-13 (1994).
Author manuscript of Clark et al., "Evidence for non-traditional activation of complement factor C3 during murine liver regeneration," available in PMC Jun. 1, 2009, published in final edited form as: Mol Immunol. 45(11):3125-32 (2008) (15 pages).
Author manuscript of Habermann et al., "Increased serum levels of complement C3a anaphylatoxin indicate the presence of colorectal tumors," available in PMC Sep. 8, 2008, published in final edited form as: Gastroenterol. 131(4):1020-9 (2006) (17 pages).
Author manuscript of Huang et al., "A novel targeted inhibitor of the alternative pathway of complement and its therapeutic application in ischemia/reperfusion injury," available in PMC Nov. 25, 2009, published in final edited form as: J Immunol. 181(11): 8068-8076 (2008) (19 pages).
Baechler et al., "Interferon-inducible gene expression signature in peripheral blood cells of patients with severe lupus," Proc Natl Acad Sci USA. 100:2610-5 (2003).
Bagshawe et al., "A cytotoxic agent can be generated selectively at cancer sites," Br J Cancer. 58:700-703 (1988).
Bagshawe, "Towards generating cytotoxic agents at cancer sites," Br J Cancer. 60:275-281(1989).
Baldo et al., "The adipsin-acylation stimulating protein system and regulation of intracellular triglyceride synthesis," J Clin Invest. 92:1543-47 (1993).
Banda et al., "Targeted inhibition of the complement alternative pathway with complement receptor 2 and factor H attenuates collagen antibody-induced arthritis in mice," J Immunol. 183:5928-37 (2009).
Baranyi et al., "Cell-surface bound complement regulatory activity is necessary for the in vivo survival of KDH-8 rat hepatoma," Immunology. 82(4):522-8 (1994).
Barlow et al., "Solution structure of a pair of complement modules by nuclear magnetic resonance," J Mol Biol. 232:268-284 (1993).
Battelli et al., "T lymphocyte killing by a xanthine-oxidase-containing immunotoxin," Cancer Immunol Immunother. 35:421-425 (1992).
Benvenuti et al., "Crystallization of soluble proteins in vapor diffusion for X-ray crystallography," Nat Protoc. 2(7):1633-1651 (2007).
Bergelson et al., "Decay-accelerating factor (CD55), a glycosylphosphatidylinositol-anchored complement regulatory protein, is a receptor for several echoviruses," Proc Nat Aced Sci USA. 91(13):6245-9 (1994).
Blank et al., "Hemoglobin interference from in vivo hemolysis," Clin Chem. 31(9):1566-9 (1985).
Bohnsack et al., "CR2 ligands modulate human B cell activation," J Immunol. 141:2569-76 (1988).
Boross et al., "Boosting antibody therapy with complement," Blood. 119(25):5945-5947 (2012).
Brauer et al., "Functional activity of anti-C6 antibodies elicited in C6-deficient rats reconstituted by liver allografts. Ability to inhibit hyperacute rejection of discordant cardiac xenografts," Transplantation 61(4):588-94 (1996).
Brodsky, "How I treat paroxysmal nocturnal hemoglobinuria," Blood. 113(26):6522-7 (2009).
Brown et al., "Molecular and cellular mechanisms of receptor-mediated endocytosis," DNA Cell Biol. 10:399-409 (1991).
Bykov, "Complement system and alcoholic liver disease," University of Helsinki 1-69 (2008).
Camargo et al., "Interleukin-6 protects liver against warm ischemia/reperfusion injury and promotes hepatocyte proliferation in the rodent," Hepatology. 26:1513-20 (1997).
Cambier, "Signalling processes in haematopoietic cells: positive and negative signal co-operativity in the immune system: the BCR, Fc gamma RIIB, CR2 paradigm," Biochem Soc Trans. 25(2):441-445 (1997).
Caragine et al., "A tumor-expressed inhibitor of the early but not late complement lytic pathway enhances tumor growth in a rat model of human breast cancer," Cancer Res. 62(4):1110-5 (2002).
Cardarelli et al., "A nonfucosylated human antibody to CD19 with potent B-cell depletive activity for therapy of B-cell malignancies," Cancer Immunol Immunother. 59(2):257-65 (2010).
Carel et al., "Structural requirements for C3d,g/Epstein-Barr virus receptor (CR2/CD21) ligand binding, internalization, and viral infection," J Biol Chem. 265(21):12293-9 (1990).
Carroll, "The role of complement and complement receptors in induction and regulation of immunity," Annu Rev Immunol. 16:545-568 (1998).
Carroll, The role of complement in B cell activation and tolerance. *Advances in Immunology*. Dixon,74:61-88 (2000).
Carter et al., "CD19: lowering the threshold for antigen receptor stimulation of B lymphocytes," Science. 256:105-7 (1992).
Carter et al., "Polymeric C3dg primes human B lymphocytes for proliferation induced by anti-IgM," J Immunol. 143(6):1755-60 (1989).
Carter et al., "Synergistic interaction between complement receptor type 2 and membrane IgM on B lymphocytes," J Immunol. 141:457-63 (1988).
Casasnovas et al., "Crystal structure of two CD46 domains reveals an extended measles virus-binding surface," EMBO J. 18(11):2911-2922 (1999).
Chavez-Cartaya et al., "Regulation of the complement cascade by soluble complement receptor type 1. Protective effect in experimental liver ischemia and reperfusion," Transplantation. 59:1047-52 (1995).
Chen et al., "CD59 expressed on a tumor cell surface modulates decay-accelerating factor expression and enhances tumor growth in a rat model of human neuroblastoma," Cancer Res. 60(11):3013-8 (2000).

(56) References Cited

OTHER PUBLICATIONS

Chen et al., "Gene therapy for brain tumors: regression of experimental gliomas by adenovirus-mediated gene transfer in vivo," Proc Natl Acad Sci USA. 91:3054-3057 (1994).
Christiansen et al., "A functional analysis of recombinant soluble CD46 in vivo and a comparison with recombinant soluble forms of CD55 and CD35 in vitro," Eur J Immunol. 26(3):578-85 (1996).
Clavien et al., "Strategies for safer liver surgery and partial liver transplantation," N Engl J Med. 356:1545-59 (2007).
Clemenza et al., "Structure-guided identification of C3d residues essential for its binding to complement receptor 2 (CD21)," J Immunol. 165:3839-3848 (2000).
Colvin, "Antibody-mediated renal allograft rejection: diagnosis and pathogenesis," J Am Soc Nephrol. 18(4):1046-56 (2007).
Cooper et al., "Immunobiology of CR2, the B lymphocyte receptor for Epstein-Barr virus and the C3d complement fragment," Ann Rev Immunol. 6:85-113 (1988).
Crumm et al., "Adenine necleotide changes in the remnant liver: an early signal for regeneration after partial hepatectomy," Hepatology. 48:898-908 (2008).
Cudney, "Protein crystallization and dumb luck," The Rigaku Journal. 16(1):1-7 (1999).
Dahm et al., "Small-for-size syndrome after partial liver transplantation: definition, mechanisms of disease and clinical implications," Am J Transplant. 5:2605-10 (2005).
Davies et al., "CD59, a Ly-6-Like protein expressed in human lymphoid cells, regulates the action of the complement membrane attack complex on homologous cells," J Exp Med. 170(3):637-54 (1989).
De Córdoba et al., "The human complement factor H: functional roles, genetic variations and disease associations," Molec Immunol. 41:355-67 (2004).
Delaglio et al., "NMRPipe: a multidimensional spectral processing system based on UNIX pipes," J Biomol NMR. 6:277-93 (1995).
Delcayre et al., "Epstein Barr virus/complement C3d receptor is an interferon alpha receptor," EMBO J. 10:919-26 (1991).
Delcayre et al., "Inhibition of Epstein-Barr virus-mediated capping of CD21/CR2 by alpha interferon (IFN-alpha): immediate antiviral activity of IFN-alpha during the early phase of infection," J Virol. 67:2918-21 (1993).
Dempsey et al., "C3d of complement as a molecular adjuvant: bridging innate and acquired immunity," Science. 271:348-350 (1996).
Dev et al., "Electrochemotherapy—A novel method of cancer treatment," Cancer Treat Rev. 20:105-115 (1994).
Diefenbach et al., "Mutation of residues in the C3dg region of human complement component C3 corresponding to a proposed binding site for complement receptor type 2 (CR2, CD21) does not abolish binding of iC3b or C3dg to CR2," J Immunol. 154(5):2303-2320 (1995).
Dierich et al., "Structural and functional relationships among receptors and regulators of the complement system," Mol Immunol. 25(11):1043-1051 (1988).
Dilillo et al., "Selective and efficient inhibition of the alternative pathway of complement by a mAb that recognizes C3b/iC3b," Mol Immunol. 43:1010-9 (2006).
Dobbie et al., "Epitope specificities and quantitative and serologic aspects of monoclonal complement (C3c and C3d) antibodies," Transfusion. 27(6):453-459 (1987).
Dominguez et al., "HADDOCK: a protein-protein docking approach based on biochemical or biophysical information," J Am Chem Soc. 125:1731-7 (2003).
Drenth, Crystalling a Protein. *Principles of Protein X-Ray Crystallography*. Springer-Verlag, 1-21 (1999).
Duits et al., "Selective enhancement of Leu-Cam expression by Interleukin 6 during differentiation of human promonocytic U937 cells," Scand J Immunol. 33(2):151-9 (1991).
Duranski et al., "Cytoprotective effects of nitrite during in vivo ischemia-reperfusion of the heart and liver," J Clin Invest. 115(5):1232-40 (2005).

Dutkowski et al., "Novel short-term hypothermic oxygenated perfusion (HOPE) system prevents injury in rat liver graft from non-heart beating donor," Ann Surg. 244(6):968-76, discussion 976-7 (2006).
Dörig et al., "The human CD46 molecule is a receptor for measles virus (Edmonston strain)," Cell. 75(2):295-305 (1993).
EBI Accession No. CQ729676, <http://ibis/IBIS/exam/dbfetch.jsp?id=EM_PAT:CQ729676>retrieved on Jan. 3, 2011(1 page).
EBI Accession No. CQ729676. Retrieved on Jan. 3, 2011 (1 page).
Edberg et al., "Quantitative analyses of the binding of soluble complement-fixing antibody/dsDNA immune complexes to CR1 on human red blood cells," J Immunol. 139:3739-47 (1987).
Edwards et al., "Complement factor H polymorphism and age-related macular degeneration," Science. 308:421-4 (2005).
Elvington et al., "A targeted complement-dependent strategy to improve the outcome of mAb therapy, and characterization in a murine model of metastatic cancer," Blood. 119(25):6043-6051 (2012).
Extended European Search Report and Written Opinion for European Application No. 11781394.9, dated Sep. 19, 2013 (11 pages).
Extended European Search Report for European Application No. 10829204.6, dated Mar. 5, 2013 (9 pages).
Fabrikant, "The kinetics of cellular proliferation in regenerating liver," J Cell Biol. 36(3):551-65 (1968).
Fausto, "Involvement of the innate immune system in liver regeneration and injury," J Hepatol. 45:347-9 (2006).
Fearon et al., "The CD19/CR2/TAPA-1 complex of B lymphocytes: Linking natural to acquired immunity," Annu Rev Immunol. 13:127-149 (1995).
Fearon, "The complement system and adaptive immunity," Semin Immunol. 10(5):355-361 (1998).
Ferreira et al., "Factor H-mediated cell surface protection from complement is critical for the survival of PNH erythrocytes," Blood. 110(6):2190-2 (2007).
Fingeroth et al., "Characterization of a T-lymphocyte Epstein-Barr virus/C3d receptor (CD21)," J Virol. 62:1442-7 (1988).
Fingeroth et al., "Epstein-Barr virus receptor of human B lymphocytes is the C3d receptor CR2," Proc Natl Acad Sci USA. 81(14):4510-4514 (1984).
Fingeroth et al., "Identification of murine complement receptor type 2," Proc Natl Acad Sci USA. 86(1):242-246 (1989).
Fiorini et al., "Development of an unbiased method for the estimation of liver steatosis," Clin Transplant. 18:700-6 (2004).
Fishelson et al., "Regulation of the alternative pathway of complement by pH," J Immunol. 138(10):3392-5 (1987).
Fondevila et al., "The membrane attack complex (C5b-9) in liver cold ischemia and reperfusion injury," Liver Transpl. 14:1133-41 (2008).
Franco-Gou et al., "Protection of reduced-size liver for transplantation," Am J Transplant. 4(9):1408-20 (2004).
Fritzinger et al., "Functional characterization of human C3/cobra venom factor hybrid proteins for therapeutic complement depletion," Develop Comp Immunol. 33(1):105-16 (2009).
Fritzinger et al., "Molecular cloning and derived primary structure of cobra venom factor," Proc Natl Acad Sci USA. 91:12775-12779 (1994); correction 92: 7065 (1995).
Frémeaux-Bacchi et al., "Soluble CD21 induces activation and differentiation of human monocytes through binding to membrane CD23," Eur J Immunol. 28:4268-4274 (1998).
Fujisaku et al., "Genomic organization and polymorphisms of the human C3d/Epstein-Barr virus receptor," J Biol Chem. 264:2118-25 (1989).
Fukuoka et al., "Molecular cloning of murine decay accelerating factor by immunoscreening," International Immunology. 8:379-385 (1996).
Girardi et al., "Complement C5a receptors and neutrophils mediate fetal injury in the antiphospholipid syndrome," J Clin Invest. 112(11):1644-54 (2003).
Gomez et al., "Role of ischaemic preconditioning in liver regeneration following major liver resection and transplantation," World J Gastroenterol. 13(5):657-70 (2007).
Goodford, "A computational procedure for determining energetically favorable binding sites on biologically important macromolecules," *J. Med. Chem.* 28: 849-857, 1985.

(56) References Cited

OTHER PUBLICATIONS

Gordon, "B-cell signalling via the C-type lectins CD23 and CD72," Immunol Today. 15(9):411-417 (1994).
Greene et al., "Partial hepatectomy in the mouse: technique and perioperative management," J Invest Surg. 16:99-102 (2003).
Greenspan et al., "Defining epitopes: It's not as easy as it seems," Nat Biotechnol. 17:936-937 (1999).
Grzesiek et al., "Improved 3D triple-resonance NMR techniques applied to a 31-kDa protein," J Magn Reson. 96:432-40 (1992).
Guthridge et al., "Epitope mapping using the X-ray crystallographic structure of complement receptor type 2 (CR2)/CD21: Identification of a highly inhibitory monoclonal antibody that directly recognizes the CR2-C3d interface," J Immunol. 167:5758-5766 (2001).
Guthridge et al., "Structural studies in solution of the recombinant N-terminal pair of short consensus/complement repeat domains of complement receptor type 2 (CR2/CD21) and interactions with its ligand C3dg," Biochemistry. 40:5931-5941 (2001).
Haan et al., "Different functional domains in the cytoplasmic tail of glycoprotein B are involved in Epstein-Barr virus-induced membrane fusion," Virology. 290:106-14 (2001).
Haddad et al., "Depletion of glycoprotein gp85 from virosomes made with Epstein-Barr virus proteins abolishes their ability to fuse with virus receptor-bearing cells," J Virol. 63:4998-5005 (1989).
Hageman et al., "A common haplotype in the complement regulatory gene factor H (HF1/CFH) predisposes individuals to age-related macular degeneration," Proc Natl Acad Sci USA. 102(20):7227-32 (2005).
Haines et al., "Complement factor H variant increases the risk of age-related macular degeneration," Science. 308(5720):419-21 (2005).
Ham et al., "Studies on destruction of red blood cells. II. Chronic hemolytic anemia with paroxysmal nocturnal hemoglobinuria: certain immunological aspects of the hemolytic mechanism with special reference to serum complement," J Clin Invest. 18:657-72 (1939).
Hampton Research, Catalog, 5 & 7 (2001).
Hampton Research, Crystal Screen User Guide, 27632 El Lazo Road, Laguna Niguel, California, 1991 (4 pages).
Hannan et al., "Mutational analysis of the complement receptor type 2 (CR2/CD21)-C3d interaction reveals a putative charged SCR1 binding site for C3d," J Mol Biol. 346(3):845-58 (2005).
Hannan et al., "Structure of complement receptor (CR) 2 and CR2-C3d complexes," Biochem Soc Trans. 30:983-9 (2002).
Harada et al., "Antithrombin reduces ischemia/reperfusion injury of rat liver by increasing the hepatic level of prostacyclin," Blood. 93:157-64 (1999).
Harlow et al., Proteolytic Fragments of Antibodies. *Antibodies: A Laboratory Manuel*. 626-629 (1988).
Harris et al., "Tailoring anti-complement therapeutics," Biochem Soc Trans. 30(6):1019-26 (2002).
Hautekeete et al., "Microvesicular steatosis of the liver," Acta Clin Belg. 45(5):311-326 (1990). Abstract Only.
He et al., "Delivery of antioxidative enzyme genes protects against ischemia/reperfusion-induced liver injury in mice," Liver Transpl. 12:1869-79 (2006).
Hebell et al., "Suppression of the immune response by a soluble complement receptor of B lymphocytes," Science. 254:102-105 (1991).
Heinen et al., "Factor H-related protein 1 (CFHR-1) inhibits complement C5 convertase activity and terminal complex formation," Blood. 114(12):2439-47 (2009).
Helling et al., "Partial hepatectomy with or without endotoxin does not promote apoptosis in the rat liver," J Surg Res. 116:1-10 (2004).
Helling, "Liver failure following partial hepatectomyn" HPB (Oxford). 8:165-74 (2006).
Heyman, "Regulation of antibody responses via antibodies, complement, and Fc receptors," Ann Rev Immunol. 18:709-737 (2000).
Higgins et al., "A soluble chimeric complement inhibitory protein that possesses both decay-accelerating and factor I cofactor activities," J Immunol. 158(6):2872-81 (1997).

Higgins et al., "Experimental pathology of the liver. 1. Restoration of the liver of the white rat following partial surgical removal," Arch Pathol. 12:186-202 (1931).
Hill et al., "Sustained response and long-term safety of eculizumab in paroxysmal nocturnal hemoglobinuria," Blood. 106:2559-65 (2005).
Hill, "Eculizumab for the treatment of paroxysmal nocturnal hemoglobinuria," Clin Adv Hematol Oncol. 3(11):849-50 (2005).
Hillmen et al., "Effect of eculizumab on hemolysis and transfusion requirements in patients with paroxysmal nocturnal hemoglobinuria," N Engl J Med. 350(6):552-9 (2004).
Holers et al., "The alternative pathway of complement in disease: Opportunities for therapeutic targeting," Mol. Immunol. 41:147-152 (2004).
Holers, "The spectrum of complement alternative pathway-mediated diseases," Immunol Rev. 223:300-316 (2008).
Holers, Complement Receptors. *The Year in Immunology 1988. Cellular, Molecular and Clinical Aspects*. Cruse et al., 4:231-240 (1989).
Holers, Complement. *Clinical Immunology, Principles and Practice*. Mosby ed. 363-91 (1996).
Homeister et al., "Soluble complement receptor type 1 prevents human complement-mediated damage of the rabbit isolated heart," J Immunol. 150(3):1055-1064 (1993).
Hori et al., "Crry, a complement regulatory protein, modulates renal interstitial disease induced by proteinuria," Kidney Int. 56:2096-2106 (1999).
Hsu et al., "Chronic progression of tubulointerstitial damage in proteinuric renal disease is mediated by complement activation: a therapeutic role for complement inhibitors?" J Am Soc Nephrol. 14:S186-91 (2003).
Huang et al., "A novel targeted inhibitor of the alternative pathway of complement," Mol Immunol. 44(16):3947 (Abstract Only: No. P31) (2007).
Huang et al., "Insights into the human CD59 complement binding interface toward engineering new therapeutics," J Biol Chem. 280(40):34073-9 (2005).
Hughes et al., "Monoclonal antibody targeting of liposomes to mouse lung in vivo," Cancer Res. 49(22):6214-20 (1989).
Humar et al., "Liver regeneration after adult living donor and deceased donor split-liver transplants," Liver Transpl. 10(3):374-8 (2004).
Humblet et al., "3D database searching and docking strategies," Topics in Drug Design and Discovery. *Annual Reports in Medicinal Chemistry*. Bristol et al., 28:275-284 (1993).
Iida et al., "Identification of the membrane receptor for the complement fragment C3d by means of a monoclonal antibody," J Exp Med. 158:1021-33 (1983).
Iimuro et al., "NFkappaB prevents apoptosis and liver dysfunction during liver regeneration," J Clin Invest. 101(4):802-11 (1998).
Imai et al., "Enhancement of antibody-dependent mechanisms of tumor cell lysis by a targeted activator of complement," Cancer Res. 67(19):9535-9541 (2007).
International Search Report for International Application No. PCT/US2011/036552, mailed Jul. 26, 2011 (7 pages).
International Search Report for International Application No. PCT/US2003/36459, mailed Sep. 15, 2004 (2 pages).
International Search Report for International Application No. PCT/US2007/014602, mailed on Mar. 6, 2008 (5 pages).
International Search Report for International Application No. PCT/US2010/040973, mailed Oct. 14, 2010 (5 pages).
International Search Report for International Application No. PCT/US2010/055745, mailed Feb. 4, 2011 (3 pages).
Jackson et al., "PI3K/Akt activation is critical for early hepatic regeneration after partial hepatectomy," Am J Physiol Gastrointest Liver Physiol. 294:G1401-10 (2008).
Jacobson et al., "Clinical and immunologic features of transient cold agglutinin-hemolytic anemia," Am J Med. 54:514-21 (1973).
Janssen et al., "Structure of C3b reveals conformational changes that underlie complement activity," Nature. 444:213-216 (2006).
Janssen et al., "Structure of compstatin in complex with complement component C3c reveals a new mechanism of complement inhibition," J Biol Chem. 282:29241-7 (2007).

(56) References Cited

OTHER PUBLICATIONS

Janzi et al., "Serum microarrays for large scale screening of protein levels," Mol Cell Proteomics. 4(12):1942-7 (2005).
Jin et al., "Interleukin-6 inhibits oxidative injury and necrosis after extreme liver resection," Hepatology. 46:802-12 (2007).
Jin et al., "Paradoxical effects of short- and long-term interleukin-6 exposure on liver injury and repair," Hepatology. 43:474-84 (2006).
Johswich et al., "Ligand specificity of the anaphylatoxin C5L2 receptor and its regulation on myeloid and epithelial cell lines," J Biol Chem. 281(51):39088-95 (2006).
Jozsi et al., "Attachment of the soluble complement regulator factor H to cell and tissue surfaces: relevance for pathology," Histol Hitopathol. 19:251-8 (2004).
Juhl et al., "Complement killing of human neuroblastoma cells: A cytotoxic monoclonal antibody and its F(ab')2-cobra venom factor conjugate are equally cytotoxic," *Mol Immunol.* 27(10):957-964 (1990).
Kadry et al., "Liver regeneration after adult living donor and deceased donor split-liver transplants," Liver Transpl. 10(8):1078 (2004).
Kalant et al., "C5L2 is a functional receptor for acylation-stimulating protein," J Biol Chem 208(25):23936-44 (2005).
Kalant et al., "The chemoattractant receptor-like protein C5L2 binds the C3a des-Arg77/acylation-stimulating protein," J Biol Chem 278(13):11123-9 (2003).
Kalli et al., "Interaction of iC3b with recombinant isotypic and chimeric forms of CR2," J Immunol. 147(2):590-594 (1991).
Kaplan, "Eculizumab Alexion," Curr Opin Investig Drugs. 3(7):1017-23 (2002).
Khurana et al., "Crystal structure of 2,5-diketo-D-gluconic acid reductase A complexed with NADPH at 2.1-A resolution," Proc Natl Acad Sci 95:6768-6773 (1998).
Kildsgaard et al., "A critical evaluation of the putative role of C3adesArg (ASP) in lipid metabolism and hyperapobetalipoproteinemia," Mol Immunol. 36:869-76 (1999).
Klein et al., "Complement factor H polymorphism in age-related macular degeneration," Science. 308(5720):385-9 (2005).
Koski et al., "Cytolysis of nucleated cells by complement: cell death displays multi-hit characteristics," Proc Natl Acad Sci USA. 80:3816-3820 (1983).
Kovacs et al., "Biophysical investigations of complement receptor 2 (CD21 and CR2)-ligand interactions reveal amino acid contacts unique to each receptor-ligand pair," J Biol Chem. 285:27251-8 (2010).
Kovacs et al., "Mapping of the C3d ligand binding site on complement receptor 2 (CR2/CD21) using nuclear magnetic resonance and chemical shift analysis," J Biol Chem. 284(14):9513-20 (2009).
Kroshus et al., "A recombinant soluble chimeric complement inhibitor composed of human CD46 and CD55 reduces acute cardiac tissue injury in models of pig-to-human heart transplantation," Transplantation. 69(11):2282-9 (2000).
Kroshus et al., "Complement inhibition with an anti-C5 monoclonal antibody prevents acute cardiac tissue injury in an ex vivo model of pig-to-human xenotransplantation," Transplantation. 60(11):1194-202 (1995).
Krushkal et al., "Evolutionary relationships among proteins encoded by the regulator of complement activation gene cluster," Mol Biol Evol. 17(11):1718-30 (2000).
Kuby et al., Antigens. *Immunology* (2nd edition). W H Freeman and Company, 85-96 (1994).
Kundrot, "Which strategy for a protein crystallization project?" Cell Mol Life Science. 61(5):525-536 (2004).
Kuraya et al., "Expression of the complement regulatory proteins CD21, CD55, and CD59 on Burkitt lymphoma lines: Their role in sensitivity to human serum-meidated lysis," Eur J Immunol. 22(7):1871-1876 (1992).
La Flamme et al., "Lack of C3 affects Th2 response development and the sequelae of chemotherapy in schistosomiasis," J Immunol. 170:470-6 (2003).

Lambris et al., "Mapping of the C3d receptor (CR2)-binding site and a neoantigenic site in the C3d domain of the third component of complement," Proc Natl Aced Sci USA. 82(12):4235-4239 (1985).
Law et al., "Action of the C3b-inactivator of the cell-bound C3b," J Immunol. 122(3):759-65 (1979).
Law et al., Complement. *In Focus*. Male, vii-ix (1995).
Lehmann et al., "Complement inhibition by soluble complement receptor type 1 improves microcirculation after rat liver transplantation," Transplantation. 66:717-22 (1998).
Lehmann et al., "Impact of inhibition of complement by sCR1 on hepatic microcirculation after warm ischemia," Microvasc Res. 62:284-92 (2001).
Leivo et al., "C3d fragment of complement interacts with laminin and binds to basement membranes of glomerulus and trophoblast," J Cell Biol. 103:1091-100 (1986).
Lemoli et al., "Immunological effects of omalizumab in chronic urticaria: a case report," J Invest Allergol Clin Immunol. 20(3):252-4 (2010).
Leu et al., "Triggering of interferon γ-primed macrophages by various known complement activators for nonspecific tumor cytotoxicity," *Cell Immunol*. 106:114-121 (1987).
Linton et al., "therapeutic efficacy of a novel membrane-targeted complement regulator in antigen-induced arthritis in the rat," Arthritis Rheum. 43(11):2590-7 (2000).
Liszewski et al., "Complement inhibitors as therapeutic agents," Clin Immunol Newsletter. 17(12):168-73 (1997).
Litzinger et al., "Biodistribution and immunotargetability of ganglioside-stabilized dioleoylphosphatidylethanolamine liposomes," Biochimica et Biophysica Acta. 1104:179-87 (1992).
Lowell et al., "Mapping of the Epstein-Barr virus and C3dg binding sites to a common domain on complement receptor type 2," J Exp Med. 170(6):1931-1946 (1989).
Luqman et al., "The antileukemia activity of a human anti-CD40 antagonist antibody, HCD122, on human chronic lymphocytic leukemia cells," Blood. 112(3):711-20 (2008).
Luxembourg et al., "Modulation of signaling via the B cell antigen receptor by CD21, the receptor for C3dg and EBV," J Immunol. 153:4448-57 (1994).
Lyubarsky et al., "Recovery phase of the murine rod photoresponse reconstructed from electroretinographic recordings," J Neurosci. 16(2):563-571 (1996).
Lyubchenko et al., "Coligation of the B cell receptor with complement receptor type 2 (CR2/CD21) using its natural ligand C3dg: activation without engagement of an inhibitory signaling pathway," J Immunol. 174:3264-72 (2005).
Mache et al., "Complement inhibitor eculizumab in atypical hemolytic uremic syndrome," Clin J Am Soc Nephrol. 4(8):1312-6 (2009).
MacLaren et al., "Adipokines and the immune system: an adipocentric view," Adv Exp Med Biol. 632:1-21 (2008).
Markiewski et al., "C3a and C3b activation products of the third component of complement (C3) are critical for normal liver recovery after toxic injury," J Immunol. 173:747-754 (2004).
Martin et al., "Determination of the role for CD21 during Epstein-Barr virus infection of B-lymphoblastoid cells," J Virol. 68(8):4716-4726 (1994).
Martin et al., "Determination of the structural basis for selective binding of Epstein-Barr virus to human complement receptor type 2," J Exp Med. 174:1299-1311 (1991).
Maslowska et al., "Novel roles for acylation stimulating protein/C3adesArg: a review of recent in vitro and in vivo evidence," Vitam Norm. 70:309-32 (2005).
Mastellos et al., "A novel role of complement: mice deficient in the fifth component of complement (C5) exhibit impaired liver regeneration," J Immunol. 166(4):2479-86 (2001).
Mastellos et al., "Novel monoclonal antibodies against mouse C3 interfering with complement activation: description of fine specificity and applications to various immunoassays," Mol Immunol. 40(16):1213-21 (2004).

(56) References Cited

OTHER PUBLICATIONS

Matsumoto et al., "Intersection of the complement and immune systems: A signal transduction complex of the B lymphocyte-containing complement receptor type 2 and CD19," J Exp Med. 173(1):55-64 (1991).
Matsuo et al., "Complement in renal tubulointerstitial injuries," Proceedings of the 35th Complement Symposium 21-22 (1998).
McPherson, "Current approaches to macromolecular crystallization," Eur J Biochem. 189(1):1-23 (1990).
Mendrick et al., "I. induction of proteinuria in the rat by a monoclonal antibody against SGP-115/107," Kidney Int. 33:818-30 (1988).
Mendrick et al., "Monoclonal antibodies against rat glomerular antigens: production and specificity," Lab Invest. 49(1):107-17 (1983).
Meri et al., "Structural composition and functional characterization of soluble CD59: heterogeneity of the oligosaccharide and glycophoshoinositol (GPI) anchor revealed by laser-desorption mass spectrometric analysis," Biochem J. 316(3):923-35 (1996).
Moir et al., "B cells of HIV-1-infected patients bind virions through CD21-complement interactions and transmit infectious virus to activated T cells," J Exp Med. 192(5):637-646 (2000).
Mold et al., "Activation of the alternative complement pathway by EBV and the viral envelope glycoprotein, gp350," J Immunol. 140(11):3867-3874 (1988).
Molesworth et al., "Epstein-Barr virus gH is essential for penetration of B cells but also plays a role in attachment of virus to epithelial cells," J Virol. 74(14):6324-32 (2000).
Molina et al., "Analysis of C3b/C3d binding sites and factor I cofactor regions within mouse complement receptor 1 and 2," J Immunol. 153(2):789-795 (1994).
Molina et al., "Analysis of Epstein-Barr virus-binding sites on complement receptor 2 (CR2/CD21) using human-mouse chimeras and peptides," J Biol Chem. 266(19-20):12173-9 (1991).
Molina et al., "Characterization of a complement receptor 2 (CR2, CD21) ligand binding site for C3. An initial model of ligand interaction with two linked short consensus repeat modules," J Immunol. 154:5426-5435 (1995).
Molina et al., "Markedly impaired humoral immune response in mice deficient in complement receptors 1 and 2," Proc Natl Acad Sci USA. 93:3357-3361 (1996).
Mollnes et al., "Identification of a human C5 beta-chain epitope exposed in the native complement component but concealed in the SC5b-9 complex," Scand J Immunol. 28:307-12 (1988).
Moongkarndi et al., "Immunological and functional properties of two monoclonal antibodies against human C5," Immunobiol. 165:323 (1983).
Moongkarndi et al., "Monoclonal antibodies against the fifth component of human complement," Immunobiol. 162:397 (1982).
Moore et al., "Hydrodynamic, electron microscopic, and ligand-binding analysis of the Epstein-Barr virus/C3dg receptor (CR2)," J Biol Chem. 264:20576-82 (1989).
Moore et al., "Inhibition of Epstein-Barr virus infection In Vitro and In Vivo by soluble CR2 (CD21) containing two short consensus repeats," J Virol. 65(7):3559-3565 (1991).
Moore et al., "Molecular cloning of the cDNA encoding the Epstein-Barr virus/C3d receptor (complement receptor type 2) of human B lymphocytes," Proc Natl Acad Sci USA. 84:9194-8 (1987).
Moran et al., "Human recombinant soluble decay accelerating factor inhibits complement activation in vitro and in vivo," J Immunol. 149:1736-1743 (1992).
Morgan, "Clinical complementology: recent progress and future trends," Eur J Clin Invest. 24(4):219-28 (1994).
Morikis et al., "The electrostatic nature of C3d-complement receptor 2 association," J Immunol. 172:7537-47 (2004).
Mullen et al., "Structure of the Epstein-Barr virus gp42 protein bound to the MHC class II receptor HLA-DR1," Mol Cell. 9:375-85 (2002).
Mulligan et al., "Endothelial targeting and enhanced antiinflammatory effects of complement inhibitors possessing sialyl Lewisx moieties," J Immunol 162(8):4952-9 (1999).
Murray et al., "Functional bioactive recombinant acylation stimulating protein is distinct from C3a anaphylatoxin," J Lipid Res. 38:2492-501 (1997).
Murray et al., "Mice lacking acylation stimulating protein (ASP) have delayed postprandial triglyceride clearance," J Lipid Res. 40:1671-6 (1999).
Murray et al., "Reduced body weight, adipose tissue, and leptin levels despite increased energy intake in female mice lacking acylation-stimulating protein," Endocrinology. 141(3):1041-9 (2000).
Müller-Eberhard, "Molecular organization and function of the complement system," Ann Rev Biochem. 57:321-47 (1988).
Nagar et al., "X-ray crystal structure of C3d: A C3 fragment and ligand for complement receptor 2," Science. 280(5367):1277-81 (1998).
NCBI Blast for Accession No. NP_001006659.1. Retrieved on Dec. 26, 2013 (5 pages).
NCBI Blast for Accession No. NP_031784.1. Retrieved on Dec. 26, 2013 (4 pages).
NCBI Blast for GenBank Accession No. U09969. Retrieved on Nov. 15, 2013 (3 pages).
NCBI Blast for UniProtKB/Swiss-Prot Accession No. O55186. Retrieved on Nov. 13, 2013 (5 pages).
NCBI Blast for UniProtKB/Swiss-Prot Accession No. P00746. Retrieved on Nov. 13, 2013 (14 pages).
NCBI Blast for UniProtKB/Swiss-Prot Accession No. P00751. Retrieved on Nov. 13, 2013 (1 page).
NCBI Blast for UniProtKB/Swiss-Prot Accession No. P01024. Retrieved on Nov. 13, 2013 (29 pages).
NCBI Blast for UniProtKB/Swiss-Prot Accession No. P01027. Retrieved on Nov. 13, 2013 (13 pages).
NCBI Blast for UniProtKB/Swiss-Prot Accession No. P03953. Retrieved on Nov. 13, 2013 (6 pages).
NCBI Blast for UniProtKB/Swiss-Prot Accession No. P04004. Retrieved on Nov. 13, 2013 (14 pages).
NCBI Blast for UniProtKB/Swiss-Prot Accession No. P04186. Retrieved on Nov. 13, 2013 (9 pages).
NCBI Blast for UniProtKB/Swiss-Prot Accession No. P05155. Retrieved on Nov. 13, 2013 (29 pages).
NCBI Blast for UniProtKB/Swiss-Prot Accession No. P06909. Retrieved on Nov. 13, 2013 (19 pages).
NCBI Blast for UniProtKB/Swiss-Prot Accession No. P08173. Retrieved on Nov. 13, 2013 (4 pages).
NCBI Blast for UniProtKB/Swiss-Prot Accession No. P08603. Retrieved on Nov. 13, 2013 (1 page).
NCBI Blast for UniProtKB/Swiss-Prot Accession No. P10909. Retrieved on Nov. 13, 2013 (21 pages).
NCBI Blast for UniProtKB/Swiss-Prot Accession No. P11680. Retrieved on Nov. 13, 2013 (5 pages).
NCBI Blast for UniProtKB/Swiss-Prot Accession No. P13987. Retrieved on Nov. 13, 2013 (16 pages).
NCBI Blast for UniProtKB/Swiss-Prot Accession No. P15529. Retrieved on Nov. 13, 2013 (30 pages).
NCBI Blast for UniProtKB/Swiss-Prot Accession No. P17927. Retrieved on Nov. 13, 2013 (1 page).
NCBI Blast for UniProtKB/Swiss-Prot Accession No. P27918. Retrieved on Nov. 13, 2013 (13 pages).
NCBI Blast for UniProtKB/Swiss-Prot Accession No. P29788. Retrieved on Nov. 13, 2013 (10 pages).
NCBI Blast for UniProtKB/Swiss-Prot Accession No. P58019. Retrieved on Nov. 13, 2013 (5 pages).
NCBI Blast for UniProtKB/Swiss-Prot Accession No. P97290. Retrieved on Nov. 13, 2013 (6 pages).
NCBI Blast for UniProtKB/Swiss-Prot Accession No. Q06890. Retrieved on Nov. 13, 2013 (9 pages).
NCBI Blast for UniProtKB/Swiss-Prot Accession No. Q61475. Retrieved on Nov. 13, 2013 (11 pages).
NCBI Blast for UniProtKB/Swiss-Prot Accession No. Q9P296. Retrieved on Nov. 13, 2013 (9 pages).

(56) References Cited

OTHER PUBLICATIONS

NCBI Protein Database Accession No. P08173. Retrieved Feb. 18, 2014 (4 pages).
NCBI Protein Database Accession No. P13987. Retrieved Feb. 18, 2014 (12 pages).
NCBI Protein Database Accession No. P15529. Retrieved Feb. 18, 2014 (21 pages).
NCBI Protein Database Accession No. P58019. Retrieved Feb. 18, 2014 (4 pages).
Nemerow et al., "Identification and characterization of the Epstein-Barr virus receptor on human B lymphocytes and its relationship to the C3d complement receptor (CR2)," J Virol. 55(2):347-51 (1985).
Nemerow et al., "Identification of an epitope in the major envelope protein of Epstein-Barr virus that mediates viral binding to the B lymphocyte EBV receptor (CR2)," Cell. 56:369-77 (1989).
Nemerow et al., "Identification of gp350 as the viral glycoprotein mediating attachment of Epstein-Barr virus (EBV) to the EBV/C3d receptor of B cells: sequence homology of gp350 and C3 complement fragment C3d," J Virol. 61(5):1416-20 (1987).
Ngo et al., Computational Complexity, Protein Structure Prediction, and the Levinthal Paradox. *The Protein Folding Problem and Tertiary Structure Prediction*. Merz et al., 491-495 (1994).
Niemann et al., "The use of monoclonal antibodies as probes of the three-dimensional structure of human complement factor D," J Immunol. 132(2):809-15 (1984).
Nozaki et al., "Drusen complement components C3a and C5a promote choroidal neovascularization," Proc Natl Acad Sci USA. 103(7):2328-2333 (2006).
Oglesby et al., "Membrane cofactor protein (CD46) protects cells from complement-mediated attack by an intrinsic mechanism," J Exp Med. 175:1547-51 (1992).
Okano, "Epstein-Barr virus infection and its role in the expanding spectrum of human diseases," Acta Paediatr. 87:11-18 (1998).
Paglialunga et al., "Reduced adipose tissue triglyceride synthesis and increased muscle fatty acid oxidation in C5L2 knockout mice," J Endocrinol. 194:293-304 (2007).
Paixao-Cavalcante et al., "Factor H facilitates the clearance of GBM bound iC3b by controlling C3 activation in fluid phase," Mol Immunol. 46:1942-50 (2009).
Pascual et al., "A monoclonal antibody which blocks the function of factor D of human complement," J Immunol Methods. 127:263-9 (1990).
Pascual et al., "Inhibition of complement alternative pathway in mice with Fab antibody to recombinant adipsin/factor D," Eur J Immunol. 23:1389-92 (1993).
Patel et al., "Pexelizumab: a novel therapy for myocardial ischemia-reperfusion," Drugs Today (Barc). 41(3):165-70 (2005).
Pervushin et al., "Attenuated T2 relaxation by mutual cancellation of dipole-dipole coupling and chemical shift anisotropy indicates an avenue to NMR structures of very large biological macromolecules in solution," Proc Natl Acad Sci USA. 94:12366-71 (1997).
Petersen et al., "The mannan-binding lectin pathway of complement activation: biology and disease association," Mol Immunol. 38:133-49 (2001).
Piatesi et al., "Immunological optimization of a generic hydrophobic pocket for high affinity hapten binding and Diels-Alder activity," Chembiochem. 5(4):460-466 (2004).
Pietersz et al., "Antibody conjugates for the treatment of cancer," Immunolog Reviews. 129:57-80 (1992).
Poznansky et al., "The difference between human C3F and C3S results from a single amino acid change from an asparagine to an aspartate residue at position 1216 on the α-chain of the complement component C3," J Immunol. 143(4):1254-1258 (1989).
Preissner, "Structure and biological role of vitronectin," Annu Rev Cell Biol. 7:275-310 (1991).
Prodeus et al., "A critical role for complement in maintenance of self-tolerance," Immunity. 9(5):721-731 (1998).
Prodinger et al., "Characterization of C3dg binding to to a recess formed between short consensus repeats 1 and 2 of complement receptor type 2 (CR2; CD21)," J Immunol. 161:4604-4610 (1998).

Prota et al., "The crystal structure of human CD21: Implications for Epstein-Barr virus and C3d binding," Proc Natl Acad Sci USA. 99:10641-6 (2002).
Quigg et al., "Blockade of antibody-induced glomerulonephritis with Crry-Ig, a soluble murine complement inhibitor," J Immunol. 160(9):4553-60 (1998).
Quigg et al., "Production and fuctional analysis of rat CD59 and chimeric CD59-Crry as active soluble proteins in Pichia pastoris," Immunol. 99(1):46-53 (2000).
Rabinovici et al., "Role of complement in endotoxin/platelet-activating factor-induced lung injury," J Immunol. 149(5):1744-50 (1992).
Ramm et al., "Transmembrane channel formation by complement: functional analysis of the number of C5b6, C7, C8, and C9 molecules required for a single channel," Pro Natl Aced Sci. 79(15):4751-5 (1982).
Rao et al., "OKB7, a monoclonal antibody that reacts at or near the C3d binding site of human CR2," Cell Immunol. 93(2):549-555 (1985).
Reeck et al., "Homology in proteins and nucleic acids: A terminology muddle and a way out of it," Cell. 50:667 (1987).
Rehrig et al., "Complement inhibitor, complement receptor 1-related gene/protein y-lg attenuates intestinal damage after the onset of mesenteric ischemia/reperfusion injury in mice," J Immunol. 167:5921-7 (2001).
Ricklin et al., "Complement-targeted therapeutics," Nat Biotechnol. 25(11):1265-75 (2007).
Rinder et al., "Blockade of C5a and C5b-9 generation inhibits leukocyte and platelet activation during extracorporeal circulation," J Clin Invest. 96(3):1564-72 (1995).
Rioux, "TP-10 AVANT immunotherapeutics," Curr Opin Invest Drugs 2(3):364-71 (2001).
Risitano et al., "Complement fraction 3 binding on erythrocytes as additional mechanism of disease in paroxysmal nocturnal hemoglobinuria patients treated by eculizumab," Blood. 113(17):4094-4100 (2009) (25 pages).
Risitano et al., "Paroxysmal nocturnal hemoglobinuria: pathophysiology, natural history and treatment options in the era of biological agents," Biologics. 2(2):205-222 (2008).
Risitano et al., "The complement receptor 2/factor H fusion protein TT30 protects paroxysmal nocturnal hemoglobinuria erythroctyes from complement-mediated hemolysis and C3 fragment opsonization," Blood. 119(26):6307-6316 (2012).
Risitano et al., "TT30, a novel regulator of the complement alternative pathway (CAP), inhibits hemolysis of paroxysmal nocturnal hemoglobinuria (PNH) erythrocytes and prevents upstream C3 binding on their surface in an in vitro model," <https://ash.confex.com/ash/2009/webprogram/Paper19102.html>, retrieved on Dec. 26, 2013 (2 pages).
Rittershaus et al., "Recombinant glycoproteins that inhibit complement activation and also bind the selectin adhesion molecules," J Biol Chem. 274(16):11237-44 (1999).
Roffler et al., "Anti-neoplastic glucuronide prodrug treatment of human tumor cells targeted with a monoclonal antibody-enzyme conjugate," Biochem Pharmacol. 42:2062-2065 (1991).
Rohrer et al., "A targeted inhibitor of the alternative complement pathway reduces angiogenesis in a mouse model of age-related macular degeneration," Invest Ophthalmol Vis Sci. 50(7):3056-3064 (2009).
Rohrer et al., "Eliminating complement factor D reduces photoreceptor susceptibility to light-induced damage," Invest Ophthalmol Vis Sci. 48(11):5282-9 (2007).
Rohrer et al., "Role of neurotrophin receptor TrkB in the maturation of rod photoreceptors and establishment of synaptic transmission to the inner retina," J Neurosci. 19(20):8919-8930 (1999).
Ross et al., "Macrophage cytoskeleton association with CR3 and CR4 regulates receptor mobility and phagocytosis of iC3b-opsonized erythrocytes," J Leukoc Biol. 51(20):109-117 (1992).
Rother et al., "Discovery and development of the complement inhibitor eculizumab for the treatment of paroxysmal nocturnal hemoglobinuria," Nat Biotechnol. 25(11):1256-64, 1488 (2007).

(56) References Cited

OTHER PUBLICATIONS

Rothlein et al., "The requirement for lymphocyte function-associated antigen 1 in homotypic leukocyte adhesion stimulated by phorbol ester," J Exp Med. 163(5):1132-49 (1986).
Rudikoff et al., "Single amino acid subsitution altering antigen-binding specificity," Proc Natl Acad Sci USA. 79(6):1979-19783 (1982).
Rushmere et al., "Production and functional characterization of a soluble recombinant form of mouse CD59," Immunol. 99(2):326-32 (2000).
Sahu et al., "Identification of multiple sites of interaction between heparin and the complement system," Mol Immunol. 30(7):679-84 (1993).
Salerno et al., "A soluble chimeric inhibitor of C3 and C5 convertases, complement activation blocker-2, prolongs graft survival in pig-to-rhesus monkey heart transplantation," Xenotransplantation. 9(2):125-34 (2002).
Santiago-Raber et al., "Type-I interferon receptor deficiency reduces lupus-like disease in NZB mice," J Exp Med. 197:777-88 (2003).
Sarnaik et al., "Periodic transfusions for sickle cell anemia and CNS infarction," Am J Dis Child. 133(12):1254-7 (1979).
Satoh et al., "Energy metabolism regeneration in transgenic mouse liver expressing creatine kinase after major hepatectomy," Gastroenterology. 101:1166-74 (1996).
Schwarzenbacher et al., "Crystal structure of human b2-glycoprotein I: implications for phospholipid binding and the antiphospholipid syndrome," EMBO J. 18:6228-39 (1999).
Scola et al., "The human complement fragment receptor, C5L2, is a recycling decoy receptor," Mol Immunol. 46:1149-62 (2009).
Selzner et al., "Failure of regeneration of the steatotic rat liver: disruption at two different levels in the regeneration pathway," Hepatology. 31:35-42 (2000).
Senter et al., "Generation of 5-fluorouracil from 5-fluorocytosine by monoclonal antibody-cytosine deaminase conjugates," Bioconjugate Chem. 2:447-451 (1991).
Senter et al., "Generation of cytotoxic agents by targeted enzymes," Bioconjugate Chem. 4:3-9 (1993).
Seya et al., "Limited proteolysis of complement protein C3b by regulatory enzyme C3b inactivator: Isolation and characterization of a biologically active fragment, C3d,g," J Biochem. 97(1):373-382 (1985).
Sharkey et al., "Biodistribution and radiation dose estimates for yttrium- and iodine-labeled monoclonal antibody IgG and fragments in nude mice bearing human colonic tumor xenografts," Cancer Res. 50:2330-2336 (1990).
Sharkey et al., "Rapid blood clearance of immunoglobulin G2a and immunoglobulin G2b in nude mice," Cancer Res. 51:3102-3107 (1991).
Sharma et al., "Identification of three physically and functionally distinct binding sites for C3b in human complement Factor H by deletion mutagenesis," Proc Natl Aced Sci USA. 93(20):10996-11001 (1996).
Sheerin et al., "Leaked protein and interstitial damage in the kidney: is complement the missing link?" Clin Exp Immunol. 130(1):1-3 (2002).
Sigala et al., "Histological and lipid peroxidation changes after administration of 2-acetylaminofluorene in a rat liver injury model following selective periportal and pericentral damage," Toxicology. 196:155-63 (2004).
Skjodt et al., "MBL/Ficolin assocaited protein-1 (MAP-1) may function as a local lectin pathway specific complement inhibitor," Mol Immunol. 47:2229-30 (2010).
Smith et al., "Membrane-targeted complement inhibitors," Mol Immunol. 38:249-55 (2001).
Sokoloff et al., "Targeting of cancer cells with monoclonal antibodies specific for C3b(ii)," Cancer Immunol and Immunother. 49(10):551-62 (2000).

Song et al., "Complement receptor 2-mediated targeting of complement inhibitors to sites of complement activation," J Clin Invest. 111(12):1875-1885 (2003).
Spriggs et al., "The extracellular domain of the Epstein-Barr virus BZLF2 protein binds the HLA-DR beta chain and inhibits antigen presentation," J Virol. 70:5557-63 (1996).
Strey et al., "The proinflammatory mediators C3a and C5a are essential for liver regeneration," J Exp Med. 198(6):913-23 (2003).
Stryer et al., Levels of Structure in Protein Architecture. *Biochemistry* (3rd edition). W H Freeman Company, 31-33 (1998).
Sugita et al., "Recombinant soluble CD59 inhibits reative haemolysis with complement," Immunol. 82(1):34-41 (1994).
Supplementary European Search Report for European Application No. 03796403.8, mailed Jul. 3, 2006 (4 pages).
Supplementary European Search Report for European Patent Application No. EP11798880.8, dated Jan. 7, 2014 (13 pages).
Supplementary Partial European Search Report for European Application No. 03796403.8, mailed Apr. 3, 2006 (3 pages).
Szakonyi et al., "Structure of complement receptor 2 in complex with its C3d ligand," Science. 292:1725-1728 (2001).
Szakonyi et al., "Structure of the Epstein-Barr virus major envelope glycoprotein," Nature Struct Mol Biol. 13:996-1001 (2006).
Takahashi et al., "Mouse complement receptors type 1 (CR1 ;CD35) and type 2 (CR2;CD21): expression on normal B cell subpopulations and decreased levels during the development of autoimmunity in MRL/Ipr mice," J Immunol. 159:1557-69 (1997).
Takeda et al., "Numbe of hits necessary for complement-mediated hemolysis," Microbiol Immunol. 30(5):461-8 (1986).
Tamerius et al., "Detection of a neoantigen on human C3bi and C3d by monoclonal antibody," J Immunol. 135(3):2015-2019 (1985).
Tanhehco et al., "The anti-factor D antibody, MAb 166-32, inhibits the alternative pathway of the human complement system," Transplant Proc. 31(55):2168-71 (1999).
Tanner et al., "Epstein-Barr virus gp350/220 binding to the B lymphocyte C3d receptor mediates adsorption, capping, and endocytosis," Cell. 50:203-13 (1987).
Taub, "Liver regeneration: from myth to mechanism," Nat Rev Mol Cell Biol. 5:836-47 (2004).
Ten et al., "The signal transduction pathway of CD23 (FceRllb) targets IkB kinase," J Immunol. 163(7):3851-7 (1999).
Teoh et al., "Dual role of tumor necrosis factor-alpha in hepatic ischemia-reperfusion injury: studies in tumor necrosis factor-alpha gene knockout mice," Hepatology. 39:412-21 (2004).
Thomas et al., "Inhibition of complement activity by humanized anti-C5 antibody and single-chain Fv," Mol Immunol. 33(17-18):1389-401 (1996).
Thurman et al., "Lack of a functional alternative complement pathway ameliorates ischemic acute renal failure in mice," J. Immunol. 170(3):1517-1523(2003).
Tian et al., "Kupffer cell-dependent TNF-alpha signaling mediates injury in the arterialized small-for-size liver transplantation in the mouse," Proc Natl Acad Sci USA. 103(12):4598-603 (2006).
Tolnay et al., "Complement receptor 2 in the regulation of the immune response," Clin Immunol Immunopathol. 88:123-32 (1998).
Tosic et al., "Preparation of monoclonal antibodies to C3b by immunization with C3b(i)-sepharose," J Immunol Methods. 120:241-9 (1989).
Tsutsumi et al., "Site-specific chemical modification with polyethylene glycol of recombinant immunotoxin anti-Tac(Fv)-PE38 (LMB-2) improves antitumor activity and reduces animal toxicity and immunogenicity," Proc Natl Acad Sci USA. 97(15):8548-53 (2000).
Tuveson et al., "Molecular interactions of complement receptors on B lymphocytes: a CR1/CR2 complex distinct from the CR2/CD19 complex," J Exp Med. 173:1083-9 (1991).
Ueda et al., "Probing Functional Sites on Complement Protein B with Monoclonal Antibodies," J. Immunol. 138(4):1143-1149(1987).
van der Eisen et al., "A crystal structure of the complex between human complement receptor 2 and its ligand C3d," Science. 332:608-611 (2011).

(56) References Cited

OTHER PUBLICATIONS

Van Harmelen et al., "Mechanisms involved in the regulation of free fatty acid release from isolated human fat cells by acylation-stimulating protein and insulin," J Biol Chem. 274(26):18243-51 (1999).

Vranken et al., "The CCPN data model for NMR spectroscopy: development of a software pipeline," Proteins. 59:687-96 (2005).

Wang et al., "Amelioration of Lupus-like autoimmune disease in NZB/W $F_1$ mice after treatment with a blocking monoclonal antibody specific for complement component C5," Proc Natl Acad Sci USA. 93(16):8563-8 (1996).

Wang et al., "Anti-C5 monoclonal antibody therapy prevents collagen-induced arthritis and ameoliorates established disease," Proc Natl Acad Sci USA. 92(19):8955-9 (1995).

Ward et al., "Decay-accelerating factor CD55 is identified as the receptor for echovirus 7 using CELICS, a rapid immuno-focal cloning method," EMBO J. 13(21):5070-4 (1994).

Watanabe et al., "Co-protective effect of Crry and CD59 in rat kidney against complement attack," Proceedings of the Joint Academic Meeting of the Complement Symposium and Japanese Society for Host Defense Research, 37(11):19-20 (2000).

Weis et al., "Identification of a 145,000 Mr membrane protein as the C3d receptor (CR2) of human B lymphocytes," Proc Natl Acad Sci USA. 81:881-5 (1984).

Weis et al., "Identification of a partial cDNA clone for the C3d/ Epstein-Barr virus receptor of human B lymphocytes: homology with the receptor for fragments C3b and C4b of the third and fourth components of complement," Proc Natl Acad Sci USA. 83:5639-43 (1986).

Weis et al., "Structure of the human B lymphocyte receptor for C3d and the Epstein-Barr virus and relatedness to other members of the family of C3/C4 binding proteins," J Exp Med. 167:1047-66 (1988).

Weisman et al., "Soluble human complement receptor type 1: in vivo inhibitor of complement suppressing post-ischemic myocardial inflammation and necrosis," Science. 249(4965):146-151 (1990).

Whiss, "Pexelizumab Alexion," Curr Opin Investig Drugs. 3(6):870-7 (2002).

Wiles et al., "NMR studies of a viral protein that mimics the regulators of complement activation," J Mol Biol. 272(2):253-265 (1997).

Wiseman et al., "Rapid measurement of binding constants and heats of binding using a new titration calorimeter," Anal Biochem. 179:131-7 (1989).

Wittekind et al., "A high sensitivity 3D NMR experiment to correlate amide-proton and nitrogen resonances with the alpha-carbon and beta-carbon resonances in proteins," J Magn Reson. 101:201-5 (1993).

Wullaert et al., "Hepatic tumor necrosis factor signaling and nuclear factor-kappaB: effects on liver homeostasis and beyond," Endocr Rev. 28(4):365-86 (2007).

Xia et al., "Acylation-stimulating protein (ASP) deficiency induces obesity resistance and increased energy expenditure in ob/ob mice," J Biol Chem. 277:45874-9 (2002).

Yamaji et al., "Up-regulation of hepatic heme oxygenase-1 expression by locally induced interleukin-6 in rats administered carbon tetrachloride intraperitoneally," Toxicol Lett. 179:124-9 (2008).

Yang et al., "An engineered complement receptor 1 composed of two functional domains can protect against immune-mediated hemolysis," Protein Expr Purif. 66(1):28-34 (2009).

Young et al., "Isolating the Epstein-Barr virus gp350/220 binding site on complement receptor type 2 (CR2/CD21)," J Biol Chem. 282(50):36614-25 (2007).

Young et al., "Molecular basis of the interaction between complement receptor type 2 (CR2/CD21) and Epstein-Barr virus glycoprotein gp350," J Virol. 82:11217-27 (2008).

Yu et al., "Protection of human breast cancer cells from complement-mediated lysis by expression of heterologous CD59," Clin Exp Immunol. 115(1):13-8 (1999).

Zhang et al., "Immunophysical exploration of C3d-CR2(CCP1-2) interaction using molecular dynamics and electrostatics," J Mol Biol. 369:567-83 (2007).

Zhang et al., "Targeting of functional antibody-CD59 fusion proteins to a cell surface," J Clin Invest. 103(1):55-61 (1999).

Zhang et al., "Targeting of functional antibody-decay-accelerating factor fusion proteins to a cell surface," J Biol Chem. 276(29):27290-5 (2001).

Zhong et al., "NIM811, a mitochondrial permeability transition inhibitor, prevents mitochondrial depolarization in small-for-size rat liver grafts," Am J Transplant. 7:1103-11 (2007).

Zhu et al., "Inhibition of tumor growth and metastasis by targeting tumor-associated angiogenesis with antagonists to the receptors of vascular endothelial growth factor," Invest New Drugs. 17(3):195-212 (1999).

Zipfel, "Complement factor H: physiology and pathophysiology," Semin Thromb Hemost. 27(3):191-9 (2001).

Zuiderweg et al., "Heteronuclear three-dimensional NMR spectroscopy of the inflammatory protein C5a," Biochemistry. 28:2387-91 (1989).

\* cited by examiner

SEQUENCE LISTING

<160> NUMBER OF SEQ ID NOS: 28

<210> SEQ ID NO 1
<211> LENGTH: 1087
<212> TYPE: PRT
<213> ORGANISM: Homo sapiens

<400> SEQUENCE: 1

```
Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
            20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
        195                 200                 205

Thr Cys Glu Glu Ala Arg Cys Lys Ser Leu Gly Arg Phe Pro Asn Gly
    210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
            260                 265                 270

Glu Ile Phe Cys Pro Ser Pro Pro Ile Leu Asn Gly Arg His Ile
        275                 280                 285

Gly Asn Ser Leu Ala Asn Val Ser Tyr Gly Ser Ile Val Thr Tyr Thr
    290                 295                 300

Cys Asp Pro Asp Pro Glu Glu Gly Val Asn Phe Ile Leu Ile Gly Glu
```

-continued

```
          305                 310                 315                 320
Ser Thr Leu Arg Cys Thr Val Asp Ser Gln Lys Thr Gly Thr Trp Ser
                325                 330                 335

Gly Pro Ala Pro Arg Cys Glu Leu Ser Thr Ser Ala Val Gln Cys Pro
                340                 345                 350

His Pro Gln Ile Leu Arg Gly Arg Met Val Ser Gly Gln Lys Asp Arg
                355                 360                 365

Tyr Thr Tyr Asn Asp Thr Val Ile Phe Ala Cys Met Phe Gly Phe Thr
        370                 375                 380

Leu Lys Gly Ser Lys Gln Ile Arg Cys Asn Ala Gln Gly Thr Trp Glu
385                 390                 395                 400

Pro Ser Ala Pro Val Cys Glu Lys Glu Cys Gln Ala Pro Pro Asn Ile
                405                 410                 415

Leu Asn Gly Gln Lys Glu Asp Arg His Met Val Arg Phe Asp Pro Gly
                420                 425                 430

Thr Ser Ile Lys Tyr Ser Cys Asn Pro Gly Tyr Val Leu Val Gly Glu
                435                 440                 445

Glu Ser Ile Gln Cys Thr Ser Glu Gly Val Trp Thr Pro Pro Val Pro
        450                 455                 460

Gln Cys Lys Val Ala Ala Cys Glu Ala Thr Gly Arg Gln Leu Leu Thr
465                 470                 475                 480

Lys Pro Gln His Gln Phe Val Arg Pro Asp Val Asn Ser Ser Cys Gly
                485                 490                 495

Glu Gly Tyr Lys Leu Ser Gly Ser Val Tyr Gln Glu Cys Gln Gly Thr
                500                 505                 510

Ile Pro Trp Phe Met Glu Ile Arg Leu Cys Lys Glu Ile Thr Cys Pro
                515                 520                 525

Pro Pro Pro Val Ile Tyr Asn Gly Ala His Thr Gly Ser Ser Leu Glu
                530                 535                 540

Asp Phe Pro Tyr Gly Thr Thr Val Thr Tyr Thr Cys Asn Pro Gly Pro
545                 550                 555                 560

Glu Arg Gly Val Glu Phe Ser Leu Ile Gly Glu Ser Thr Ile Arg Cys
                565                 570                 575

Thr Ser Asn Asp Gln Glu Arg Gly Thr Trp Ser Gly Pro Ala Pro Leu
                580                 585                 590

Cys Lys Leu Ser Leu Leu Ala Val Gln Cys Ser His Val His Ile Ala
                595                 600                 605

Asn Gly Tyr Lys Ile Ser Gly Lys Glu Ala Pro Tyr Phe Tyr Asn Asp
                610                 615                 620

Thr Val Thr Phe Lys Cys Tyr Ser Gly Phe Thr Leu Lys Gly Ser Ser
625                 630                 635                 640

Gln Ile Arg Cys Lys Arg Asp Asn Thr Trp Asp Pro Glu Ile Pro Val
                645                 650                 655

Cys Glu Lys Gly Cys Gln Pro Pro Gly Leu His His Gly Arg His
                660                 665                 670

Thr Gly Gly Asn Thr Val Phe Phe Val Ser Gly Met Thr Val Asp Tyr
                675                 680                 685

Thr Cys Asp Pro Gly Tyr Leu Leu Val Gly Asn Lys Ser Ile His Cys
        690                 695                 700

Met Pro Ser Gly Asn Trp Ser Pro Ser Ala Pro Arg Cys Glu Glu Thr
705                 710                 715                 720

Cys Gln His Val Arg Gln Ser Leu Gln Glu Leu Pro Ala Gly Ser Arg
                725                 730                 735
```

```
Val Glu Leu Val Asn Thr Ser Cys Gln Asp Gly Tyr Gln Leu Thr Gly
            740                 745                 750

His Ala Tyr Gln Met Cys Gln Asp Ala Glu Asn Gly Ile Trp Phe Lys
            755                 760                 765

Lys Ile Pro Leu Cys Lys Val Ile His Cys His Pro Pro Pro Val Ile
770                 775                 780

Val Asn Gly Lys His Thr Gly Met Met Ala Glu Asn Phe Leu Tyr Gly
785                 790                 795                 800

Asn Glu Val Ser Tyr Glu Cys Asp Gln Gly Phe Tyr Leu Leu Gly Glu
                805                 810                 815

Lys Asn Cys Ser Ala Glu Val Ile Leu Lys Ala Trp Ile Leu Glu Arg
            820                 825                 830

Ala Phe Pro Gln Cys Leu Arg Ser Leu Cys Pro Asn Pro Glu Val Lys
            835                 840                 845

His Gly Tyr Lys Leu Asn Lys Thr His Ser Ala Tyr Ser His Asn Asp
            850                 855                 860

Ile Val Tyr Val Asp Cys Asn Pro Gly Phe Ile Met Asn Gly Ser Arg
865                 870                 875                 880

Val Ile Arg Cys His Thr Asp Asn Thr Trp Val Pro Gly Val Pro Thr
                885                 890                 895

Cys Ile Lys Lys Ala Phe Ile Gly Cys Pro Pro Pro Lys Thr Pro
                900                 905                 910

Asn Gly Asn His Thr Gly Gly Asn Ile Ala Arg Phe Ser Pro Gly Met
            915                 920                 925

Ser Ile Leu Tyr Ser Cys Asp Gln Gly Tyr Leu Val Val Gly Glu Pro
            930                 935                 940

Leu Leu Leu Cys Thr His Glu Gly Thr Trp Ser Gln Pro Ala Pro His
945                 950                 955                 960

Cys Lys Glu Val Asn Cys Ser Ser Pro Ala Asp Met Asp Gly Ile Gln
                965                 970                 975

Lys Gly Leu Glu Pro Arg Lys Met Tyr Gln Tyr Gly Ala Val Val Thr
            980                 985                 990

Leu Glu Cys Glu Asp Gly Tyr Met Leu Glu Gly Ser Pro Gln Ser Gln
            995                 1000                1005

Cys Gln Ser Asp His Gln Trp Asn Pro Pro Leu Ala Val Cys Arg
    1010                1015                1020

Ser Arg Ser Leu Ala Pro Val Leu Cys Gly Ile Ala Ala Gly Leu
    1025                1030                1035

Ile Leu Leu Thr Phe Leu Ile Val Ile Thr Leu Tyr Val Ile Ser
    1040                1045                1050

Lys His Arg Glu Arg Asn Tyr Tyr Thr Asp Thr Ser Gln Lys Glu
    1055                1060                1065

Ala Phe His Leu Glu Ala Arg Glu Val Tyr Ser Val Asp Pro Tyr
    1070                1075                1080

Asn Pro Ala Ser
    1085

<210> SEQ ID NO 2
<211> LENGTH: 128
<212> TYPE: PRT
<213> ORGANISM: Homo sapiens

<400> SEQUENCE: 2

Ile Ser Cys Gly Ser Pro Pro Pro Ile Leu Asn Gly Arg Ile Ser Tyr
```

```
         1               5                  10                 15
Tyr Ser Thr Pro Ile Ala Val Gly Thr Val Ile Arg Tyr Ser Cys Ser
                    20                 25                 30

Gly Thr Phe Arg Leu Ile Gly Glu Lys Ser Leu Leu Cys Ile Thr Lys
                    35                 40                 45

Asp Lys Val Asp Gly Thr Trp Asp Lys Pro Ala Pro Lys Cys Glu Tyr
                50                 55                 60

Phe Asn Lys Tyr Ser Ser Cys Pro Glu Pro Ile Val Pro Gly Gly Tyr
 65                 70                 75                 80

Lys Ile Arg Gly Ser Thr Pro Tyr Arg His Gly Asp Ser Val Thr Phe
                    85                 90                 95

Ala Cys Lys Thr Asn Phe Ser Met Asn Gly Asn Lys Ser Val Trp Cys
                   100                105                110

Gln Ala Asn Asn Met Trp Gly Pro Thr Arg Leu Pro Thr Cys Val Ser
                   115                120                125

<210> SEQ ID NO 3
<211> LENGTH: 128
<212> TYPE: PRT
<213> ORGANISM: Homo sapiens

<400> SEQUENCE: 3

Met Gly Ile Gln Gly Gly Ser Val Leu Phe Gly Leu Leu Leu Val Leu
 1               5                  10                 15

Ala Val Phe Cys His Ser Gly His Ser Leu Gln Cys Tyr Asn Cys Pro
                    20                 25                 30

Asn Pro Thr Ala Asp Cys Lys Thr Ala Val Asn Cys Ser Ser Asp Phe
                    35                 40                 45

Asp Ala Cys Leu Ile Thr Lys Ala Gly Leu Gln Val Tyr Asn Lys Cys
                50                 55                 60

Trp Lys Phe Glu His Cys Asn Phe Asn Asp Val Thr Thr Arg Leu Arg
 65                 70                 75                 80

Glu Asn Glu Leu Thr Tyr Tyr Cys Cys Lys Lys Asp Leu Cys Asn Phe
                    85                 90                 95

Asn Glu Gln Leu Glu Asn Gly Gly Thr Ser Leu Ser Glu Lys Thr Val
                   100                105                110

Leu Leu Leu Val Thr Pro Phe Leu Ala Ala Ala Trp Ser Leu His Pro
                   115                120                125

<210> SEQ ID NO 4
<211> LENGTH: 483
<212> TYPE: PRT
<213> ORGANISM: Mus musculus

<400> SEQUENCE: 4

Met Glu Val Ser Ser Arg Ser Ser Glu Pro Leu Asp Pro Val Trp Leu
 1               5                  10                 15

Leu Val Ala Phe Gly Arg Gly Gly Val Lys Leu Glu Val Leu Leu Leu
                    20                 25                 30

Phe Leu Leu Pro Phe Thr Leu Gly Glu Leu Arg Gly Leu Gly Leu Lys
                    35                 40                 45

His Gly His Thr Val His Arg Glu Pro Ala Val Asn Arg Leu Cys Ala
                50                 55                 60

Asp Ser Lys Arg Trp Ser Gly Leu Pro Val Ser Ala Gln Arg Pro Phe
 65                 70                 75                 80

Pro Met Gly His Cys Pro Ala Pro Ser Gln Leu Pro Ser Ala Lys Pro
```

```
                        85                  90                  95
Ile Asn Leu Thr Asp Glu Ser Met Phe Pro Ile Gly Thr Tyr Leu Leu
                    100                 105                 110
Tyr Glu Cys Leu Pro Gly Tyr Ile Lys Arg Gln Phe Ser Ile Thr Cys
                115                 120                 125
Lys Gln Asp Ser Thr Trp Thr Ser Ala Glu Asp Lys Cys Ile Arg Lys
            130                 135                 140
Gln Cys Lys Thr Pro Ser Asp Pro Glu Asn Gly Leu Val His Val His
145                 150                 155                 160
Thr Gly Ile Gln Phe Gly Ser Arg Ile Asn Tyr Thr Cys Asn Gln Gly
                165                 170                 175
Tyr Arg Leu Ile Gly Ser Ser Ala Val Cys Val Ile Thr Asp Gln
            180                 185                 190
Ser Val Asp Trp Asp Thr Glu Ala Pro Ile Cys Glu Trp Ile Pro Cys
        195                 200                 205
Glu Ile Pro Pro Gly Ile Pro Asn Gly Asp Phe Phe Ser Ser Thr Arg
    210                 215                 220
Glu Asp Phe His Tyr Gly Met Val Val Thr Tyr Arg Cys Asn Thr Asp
225                 230                 235                 240
Ala Arg Gly Lys Ala Leu Phe Asn Leu Val Gly Glu Pro Ser Leu Tyr
                245                 250                 255
Cys Thr Ser Asn Asp Gly Glu Ile Gly Val Trp Ser Gly Pro Pro Pro
            260                 265                 270
Gln Cys Ile Glu Leu Asn Lys Cys Thr Pro Pro Tyr Val Glu Asn
        275                 280                 285
Ala Val Met Leu Ser Glu Asn Arg Ser Leu Phe Ser Leu Arg Asp Ile
    290                 295                 300
Val Glu Phe Arg Cys His Pro Gly Phe Ile Met Lys Gly Ala Ser Ser
305                 310                 315                 320
Val His Cys Gln Ser Leu Asn Lys Trp Glu Pro Glu Leu Pro Ser Cys
                325                 330                 335
Phe Lys Gly Val Ile Cys Arg Leu Pro Gln Glu Met Ser Gly Phe Gln
            340                 345                 350
Lys Gly Leu Gly Met Lys Lys Glu Tyr Tyr Gly Glu Asn Val Thr
        355                 360                 365
Leu Glu Cys Glu Asp Gly Tyr Thr Leu Glu Gly Ser Ser Gln Ser Gln
    370                 375                 380
Cys Gln Ser Asp Gly Ser Trp Asn Pro Leu Leu Ala Lys Cys Val Ser
385                 390                 395                 400
Arg Ser Ile Ser Gly Leu Ile Val Gly Ile Phe Ile Gly Ile Val
                405                 410                 415
Phe Ile Leu Val Ile Ile Val Phe Ile Trp Met Ile Leu Lys Tyr Lys
            420                 425                 430
Lys Arg Asn Thr Thr Asp Glu Lys Tyr Lys Glu Val Gly Ile His Leu
        435                 440                 445
Asn Tyr Lys Glu Asp Ser Cys Val Arg Leu Gln Ser Leu Leu Thr Ser
    450                 455                 460
Gln Glu Asn Ser Ser Thr Thr Ser Pro Ala Arg Asn Ser Leu Thr Gln
465                 470                 475                 480
Glu Val Ser

<210> SEQ ID NO 5
<211> LENGTH: 1231
```

<212> TYPE: PRT
<213> ORGANISM: Homo sapiens

<400> SEQUENCE: 5

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400
```

-continued

```
Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
                420                 425                 430

Glu Asn Gly Trp Ser Pro Thr Pro Arg Cys Ile Arg Val Lys Thr Cys
                435                 440                 445

Ser Lys Ser Ser Ile Asp Ile Glu Asn Gly Phe Ile Ser Glu Ser Gln
            450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
                500                 505                 510

Val Phe Met Asn Ala Arg Thr Lys Asn Asp Phe Thr Trp Phe Lys Leu
            515                 520                 525

Asn Asp Thr Leu Asp Tyr Glu Cys His Asp Gly Tyr Glu Ser Asn Thr
            530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
                580                 585                 590

Leu Lys Phe Ser Cys Lys Pro Gly Phe Thr Ile Val Gly Pro Asn Ser
            595                 600                 605

Val Gln Cys Tyr His Phe Gly Leu Ser Pro Asp Leu Pro Ile Cys Lys
            610                 615                 620

Glu Gln Val Gln Ser Cys Gly Pro Pro Glu Leu Leu Asn Gly Asn
625                 630                 635                 640

Val Lys Glu Lys Thr Lys Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
            675                 680                 685

Ser Thr Cys Gly Asp Ile Pro Glu Leu Glu His Gly Trp Ala Gln Leu
            690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
                740                 745                 750

Cys Lys Ser Ser Asn Leu Ile Ile Leu Glu Glu His Leu Lys Asn Lys
            755                 760                 765

Lys Glu Phe Asp His Asn Ser Asn Ile Arg Tyr Arg Cys Arg Gly Lys
            770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Pro Gln
                805                 810                 815
```

-continued

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
            835                 840                 845

Glu Glu Ile Thr Cys Lys Asp Gly Arg Trp Gln Ser Ile Pro Leu Cys
850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
            915                 920                 925

Leu Pro Cys Lys Ser Pro Pro Glu Ile Ser His Gly Val Val Ala His
930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
            995                 1000                1005

Lys Ala Gly Glu Gln Val Thr Tyr Thr Cys Ala Thr Tyr Tyr Lys
            1010                1015                1020

Met Asp Gly Ala Ser Asn Val Thr Cys Ile Asn Ser Arg Trp Thr
            1025                1030                1035

Gly Arg Pro Thr Cys Arg Asp Thr Ser Cys Val Asn Pro Pro Thr
            1040                1045                1050

Val Gln Asn Ala Tyr Ile Val Ser Arg Gln Met Ser Lys Tyr Pro
            1055                1060                1065

Ser Gly Glu Arg Val Arg Tyr Gln Cys Arg Ser Pro Tyr Glu Met
            1070                1075                1080

Phe Gly Asp Glu Glu Val Met Cys Leu Asn Gly Asn Trp Thr Glu
            1085                1090                1095

Pro Pro Gln Cys Lys Asp Ser Thr Gly Lys Cys Gly Pro Pro Pro
            1100                1105                1110

Pro Ile Asp Asn Gly Asp Ile Thr Ser Phe Pro Leu Ser Val Tyr
            1115                1120                1125

Ala Pro Ala Ser Ser Val Glu Tyr Gln Cys Gln Asn Leu Tyr Gln
            1130                1135                1140

Leu Glu Gly Asn Lys Arg Ile Thr Cys Arg Asn Gly Gln Trp Ser
            1145                1150                1155

Glu Pro Pro Lys Cys Leu His Pro Cys Val Ile Ser Arg Glu Ile
            1160                1165                1170

Met Glu Asn Tyr Asn Ile Ala Leu Arg Trp Thr Ala Lys Gln Lys
            1175                1180                1185

Leu Tyr Ser Arg Thr Gly Glu Ser Val Glu Phe Val Cys Lys Arg
            1190                1195                1200

Gly Tyr Arg Leu Ser Ser Arg Ser His Thr Leu Arg Thr Thr Cys
            1205                1210                1215

Trp Asp Gly Lys Leu Glu Tyr Pro Thr Cys Ala Lys Arg

-continued

```
             1220                1225              1230
```

<210> SEQ ID NO 6
<211> LENGTH: 123
<212> TYPE: PRT
<213> ORGANISM: Mus musculus

<400> SEQUENCE: 6

```
Met Arg Ala Gln Arg Gly Leu Ile Leu Leu Leu Leu Leu Ala Val
1               5                   10                  15

Phe Cys Ser Thr Ala Val Ser Leu Thr Cys Tyr His Cys Phe Gln Pro
                20                  25                  30

Val Val Ser Ser Cys Asn Met Asn Ser Thr Cys Ser Pro Asp Gln Asp
                35                  40                  45

Ser Cys Leu Tyr Ala Val Ala Gly Met Gln Val Tyr Gln Arg Cys Trp
        50                  55                  60

Lys Gln Ser Asp Cys His Gly Glu Ile Ile Met Asp Gln Leu Glu Glu
65                  70                  75                  80

Thr Lys Leu Lys Phe Arg Cys Cys Gln Phe Asn Leu Cys Asn Lys Ser
                85                  90                  95

Asp Gly Ser Leu Gly Lys Thr Pro Leu Leu Gly Thr Ser Val Leu Val
                100                 105                 110

Ala Ile Leu Asn Leu Cys Phe Leu Ser His Leu
            115                 120
```

<210> SEQ ID NO 7
<211> LENGTH: 129
<212> TYPE: PRT
<213> ORGANISM: Mus musculus

<400> SEQUENCE: 7

```
Met Arg Ala Gln Arg Gly Leu Ile Leu Leu Leu Leu Leu Ala Val
1               5                   10                  15

Phe Cys Ser Thr Ala Val Ser Leu Lys Cys Tyr Asn Cys Phe Gln Phe
                20                  25                  30

Val Ser Ser Cys Lys Ile Asn Thr Thr Cys Ser Pro Asn Leu Asp Ser
                35                  40                  45

Cys Leu Tyr Ala Val Ala Gly Arg Gln Val Tyr Gln Gln Cys Trp Lys
        50                  55                  60

Leu Ser Asp Cys Asn Ser Asn Tyr Ile Met Ser Arg Leu Asp Val Ala
65                  70                  75                  80

Gly Ile Gln Ser Lys Cys Cys Gln Trp Gly Leu Cys Asn Lys Asn Leu
                85                  90                  95

Asp Gly Leu Glu Glu Pro Asn Asn Ala Glu Thr Ser Ser Leu Arg Lys
                100                 105                 110

Thr Ala Leu Leu Gly Thr Ser Val Leu Val Ala Ile Leu Lys Phe Cys
            115                 120                 125

Phe
```

<210> SEQ ID NO 8
<211> LENGTH: 1234
<212> TYPE: PRT
<213> ORGANISM: Mus musculus

<400> SEQUENCE: 8

```
Met Arg Leu Ser Ala Arg Ile Ile Trp Leu Ile Leu Trp Thr Val Cys
1               5                   10                  15
```

-continued

```
Ala Ala Glu Asp Cys Lys Gly Pro Pro Arg Glu Asn Ser Glu Ile
         20                  25                  30
Leu Ser Gly Ser Trp Ser Glu Gln Leu Tyr Pro Glu Gly Thr Gln Ala
     35                  40                  45
Thr Tyr Lys Cys Arg Pro Gly Tyr Arg Thr Leu Gly Thr Ile Val Lys
 50                  55                  60
Val Cys Lys Asn Gly Lys Trp Val Ala Ser Asn Pro Ser Arg Ile Cys
 65                  70                  75                  80
Arg Lys Lys Pro Cys Gly His Pro Gly Asp Thr Pro Phe Gly Ser Phe
             85                  90                  95
Arg Leu Ala Val Gly Ser Gln Phe Glu Phe Gly Ala Lys Val Val Tyr
            100                 105                 110
Thr Cys Asp Asp Gly Tyr Gln Leu Leu Gly Glu Ile Asp Tyr Arg Glu
        115                 120                 125
Cys Gly Ala Asp Gly Trp Ile Asn Asp Ile Pro Leu Cys Glu Val Val
        130                 135                 140
Lys Cys Leu Pro Val Thr Glu Leu Glu Asn Gly Arg Ile Val Ser Gly
145                 150                 155                 160
Ala Ala Glu Thr Asp Gln Glu Tyr Tyr Phe Gly Gln Val Val Arg Phe
                165                 170                 175
Glu Cys Asn Ser Gly Phe Lys Ile Glu Gly His Lys Glu Ile His Cys
            180                 185                 190
Ser Glu Asn Gly Leu Trp Ser Asn Glu Lys Pro Arg Cys Val Glu Ile
        195                 200                 205
Leu Cys Thr Pro Pro Arg Val Glu Asn Gly Asp Gly Ile Asn Val Lys
210                 215                 220
Pro Val Tyr Lys Glu Asn Glu Arg Tyr His Tyr Lys Cys Lys His Gly
225                 230                 235                 240
Tyr Val Pro Lys Glu Arg Gly Asp Ala Val Cys Thr Gly Ser Gly Trp
                245                 250                 255
Ser Ser Gln Pro Phe Cys Glu Glu Lys Arg Cys Ser Pro Pro Tyr Ile
            260                 265                 270
Leu Asn Gly Ile Tyr Thr Pro His Arg Ile Ile His Arg Ser Asp Asp
        275                 280                 285
Glu Ile Arg Tyr Glu Cys Asn Tyr Gly Phe Tyr Pro Val Thr Gly Ser
290                 295                 300
Thr Val Ser Lys Cys Thr Pro Thr Gly Trp Ile Pro Val Pro Arg Cys
305                 310                 315                 320
Thr Leu Lys Pro Cys Glu Phe Pro Gln Phe Lys Tyr Gly Arg Leu Tyr
                325                 330                 335
Tyr Glu Glu Ser Leu Arg Pro Asn Phe Pro Val Ser Ile Gly Asn Lys
            340                 345                 350
Tyr Ser Tyr Lys Cys Asp Asn Gly Phe Ser Pro Pro Ser Gly Tyr Ser
        355                 360                 365
Trp Asp Tyr Leu Arg Cys Thr Ala Gln Gly Trp Glu Pro Glu Val Pro
370                 375                 380
Cys Val Arg Lys Cys Val Phe His Tyr Val Glu Asn Gly Asp Ser Ala
385                 390                 395                 400
Tyr Trp Glu Lys Val Tyr Gln Gly Gln Ser Leu Lys Val Gln Cys
                405                 410                 415
Tyr Asn Gly Tyr Ser Leu Gln Asn Gly Gln Asp Thr Met Thr Cys Thr
            420                 425                 430
Glu Asn Gly Trp Ser Pro Pro Pro Lys Cys Ile Arg Ile Lys Thr Cys
```

```
            435                 440                 445
Ser Ala Ser Asp Ile His Ile Asp Asn Gly Phe Leu Ser Glu Ser Ser
450                     455                 460

Ser Ile Tyr Ala Leu Asn Arg Glu Thr Ser Tyr Arg Cys Lys Gln Gly
465                 470                  475                 480

Tyr Val Thr Asn Thr Gly Glu Ile Ser Gly Ser Ile Thr Cys Leu Gln
                    485                 490                 495

Asn Gly Trp Ser Pro Gln Pro Ser Cys Ile Lys Ser Cys Asp Met Pro
                500                 505                 510

Val Phe Glu Asn Ser Ile Thr Lys Asn Thr Arg Thr Trp Phe Lys Leu
            515                 520                 525

Asn Asp Lys Leu Asp Tyr Glu Cys Leu Val Gly Phe Glu Asn Glu Tyr
        530                 535                 540

Lys His Thr Lys Gly Ser Ile Thr Cys Thr Tyr Tyr Gly Trp Ser Asp
545                 550                 555                 560

Thr Pro Ser Cys Tyr Glu Arg Glu Cys Ser Val Pro Thr Leu Asp Arg
                565                 570                 575

Lys Leu Val Val Ser Pro Arg Lys Glu Lys Tyr Arg Val Gly Asp Leu
            580                 585                 590

Leu Glu Phe Ser Cys His Ser Gly His Arg Val Gly Pro Asp Ser Val
        595                 600                 605

Gln Cys Tyr His Phe Gly Trp Ser Pro Gly Phe Pro Thr Cys Lys Gly
610                 615                 620

Gln Val Ala Ser Cys Ala Pro Pro Leu Glu Ile Leu Asn Gly Glu Ile
625                 630                 635                 640

Asn Gly Ala Lys Lys Val Glu Tyr Ser His Gly Glu Val Val Lys Tyr
                645                 650                 655

Asp Cys Lys Pro Arg Phe Leu Leu Lys Gly Pro Asn Lys Ile Gln Cys
                660                 665                 670

Val Asp Gly Asn Trp Thr Thr Leu Pro Val Cys Ile Glu Glu Arg
            675                 680                 685

Thr Cys Gly Asp Ile Pro Glu Leu Glu His Gly Ser Ala Lys Cys Ser
        690                 695                 700

Val Pro Pro Tyr His His Gly Asp Ser Val Glu Phe Ile Cys Glu Glu
705                 710                 715                 720

Asn Phe Thr Met Ile Gly His Gly Ser Val Ser Cys Ile Ser Gly Lys
                725                 730                 735

Trp Thr Gln Leu Pro Lys Cys Val Ala Thr Asp Gln Leu Glu Lys Cys
                740                 745                 750

Arg Val Leu Lys Ser Thr Gly Ile Glu Ala Ile Lys Pro Lys Leu Thr
            755                 760                 765

Glu Phe Thr His Asn Ser Thr Met Asp Tyr Lys Cys Arg Asp Lys Gln
        770                 775                 780

Glu Tyr Glu Arg Ser Ile Cys Ile Asn Gly Lys Trp Asp Pro Glu Pro
785                 790                 795                 800

Asn Cys Thr Ser Lys Thr Ser Cys Pro Pro Pro Gln Ile Pro Asn
                805                 810                 815

Thr Gln Val Ile Glu Thr Thr Val Lys Tyr Leu Asp Gly Glu Lys Leu
                820                 825                 830

Ser Val Leu Cys Gln Asp Asn Tyr Leu Thr Gln Asp Ser Glu Glu Met
            835                 840                 845

Val Cys Lys Asp Gly Arg Trp Gln Ser Leu Pro Arg Cys Ile Glu Lys
850                 855                 860
```

-continued

```
Ile Pro Cys Ser Gln Pro Pro Thr Ile Glu His Gly Ser Ile Asn Leu
865                 870                 875                 880

Pro Arg Ser Ser Glu Glu Arg Arg Asp Ser Ile Glu Ser Ser Ser His
            885                 890                 895

Glu His Gly Thr Thr Phe Ser Tyr Val Cys Asp Asp Gly Phe Arg Ile
        900                 905                 910

Pro Glu Glu Asn Arg Ile Thr Cys Tyr Met Gly Lys Trp Ser Thr Pro
    915                 920                 925

Pro Arg Cys Val Gly Leu Pro Cys Gly Pro Pro Ser Ile Pro Leu
930                 935                 940

Gly Thr Val Ser Leu Glu Leu Glu Ser Tyr Gln His Gly Glu Glu Val
945                 950                 955                 960

Thr Tyr His Cys Ser Thr Gly Phe Gly Ile Asp Gly Pro Ala Phe Ile
                965                 970                 975

Ile Cys Glu Gly Gly Lys Trp Ser Asp Pro Pro Lys Cys Ile Lys Thr
                980                 985                 990

Asp Cys Asp Val Leu Pro Thr Val  Lys Asn Ala Ile Ile Arg Gly Lys
                995                 1000                1005

Ser Lys Lys Ser Tyr Arg Thr  Gly Glu Gln Val Thr  Phe Arg Cys
    1010                1015                1020

Gln Ser  Pro Tyr Gln Met Asn  Gly Ser Asp Thr Val  Thr Cys Val
    1025                1030                1035

Asn Ser  Arg Trp Ile Gly Gln  Pro Val Cys Lys Asp  Asn Ser Cys
    1040                1045                1050

Val Asp  Pro Pro His Val Pro  Asn Ala Thr Ile Val  Thr Arg Thr
    1055                1060                1065

Lys Asn  Lys Tyr Leu His Gly  Asp Arg Val Arg Tyr  Glu Cys Asn
    1070                1075                1080

Lys Pro  Leu Glu Leu Phe Gly  Gln Val Glu Val Met  Cys Glu Asn
    1085                1090                1095

Gly Ile  Trp Thr Glu Lys Pro  Lys Cys Arg Asp Ser  Thr Gly Lys
    1100                1105                1110

Cys Gly  Pro Pro Pro Ile Asp  Asn Gly Asp Ile  Thr Ser Leu
    1115                1120                1125

Ser Leu  Pro Val Tyr Glu Pro  Leu Ser Ser Val Glu  Tyr Gln Cys
    1130                1135                1140

Gln Lys  Tyr Tyr Leu Leu Lys  Gly Lys Lys Thr Ile  Thr Cys Thr
    1145                1150                1155

Asn Gly  Lys Trp Ser Glu Pro  Pro Thr Cys Leu His  Ala Cys Val
    1160                1165                1170

Ile Pro  Glu Asn Ile Met Glu  Ser His Asn Ile Ile  Leu Lys Trp
    1175                1180                1185

Arg His  Thr Glu Lys Ile Tyr  Ser His Ser Gly Glu  Asp Ile Glu
    1190                1195                1200

Phe Gly  Cys Lys Tyr Gly Tyr  Tyr Lys Ala Arg Asp  Ser Pro Pro
    1205                1210                1215

Phe Arg  Thr Lys Cys Ile Asn  Gly Thr Ile Asn Tyr  Pro Thr Cys
    1220                1225                1230

Val
```

<210> SEQ ID NO 9
<211> LENGTH: 2039
<212> TYPE: PRT

<213> ORGANISM: Homo sapiens

<400> SEQUENCE: 9

```
Met Gly Ala Ser Ser Pro Arg Ser Pro Glu Pro Val Gly Pro Pro Ala
1               5                   10                  15
Pro Gly Leu Pro Phe Cys Cys Gly Gly Ser Leu Leu Ala Val Val Val
            20                  25                  30
Leu Leu Ala Leu Pro Val Ala Trp Gly Gln Cys Asn Ala Pro Glu Trp
        35                  40                  45
Leu Pro Phe Ala Arg Pro Thr Asn Leu Thr Asp Glu Phe Glu Phe Pro
    50                  55                  60
Ile Gly Thr Tyr Leu Asn Tyr Glu Cys Arg Pro Gly Tyr Ser Gly Arg
65                  70                  75                  80
Pro Phe Ser Ile Ile Cys Leu Lys Asn Ser Val Trp Thr Gly Ala Lys
                85                  90                  95
Asp Arg Cys Arg Arg Lys Ser Cys Arg Asn Pro Pro Asp Pro Val Asn
            100                 105                 110
Gly Met Val His Val Ile Lys Gly Ile Gln Phe Gly Ser Gln Ile Lys
        115                 120                 125
Tyr Ser Cys Thr Lys Gly Tyr Arg Leu Ile Gly Ser Ser Ser Ala Thr
    130                 135                 140
Cys Ile Ile Ser Gly Asp Thr Val Ile Trp Asp Asn Glu Thr Pro Ile
145                 150                 155                 160
Cys Asp Arg Ile Pro Cys Gly Leu Pro Pro Thr Ile Thr Asn Gly Asp
                165                 170                 175
Phe Ile Ser Thr Asn Arg Glu Asn Phe His Tyr Gly Ser Val Val Thr
            180                 185                 190
Tyr Arg Cys Asn Pro Gly Ser Gly Gly Arg Lys Val Phe Glu Leu Val
        195                 200                 205
Gly Glu Pro Ser Ile Tyr Cys Thr Ser Asn Asp Asp Gln Val Gly Ile
    210                 215                 220
Trp Ser Gly Pro Ala Pro Gln Cys Ile Ile Pro Asn Lys Cys Thr Pro
225                 230                 235                 240
Pro Asn Val Glu Asn Gly Ile Leu Val Ser Asp Asn Arg Ser Leu Phe
                245                 250                 255
Ser Leu Asn Glu Val Val Glu Phe Arg Cys Gln Pro Gly Phe Val Met
            260                 265                 270
Lys Gly Pro Arg Arg Val Lys Cys Gln Ala Leu Asn Lys Trp Glu Pro
        275                 280                 285
Glu Leu Pro Ser Cys Ser Arg Val Cys Gln Pro Pro Pro Asp Val Leu
    290                 295                 300
His Ala Glu Arg Thr Gln Arg Asp Lys Asp Asn Phe Ser Pro Gly Gln
305                 310                 315                 320
Glu Val Phe Tyr Ser Cys Glu Pro Gly Tyr Asp Leu Arg Gly Ala Ala
                325                 330                 335
Ser Met Arg Cys Thr Pro Gln Gly Asp Trp Ser Pro Ala Ala Pro Thr
            340                 345                 350
Cys Glu Val Lys Ser Cys Asp Asp Phe Met Gly Gln Leu Leu Asn Gly
        355                 360                 365
Arg Val Leu Phe Pro Val Asn Leu Gln Leu Gly Ala Lys Val Asp Phe
    370                 375                 380
Val Cys Asp Glu Gly Phe Gln Leu Lys Gly Ser Ser Ala Ser Tyr Cys
385                 390                 395                 400
```

-continued

Val Leu Ala Gly Met Glu Ser Leu Trp Asn Ser Ser Val Pro Val Cys
                405                 410                 415

Glu Gln Ile Phe Cys Pro Ser Pro Val Ile Pro Asn Gly Arg His
            420                 425                 430

Thr Gly Lys Pro Leu Glu Val Phe Pro Phe Gly Lys Ala Val Asn Tyr
        435                 440                 445

Thr Cys Asp Pro His Pro Asp Arg Gly Thr Ser Phe Asp Leu Ile Gly
    450                 455                 460

Glu Ser Thr Ile Arg Cys Thr Ser Asp Pro Gln Gly Asn Gly Val Trp
465                 470                 475                 480

Ser Ser Pro Ala Pro Arg Cys Gly Ile Leu Gly His Cys Gln Ala Pro
                485                 490                 495

Asp His Phe Leu Phe Ala Lys Leu Lys Thr Gln Thr Asn Ala Ser Asp
            500                 505                 510

Phe Pro Ile Gly Thr Ser Leu Lys Tyr Glu Cys Arg Pro Glu Tyr Tyr
        515                 520                 525

Gly Arg Pro Phe Ser Ile Thr Cys Leu Asp Asn Leu Val Trp Ser Ser
    530                 535                 540

Pro Lys Asp Val Cys Lys Arg Lys Ser Cys Lys Thr Pro Pro Asp Pro
545                 550                 555                 560

Val Asn Gly Met Val His Val Ile Thr Asp Ile Gln Val Gly Ser Arg
                565                 570                 575

Ile Asn Tyr Ser Cys Thr Thr Gly His Arg Leu Ile Gly His Ser Ser
            580                 585                 590

Ala Glu Cys Ile Leu Ser Gly Asn Ala Ala His Trp Ser Thr Lys Pro
        595                 600                 605

Pro Ile Cys Gln Arg Ile Pro Cys Gly Leu Pro Pro Thr Ile Ala Asn
    610                 615                 620

Gly Asp Phe Ile Ser Thr Asn Arg Glu Asn Phe His Tyr Gly Ser Val
625                 630                 635                 640

Val Thr Tyr Arg Cys Asn Pro Gly Ser Gly Gly Arg Lys Val Phe Glu
                645                 650                 655

Leu Val Gly Glu Pro Ser Ile Tyr Cys Thr Ser Asn Asp Asp Gln Val
            660                 665                 670

Gly Ile Trp Ser Gly Pro Ala Pro Gln Cys Ile Ile Pro Asn Lys Cys
        675                 680                 685

Thr Pro Pro Asn Val Glu Asn Gly Ile Leu Val Ser Asp Asn Arg Ser
    690                 695                 700

Leu Phe Ser Leu Asn Glu Val Val Glu Phe Arg Cys Gln Pro Gly Phe
705                 710                 715                 720

Val Met Lys Gly Pro Arg Arg Val Lys Cys Gln Ala Leu Asn Lys Trp
                725                 730                 735

Glu Pro Glu Leu Pro Ser Cys Ser Arg Val Cys Gln Pro Pro Pro Asp
            740                 745                 750

Val Leu His Ala Glu Arg Thr Gln Arg Asp Lys Asp Asn Phe Ser Pro
        755                 760                 765

Gly Gln Glu Val Phe Tyr Ser Cys Glu Pro Gly Tyr Asp Leu Arg Gly
    770                 775                 780

Ala Ala Ser Met Arg Cys Thr Pro Gln Gly Asp Trp Ser Pro Ala Ala
785                 790                 795                 800

Pro Thr Cys Glu Val Lys Ser Cys Asp Asp Phe Met Gly Gln Leu Leu
                805                 810                 815

Asn Gly Arg Val Leu Phe Pro Val Asn Leu Gln Leu Gly Ala Lys Val

-continued

```
                820                 825                 830
Asp Phe Val Cys Asp Glu Gly Phe Gln Leu Lys Gly Ser Ser Ala Ser
            835                 840                 845
Tyr Cys Val Leu Ala Gly Met Glu Ser Leu Trp Asn Ser Ser Val Pro
        850                 855                 860
Val Cys Glu Gln Ile Phe Cys Pro Ser Pro Val Ile Pro Asn Gly
865                 870                 875                 880
Arg His Thr Gly Lys Pro Leu Glu Val Phe Pro Phe Gly Lys Ala Val
                885                 890                 895
Asn Tyr Thr Cys Asp Pro His Pro Asp Arg Gly Thr Ser Phe Asp Leu
            900                 905                 910
Ile Gly Glu Ser Thr Ile Arg Cys Thr Ser Asp Pro Gln Gly Asn Gly
        915                 920                 925
Val Trp Ser Ser Pro Ala Pro Arg Cys Gly Ile Leu Gly His Cys Gln
    930                 935                 940
Ala Pro Asp His Phe Leu Phe Ala Lys Leu Lys Thr Gln Thr Asn Ala
945                 950                 955                 960
Ser Asp Phe Pro Ile Gly Thr Ser Leu Lys Tyr Glu Cys Arg Pro Glu
                965                 970                 975
Tyr Tyr Gly Arg Pro Phe Ser Ile Thr Cys Leu Asp Asn Leu Val Trp
            980                 985                 990
Ser Ser Pro Lys Asp Val Cys Lys Arg Lys Ser Cys Lys Thr Pro Pro
        995                 1000                1005
Asp Pro Val Asn Gly Met Val His Val Ile Thr Asp Ile Gln Val
    1010                1015                1020
Gly Ser Arg Ile Asn Tyr Ser Cys Thr Thr Gly His Arg Leu Ile
    1025                1030                1035
Gly His Ser Ser Ala Glu Cys Ile Leu Ser Gly Asn Thr Ala His
    1040                1045                1050
Trp Ser Thr Lys Pro Pro Ile Cys Gln Arg Ile Pro Cys Gly Leu
    1055                1060                1065
Pro Pro Thr Ile Ala Asn Gly Asp Phe Ile Ser Thr Asn Arg Glu
    1070                1075                1080
Asn Phe His Tyr Gly Ser Val Val Thr Tyr Arg Cys Asn Leu Gly
    1085                1090                1095
Ser Arg Gly Arg Lys Val Phe Glu Leu Val Gly Glu Pro Ser Ile
    1100                1105                1110
Tyr Cys Thr Ser Asn Asp Asp Gln Val Gly Ile Trp Ser Gly Pro
    1115                1120                1125
Ala Pro Gln Cys Ile Ile Pro Asn Lys Cys Thr Pro Pro Asn Val
    1130                1135                1140
Glu Asn Gly Ile Leu Val Ser Asp Asn Arg Ser Leu Phe Ser Leu
    1145                1150                1155
Asn Glu Val Val Glu Phe Arg Cys Gln Pro Gly Phe Val Met Lys
    1160                1165                1170
Gly Pro Arg Arg Val Lys Cys Gln Ala Leu Asn Lys Trp Glu Pro
    1175                1180                1185
Glu Leu Pro Ser Cys Ser Arg Val Cys Gln Pro Pro Glu Ile
    1190                1195                1200
Leu His Gly Glu His Thr Pro Ser His Gln Asp Asn Phe Ser Pro
    1205                1210                1215
Gly Gln Glu Val Phe Tyr Ser Cys Glu Pro Gly Tyr Asp Leu Arg
    1220                1225                1230
```

```
Gly Ala Ala Ser Leu His Cys Thr Pro Gln Gly Asp Trp Ser Pro
1235                1240                1245

Glu Ala Pro Arg Cys Ala Val Lys Ser Cys Asp Asp Phe Leu Gly
1250                1255                1260

Gln Leu Pro His Gly Arg Val Leu Phe Pro Leu Asn Leu Gln Leu
1265                1270                1275

Gly Ala Lys Val Ser Phe Val Cys Asp Glu Gly Phe Arg Leu Lys
1280                1285                1290

Gly Ser Ser Val Ser His Cys Val Leu Val Gly Met Arg Ser Leu
1295                1300                1305

Trp Asn Asn Ser Val Pro Val Cys Glu His Ile Phe Cys Pro Asn
1310                1315                1320

Pro Pro Ala Ile Leu Asn Gly Arg His Thr Gly Thr Pro Ser Gly
1325                1330                1335

Asp Ile Pro Tyr Gly Lys Glu Ile Ser Tyr Thr Cys Asp Pro His
1340                    1345                1350

Pro Asp Arg Gly Met Thr Phe Asn Leu Ile Gly Glu Ser Thr Ile
1355                1360                1365

Arg Cys Thr Ser Asp Pro His Gly Asn Gly Val Trp Ser Ser Pro
1370                1375                1380

Ala Pro Arg Cys Glu Leu Ser Val Arg Ala Gly His Cys Lys Thr
1385                1390                1395

Pro Glu Gln Phe Pro Phe Ala Ser Pro Thr Ile Pro Ile Asn Asp
1400                1405                1410

Phe Glu Phe Pro Val Gly Thr Ser Leu Asn Tyr Glu Cys Arg Pro
1415                1420                1425

Gly Tyr Phe Gly Lys Met Phe Ser Ile Ser Cys Leu Glu Asn Leu
1430                1435                1440

Val Trp Ser Ser Val Glu Asp Asn Cys Arg Arg Lys Ser Cys Gly
1445                1450                1455

Pro Pro Pro Glu Pro Phe Asn Gly Met Val His Ile Asn Thr Asp
1460                1465                1470

Thr Gln Phe Gly Ser Thr Val Asn Tyr Ser Cys Asn Glu Gly Phe
1475                1480                1485

Arg Leu Ile Gly Ser Pro Ser Thr Thr Cys Leu Val Ser Gly Asn
1490                1495                1500

Asn Val Thr Trp Asp Lys Lys Ala Pro Ile Cys Glu Ile Ile Ser
1505                1510                1515

Cys Glu Pro Pro Pro Thr Ile Ser Asn Gly Asp Phe Tyr Ser Asn
1520                1525                1530

Asn Arg Thr Ser Phe His Asn Gly Thr Val Val Thr Tyr Gln Cys
1535                1540                1545

His Thr Gly Pro Asp Gly Glu Gln Leu Phe Glu Leu Val Gly Glu
1550                1555                1560

Arg Ser Ile Tyr Cys Thr Ser Lys Asp Asp Gln Val Gly Val Trp
1565                1570                1575

Ser Ser Pro Pro Pro Arg Cys Ile Ser Thr Asn Lys Cys Thr Ala
1580                1585                1590

Pro Glu Val Glu Asn Ala Ile Arg Val Pro Gly Asn Arg Ser Phe
1595                1600                1605

Phe Ser Leu Thr Glu Ile Ile Arg Phe Arg Cys Gln Pro Gly Phe
1610                1615                1620
```

```
Val Met Val Gly Ser His Thr Val Gln Cys Gln Thr Asn Gly Arg
    1625            1630            1635

Trp Gly Pro Lys Leu Pro His Cys Ser Arg Val Cys Gln Pro Pro
    1640            1645            1650

Pro Glu Ile Leu His Gly Glu His Thr Leu Ser His Gln Asp Asn
    1655            1660            1665

Phe Ser Pro Gly Gln Glu Val Phe Tyr Ser Cys Glu Pro Ser Tyr
    1670            1675            1680

Asp Leu Arg Gly Ala Ala Ser Leu His Cys Thr Pro Gln Gly Asp
    1685            1690            1695

Trp Ser Pro Glu Ala Pro Arg Cys Thr Val Lys Ser Cys Asp Asp
    1700            1705            1710

Phe Leu Gly Gln Leu Pro His Gly Arg Val Leu Leu Pro Leu Asn
    1715            1720            1725

Leu Gln Leu Gly Ala Lys Val Ser Phe Val Cys Asp Glu Gly Phe
    1730            1735            1740

Arg Leu Lys Gly Arg Ser Ala Ser His Cys Val Leu Ala Gly Met
    1745            1750            1755

Lys Ala Leu Trp Asn Ser Ser Val Pro Val Cys Glu Gln Ile Phe
    1760            1765            1770

Cys Pro Asn Pro Pro Ala Ile Leu Asn Gly Arg His Thr Gly Thr
    1775            1780            1785

Pro Phe Gly Asp Ile Pro Tyr Gly Lys Glu Ile Ser Tyr Ala Cys
    1790            1795            1800

Asp Thr His Pro Asp Arg Gly Met Thr Phe Asn Leu Ile Gly Glu
    1805            1810            1815

Ser Ser Ile Arg Cys Thr Ser Asp Pro Gln Gly Asn Gly Val Trp
    1820            1825            1830

Ser Ser Pro Ala Pro Arg Cys Glu Leu Ser Val Pro Ala Ala Cys
    1835            1840            1845

Pro His Pro Pro Lys Ile Gln Asn Gly His Tyr Ile Gly Gly His
    1850            1855            1860

Val Ser Leu Tyr Leu Pro Gly Met Thr Ile Ser Tyr Thr Cys Asp
    1865            1870            1875

Pro Gly Tyr Leu Leu Val Gly Lys Gly Phe Ile Phe Cys Thr Asp
    1880            1885            1890

Gln Gly Ile Trp Ser Gln Leu Asp His Tyr Cys Lys Glu Val Asn
    1895            1900            1905

Cys Ser Phe Pro Leu Phe Met Asn Gly Ile Ser Lys Glu Leu Glu
    1910            1915            1920

Met Lys Lys Val Tyr His Tyr Gly Asp Tyr Val Thr Leu Lys Cys
    1925            1930            1935

Glu Asp Gly Tyr Thr Leu Glu Gly Ser Pro Trp Ser Gln Cys Gln
    1940            1945            1950

Ala Asp Asp Arg Trp Asp Pro Pro Leu Ala Lys Cys Thr Ser Arg
    1955            1960            1965

Ala His Asp Ala Leu Ile Val Gly Thr Leu Ser Gly Thr Ile Phe
    1970            1975            1980

Phe Ile Leu Leu Ile Ile Phe Leu Ser Trp Ile Ile Leu Lys His
    1985            1990            1995

Arg Lys Gly Asn Asn Ala His Glu Asn Pro Lys Glu Val Ala Ile
    2000            2005            2010

His Leu His Ser Gln Gly Gly Ser Ser Val His Pro Arg Thr Leu
```

Gln Thr Asn Glu Glu Asn Ser Arg Val Leu Pro
    2030                2035

<210> SEQ ID NO 10
<211> LENGTH: 392
<212> TYPE: PRT
<213> ORGANISM: Homo sapiens

<400> SEQUENCE: 10

Met Glu Pro Pro Gly Arg Arg Glu Cys Pro Phe Pro Ser Trp Arg Phe
1               5                   10                  15

Pro Gly Leu Leu Leu Ala Ala Met Val Leu Leu Leu Tyr Ser Phe Ser
            20                  25                  30

Asp Ala Cys Glu Glu Pro Pro Thr Phe Glu Ala Met Glu Leu Ile Gly
        35                  40                  45

Lys Pro Lys Pro Tyr Tyr Glu Ile Gly Glu Arg Val Asp Tyr Lys Cys
    50                  55                  60

Lys Lys Gly Tyr Phe Tyr Ile Pro Pro Leu Ala Thr His Thr Ile Cys
65                  70                  75                  80

Asp Arg Asn His Thr Trp Leu Pro Val Ser Asp Ala Cys Tyr Arg
                85                  90                  95

Glu Thr Cys Pro Tyr Ile Arg Asp Pro Leu Asn Gly Gln Ala Val Pro
            100                 105                 110

Ala Asn Gly Thr Tyr Glu Phe Gly Tyr Gln Met His Phe Ile Cys Asn
        115                 120                 125

Glu Gly Tyr Tyr Leu Ile Gly Glu Glu Ile Leu Tyr Cys Glu Leu Lys
    130                 135                 140

Gly Ser Val Ala Ile Trp Ser Gly Lys Pro Pro Ile Cys Glu Lys Val
145                 150                 155                 160

Leu Cys Thr Pro Pro Pro Lys Ile Lys Asn Gly Lys His Thr Phe Ser
                165                 170                 175

Glu Val Glu Val Phe Glu Tyr Leu Asp Ala Val Thr Tyr Ser Cys Asp
            180                 185                 190

Pro Ala Pro Gly Pro Asp Pro Phe Ser Leu Ile Gly Glu Ser Thr Ile
        195                 200                 205

Tyr Cys Gly Asp Asn Ser Val Trp Ser Arg Ala Ala Pro Glu Cys Lys
    210                 215                 220

Val Val Lys Cys Arg Phe Pro Val Val Glu Asn Gly Lys Gln Ile Ser
225                 230                 235                 240

Gly Phe Gly Lys Lys Phe Tyr Tyr Lys Ala Thr Val Met Phe Glu Cys
                245                 250                 255

Asp Lys Gly Phe Tyr Leu Asp Gly Ser Asp Thr Ile Val Cys Asp Ser
            260                 265                 270

Asn Ser Thr Trp Asp Pro Pro Val Pro Lys Cys Leu Lys Val Leu Pro
        275                 280                 285

Pro Ser Ser Thr Lys Pro Pro Ala Leu Ser His Ser Val Ser Thr Ser
    290                 295                 300

Ser Thr Thr Lys Ser Pro Ala Ser Ser Ala Ser Gly Pro Arg Pro Thr
305                 310                 315                 320

Tyr Lys Pro Pro Val Ser Asn Tyr Pro Gly Tyr Pro Lys Pro Glu Glu
                325                 330                 335

Gly Ile Leu Asp Ser Leu Asp Val Trp Val Ile Ala Val Ile Val Ile
            340                 345                 350

```
Ala Ile Val Val Gly Val Ala Val Ile Cys Val Val Pro Tyr Arg Tyr
        355                 360                 365

Leu Gln Arg Arg Lys Lys Gly Thr Tyr Leu Thr Asp Glu Thr His
370                 375                 380

Arg Glu Val Lys Phe Thr Ser Leu
385                 390

<210> SEQ ID NO 11
<211> LENGTH: 381
<212> TYPE: PRT
<213> ORGANISM: Homo sapiens

<400> SEQUENCE: 11

Met Thr Val Ala Arg Pro Ser Val Pro Ala Leu Pro Leu Leu Gly
1               5                   10                  15

Glu Leu Pro Arg Leu Leu Leu Val Leu Leu Cys Leu Pro Ala Val
                20                  25                  30

Trp Gly Asp Cys Gly Leu Pro Pro Asp Val Pro Asn Ala Gln Pro Ala
            35                  40                  45

Leu Glu Gly Arg Thr Ser Phe Pro Glu Asp Thr Val Ile Thr Tyr Lys
50                  55                  60

Cys Glu Glu Ser Phe Val Lys Ile Pro Gly Glu Lys Asp Ser Val Ile
65                  70                  75                  80

Cys Leu Lys Gly Ser Gln Trp Ser Asp Ile Glu Glu Phe Cys Asn Arg
                85                  90                  95

Ser Cys Glu Val Pro Thr Arg Leu Asn Ser Ala Ser Leu Lys Gln Pro
            100                 105                 110

Tyr Ile Thr Gln Asn Tyr Phe Pro Val Gly Thr Val Val Glu Tyr Glu
            115                 120                 125

Cys Arg Pro Gly Tyr Arg Arg Glu Pro Ser Leu Ser Pro Lys Leu Thr
130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
            180                 185                 190

Gly Tyr Lys Leu Phe Gly Ser Thr Ser Ser Phe Cys Leu Ile Ser Gly
            195                 200                 205

Ser Ser Val Gln Trp Ser Asp Pro Leu Pro Glu Cys Arg Glu Ile Tyr
210                 215                 220

Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp
            260                 265                 270

Glu Gly Glu Trp Ser Gly Pro Pro Glu Cys Arg Gly Lys Ser Leu
            275                 280                 285

Thr Ser Lys Val Pro Pro Thr Val Gln Lys Pro Thr Thr Val Asn Val
        290                 295                 300

Pro Thr Thr Glu Val Ser Pro Thr Ser Gln Lys Thr Thr Thr Lys Thr
305                 310                 315                 320

Thr Thr Pro Asn Ala Gln Ala Thr Arg Ser Thr Pro Val Ser Arg Thr
                325                 330                 335
```

```
Thr Lys His Phe His Glu Thr Thr Pro Asn Lys Gly Ser Gly Thr Thr
                340                 345                 350

Ser Gly Thr Thr Arg Leu Leu Ser Gly His Thr Cys Phe Thr Leu Thr
            355                 360                 365

Gly Leu Leu Gly Thr Leu Val Thr Met Gly Leu Leu Thr
        370                 375                 380

<210> SEQ ID NO 12
<211> LENGTH: 390
<212> TYPE: PRT
<213> ORGANISM: Mus musculus

<400> SEQUENCE: 12

Met Ile Arg Gly Arg Ala Pro Arg Thr Arg Pro Ser Pro Pro Pro Pro
1               5                   10                  15

Leu Leu Pro Leu Leu Ser Leu Ser Leu Leu Leu Ser Pro Thr Val
            20                  25                  30

Arg Gly Asp Cys Gly Pro Pro Asp Ile Pro Asn Ala Arg Pro Ile
        35                  40                  45

Leu Gly Arg His Ser Lys Phe Ala Glu Gln Ser Lys Val Ala Tyr Ser
    50                  55                  60

Cys Asn Asn Gly Phe Lys Gln Val Pro Asp Lys Ser Asn Ile Val Val
65                  70                  75                  80

Cys Leu Glu Asn Gly Gln Trp Ser Ser His Glu Thr Phe Cys Glu Lys
                85                  90                  95

Ser Cys Val Ala Pro Glu Arg Leu Ser Phe Ala Ser Leu Lys Lys Glu
            100                 105                 110

Tyr Leu Asn Met Asn Phe Phe Pro Val Gly Thr Ile Val Glu Tyr Glu
        115                 120                 125

Cys Arg Pro Gly Phe Arg Lys Gln Pro Pro Leu Pro Gly Lys Ala Thr
    130                 135                 140

Cys Leu Glu Asp Leu Val Trp Ser Pro Val Ala Gln Phe Cys Lys Lys
145                 150                 155                 160

Lys Ser Cys Pro Asn Pro Lys Asp Leu Asp Asn Gly His Ile Asn Ile
                165                 170                 175

Pro Thr Gly Ile Leu Phe Gly Ser Glu Ile Phe Asn Ser Cys Asn Pro
            180                 185                 190

Gly Tyr Arg Leu Val Gly Val Ser Ser Thr Phe Cys Ser Val Thr Gly
        195                 200                 205

Asn Thr Val Asp Trp Asp Asp Glu Phe Pro Val Cys Thr Glu Ile His
    210                 215                 220

Cys Pro Glu Pro Pro Lys Ile Asn Asn Gly Ile Met Arg Gly Glu Ser
225                 230                 235                 240

Asp Ser Tyr Thr Tyr Ser Gln Val Val Thr Tyr Ser Cys Asp Lys Gly
                245                 250                 255

Phe Ile Leu Val Gly Asn Ala Ser Ile Tyr Cys Thr Val Ser Lys Ser
            260                 265                 270

Asp Val Gly Gln Trp Ser Ser Pro Pro Arg Cys Ile Glu Lys Ser
        275                 280                 285

Lys Val Pro Thr Lys Pro Thr Ile Asn Val Pro Ser Thr Gly Thr
    290                 295                 300

Pro Ser Thr Pro Gln Lys Pro Thr Glu Ser Val Pro Asn Pro Gly
305                 310                 315                 320

Asp Gln Pro Thr Pro Gln Lys Pro Ser Thr Val Lys Val Ser Ala Thr
```

```
            325                 330                 335
Gln His Val Pro Val Thr Lys Thr Thr Val Arg His Pro Ile Arg Thr
                340                 345                 350

Ser Thr Asp Lys Gly Glu Pro Asn Thr Gly Gly Asp Arg Tyr Ile Tyr
                355                 360                 365

Gly His Thr Cys Leu Ile Thr Leu Thr Val Leu His Val Met Leu Ser
370                 375                 380

Leu Ile Gly Tyr Leu Thr
385                 390

<210> SEQ ID NO 13
<211> LENGTH: 1642
<212> TYPE: PRT
<213> ORGANISM: Naja kaouthia

<400> SEQUENCE: 13

Met Glu Arg Met Ala Leu Tyr Leu Val Ala Leu Leu Ile Gly Phe
1               5                   10                  15

Pro Gly Ser Ser His Gly Ala Leu Tyr Thr Leu Ile Thr Pro Ala Val
                20                  25                  30

Leu Arg Thr Asp Thr Glu Glu Gln Ile Leu Val Glu Ala His Gly Asp
            35                  40                  45

Ser Thr Pro Lys Gln Leu Asp Ile Phe Val His Asp Phe Pro Arg Lys
50                  55                  60

Gln Lys Thr Leu Phe Gln Thr Arg Val Asp Met Asn Pro Ala Gly Gly
65                  70                  75                  80

Met Leu Val Thr Pro Thr Ile Glu Ile Pro Ala Lys Glu Val Ser Thr
                85                  90                  95

Asp Ser Arg Gln Asn Gln Tyr Val Val Val Gln Val Thr Gly Pro Gln
            100                 105                 110

Val Arg Leu Glu Lys Val Val Leu Ser Tyr Gln Ser Ser Phe Leu
            115                 120                 125

Phe Ile Gln Thr Asp Lys Gly Ile Tyr Thr Pro Gly Ser Pro Val Leu
130                 135                 140

Tyr Arg Val Phe Ser Met Asp His Asn Thr Ser Lys Met Asn Lys Thr
145                 150                 155                 160

Val Ile Val Glu Phe Gln Thr Pro Glu Gly Ile Leu Val Ser Ser Asn
                165                 170                 175

Ser Val Asp Leu Asn Phe Phe Trp Pro Tyr Asn Leu Pro Asp Leu Val
            180                 185                 190

Ser Leu Gly Thr Trp Arg Ile Val Ala Lys Tyr Glu His Ser Pro Glu
            195                 200                 205

Asn Tyr Thr Ala Tyr Phe Asp Val Arg Lys Tyr Val Leu Pro Ser Phe
210                 215                 220

Glu Val Arg Leu Gln Pro Ser Glu Lys Phe Phe Tyr Ile Asp Gly Asn
225                 230                 235                 240

Glu Asn Phe His Val Ser Ile Thr Ala Arg Tyr Leu Tyr Gly Glu Glu
                245                 250                 255

Val Glu Gly Val Ala Phe Val Leu Phe Gly Val Lys Ile Asp Asp Ala
            260                 265                 270

Lys Lys Ser Ile Pro Asp Ser Leu Thr Arg Ile Pro Ile Ile Asp Gly
            275                 280                 285

Asp Gly Lys Ala Thr Leu Lys Arg Asp Thr Phe Arg Ser Arg Phe Pro
290                 295                 300
```

-continued

```
Asn Leu Asn Glu Leu Val Gly His Thr Leu Tyr Ala Ser Val Thr Val
305                 310                 315                 320

Met Thr Glu Ser Gly Ser Asp Met Val Thr Glu Gln Ser Gly Ile
            325                 330                 335

His Ile Val Ala Ser Pro Tyr Gln Ile His Phe Thr Lys Thr Pro Lys
        340                 345                 350

Tyr Phe Lys Pro Gly Met Pro Tyr Glu Leu Thr Val Tyr Val Thr Asn
            355                 360                 365

Pro Asp Gly Ser Pro Ala Ala His Val Pro Val Ser Glu Ala Phe
370                 375                 380

His Ser Met Gly Thr Thr Leu Ser Asp Gly Thr Ala Lys Leu Ile Leu
385                 390                 395                 400

Asn Ile Pro Leu Asn Ala Gln Ser Leu Pro Ile Thr Val Arg Thr Asn
            405                 410                 415

His Gly Asp Leu Pro Arg Glu Arg Gln Ala Thr Lys Ser Met Thr Ala
            420                 425                 430

Ile Ala Tyr Gln Thr Gln Gly Gly Ser Gly Asn Tyr Leu His Val Ala
        435                 440                 445

Ile Thr Ser Thr Glu Ile Lys Pro Gly Asp Asn Leu Pro Val Asn Phe
450                 455                 460

Asn Val Lys Gly Asn Ala Asn Ser Leu Lys Gln Ile Lys Tyr Phe Thr
465                 470                 475                 480

Tyr Leu Ile Leu Asn Lys Gly Lys Ile Phe Lys Val Gly Arg Gln Pro
            485                 490                 495

Arg Arg Asp Gly Gln Asn Leu Val Thr Met Asn Leu His Ile Thr Pro
            500                 505                 510

Asp Leu Ile Pro Ser Phe Arg Phe Val Ala Tyr Tyr Gln Val Gly Asn
        515                 520                 525

Asn Glu Ile Val Ala Asp Ser Val Trp Val Asp Val Lys Asp Thr Cys
530                 535                 540

Met Gly Thr Leu Val Val Lys Gly Asp Asn Leu Ile Gln Met Pro Gly
545                 550                 555                 560

Ala Ala Met Lys Ile Lys Leu Glu Gly Asp Pro Gly Ala Arg Val Gly
            565                 570                 575

Leu Val Ala Val Asp Lys Ala Val Tyr Val Leu Asn Asp Lys Tyr Lys
            580                 585                 590

Ile Ser Gln Ala Lys Ile Trp Asp Thr Ile Glu Lys Ser Asp Phe Gly
        595                 600                 605

Cys Thr Ala Gly Ser Gly Gln Asn Asn Leu Gly Val Phe Glu Asp Ala
610                 615                 620

Gly Leu Ala Leu Thr Thr Ser Thr Asn Leu Asn Thr Lys Gln Arg Ser
625                 630                 635                 640

Ala Ala Lys Cys Pro Gln Pro Ala Asn Arg Arg Arg Ser Ser Val
            645                 650                 655

Leu Leu Leu Asp Ser Asn Ala Ser Lys Ala Ala Glu Phe Gln Asp Gln
            660                 665                 670

Asp Leu Arg Lys Cys Cys Glu Asp Val Met His Glu Asn Pro Met Gly
        675                 680                 685

Tyr Thr Cys Glu Lys Arg Ala Lys Tyr Ile Gln Glu Gly Asp Ala Cys
            690                 695                 700

Lys Ala Ala Phe Leu Glu Cys Cys Arg Tyr Ile Lys Gly Val Arg Asp
705                 710                 715                 720

Glu Asn Gln Arg Glu Ser Glu Leu Phe Leu Ala Arg Asp Asp Asn Glu
```

```
                    725                 730                 735
Asp Gly Phe Ile Ala Asp Ser Asp Ile Ile Ser Arg Ser Asp Phe Pro
                740                 745                 750
Lys Ser Trp Leu Trp Leu Thr Lys Asp Leu Thr Glu Glu Pro Asn Ser
            755                 760                 765
Gln Gly Ile Ser Ser Lys Thr Met Ser Phe Tyr Leu Arg Asp Ser Ile
        770                 775                 780
Thr Thr Trp Val Val Leu Ala Val Ser Phe Thr Pro Thr Lys Gly Ile
785                 790                 795                 800
Cys Val Ala Glu Pro Tyr Glu Ile Arg Val Met Lys Val Phe Phe Ile
                805                 810                 815
Asp Leu Gln Met Pro Tyr Ser Val Val Lys Asn Glu Gln Val Glu Ile
                820                 825                 830
Arg Ala Ile Leu His Asn Tyr Val Asn Glu Asp Ile Tyr Val Arg Val
                835                 840                 845
Glu Leu Leu Tyr Asn Pro Ala Phe Cys Ser Ala Ser Thr Lys Gly Gln
            850                 855                 860
Arg Tyr Arg Gln Gln Phe Pro Ile Lys Ala Leu Ser Ser Arg Ala Val
865                 870                 875                 880
Pro Phe Val Ile Val Pro Leu Glu Gln Gly Leu His Asp Val Glu Ile
                885                 890                 895
Lys Ala Ser Val Gln Glu Ala Leu Trp Ser Asp Gly Val Arg Lys Lys
                900                 905                 910
Leu Lys Val Val Pro Glu Gly Val Gln Lys Ser Ile Val Thr Ile Val
            915                 920                 925
Lys Leu Asp Pro Arg Ala Lys Gly Val Gly Gly Thr Gln Leu Glu Val
        930                 935                 940
Ile Lys Ala Arg Lys Leu Asp Asp Arg Val Pro Asp Thr Glu Ile Glu
945                 950                 955                 960
Thr Lys Ile Ile Ile Gln Gly Asp Pro Val Ala Gln Ile Ile Glu Asn
                965                 970                 975
Ser Ile Asp Gly Ser Lys Leu Asn His Leu Ile Ile Thr Pro Ser Gly
            980                 985                 990
Cys Gly Glu Gln Asn Met Ile Arg Met Ala Ala Pro Val Ile Ala Thr
        995                1000                1005
Tyr Tyr Leu Asp Thr Thr Glu Gln Trp Glu Thr Leu Gly Ile Asn
        1010                1015                1020
Arg Arg Thr Glu Ala Val Asn Gln Ile Val Thr Gly Tyr Ala Gln
        1025                1030                1035
Gln Met Val Tyr Lys Lys Ala Asp His Ser Tyr Ala Ala Phe Thr
        1040                1045                1050
Asn Arg Ala Ser Ser Ser Trp Leu Thr Ala Tyr Val Val Lys Val
        1055                1060                1065
Phe Ala Met Ala Ala Lys Met Val Ala Gly Ile Ser His Glu Ile
        1070                1075                1080
Ile Cys Gly Gly Val Arg Trp Leu Ile Leu Asn Arg Gln Gln Pro
        1085                1090                1095
Asp Gly Ala Phe Lys Glu Asn Ala Pro Val Leu Ser Gly Thr Met
        1100                1105                1110
Gln Gly Gly Ile Gln Gly Ala Glu Glu Glu Val Tyr Leu Thr Ala
        1115                1120                1125
Phe Ile Leu Val Ala Leu Leu Glu Ser Lys Thr Ile Cys Asn Asp
        1130                1135                1140
```

```
Tyr Val Asn Ser Leu Asp Ser Ser Ile Lys Lys Ala Thr Asn Tyr
1145                1150                1155

Leu Leu Lys Lys Tyr Glu Lys Leu Gln Arg Pro Tyr Thr Thr Ala
1160                1165                1170

Leu Thr Ala Tyr Ala Leu Ala Ala Ala Asp Gln Leu Asn Asp Asp
1175                1180                1185

Arg Val Leu Met Ala Ala Ser Thr Gly Arg Asp His Trp Glu Glu
1190                1195                1200

Tyr Asn Ala His Thr His Asn Ile Glu Gly Thr Ser Tyr Ala Leu
1205                1210                1215

Leu Ala Leu Leu Lys Met Lys Lys Phe Asp Gln Thr Gly Pro Ile
1220                1225                1230

Val Arg Trp Leu Thr Asp Gln Asn Phe Tyr Gly Glu Thr Tyr Gly
1235                1240                1245

Gln Thr Gln Ala Thr Val Met Ala Phe Gln Ala Leu Ala Glu Tyr
1250                1255                1260

Glu Ile Gln Met Pro Thr His Lys Asp Leu Asn Leu Asp Ile Thr
1265                1270                1275

Ile Glu Leu Pro Asp Arg Glu Val Pro Ile Arg Tyr Arg Ile Asn
1280                1285                1290

Tyr Glu Asn Ala Leu Leu Ala Arg Thr Val Glu Thr Lys Leu Asn
1295                1300                1305

Gln Asp Ile Thr Val Thr Ala Ser Gly Asp Gly Lys Ala Thr Met
1310                1315                1320

Thr Ile Leu Thr Phe Tyr Asn Ala Gln Leu Gln Glu Lys Ala Asn
1325                1330                1335

Val Cys Asn Lys Phe His Leu Asn Val Ser Val Glu Asn Ile His
1340                1345                1350

Leu Asn Ala Met Gly Ala Lys Gly Ala Leu Met Leu Lys Ile Cys
1355                1360                1365

Thr Arg Tyr Leu Gly Glu Val Asp Ser Thr Met Thr Ile Ile Asp
1370                1375                1380

Ile Ser Met Leu Thr Gly Phe Leu Pro Asp Ala Glu Asp Leu Thr
1385                1390                1395

Arg Leu Ser Lys Gly Val Asp Arg Tyr Ile Ser Arg Tyr Glu Val
1400                1405                1410

Asp Asn Asn Met Ala Gln Lys Val Ala Val Ile Ile Tyr Leu Asn
1415                1420                1425

Lys Val Ser His Ser Glu Asp Glu Cys Leu His Phe Lys Ile Leu
1430                1435                1440

Lys His Phe Glu Val Gly Phe Ile Gln Pro Gly Ser Val Lys Val
1445                1450                1455

Tyr Ser Tyr Tyr Asn Leu Asp Glu Lys Cys Thr Lys Phe Tyr His
1460                1465                1470

Pro Asp Lys Gly Thr Gly Leu Leu Asn Lys Ile Cys Ile Gly Asn
1475                1480                1485

Val Cys Arg Cys Ala Gly Glu Thr Cys Ser Ser Leu Asn His Gln
1490                1495                1500

Glu Arg Ile Asp Val Pro Leu Gln Ile Glu Lys Ala Cys Glu Thr
1505                1510                1515

Asn Val Asp Tyr Val Tyr Lys Thr Lys Leu Leu Arg Ile Glu Glu
1520                1525                1530
```

```
Gln Asp Gly Asn Asp Ile Tyr Val Met Asp Val Leu Glu Val Ile
    1535                1540                1545

Lys Gln Gly Thr Asp Glu Asn Pro Arg Ala Lys Thr His Gln Tyr
    1550                1555                1560

Ile Ser Gln Arg Lys Cys Gln Glu Ala Leu Asn Leu Lys Val Asn
    1565                1570                1575

Asp Asp Tyr Leu Ile Trp Gly Ser Arg Ser Asp Leu Leu Pro Thr
    1580                1585                1590

Lys Asp Lys Ile Ser Tyr Ile Ile Thr Lys Asn Thr Trp Ile Glu
    1595                1600                1605

Arg Trp Pro His Glu Asp Glu Cys Gln Glu Glu Phe Gln Lys
    1610                1615                1620

Leu Cys Asp Asp Phe Ala Gln Phe Ser Tyr Thr Leu Thr Glu Phe
    1625                1630                1635

Gly Cys Pro Thr
    1640

<210> SEQ ID NO 14
<211> LENGTH: 330
<212> TYPE: PRT
<213> ORGANISM: Homo sapiens

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 106
<212> TYPE: PRT
<213> ORGANISM: Homo sapiens

<400> SEQUENCE: 15

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 16
<211> LENGTH: 232
<212> TYPE: PRT
<213> ORGANISM: Homo sapiens

<400> SEQUENCE: 16

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140
```

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Pro Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 17
<211> LENGTH: 452
<212> TYPE: PRT
<213> ORGANISM: Homo sapiens

<400> SEQUENCE: 17

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Leu Ser Trp Lys Tyr Lys Asn Asn Ser
            35                  40                  45

Asp Ile Ser Ser Thr Arg Gly Phe Pro Ser Val Leu Arg Gly Gly Lys
50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
```

```
                275                 280                 285
Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
        435                 440                 445

Gly Thr Cys Tyr
    450

<210> SEQ ID NO 18
<211> LENGTH: 105
<212> TYPE: PRT
<213> ORGANISM: Homo sapiens

<400> SEQUENCE: 18

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val
            100                 105

<210> SEQ ID NO 19
<211> LENGTH: 454
<212> TYPE: PRT
<213> ORGANISM: Homo sapiens

<400> SEQUENCE: 19

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
```

```
              35                  40                  45
Asp Ile Ser Ser Thr Arg Gly Phe Pro Ser Val Leu Arg Gly Gly Lys
 50                  55                  60

Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                 85                  90                  95

Lys Glu Lys Asn Val Pro Leu Pro Val Ile Ala Glu Leu Pro Pro Lys
             100                 105                 110

Val Ser Val Phe Val Pro Pro Arg Asp Gly Phe Phe Gly Asn Pro Arg
         115                 120                 125

Ser Lys Ser Lys Leu Ile Cys Gln Ala Thr Gly Phe Ser Pro Arg Gln
     130                 135                 140

Ile Gln Val Ser Trp Leu Arg Glu Gly Lys Gln Val Gly Ser Gly Val
145                 150                 155                 160

Thr Thr Asp Gln Val Gln Ala Glu Ala Lys Glu Ser Gly Pro Thr Thr
                165                 170                 175

Tyr Lys Val Thr Ser Thr Leu Thr Ile Lys Glu Ser Asp Trp Leu Ser
            180                 185                 190

Gln Ser Met Phe Thr Cys Arg Val Asp His Arg Gly Leu Thr Phe Gln
        195                 200                 205

Gln Asn Ala Ser Ser Met Cys Val Pro Asp Gln Asp Thr Ala Ile Arg
    210                 215                 220

Val Phe Ala Ile Pro Pro Ser Phe Ala Ser Ile Phe Leu Thr Lys Ser
225                 230                 235                 240

Thr Lys Leu Thr Cys Leu Val Thr Asp Leu Thr Thr Tyr Asp Ser Val
                245                 250                 255

Thr Ile Ser Trp Thr Arg Gln Asn Gly Glu Ala Val Lys Thr His Thr
            260                 265                 270

Asn Ile Ser Glu Ser His Pro Asn Ala Thr Phe Ser Ala Val Gly Glu
        275                 280                 285

Ala Ser Ile Cys Glu Asp Asp Trp Asn Ser Gly Glu Arg Phe Thr Cys
    290                 295                 300

Thr Val Thr His Thr Asp Leu Pro Ser Pro Leu Lys Gln Thr Ile Ser
305                 310                 315                 320

Arg Pro Lys Gly Val Ala Leu His Arg Pro Asp Val Tyr Leu Leu Pro
                325                 330                 335

Pro Ala Arg Glu Gln Leu Asn Leu Arg Glu Ser Ala Thr Ile Thr Cys
            340                 345                 350

Leu Val Thr Gly Phe Ser Pro Ala Asp Val Phe Val Gln Trp Met Gln
        355                 360                 365

Arg Gly Gln Pro Leu Ser Pro Glu Lys Tyr Val Thr Ser Ala Pro Met
    370                 375                 380

Pro Glu Pro Gln Ala Pro Gly Arg Tyr Phe Ala His Ser Ile Leu Thr
385                 390                 395                 400

Val Ser Glu Glu Glu Trp Asn Thr Gly Glu Thr Tyr Thr Cys Val Val
                405                 410                 415

Ala His Glu Ala Leu Pro Asn Arg Val Thr Glu Arg Thr Val Asp Lys
            420                 425                 430

Ser Thr Gly Lys Pro Thr Leu Tyr Asn Val Ser Leu Val Met Ser Asp
        435                 440                 445

Thr Ala Gly Thr Cys Tyr
    450
```

<210> SEQ ID NO 20
<211> LENGTH: 327
<212> TYPE: PRT
<213> ORGANISM: Mus musculus

<400> SEQUENCE: 20

```
Thr Thr Thr Ala Pro Ser Val Tyr Pro Leu Val Pro Gly Cys Ser Asp
1               5                   10                  15
Thr Ser Gly Ser Ser Val Thr Leu Gly Cys Leu Val Lys Gly Tyr Phe
            20                  25                  30
Pro Glu Pro Val Thr Val Lys Trp Asn Tyr Gly Ala Leu Ser Ser Gly
        35                  40                  45
Val Arg Thr Val Ser Ser Val Leu Gln Ser Gly Phe Tyr Ser Leu Ser
    50                  55                  60
Ser Leu Val Thr Val Pro Ser Ser Thr Trp Pro Ser Gln Thr Val Ile
65                  70                  75                  80
Cys Asn Val Ala His Pro Ala Ser Lys Thr Glu Leu Ile Lys Arg Ile
                85                  90                  95
Glu Pro Arg Ile Pro Lys Pro Ser Thr Pro Pro Gly Ser Ser Cys Pro
            100                 105                 110
Pro Gly Asn Ile Leu Gly Gly Pro Ser Val Phe Ile Phe Pro Pro Lys
        115                 120                 125
Pro Lys Asp Ala Leu Met Ile Ser Leu Thr Pro Lys Val Thr Cys Val
    130                 135                 140
Val Val Asp Val Ser Glu Asp Pro Asp Val His Val Ser Trp Phe
145                 150                 155                 160
Val Asp Asn Lys Glu Val His Thr Ala Trp Thr Gln Pro Arg Glu Ala
                165                 170                 175
Gln Tyr Asn Ser Thr Phe Arg Val Val Ser Ala Leu Pro Ile Gln His
            180                 185                 190
Gln Asp Trp Met Arg Gly Lys Glu Phe Lys Cys Lys Val Asn Asn Lys
        195                 200                 205
Ala Leu Pro Ala Pro Ile Glu Arg Thr Ile Ser Lys Pro Lys Gly Arg
    210                 215                 220
Ala Gln Thr Pro Gln Val Tyr Thr Ile Pro Pro Arg Glu Gln Met
225                 230                 235                 240
Ser Lys Lys Lys Val Ser Leu Thr Cys Leu Val Thr Asn Phe Phe Ser
                245                 250                 255
Glu Ala Ile Ser Val Glu Trp Glu Arg Asn Gly Glu Leu Glu Gln Asp
            260                 265                 270
Tyr Lys Asn Thr Pro Pro Ile Leu Asp Ser Asp Gly Thr Tyr Phe Leu
        275                 280                 285
Tyr Ser Lys Leu Thr Val Asp Thr Asp Ser Trp Leu Gln Gly Glu Ile
    290                 295                 300
Phe Thr Cys Ser Val Val His Glu Ala Leu His Asn His His Thr Gln
305                 310                 315                 320
Lys Asn Leu Ser Arg Ser Pro
                325
```

<210> SEQ ID NO 21
<211> LENGTH: 108
<212> TYPE: PRT
<213> ORGANISM: Mus musculus

<400> SEQUENCE: 21

```
Ile Val Leu Thr Gln Ser Pro Ala Ile Met Ser Ala Ser Pro Gly Glu
1               5                   10                  15

Lys Val Thr Met Thr Cys Arg Ala Ser Ser Val Arg Ser Ser Tyr
            20                  25                  30

Leu His Trp Tyr Gln Gln Lys Pro Gly Ser Ser Pro Lys Leu Trp Ile
        35                  40                  45

Tyr Ser Thr Ser Asn Leu Ala Ser Gly Val Pro Val Arg Phe Ser Gly
    50                  55                  60

Ser Gly Ser Gly Thr Ser Tyr Ser Leu Thr Ile Ser Ser Val Glu Ala
65                  70                  75                  80

Glu Asp Ala Ala Thr Tyr Tyr Cys Gln Gln Tyr Asp Ser Ser Pro Ser
                85                  90                  95

Ile Thr Phe Gly Ala Gly Thr Lys Leu Glu Leu Lys
            100                 105
```

<210> SEQ ID NO 22
<211> LENGTH: 233
<212> TYPE: PRT
<213> ORGANISM: Mus musculus

<400> SEQUENCE: 22

```
Glu Pro Arg Ile Pro Lys Pro Ser Thr Pro Pro Gly Ser Ser Cys Pro
1               5                   10                  15

Pro Gly Asn Ile Leu Gly Gly Pro Ser Val Phe Ile Phe Pro Pro Lys
            20                  25                  30

Pro Lys Asp Ala Leu Met Ile Ser Leu Thr Pro Lys Val Thr Cys Val
        35                  40                  45

Val Val Asp Val Ser Glu Asp Asp Pro Asp Val His Val Ser Trp Phe
    50                  55                  60

Val Asp Asn Lys Glu Val His Thr Ala Trp Thr Gln Pro Arg Glu Ala
65                  70                  75                  80

Gln Tyr Asn Ser Thr Phe Arg Val Val Ser Ala Leu Pro Ile Gln His
                85                  90                  95

Gln Asp Trp Met Arg Gly Lys Glu Phe Lys Cys Lys Val Asn Asn Lys
            100                 105                 110

Ala Leu Pro Ala Pro Ile Glu Arg Thr Ile Ser Lys Pro Lys Gly Arg
        115                 120                 125

Ala Gln Thr Pro Gln Val Tyr Thr Ile Pro Pro Arg Glu Gln Met
    130                 135                 140

Ser Lys Lys Lys Val Ser Leu Thr Cys Leu Val Thr Asn Phe Phe Ser
145                 150                 155                 160

Glu Ala Ile Ser Val Glu Trp Glu Arg Asn Gly Glu Leu Glu Gln Asp
                165                 170                 175

Tyr Lys Asn Thr Pro Pro Ile Leu Asp Ser Asp Gly Thr Tyr Phe Leu
            180                 185                 190

Tyr Ser Lys Leu Thr Val Asp Thr Asp Ser Trp Leu Gln Gly Glu Ile
        195                 200                 205

Phe Thr Cys Ser Val Val His Glu Ala Leu His Asn His His Thr Gln
    210                 215                 220

Lys Asn Leu Ser Arg Ser Pro Gly Lys
225                 230
```

<210> SEQ ID NO 23
<211> LENGTH: 454
<212> TYPE: PRT

<213> ORGANISM: Mus musculus

<400> SEQUENCE: 23

```
Ser Gln Ser Phe Pro Asn Val Phe Pro Leu Val Ser Cys Glu Ser Pro
1               5                   10                  15

Leu Ser Asp Lys Asn Leu Val Ala Met Gly Cys Leu Ala Arg Asp Phe
            20                  25                  30

Leu Pro Ser Thr Ile Ser Phe Thr Trp Asn Tyr Gln Asn Asn Thr Glu
        35                  40                  45

Val Ile Gln Gly Ile Arg Thr Phe Pro Thr Leu Arg Thr Gly Gly Lys
    50                  55                  60

Tyr Leu Ala Thr Ser Gln Val Leu Leu Ser Pro Lys Ser Ile Leu Glu
65                  70                  75                  80

Gly Ser Asp Glu Tyr Leu Val Cys Lys Ile His Tyr Gly Gly Lys Asn
                85                  90                  95

Arg Asp Leu His Val Pro Ile Pro Ala Val Ala Glu Met Asn Pro Asn
            100                 105                 110

Val Asn Val Phe Val Pro Pro Arg Asp Gly Phe Ser Gly Pro Ala Pro
        115                 120                 125

Arg Lys Ser Lys Leu Ile Cys Glu Ala Thr Asn Phe Thr Pro Lys Pro
130                 135                 140

Ile Thr Val Ser Trp Leu Lys Asp Gly Lys Leu Val Glu Ser Gly Phe
145                 150                 155                 160

Thr Thr Asp Pro Val Thr Ile Glu Asn Lys Gly Ser Thr Pro Gln Thr
                165                 170                 175

Tyr Lys Val Ile Ser Thr Leu Thr Ile Ser Glu Ile Asp Trp Leu Asn
            180                 185                 190

Leu Asn Val Tyr Thr Cys Arg Val Asp His Arg Gly Leu Thr Phe Leu
        195                 200                 205

Lys Asn Val Ser Ser Thr Cys Ala Ala Ser Pro Ser Thr Asp Ile Leu
210                 215                 220

Thr Phe Thr Ile Pro Pro Ser Phe Ala Asp Ile Phe Leu Ser Lys Ser
225                 230                 235                 240

Ala Asn Leu Thr Cys Leu Val Ser Asn Leu Ala Thr Tyr Glu Thr Leu
                245                 250                 255

Asn Ile Ser Trp Ala Ser Gln Ser Gly Glu Pro Leu Glu Thr Lys Ile
            260                 265                 270

Lys Ile Met Glu Ser His Pro Asn Gly Thr Phe Ser Ala Lys Gly Val
        275                 280                 285

Ala Ser Val Cys Val Glu Asp Trp Asn Asn Arg Lys Glu Phe Val Cys
290                 295                 300

Thr Val Thr His Arg Asp Leu Pro Ser Pro Gln Lys Lys Phe Ile Ser
305                 310                 315                 320

Lys Pro Asn Glu Val His Lys His Pro Pro Ala Val Tyr Leu Leu Pro
                325                 330                 335

Pro Ala Arg Glu Gln Leu Asn Leu Arg Glu Ser Ala Thr Val Thr Cys
            340                 345                 350

Leu Val Lys Gly Phe Ser Pro Ala Asp Ile Ser Val Gln Trp Leu Gln
        355                 360                 365

Arg Gly Gln Leu Leu Pro Gln Glu Lys Tyr Val Thr Ser Ala Pro Met
370                 375                 380

Pro Glu Pro Gly Ala Pro Gly Phe Tyr Phe Thr His Ser Ile Leu Thr
385                 390                 395                 400
```

```
Val Thr Glu Glu Trp Asn Ser Gly Glu Thr Tyr Thr Cys Val Val
                405                 410                 415

Gly His Glu Ala Leu Pro His Leu Val Thr Glu Arg Thr Val Asp Lys
            420                 425                 430

Ser Thr Gly Lys Pro Thr Leu Tyr Asn Val Ser Leu Ile Met Ser Asp
        435                 440                 445

Thr Gly Gly Thr Cys Tyr
        450
```

<210> SEQ ID NO 24
<211> LENGTH: 104
<212> TYPE: PRT
<213> ORGANISM: Mus musculus

<400> SEQUENCE: 24

```
Ser Gln Ser Phe Pro Asn Val Phe Pro Leu Val Ser Cys Glu Ser Pro
1               5                   10                  15

Leu Ser Asp Lys Asn Leu Val Ala Met Gly Cys Leu Ala Arg Asp Phe
            20                  25                  30

Leu Pro Ser Thr Ile Ser Phe Thr Trp Asn Tyr Gln Asn Asn Thr Glu
        35                  40                  45

Val Ile Gln Gly Ile Arg Thr Phe Pro Thr Leu Arg Thr Gly Gly Lys
    50                  55                  60

Tyr Leu Ala Thr Ser Gln Val Leu Leu Ser Pro Lys Ser Ile Leu Glu
65                  70                  75                  80

Gly Ser Asp Glu Tyr Leu Val Cys Lys Ile His Tyr Gly Gly Lys Asn
                85                  90                  95

Arg Asp Leu His Val Pro Ile Pro
            100
```

<210> SEQ ID NO 25
<211> LENGTH: 238
<212> TYPE: PRT
<213> ORGANISM: Mus musculus

<400> SEQUENCE: 25

```
Ala Ser Pro Ser Thr Asp Ile Leu Thr Phe Thr Ile Pro Pro Ser Phe
1               5                   10                  15

Ala Asp Ile Phe Leu Ser Lys Ser Ala Asn Leu Thr Cys Leu Val Ser
            20                  25                  30

Asn Leu Ala Thr Tyr Glu Thr Leu Asn Ile Ser Trp Ala Ser Gln Ser
        35                  40                  45

Gly Glu Pro Leu Glu Thr Lys Ile Lys Ile Met Glu Ser His Pro Asn
    50                  55                  60

Gly Thr Phe Ser Ala Lys Gly Val Ala Ser Val Cys Val Glu Asp Trp
65                  70                  75                  80

Asn Asn Arg Lys Glu Phe Val Cys Thr Val Thr His Arg Asp Leu Pro
                85                  90                  95

Ser Pro Gln Lys Lys Phe Ile Ser Lys Pro Asn Glu Val His Lys His
            100                 105                 110

Pro Pro Ala Val Tyr Leu Leu Pro Pro Ala Arg Glu Gln Leu Asn Leu
        115                 120                 125

Arg Glu Ser Ala Thr Val Thr Cys Leu Val Lys Gly Phe Ser Pro Ala
    130                 135                 140

Asp Ile Ser Val Gln Trp Leu Gln Arg Gly Gln Leu Leu Pro Gln Glu
145                 150                 155                 160
```

```
Lys Tyr Val Thr Ser Ala Pro Met Pro Glu Pro Gly Ala Pro Gly Phe
                165                 170                 175

Tyr Phe Thr His Ser Ile Leu Thr Val Thr Glu Glu Glu Trp Asn Ser
            180                 185                 190

Gly Glu Thr Tyr Thr Cys Val Val Gly His Glu Ala Leu Pro His Leu
            195                 200                 205

Val Thr Glu Arg Thr Val Asp Lys Ser Thr Gly Lys Pro Thr Leu Tyr
        210                 215                 220

Asn Val Ser Leu Ile Met Ser Asp Thr Gly Gly Thr Cys Tyr
225                 230                 235

<210> SEQ ID NO 26
<211> LENGTH: 7
<212> TYPE: PRT
<213> ORGANISM: Homo sapiens

<400> SEQUENCE: 26

Val Ser Val Phe Pro Leu Glu
1               5

<210> SEQ ID NO 27
<211> LENGTH: 8
<212> TYPE: PRT
<213> ORGANISM: Homo sapiens

<400> SEQUENCE: 27

Glu Tyr Phe Asn Lys Tyr Ser Ser
1               5

<210> SEQ ID NO 28
<211> LENGTH: 4
<212> TYPE: PRT
<213> ORGANISM: Homo sapiens

<400> SEQUENCE: 28

Glu Glu Ile Phe
1
```

COMPLEMENT RECEPTOR 2 (CR2) TARGETING GROUPS

CROSS-REFERENCE TO RELATED APPLICATIONS

This application is the U.S. National Stage filing under 35 U.S.C. §371 of International Application No. PCT/US2011/036552, filed May 13, 2011, which claims priority benefit to U.S. Provisional Patent Application No. 61/345,035, filed May 14, 2010, the disclosure of which is hereby incorporated herein by reference in its entirety.

STATEMENT REGARDING FEDERALLY SPONSORED RESEARCH OR DEVELOPMENT

This invention was made in part during work supported by Grant No. RO1-CA53617 from the National Institutes of Health. The government has certain rights in the invention.

TECHNICAL FIELD

This application pertains to improved compositions for targeted delivery of therapeutics, including complement inhibitors, to sites of inflammation.

BACKGROUND

Human complement receptor 2 (CR2/CD21) is a 145 kiloDalton ("kDa") transmembrane protein comprised of 15 or 16 short consensus repeat (SCR) extracellular domains, a 28 amino acid single pass transmembrane domain and a short 34 amino acid intracellular domain (1-5). Each of the extracellular SCRs comprises approximately 60-70 amino acid residues and is connected by linker regions of three to eight amino acid residues. All SCRs contain a number of conserved amino acid residues including four cysteine residues, which form a pattern of disulfide bridges connecting Cys1-Cys3 and Cys2-Cys4. CR2 is primarily present on B cells, where it is found in complex with other membrane proteins that promote normal humoral and cellular immune responses (6-9). Using the most distally located (i.e., amino-terminal) SCR domains, SCR1-2, CR2 binds four classes of ligands—complement component 3 (C3) proteolytic fragments iC3b, C3dg and C3d (10, 11); the Epstein-Barr virus (EBV) glycoprotein gp350/220 (gp350) (12-14); the low affinity IgE receptor CD23 (15, 16); and the cytokine interferon alpha (IFNα) (17-19).

The primary role of CR2 is to function as a B cell co-receptor for antigen-mediated B cell activation through enhanced signal transduction (20, 21). This function is carried out through co-ligation via C3d and surface IgM, when C3d is covalently attached to an antigen (22-28). CR2 is also the obligate cellular receptor for EBV through its envelope surface glycoprotein gp350 (12, 20, 29-31). Actual cellular EBV infection is achieved after the ligation of CR2 to gp350 tethers the virus close enough to the cell surface (14, 32, 33), allowing viral gp42 to bind human leukocyte antigen class II molecules (34, 35) and subsequently triggering host cell fusion via three additional viral glycoproteins gB, gH and gL (36-38). IFNα has been shown to be a ligand of CR2, though the physiologic importance of this interaction remains unclear (17-19). It has been suggested, however, that IFNα and CR2 may be involved in the development of the autoimmune disease systemic lupus erythematosus (39-41).

Mutagenesis studies along with structural studies of the CR2-gp350 interaction have suggested residues on CR2 that are required for the interaction (20, 42, 43). ELISA and flow cytometry was used to test candidate CR2 mutants for the binding of gp350 and CR2 (20, 42, 43). In recent studies specific residues on CR2 which were found to have a deleterious effect on gp350-binding when mutated included R13, S15, R28, R36, K41, K57, K67, R83 and R89 (42, 43). In separate work residues P8-S15 within the first conserved inter-cysteine region of SCR1 and the linker region between SCR1 and SCR2 were also highlighted as being essential for gp350-binding to occur (20). These data, in conjunction with separate mutagenesis analyses targeting the gp350 molecule were used to drive an in silico model of the CR2-gp350 interaction utilizing the soft docking program HADDOCK (43-45). This analysis suggested that the primary interaction on CR2 was between SCR1 and the linker region joining SCR1 to SCR2, and for gp350, the linker region between domain 1 and domain 2 (43).

CR2 has been suggested as a receptor for IFNα by the finding that IFNα mimics both gp350 and C3d binding, and the observation that all three ligands bind a similar region on CR2 (18, 19). The mimicry was shown to be functional as well (18). After both the C3d and IFNα structures were solved, the putative CR2 binding sequence was found to have similar structural motifs. IFNα has been described as being able to bind to multiple forms of CR2 from full length to SCR1-2, although to varying degrees (17). Though CR2 has been shown to be a receptor for IFNα, the IFNα binding site within CR2SCR1-2 is unknown.

Further analysis of CR2 interactions with known ligands to identify specific amino acid residues involved in binding to these ligands would enable the design of modified CR2 molecules with defined binding specificity for each known CR2 ligand (e.g., C3 proteolytic fragments iC3b, C3dg and C3d; EBV glycoprotein gp350; CD23; and IFNα.

BRIEF SUMMARY

Provided herein are compositions and methods directed to soluble proteins which can selectively deliver modulators of complement activity. Targeted delivery of these modulators is accomplished by selectively mutating particular amino acids in a targeting protein portion of the composition corresponding to at least the first two N-terminal SCR domains of CR2. Depending on the particular combination of mutations introduced into the targeting portion, a complement activity modulator can be selectively delivered to particular ligands of CR2 at sites where complement system activation or suppression is desired.

Accordingly, in one aspect, provided herein are soluble compositions comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least one amino acid substitution at an amino acid residue selected from the group consisting of: N11, R36, K41, Y64 and K67. In certain embodiments, the construct is a fusion protein.

In certain embodiments, the complement modulator portion comprises a complement inhibitor or biologically-active fragment thereof. In certain embodiments, the complement inhibitor or biologically active fragment thereof is selected from the group consisting of human membrane complement protein (MCP) (SEQ ID NO:10), human decay accelerating factor (DAF) (SEQ ID NO:11), mouse DAF (SEQ ID NO:12), mouse complement receptor 1-related gene/protein y (Crry) (SEQ ID NO:4), human CD59 (SEQ ID NO:3), mouse CD59 isoform A (SEQ ID NO:6), mouse CD59 isoform B (SEQ ID NO:7), human complement receptor 1 (CR1) (SEQ ID NO:9), human factor H (SEQ ID NO:5), and mouse factor H (SEQ ID NO:8).

In certain embodiments, the complement inhibitor comprises human membrane complement protein (MCP) (SEQ ID NO:10) or a biologically-active fragment thereof. In certain embodiments, the biologically active fragment of human MCP (SEQ ID NO:10) is selected from the group consisting of SCR1-4 (amino acids 35-285 of SEQ ID NO:10), SCR1-4 plus the serine/threonine-rich domain (amino acids 35-326 of SEQ ID NO:10), and the extracellular domain of MCP (amino acids 35-343 of SEQ ID NO:10). In certain embodiments, the complement inhibitor comprises human DAF (SEQ ID NO:11) or a biologically-active fragment thereof. In certain embodiments, the biologically active fragment of human DAF (SEQ ID NO:11) is selected from the group consisting of SCR1-4 (amino acids 25-285 of SEQ ID NO:11) and SCR1-4 plus the O-glycosylated serine/threonine-rich domain (amino acids 25-353 of SEQ ID NO:11). In certain embodiments, the complement inhibitor comprises mouse DAF (SEQ ID NO:12) or a biologically-active fragment thereof. In certain embodiments, the biologically active fragment of mouse DAF (SEQ ID NO:12) is selected from the group consisting of SCR1-4 (amino acids 35-286 of SEQ ID NO:12) and SCR1-4 plus the O-glycosylated serine/threonine-rich domain (amino acids 35-362 of SEQ ID NO:12). In certain embodiments, the complement inhibitor comprises Crry (SEQ ID NO:4) or a biologically-active fragment thereof. In certain embodiments, the biologically-active fragment of Crry (SEQ ID NO:4) is selected from the group consisting of SCR1-5 (amino acids 41-400 of SEQ ID NO:4) and the extracellular domain mouse Crry protein (amino acids 41-405 of SEQ ID NO:4). In certain embodiments, the complement inhibitor comprises human CD59 (SEQ ID NO:3) or a biologically-active fragment thereof. In certain embodiments, the biologically-active fragment of human CD59 (SEQ ID NO:3) comprises the extracellular domain of human CD59 lacking its GPI anchor (amino acids 26-101 of SEQ ID NO:3). In certain embodiments, the complement inhibitor comprises mouse CD59 isoform A (SEQ ID NO:6) or a biologically-active fragment thereof. In certain embodiments, the biologically-active fragment of mouse CD59 isoform A (SEQ ID NO:6) comprises the extracellular domain of mouse CD59, isoform A lacking its GPI anchor (amino acids 24-95 of SEQ ID NO:6). In certain embodiments, the complement inhibitor comprises mouse CD59 isoform B (SEQ ID NO:7) or a biologically-active fragment thereof. In certain embodiments, the biologically-active fragment of mouse CD59 isoform B (SEQ ID NO:7) comprises the extracellular domain of mouse CD59, isoform B lacking its GPI anchor (amino acids 24-103 of SEQ ID NO:7). In certain embodiments, the complement inhibitor comprises human CR1 (SEQ ID NO:9) or a biologically-active fragment thereof. In certain embodiments, the biologically-active fragment of human CR1 (SEQ ID NO:9) is selected from the group consisting of SCR1-3 (amino acids of 42-234 of SEQ ID NO:9), SCR1-4 (amino acids 42-295 of SEQ ID NO:9), SCR1-10 (amino acids 42-684 of SEQ ID NO:9), SCR8-10 (amino acids of 491-684 of SEQ ID NO:9), SCR 8-11 (amino acids 491-745 of SEQ ID NO:9), SCR15-17 (amino acids of 941-1134 of SEQ ID NO:9), SCR15-18 (amino acids 941-1195 of SEQ ID NO:9), and SCR22-28 (amino acids 1394-1842 of SEQ ID NO:9). In certain embodiments, the complement inhibitor comprises human factor H (SEQ ID NO:5) or a biologically-active fragment thereof. In certain embodiments, the biologically-active fragment of human factor H (SEQ ID NO:5) is selected from the group consisting of SCR1-4 (amino acids 21-262 of SEQ ID NO:5), SCR1-5 (amino acids 21-320 of SEQ ID NO:5), SCR1-8 (amino acids 21-507 of SEQ ID NO:5), and SCR1-18 (amino acids 21-1104 of SEQ ID NO:5). In certain embodiments, the complement inhibitor comprises mouse factor H (SEQ ID NO:8) or a biologically-active fragment thereof. In certain embodiments, the biologically-active fragment of mouse factor H (SEQ ID NO:8) is selected from the group consisting of SCR1-4 (amino acids 19-264 of SEQ ID NO:8), SCR1-5 (amino acids 19-322 of SEQ ID NO:8), SCR1-8 (amino acids 19-507 of SEQ ID NO:8), and SCR1-18 (amino acids 19-1109 of SEQ ID NO:8).

In certain embodiments, the complement modulator portion comprises a complement activator or biologically-active fragment thereof. In certain embodiments, the complement activator or biologically-active fragment thereof is selected from the group consisting of human IgG$_1$, human IgG$_1$ Fc domain, human IgM, human IgM Fc domain, mouse IgG$_3$, mouse IgG$_3$ Fc domain, mouse IgM, mouse IgM Fc domain, and cobra venom factor (CVF).

In certain embodiments, the construct exhibits decreased binding affinity for EBV-gp350 or IFNα compared to a construct in which the CR2 or biologically active fragment thereof does not contain any amino acid substitution. In certain embodiments, the construct exhibits decreased binding affinity for EBV-gp350 compared to a construct in which the CR2 or biologically active fragment thereof does not contain any amino acid substitution. In certain embodiments, the CR2 or biologically active fragment thereof contains at least one amino acid substitution of an amino acid residue selected from the group consisting of: N11, R36, K41, Y64 and K67. In certain embodiments, the construct exhibits decreased binding affinity for IFNα compared to a construct in which the CR2 or biologically active fragment thereof does not contain any amino acid substitution. In certain embodiments, the CR2 or fragment thereof contains at least one amino acid substitution to an amino acid residue selected from the group consisting of: S42 and K50.

In another aspect, provided herein are methods of reducing the binding affinity of a construct comprising: (a) a complement receptor 2 (CR2) portion comprising a CR2 protein of SEQ ID NO:1 or a biologically active fragment thereof, wherein the CR2 portion contains at least the first two N-terminal SCR domains of the CR2 portion; and (b) a complement modulator portion, for EBV-gp350, comprising mutating at least one amino acid residue selected from the group consisting of N11, R36, K41, Y64 and K67.

In another aspect, provided herein are methods of reducing the binding affinity of a construct comprising: (a) a complement receptor 2 (CR2) portion comprising a CR2 protein of SEQ ID NO:1 or a biologically active fragment thereof, wherein the CR2 portion contains at least the first two N-terminal SCR domains of the CR2 portion; and (b) a complement modulator portion, for IFNα, comprising mutating at least one amino acid residue selected from the group consisting of S42 and K50.

BRIEF DESCRIPTION OF THE DRAWINGS

FIG. 4A. NMR-determined gp350 binding residues. Gray residues represent residues unaffected by gp350 titration. The black residues on SCR1, the linker region and SCR2 represent residues involved in gp350 binding to CR2 SCR1-2. FIG. 4B. NMR determined IFNα binding residues. Gray residues represent residues unaffected by IFNα titration. The black residues on SCR1, the linker region and SCR2 represent residues involved in IFNα binding to CR2 SCR1-2. FIG. 4C. NMR determined ligand unique and shared binding residues. The black residues represent residues that are uniquely involved in CR2 binding to IFNα and gp350. The dark grey residues represent residues that are uniquely involved in CR2 binding to C3d. The light grey residues represent residues that are involved in all three CR2 ligand binding events.

BRIEF DESCRIPTION OF THE SEQUENCES

Figure 1:
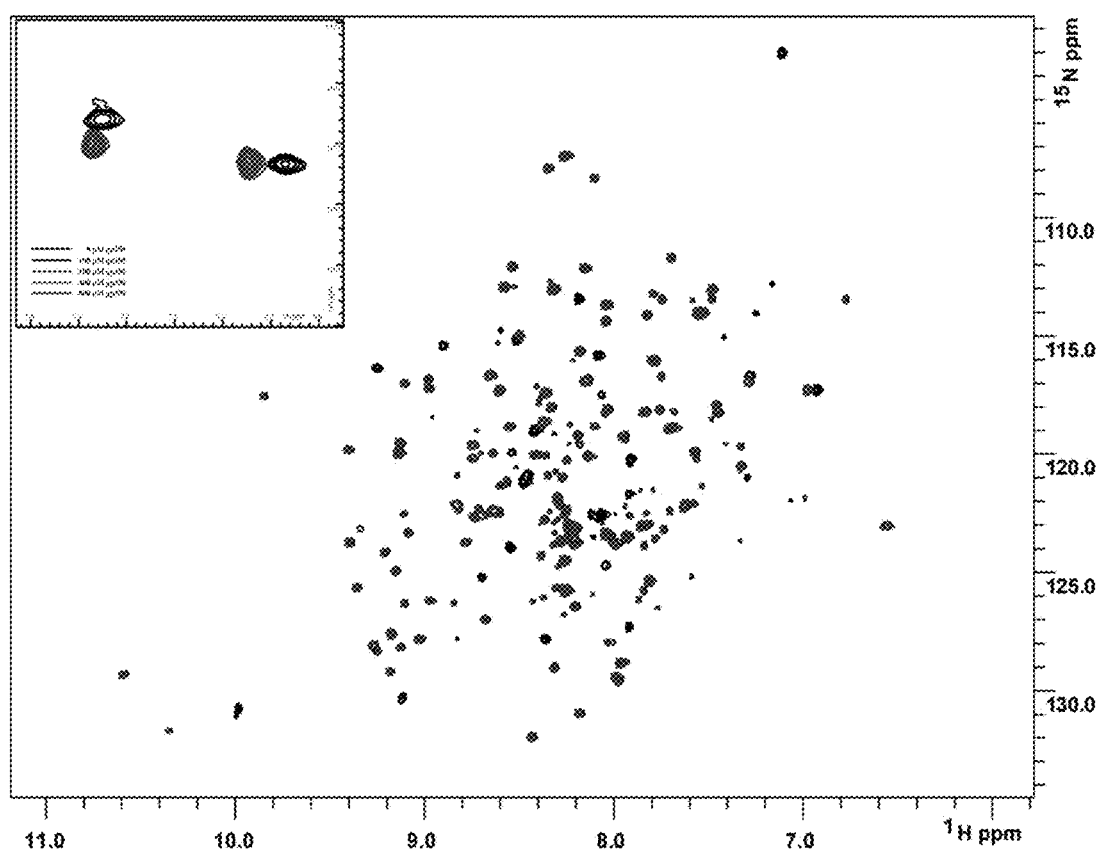
FIG. 1. NMR titration analysis reveals that SCR1 and SCR2 of CR2 are both involved in ligating gp350. Two superimposed ¹H-¹⁵N Transverse Relaxation Optimized Spectroscopy-Heteronuclear Single Quantum Coherence (TROSY-HSQC) spectra of ¹⁵N-labeled CR2SCR1-2 (0.6 mM in ⅓×PBS) collected during titration with increasing amounts of gp350. Black, no gp350 and grey, saturating amounts of gp350. Inset, detailed view of chemical shift change. The numbering scheme used here for CR2 is based on the amino acid sequence for the mature protein.

SEQ ID NO:1 is the complete amino acid sequence of human complement receptor 2 (CR2).

SEQ ID NO:2 is the complete amino acid sequence of short consensus repeat (SCR) domains 1 and 2 of human CR2.

SEQ ID NO:3 is the complete amino acid sequence of human CD59 protein.

SEQ ID NO:4 is the complete amino acid sequence of mouse complement receptor 1-related gene/protein y (Crry).

SEQ ID NO:5 is the complete amino acid sequence of human factor H.

SEQ ID NO:6 is the complete amino acid sequence of mouse CD59A protein.

SEQ ID NO:7 is the complete amino acid sequence of mouse CD59B protein.

SEQ ID NO:8 is the complete amino acid sequence of mouse factor H.

SEQ ID NO:9 is the complete amino acid sequence of human complement receptor 1 (CR1).

SEQ ID NO:10 is the complete amino acid sequence of human membrane cofactor protein (MCP).

SEQ ID NO:11 is the complete amino acid sequence of human decay accelerating factor (DAF/CD55).

SEQ ID NO:12 is the complete amino acid sequence of mouse decay accelerating factor (DAF/CD55).

SEQ ID NO:13 is the complete amino acid sequence of cobra venom factor (CVF) from the monocled cobra (*Naja kaouthia*).

SEQ ID NO:14 is the complete amino acid sequence of the human IgG₁ heavy chain, C domain.

SEQ ID NO:15 is the complete amino acid sequence of the human IgG₁ light chain, C domain.

SEQ ID NO:16 is the complete amino acid sequence of the Fc domain of human IgG₁.

SEQ ID NO:17 is the complete amino acid sequence of human IgM heavy chain, C domain.

SEQ ID NO:18 is the complete amino acid sequence of human IgM light chain, C domain.

SEQ ID NO:19 is the complete amino acid sequence of the Fc domain of human IgM.

SEQ ID NO:20 is the complete amino acid sequence of mouse IgG₃ heavy chain, C domain.

SEQ ID NO:21 is the complete amino acid sequence of mouse IgG₃ light chain, C domain.

SEQ ID NO:22 is the complete amino acid sequence of mouse IgG₃ Fc domain.

SEQ ID NO:23 is the complete amino acid sequence of mouse IgM heavy chain, C domain.

SEQ ID NO:24 is the complete amino acid sequence of mouse IgM light chain, C domain.

SEQ ID NO:25 is the complete amino acid sequence of mouse IgM Fc domain.

SEQ ID NO:26 is a linking sequence between the first two N-terminal SCRs of human CR2.

SEQ ID NO:27 is a linking sequences between the first two N-terminal SCRs of human CR2.

SEQ ID NO:28 is a linking sequence between the fourth and the fifth N-terminal short consensus repeat domains of human CR2.

DETAILED DESCRIPTION

Complement is an important component of immunity, but inappropriate and excessive activation of the complement system is involved in numerous pathological and inflammatory conditions. Complement activation products that mediate tissue injury are generated at various points in the complement pathway. Complement activation on cell surfaces results in the cleavage of serum complement component 3 (C3) and the covalent attachment of C3 fragments that serve as opsonins for immune effector cells to the cell surfaces. The resulting C3 fragments include C3a, a soluble peptide that is a potent anaphylatoxin, and C3b, a component of the alternative complement pathway C3 convertase. Later in the pathway, serum complement component 5 (C5) is cleaved to release soluble C5a, another potent anaphylatoxin and chemoattractant with a wide range of bioactive properties. Cleavage of C5 also initiates formation of the membrane attack complex (MAC), a cytolytic protein complex that assembles in cell membranes, ultimately resulting in lysis of opsonized cells.

Complement component 3 (C3) is a zymogen. Intact C3 circulates at high concentrations (1-2 mg/ml). M. Janzi et al., *Mol. Cell. Proteomics* (2005) 4(12):1942-1947. During complement activation, whole C3 is cleaved to form C3b, a component of the alternative complement pathway C3 convertase, which becomes covalently bound to target surfaces. Endogenous complement regulatory proteins inactivate tissue-bound C3b to form iC3b and eventually the 35 kilodalton ("kD") C3d fragment. The C3d fragment remains fixed to tissues and serves as a durable marker of complement-mediated inflammation. I. Leivo et al., *J. Cell. Biol.* (1986) 103:1091-1100.

Targeted delivery of complement inhibitors to sites of complement activation and disease can improve their efficacy. Since complement plays an important role in host defense and the shaping of immunity, as well as in immune homeostatic mechanisms such as immune complex catabolism and apoptotic cell clearance, targeted delivery of complement inhibitors reduces potentially serious side effects resulting from systemic complement inhibition, particularly long-term complement inhibition.

General Techniques

The practice of the present invention will employ, unless otherwise indicated, conventional techniques of molecular biology, microbiology, cell biology, biochemistry, and nucleic acid chemistry which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russell, 2001), (jointly referred to herein as "Sambrook"); *Current Protocols in Molecular Biology* (F. M. Ausubel et al., eds., 1987, including supplements through 2001); *PCR: The Polymerase Chain Reaction* (Mullis et al., eds., 1994); *Current Protocols in Nucleic Acid Chemistry* John Wiley & Sons, Inc., New York, 2000), *Handbook of Experimental Immunology*, 4th edition (D. M. Weir & C. C. Blackwell, eds., Blackwell Science Inc., 1987); and *Gene Transfer Vectors for Mammalian Cells* (J. M. Miller & M. P. Calos, eds., 1987).

Complement Receptor 2

Human complement receptor 2, also referred to as CD21 (CR2/CD21) (SEQ ID NO:1 and SEQ ID NO:2), is a ~145 kD transmembrane protein of the C3 binding protein family comprising 15 or 16 short consensus repeat (SCR) domains, structural units characteristic of such proteins. CR2 is expressed on mature B cells and follicular dendritic cells, and plays an important role in humoral immunity. J. Hannan et al., *Biochem. Soc. Trans.* (2002) 30:983-989; K. A. Young et al., *J. Biol. Chem.* (2007) 282(50):36614-36625. CR2 protein does not bind intact C3 protein, but binds its breakdown products, including the C3b, iC3b, and C3d cleavage fragments, via a binding site located within the first two amino-terminal short consensus repeats ("SCRs 1-2") of the CR2 protein. Consequently, the SCR1-2 domain of CR2 discriminates between cleaved (i.e., activated) forms of C3 and intact circulating C3. As a targeting group, SCRs 1-2 of CR2 are therefore able to discriminate between circulating C3 and the C3 fragments generated during complement activation. While the affinity of CR2 for C3d is only 620-658 nM (J. Hannan et al., *Biochem. Soc. Trans.* (2002) 30:983-989; J. M. Guthridge et al., *Biochem.* (2001) 40:5931-5941), the avidity of CR2 for clustered C3d makes it an effective method of targeting molecules to sites of complement activation.

Cleavage of C3 results initially in the generation and deposition of C3b on the activating cell surface. The C3b fragment is involved in the generation of enzymatic complexes that amplify the complement cascade. On a cell surface, C3b is rapidly converted to inactive iC3b, particularly when deposited on a host surface containing regulators of complement activation (i.e., most host tissue). Even in the absence of membrane-bound complement regulators, substantial levels of iC3b are formed because of the action of serum factor H and serum factor I. iC3b is subsequently digested to the membrane-bound fragments C3dg and then C3d by factor I and other proteases and cofactors, but this process is relatively slow. Thus, the C3 ligands for CR2 are relatively long lived once they are generated and are present in high concentrations at sites of complement activation.

DEFINITIONS

General reference to "the composition" or "compositions" includes and is applicable to compositions of the invention.

As used herein, the singular form of the articles "a," "an," and "the" includes plural references unless indicated otherwise. For example, the phrase "a biologically active CR2 fragment" includes one or more biologically active CR2 fragments.

Reference to "about" a value or parameter herein includes (and describes) embodiments that are directed to that value or parameter per se. For example, description referring to "about X" includes description of "X."

It is understood that aspects and embodiments of the invention described herein include consisting and/or consisting essentially of aspects and embodiments.

As used herein, the term "individual" refers to a vertebrate, preferably a mammal, more preferably a human. Mammals include, but are not limited to, research animals, domestic animals, farm animals, sport animals, pets, primates, mice and rats. In certain embodiments, the individual is human. In certain embodiments, the individual is an individual other than a human. In certain embodiments, the individual is an animal model for the study of a disease in which the alternative complement pathway is implicated.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Amino Acid Substitutions

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. Substitution of one amino acid residue for another from a different class or group is referred to herein as a "non-conservative" substitution. In contrast, non-conservative amino acid substitutions tend to disrupt conformation and function of a protein.

TABLE 3

| Example of amino acid classification | |
|---|---|
| Small/Aliphatic residues: | Gly, Ala, Val, Leu, Ile |
| Cyclic Imino Acid: | Pro |
| Hydroxyl-containing Residues: | Ser, Thr |
| Acidic Residues: | Asp, Glu |
| Amide Residues: | Asn, Gln |
| Basic Residues: | Lys, Arg |
| Imidazole Residue: | His |

TABLE 3-continued

Example of amino acid classification

| Aromatic Residues: | Phe, Tyr, Trp |
| Sulfur-containing Residues: | Met, Cys |

In certain embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., BIOCHEMISTRY at pp. 13-15, $2^{nd}$ ed. Lubert Stryer ed. (Stanford University); Henikoff et al., *Proc. Nat'l Acad. Sci. USA* (1992) 89:10915-10919; Lei et al., *J. Biol. Chem.* (1995) 270(20):11882-11886).

In certain embodiments, the non-conservative amino acid substitution comprises substituting any of glycine (G), alanine (A), isoleucine (I), valine (V), and leucine (L) for any of serine (S), threonine (T), aspartic acid (D), glutamic acid (E), glutamine (Q), asparagine (N), lysine (K), arginine (R), phenylalanine (F), tyrosine (Y), tryptophan (W), methionine (M), cysteine (C), histidine (H), and proline (P). In certain embodiments, the non-conservative amino acid substitution comprises substituting any of serine (S) and threonine (T) for any of glycine (G), alanine (A), isoleucine (I), valine (V), leucine (L), aspartic acid (D), glutamic acid (E), glutamine (Q), asparagine (N), lysine (K), arginine (R), phenylalanine (F), tyrosine (Y), tryptophan (W), methionine (M), cysteine (C), histidine (H) and proline (P). In certain embodiments, the non-conservative amino acid substitution comprises substituting any of aspartic acid (D) and glutamic acid (E) for any of glycine (G), alanine (A), isoleucine (I), valine (V), leucine (L), serine (S), threonine (T), glutamine (Q), asparagine (N), lysine (K), arginine (R), phenylalanine (F), tyrosine (Y), tryptophan (W), methionine (M), cysteine (C), histidine (H), and proline (P). In certain embodiments, the non-conservative amino acid substitution comprises substituting any of glutamine (Q) and asparagine (N) for any of glycine (G), alanine (A), isoleucine (I), valine (V), leucine (L), serine (S), threonine (T), aspartic acid (D), glutamic acid (E), lysine (K), arginine (R), phenylalanine (F), tyrosine (Y), tryptophan (W), methionine (M), cysteine (C), histidine (H), and proline (P). In certain embodiments, the non-conservative amino acid substitution comprises substituting any of lysine (K) and arginine (R) for any of glycine (G), alanine (A), isoleucine (I), valine (V), leucine (L), serine (S), threonine (T), aspartic acid (D), glutamic acid (E), glutamine (Q), asparagine (N), phenylalanine (F), tyrosine (Y), tryptophan (W), methionine (M), cysteine (C), histidine (H), and proline (P). In certain embodiments, the non-conservative amino acid substitution comprises substituting any of phenylalanine (F), tyrosine (Y), and tryptophan (W) for any of glycine (G), alanine (A), isoleucine (I), valine (V), leucine (L), serine (S), threonine (T), aspartic acid (D), glutamic acid (E), glutamine (Q), asparagine (N), lysine (K), arginine (R), methionine (M), cysteine (C), histidine (H), and proline (P). In certain embodiments, the non-conservative amino acid substitution comprises substituting any of methionine (M) and cysteine (C) for any of glycine (G), alanine (A), isoleucine (I), valine (V), leucine (L), serine (S), threonine (T), aspartic acid (D), glutamic acid (E), glutamine (Q), asparagine (N), lysine (K), arginine (R), phenylalanine (F), tyrosine (Y), tryptophan (W), histidine (H), and proline (P). In certain embodiments, the non-conservative amino acid substitution comprises substituting histidine (H) for any of glycine (G), alanine (A), isoleucine (I), valine (V), leucine (L), serine (S), threonine (T), aspartic acid (D), glutamic acid (E), glutamine (Q), asparagine (N), lysine (K), arginine (R), phenylalanine (F), tyrosine (Y), tryptophan (W), methionine (M), cysteine (C), and proline (P). In certain embodiments, the non-conservative amino acid substitution comprises substituting proline (P) for any of glycine (G), alanine (A), isoleucine (I), valine (V), leucine (L), serine (S), threonine (T), aspartic acid (D), glutamic acid (E), glutamine (Q), asparagine (N), lysine (K), arginine (R), phenylalanine (F), tyrosine (Y), tryptophan (W), methionine (M), cysteine (C), and histidine (H).

Modulators of Complement Activity

As used herein, the term "complement modulator" refers to a compound, composition, or protein that modulates (e.g., inhibits or activates) complement activity or a biologically active fragment thereof. A complement modulator can be a complement inhibitor or a complement activator.

As used herein, the term "complement inhibitor" refers to any compound, composition, or protein that reduces or eliminates complement activity or a biologically active fragment thereof. The reduction in complement activity may be incremental (e.g., a 10%, 20%, 30%, 40%, 50%, 60%, 70%, 80%, or 90% reduction in activity) or complete. A complement inhibitor may be a soluble or membrane-bound protein such as, for example, membrane cofactor protein (MCP), decay accelerating factor (DAF/CD55), CD59, mouse complement receptor 1-related gene/protein y (Crry), human complement receptor 1 (CR1) and factor H, or an antibody specific for a component of a complement pathway such as, for example, eculizumab (an anti-C5 antibody marketed under the trade name Soliris®), pexelizumab (a single-chain antibody (scFv) comprising the antigen-binding fragment of eculizumab), an anti-factor B antibody (such as the monoclonal antibody 1379 produced by ATCC Deposit No. PTA-6230), an anti-properdin antibody, an anti-factor D antibody, and the like. Alternatively, a complement inhibitor may be a small molecule or a linear or cyclic peptide such as, for example, compstatin, N-acetylaspartylglutamic acid (NAAGA), and the like.

As used herein the term "complement activator" refers to any compound, composition, or protein that increases or activates complement activity or a biologically active fragment thereof. The increase in complement activity may be incremental (e.g., a 10%, 20%, 30%, 40%, 50%, 60%, 70%, 80%, or 90% increase in activity). A complement activator may be a soluble or membrane-bound protein such as, for example, human Ig isotype $G_1$ (Ig$G_1$), human Ig isotype M (IgM), mouse Ig isotype $G_3$ (Ig$G_3$), and mouse IgM Fc, as well as cobra venom factor (CVF) and biologically-active fragments thereof, such as the Fc domain of Ig proteins, such as human IgG$_1$ Fc domain, human IgM Fc domain, mouse IgG$_3$ Fc domain, and mouse IgM Fc domain. Complement activators may also include, for example, hybrid CVF molecules comprising a CVF portion and a complement component 3 (C3) portion, such as those described in Fritzinger et al., "Functional characterization of human C3/cobra venom factor hybrid proteins for therapeutic complement depletion," *Develop. Comp. Immunol.* 33(1):105-116 (2009). Those hybrids comprise proteins in which the 113 or 315 C-terminal residues of C3 were replaced with corresponding CVF sequences.

Complement Inhibitor Proteins

Provided herein are soluble compositions comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement inhibitor portion; wherein the CR2 portion contains at least one amino acid substitution. In certain embodiments, the construct is a fusion protein. A number of endogenous soluble and membrane-bound proteins that inhibit complement have been identified. These complement inhibitor proteins include, but are not limited to, membrane cofactor protein (MCP), decay accelerating factor (DAF/CD55), CD59, mouse complement receptor 1-related gene/protein y (Crry), human complement receptor 1 (CR1) and factor H. In certain embodiments, the complement modulator portion of the construct comprises a complement inhibitor or biologically active fragment thereof. In certain embodiments, the complement inhibitor is selected from the group consisting of human MCP, human DAF, mouse DAF, human CD59, mouse CD59 isoform A, mouse CD59 isoform B, mouse Crry protein, human CR1, human factor H, or mouse factor H, or a biologically active fragment thereof.

Membrane Cofactor Protein (MCP)

As used herein, the term "membrane cofactor protein," "MCP," or "CD46" refers to a widely distributed C3b/C4b-binding cell surface glycoprotein which inhibits complement activation on host cells and serves as a cofactor for the factor I-mediated cleavage of C3b and C4b, including homologs thereof. T. J. Oglesby et al., *J. Exp. Med.* (1992) 175:1547-1551. MCP belongs to a family known as the regulators of complement activation ("RCA"). Family members share certain structural features, comprising varying numbers of short consensus repeat (SCR) domains, which are typically between 60 and 70 amino acids in length. Beginning at its amino-terminus, MCP comprises four SCRs, a serine/threonine/proline-enriched region, an area of undefined function, a transmembrane hydrophobic domain, a cytoplasmic anchor and a cytoplasmic tail. It is understood that species and strain variations exist for the disclosed peptides, polypeptides, and proteins, and that human MCP or biologically active fragments thereof encompasses all species and strain variations.

SEQ ID NO:10 represents the full-length human MCP amino acid sequence (see, e.g., UniProtKB/Swiss-Prot. Accession No. P15529). Amino acids 1-34 correspond to the signal peptide, amino acids 35-343 correspond to the extracellular domain, amino acids 344-366 correspond to the transmembrane domain, and amino acids 367-392 correspond to the cytoplasmic domain. In the extracellular domain, amino acids 35-96 correspond to SCR 1, amino acids 97-159 correspond to SCR 2, amino acids 160-225 correspond to SCR 3, amino acids 226-285 correspond to SCR 4, and amino acids 302-326 correspond to the serine/threonine-rich domain. It is understood that species and strain variations exist for the disclosed peptides, polypeptides, and proteins, and that MCP or biologically active fragments thereof encompasses all species and strain variations. As used herein, the term "biologically active" fragment of MCP refers to any soluble fragment lacking both the cytoplasmic domain and the transmembrane domain, including fragments comprising, consisting essentially of or consisting of 1, 2, 3, or 4 SCR domains, with or without the serine/threonine-rich domain, having some or all the complement inhibitory activity of the full-length human MCP protein. In certain embodiments, the complement inhibitor portion comprises full-length human MCP (amino acids 35-392 of SEQ ID NO:10), the extracellular domain of human MCP (amino acids 35-343 of SEQ ID NO:10), or SCRs 1-4 of human MCP (amino acids 35-285 of SEQ ID NO:10).

In one aspect, there is provided a soluble composition comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) MCP; wherein the CR2 portion contains at least one amino acid substitution. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds EBV gp350. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds IFNα. In some embodiments, the CR2 portion selectively binds IFNα. In some embodiments, the CR2 portion selectively binds IFNα and also selectively binds EBV gp350. In some embodiments, the CR2 portion selectively binds EBV gp350. As used herein, "selectively binds" means that a construct exhibits enhanced binding to one ligand and/or decreased binding to a different ligand. For example, "selectively binds" can mean: 1) that a construct which has been altered has a binding affinity for a first ligand that is similar to the binding affinity of the unaltered construct for the first ligand whereas the construct that has been altered has a lower affinity for a second ligand than does the unaltered construct, and therefore the altered construct "selectively binds" the first ligand as compared to the binding of the unaltered construct to the two ligands; 2) that a construct which has been altered has increased binding to a first ligand as compared to the binding of the unaltered construct to the first ligand while retaining binding to a second ligand that is similar to the binding of the unaltered construct to the second ligand, and therefore the construct "selectively binds" the first ligand as compared to the binding of the unaltered construct to the two ligands; or 3) that a construct which has been altered has increased binding to a first ligand as compared to the binding of the unaltered construct to the first ligand and also has a lower binding affinity for a second ligand as compared to the binding of the unaltered construct to the second ligand, and therefore the altered construct "selectively binds" the first ligand and not the second ligand as compared to the binding of the unaltered construct to the two ligands. In certain embodiments, the construct is a fusion protein. In certain embodiments, the complement inhibitor portion of the construct comprises full-length human MCP (SEQ ID NO:10). In certain embodiments, the complement inhibitor portion of the construct comprises a biologically active fragment of human MCP (SEQ ID NO:10). In certain embodiments, the biologically active fragment of human MCP is selected from the group consisting of SCR1-4 (amino acids 35-285 of SEQ ID NO:10), SCR1-4 plus the serine/threonine-rich domain (amino acids 35-326 of SEQ ID NO:10), and the extracellular domain of MCP (amino acids 35-343 of SEQ ID NO:10).

Decay Accelerating Factor (DAF)

Decay accelerating factor, also referred to as CD55 (DAF/CD55) (SEQ ID NO:11 and SEQ ID NO:12), is a ~70 kiloDalton (kDa) membrane-bound glycoprotein which inhibits complement activation on host cells Like several other complement regulatory proteins, DAF comprises several approximately 60 amino acid repeating motifs termed short consensus repeats (SCR).

As used herein, the term "decay accelerating factor," "DAF," or "CD55" refers to a seventy kilodalton ("kD") membrane glycoprotein comprising four short consensus repeat (SCR) domains followed by a heavily O-glycosylated serine/threonine-rich domain at the C-terminus that elevates the molecule from the membrane surface, followed by a glycosylphosphatidylinositol ("GPI") anchor. DAF protects the cell surface from complement activation by dissociating membrane-bound C3 convertases that are required to cleave complement protein C3 and to amplify the complement cascade. DAF prevents assembly or accelerates decay of both the C3- and C5-convertases of the alternative and classical complement pathways.

SEQ ID NO:11 represents the full-length human DAF amino acid sequence (see, e.g., UniProtKB/Swiss-Prot. Accession No. P08173); SEQ ID NO:12 represents the full-length mouse DAF amino acid sequence (see, e.g., UniProtKB/Swiss-Prot. Accession No. Q61475). In the human DAF sequence, amino acids 1-34 correspond to the signal peptide, amino acids 35-353 appear in the mature protein, and amino acids 354-381 are removed from the polypeptide after translation. Within the mature protein, amino acids 35-96 correspond to SCR 1, amino acids 96-160 correspond to SCR 2, amino acids 161-222 correspond to SCR 3, amino acids 223-285 correspond to SCR 4, and amino acids 287-353 correspond to the O-glycosylated serine/threonine-rich domain. The GPI anchor is attached to human DAF at a serine at position 353. In the mouse DAF sequence, amino acids 1-34 correspond to the signal peptide, amino acids 35-362 appear in the mature protein, and amino acids 363-390 are removed from the polypeptide after translation. Within the mature protein, amino acids 35-96 correspond to SCR 1, amino acids 97-160 correspond to SCR 2, amino acids 161-222 correspond to SCR 3, amino acids 223-286 correspond to SCR 4, and amino acids 288-362 correspond to the O-glycosylated serine/threonine-rich domain. The GPI anchor is attached to mouse DAF at a serine at position 362. It is understood that species and strain variations exist for the disclosed peptides, polypeptides, and proteins, and that DAF or biologically active fragments thereof encompasses all species and strain variations. As used herein, the term "biologically active" fragment of DAF refers to any fragment of DAF lacking a GPI anchor and/or the amino acid to which it is attached (i.e., Ser-353), including any fragments of the full-length DAF protein comprising, consisting essentially of or consisting of 1, 2, 3, or 4 SCR domains, with or without the O-glycosylated serine/threonine-rich domain, having some or all the complement inhibitory activity of the full-length DAF protein.

In one aspect, there is provided a soluble composition comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) DAF; wherein the CR2 portion contains at least one amino acid substitution. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds EBV gp350. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds IFNα. In some embodiments, the CR2 portion selectively binds IFNα. In some embodiments, the CR2 portion selectively binds IFNα and also selectively binds EBV gp350. In some embodiments, the CR2 portion selectively binds EBV gp350. As used herein, "selectively binds" means that a construct exhibits enhanced binding to one ligand and/or decreased binding to a different ligand. For example, "selectively binds" can mean: 1) that a construct which has been altered has a binding affinity for a first ligand that is similar to the binding affinity of the unaltered construct for the first ligand whereas the construct that has been altered has a lower affinity for a second ligand than does the unaltered construct, and therefore the altered construct "selectively binds" the first ligand as compared to the binding of the unaltered construct to the two ligands; 2) that a construct which has been altered has increased binding to a first ligand as compared to the binding of the unaltered construct to the first ligand while retaining binding to a second ligand that is similar to the binding of the unaltered construct to the second ligand, and therefore the construct "selectively binds" the first ligand as compared to the binding of the unaltered construct to the two ligands; or 3) that a construct which has been altered has increased binding to a first ligand as compared to the binding of the unaltered construct to the first ligand and also has a lower binding affinity for a second ligand as compared to the binding of the unaltered construct to the second ligand, and therefore the altered construct "selectively binds" the first ligand and not the second ligand as compared to the binding of the unaltered construct to the two ligands. In certain embodiments, the construct is a fusion protein. In certain embodiments, the complement inhibitor portion of the construct comprises full-length human DAF. In certain embodiments, the complement inhibitor portion of the construct comprises a biologically active fragment of human DAF (SEQ ID NO:11). In certain embodiments, the biologically active fragment of human DAF is selected from the group consisting of SCR1-4 (amino acids 25-285 of SEQ ID NO:11) and SCR1-4 plus the O-glycosylated serine/threonine-rich domain (amino acids 25-353 of SEQ ID NO:11). In certain embodiments, the complement inhibitor portion of the construct comprises full-length mouse DAF (SEQ ID NO:12). In certain embodiments, the complement inhibitor portion of the construct comprises a biologically active fragment of mouse DAF. In certain embodiments, the biologically active fragment of mouse DAF is selected from the group consisting of SCR1-4 (amino acids 35-286 of SEQ ID NO:12) and SCR1-4 plus the O-glycosylated serine/threonine-rich domain (amino acids 35-362 of SEQ ID NO:12).

CD59

As used herein, the term "CD59" refers to a membrane-bound 128 amino acid glycoprotein that potently inhibits the membrane attack complex (MAC) of complement. CD59 acts by binding to the C8 and/or C9 components of the MAC during assembly, ultimately preventing incorporation of the multiple copies of C9 required for complete formation of the osmolytic pore at the heart of the MAC. CD59 is both N- and O-glycosylated. The N-glycosylation comprises primarily of bi- or tri-antennary structures with and without lactosamine and outer arm fucose residues, with variable sialylation present at some sites. Like DAF, CD59 is anchored in the cell membrane by a glycosylphosphatidylinositol ("GPI") anchor, which is attached to an asparagine at amino acid 102. Soluble forms of CD59 (sCD59) have been produced, but they generally have low functional activity in vitro, particularly in the presence of serum, suggesting that unmodified sCD59 has little or no therapeutic efficacy. See, e.g., S. Meri et al., "Structural composition and functional characterization of soluble CD59: heterogeneity of the oligosaccharide and glycophosphoinositol (GPI) anchor revealed by laser-desorption mass spectrometric analysis," *Biochem. J.* 316: 923-935 (1996).

SEQ ID NO:3 represents the full-length human CD59 amino acid sequence (see, e.g., UniProtKB/Swiss-Prot. Accession No. P13987); SEQ ID NO:6 represents the full-length mouse CD59 sequence, isoform A (see, e.g., UniProtKB/Swiss-Prot. Accession No. O55186); SEQ ID NO:7 represents the full-length mouse CD59 sequence, isoform B (see, e.g., UniProtKB/Swiss-Prot. Accession No. P58019). In the human CD59 sequence, amino acids 1-25 of SEQ ID NO:3 correspond to the leader peptide, amino acids 26-102 of SEQ ID NO:3 correspond to the mature protein, and amino acids 103-128 of SEQ ID NO:3 are removed after translation. The GPI anchor is attached to CD59 at an asparagine at position 102 of SEQ ID NO:3. In isoform A of the mouse CD59 sequence, amino acids 1-23 of SEQ ID NO:6 correspond to the leader peptide, amino acids 24-96 of SEQ ID NO:6 correspond to the mature protein, and amino acids 97-123 of SEQ ID NO:6 are removed after translation. The GPI anchor is attached to CD59 at a serine at position 96 of SEQ ID NO:6. In isoform B of the mouse CD59 sequence, amino acids 1-23 of SEQ ID NO:7 correspond to the leader peptide, amino acids 24-104 of SEQ ID NO:7 correspond to the mature protein, and amino acids 105-129 of SEQ ID NO:7 are removed after translation. The GPI anchor is attached to CD59 at an asparagine at position 104 of SEQ ID NO:7. It is understood that species and strain variations exist for the disclosed peptides, polypeptides, and proteins, and that CD59 or biologically active fragments thereof encompasses all species and strain variations.

As used herein, the term "biologically active" fragment of human CD59 refers to any fragment of human CD59 lacking a GPI anchor and/or the amino acid to which it is attached (i.e., Asn-102), including any fragments of the full-length human CD59 protein having some or all the complement inhibitory activity of the full-length CD59 protein; and the term "biologically active" fragment of mouse CD59 refers to any fragment of mouse CD59 isoform A or isoform B lacking a GPI anchor and/or the amino acid to which it is attached (i.e., Ser-96 of isoform A, or Asp-104 of isoform B), including any fragments of either full-length mouse CD59 protein isoform having some or all the complement inhibitory activity of the full-length CD59 protein.

In one aspect, there is provided a soluble composition comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) CD59; wherein the CR2 portion contains at least one amino acid substitution. In certain embodiments, the construct is a fusion protein. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds EBV gp350. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds IFNα. In some embodiments, the CR2 portion selectively binds IFNα. In some embodiments, the CR2 portion selectively binds IFNα and also selectively binds EBV gp350. In some embodiments, the CR2 portion selectively binds EBV gp350. As used herein, "selectively binds" means that a construct exhibits enhanced binding to one ligand and/or decreased binding to a different ligand. For example, "selectively binds" can mean: 1) that a construct which has been altered has a binding affinity for a first ligand that is similar to the binding affinity of the unaltered construct for the first ligand whereas the construct that has been altered has a lower affinity for a second ligand than does the unaltered construct, and therefore the altered construct "selectively binds" the first ligand as compared to the binding of the unaltered construct to the two ligands; 2) that a construct which has been altered has increased binding to a first ligand as compared to the binding of the unaltered construct to the first ligand while retaining binding to a second ligand that is similar to the binding of the unaltered construct to the second ligand, and therefore the construct "selectively binds" the first ligand as compared to the binding of the unaltered construct to the two ligands; or 3) that a construct which has been altered has increased binding to a first ligand as compared to the binding of the unaltered construct to the first ligand and also has a lower binding affinity for a second ligand as compared to the binding of the unaltered construct to the second ligand, and therefore the altered construct "selectively binds" the first ligand and not the second ligand as compared to the binding of the unaltered construct to the two ligands. In certain embodiments, the complement inhibitor portion of the construct comprises full-length human CD59 (SEQ ID NO:3). In certain embodiments, the complement inhibitor portion of the construct comprises a biologically active fragment of human CD59 (SEQ ID NO:3). In certain embodiments, the biologically active fragment of human CD59 comprises the extracellular domain of human CD59 lacking its GPI anchor (amino acids 26-101 of SEQ ID NO:3). In certain embodiments, the complement inhibitor portion of the construct comprises full-length mouse CD59, isoform A (SEQ ID NO:6). In certain embodiments, the complement inhibitor portion of the construct comprises a biologically active fragment of mouse CD59, isoform A (SEQ ID NO:6). In certain embodiments, the biologically active fragment of mouse CD59, isoform A comprises the extracellular domain of mouse CD59, isoform A lacking its GPI anchor (amino acids 24-95 of SEQ ID NO:6). In certain embodiments, the complement inhibitor portion of the construct comprises full-length mouse CD59, isoform B (SEQ ID NO:7). In certain embodiments, the complement inhibitor portion of the construct comprises a biologically active fragment of mouse CD59, isoform B (SEQ ID NO:7). In certain embodiments, the biologically active fragment of mouse CD59, isoform B comprises the extracellular domain of mouse CD59, isoform B lacking its GPI anchor (amino acids 24-103 of SEQ ID NO:7).

Mouse Complement Receptor 1-Related Gene/Protein y (Crry)

As used herein, the term "mouse complement receptor 1-related gene/protein y" or "Crry" refers to a membrane-bound mouse glycoprotein that regulates complement activation, including homologs thereof. Crry regulates complement activation by serving as a cofactor for complement factor I, a serine protease which cleaves C3b and C4b deposited on host tissue. Crry also acts as a decay-accelerating factor, preventing the formation of C4b2a and C3bBb, the amplification convertases of the complement cascade.

SEQ ID NO:4 represents the full-length mouse Crry protein amino acid sequence. Amino acids 1-40 correspond to the leader peptide, amino acids 41-483 of SEQ ID NO:4 correspond to the mature protein, comprising amino acids 41-405 of SEQ ID NO:4, corresponding to the extracellular domain, amino acids 406-426 of SEQ ID NO:4, corresponding to the transmembrane domain, and amino acids 427-483 of SEQ ID NO:4, corresponding to the cytoplasmic domain. In the extracellular domain, amino acids 83-143 of SEQ ID NO:4 correspond to SCR 1, amino acids 144-205 of SEQ ID NO:4 correspond to SCR2, amino acids 206-276 of SEQ ID NO:4 correspond to SCR3, amino acids 277-338 of SEQ ID NO:4 correspond to SCR4, and amino acids 339-400 of SEQ ID NO:4 correspond to SCR5. It is understood that species and strain variations exist for the disclosed peptides, polypeptides, and proteins, and that mouse Crry protein or biologically active fragments thereof encompasses all species and strain variations. As used herein, the term "biologically active" fragment of mouse Crry protein refers to refers to any soluble fragment of mouse Crry lacking the transmembrane domain and the cytoplasmic domain, including fragments comprising, consisting essentially of or consisting of 1, 2, 3, 4, or 5 SCR domains, including any fragments of the full-length mouse Crry protein having some or all the complement inhibitory activity of the full-length Crry protein.

In one aspect, there is provided a soluble composition comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) Crry; wherein the CR2 portion contains at least one amino acid substitution. In certain embodiments, the construct is a fusion protein. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds EBV gp350. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds IFNα. In some embodiments, the CR2 portion selectively binds IFNα. In some embodiments, the CR2 portion selectively binds IFNα and also selectively binds EBV gp350. In some embodiments, the CR2 portion selectively binds EBV gp350. As used herein, "selectively binds" means that a construct exhibits enhanced binding to one ligand and/or decreased binding to a different ligand. For example, "selectively binds" can mean: 1) that a construct which has been altered has a binding affinity for a first ligand that is similar to the binding affinity of the unaltered construct for the first ligand whereas the construct that has been altered has a lower affinity for a second ligand than does the unaltered construct, and therefore the altered construct "selectively binds" the first ligand as compared to the binding of the unaltered construct to the two ligands; 2) that a construct which has been altered has increased binding to a first ligand as compared to the binding of the unaltered construct to the first ligand while retaining binding to a second ligand that is similar to the binding of the unaltered construct to the second ligand, and therefore the construct "selectively binds" the first ligand as compared to the binding of the unaltered construct to the two ligands; or 3) that a construct which has been altered has increased binding to a first ligand as compared to the binding of the unaltered construct to the first ligand and also has a lower binding affinity for a second ligand as compared to the binding of the unaltered construct to the second ligand, and therefore the altered construct "selectively binds" the first ligand and not the second ligand as compared to the binding of the unaltered construct to the two ligands. In certain embodiments, the complement inhibitor portion of the construct comprises full-length mouse Crry protein (SEQ ID NO:4). In certain embodiments, the complement inhibitor portion of the construct comprises a biologically active fragment of mouse Crry protein (SEQ ID NO:4). In certain embodiments, the biologically active fragment of mouse Crry protein is selected from the group consisting of SCR1-5 (amino acids 41-400 of SEQ ID NO:4) and the extracellular domain of mouse Crry protein (amino acids 41-405 of SEQ ID NO:4).

Complement Receptor 1 (CR1)

As used herein, the term "complement receptor 1," "CR1," or "CD35" refers to a human gene encoding a protein of 2039 amino acids, with a predicted molecular weight of 220 kilodaltons ("kD"), including homologs thereof. The gene is expressed principally on erythrocytes, monocytes, neutrophils, and B cells, but is also present on some T lymphocytes, mast cells, and glomerular podocytes. CR1 protein is typically expressed at between 100 and 1000 copies per cell. CR1 is the main system for processing and clearance of complement-opsonized immune complexes. CR1 negatively regulates the complement cascade, mediates immune adherence and phagocytosis, and inhibits both the classic and alternative complement pathways. The full-length CR1 protein comprises a 42 amino acid signal peptide, an extracellular domain of 1930 amino acids, a 25 amino acid transmembrane domain, and a 43 amino acid C-terminal cytoplasmic domain. The extracellular domain of CR1 has 25 potential N-glycosylation signal sequences, and comprises 30 short consensus ("SCR") domains, also known as complement control protein (CCP) repeats, or sushi domains, each 60 to 70 amino acids long. The sequence homology between SCRs ranges between 60-99 percent.

The 30 SCR domains are further grouped into four longer regions termed long homologous repeats ("LHRs"), each encoding approximately 45 kD segments of the CR1 protein, designated LHR-A, -B, -C, and -D. The first three comprise seven SCR domains each, while LHR-D comprises 9 SCR domains. The active sites on the extracellular domain of CR1 protein include a C4b-binding site with lower affinity for C3b in SCRs 1-4 comprising amino acids 42-295, a C3b-binding site with lower affinity for C4b in SCRs 8-11 comprising amino acids 490-745, a C3b-binding site with lower affinity for C4b in SCRs 15-18 comprising amino acids 940-1196, and a C1q-binding site in SCRs 22-28 comprising amino acids 1394-1842.

SEQ ID NO:9 represents the full-length human CR1 amino acid sequence (see, e.g., UniProtKB/Swiss-Prot. Accession No. P17927). Amino acids 1-41 correspond to the signal peptide, amino acids 42-2039 correspond to the mature protein, comprising amino acids 42-1971, corresponding to the extracellular domain, amino acids 1972-1996, corresponding to the transmembrane domain, and amino acids 1997-2039, corresponding to the cytoplasmic domain. In the extracellular domain, amino acids 42-101 correspond to SCR 1, 102-163 correspond to SCR2, amino acids 164-234 correspond to SCR3, amino acids 236-295 correspond to SCR4, amino acids 295-355 correspond to SCR5, amino acids 356-418 correspond to SCR6, amino acids 419-489 correspond to SCR7, amino acids 491-551 correspond to SCR8, amino acids 552-613 correspond to SCR9, amino acids 614-684 correspond to SCR10, amino acids 686-745 correspond to SCR11, amino acids 745-805 correspond to SCR12, amino acids 806-868 correspond to SCR13, amino acids 869-939 correspond to SCR14, amino acids 941-1001 correspond to SCR15, amino acids 1002-1063 correspond to SCR16, amino acids 1064-1134 correspond to SCR17, amino acids 1136-1195 correspond to SCR18, amino acids 1195-1255 correspond to SCR 19, amino acids 1256-1318 correspond to SCR 20, amino acids 1319-1389 correspond to SCR 21, amino acids 1394-1454 correspond to SCR 22, amino acids 1455-1516 correspond to SCR 23, amino acids 1517-1587 correspond to SCR 24, amino acids 1589-1648 correspond to SCR 25, amino acids 1648-1708 correspond to SCR 26, amino acids 1709-1771 correspond to SCR 27, amino acids 1772-1842 correspond to SCR 28, amino acids 1846-1906 correspond to SCR 29, amino acids 1907-1967 correspond to SCR 30. It is understood that species and strain variations exist for the disclosed peptides, polypeptides, and proteins, and that CR1 protein or biologically active fragments thereof encompasses all species and strain variations. As used herein, the term "biologically active" fragment of CR1 protein refers to refers to any soluble fragment of CR1 lacking the transmembrane domain and the cytoplasmic domain, including fragments comprising, consisting essentially of or consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 SCR domains, including any fragments of the full-length CR1 protein having some or all the complement inhibitory activity of the full-length CR1 protein.

In one aspect, there is provided a soluble composition comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) CR1; wherein the CR2 portion contains at least one amino acid substitution. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds EBV gp350. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds IFNα. In some embodiments, the CR2 portion selectively binds IFNα. In some embodiments, the CR2 portion selectively binds IFNα and also selectively binds EBV gp350. In some embodiments, the CR2 portion selectively binds EBV gp350. As used herein, "selectively binds" means that a construct exhibits enhanced binding to one ligand and/or decreased binding to a different ligand. For example, "selectively binds" can mean: 1) that a construct which has been altered has a binding affinity for a first ligand that is similar to the binding affinity of the unaltered construct for the first ligand whereas the construct that has been altered has a lower affinity for a second ligand than does the unaltered construct, and therefore the altered construct "selectively binds" the first ligand as compared to the binding of the unaltered construct to the two ligands; 2) that a construct which has been altered has increased binding to a first ligand as compared to the binding of the unaltered construct to the first ligand while retaining binding to a second ligand that is similar to the binding of the unaltered construct to the second ligand, and therefore the construct "selectively binds" the first ligand as compared to the binding of the unaltered construct to the two ligands; or 3) that a construct which has been altered has increased binding to a first ligand as compared to the binding of the unaltered construct to the first ligand and also has a lower binding affinity for a second ligand as compared to the binding of the unaltered construct to the second ligand, and therefore the altered construct "selectively binds" the first ligand and not the second ligand as compared to the binding of the unaltered construct to the two ligands. In certain embodiments, the construct is a fusion protein. In certain embodiments, the complement inhibitor portion of the construct comprises full-length human CR1 protein (SEQ ID NO:9). In certain embodiments, the complement inhibitor portion of the construct comprises a biologically active fragment of human CR1 protein (SEQ ID NO:9). In certain embodiments, the biologically active fragment of human CR1 protein is selected from the group consisting of SCR1-3 (amino acids of 42-234 of SEQ ID NO:9), SCR1-4 (amino acids 42-295 of SEQ ID NO:9), SCR1-10 (amino acids 42-684 of SEQ ID NO:9), SCR8-10 (amino acids of 491-684 of SEQ ID NO:9), SCR 8-11 (amino acids 491-745 of SEQ ID NO:9), SCR15-17 (amino acids of 941-1134 of SEQ ID NO:9), SCR15-18 (amino acids 941-1195 of SEQ ID NO:9), and SCR22-28 (amino acids 1394-1842 of SEQ ID NO:9).

Factor H (FH)

As used herein, the term "complement factor H," "factor H," or "FH" refers to complement factor H, a single polypeptide chain plasma glycoprotein, including homologs thereof. The protein is composed of 20 conserved short consensus repeat (SCR) domains of approximately 60 amino acids, arranged in a continuous fashion like a string of beads, separated by short linker sequences of 2-6 amino acids each. Factor H binds to C3b, accelerates the decay of the alternative pathway C3-convertase (C3bBb), and acts as a cofactor for the proteolytic inactivation of C3b. In the presence of factor H, proteolysis by factor I results in the cleavage and inactivation of C3b. Factor H has at least three distinct binding domains for C3b, which are located within SCRs 1-4, SCRs 5-8, and SCRs 19-20. Each site of factor H binds to a distinct region within the C3b protein: the N-terminal sites bind to native C3b; the second site, located in the middle region of factor H, binds to the C3c fragment and the site located within SCR19 and 20 binds to the C3d region. In addition, factor H also contains binding sites for heparin, which are located within SCR 7, SCRs 5-12, and SCR 20 of factor H and overlap with those of the C3b binding sites. Structural and functional analyses have shown that the domains for the complement inhibitory activity of factor H are located within the first four N-terminal SCR domains.

SEQ ID NO:5 represents the full-length human factor H amino acid sequence (see, e.g., UniProtKB/Swiss-Prot. Accession No. P08603); SEQ ID NO:8 represents the full-length mouse factor H amino acid sequence (see, e.g., UniProtKB/Swiss-Prot. Accession No. P06909). In the human factor H sequence, amino acids 1-18 of SEQ ID NO:5 correspond to the signal peptide, and amino acids 19-1231 of SEQ ID NO:5 correspond to the mature protein. Within that protein, amino acids 21-80 of SEQ ID NO:5 correspond to SCR 1, amino acids 85-141 of SEQ ID NO:5 correspond to SCR 2, amino acids 146-205 of SEQ ID NO:5 correspond to SCR 3, amino acids 210-262 of SEQ ID NO:5 correspond to SCR 4, and amino acids 267-320 of SEQ ID NO:5 correspond to SCR 5. In the mouse factor H sequence, amino acids 1-18 of SEQ ID NO:8 correspond to the signal peptide, and amino acids 19-1234 of SEQ ID NO:8 correspond to the mature protein. Within that protein, amino acids 19-82 of SEQ ID NO:8 correspond to SCR 1, amino acids 83-143 of SEQ ID NO:8 correspond to SCR 2, amino acids 144-207 of SEQ ID NO:8 correspond to SCR 3, amino acids 208-264 of SEQ ID NO:8 correspond to SCR 4, and amino acids 265-322 of SEQ ID NO:8 correspond to SCR 5. It is understood that species and strain variations exist for the disclosed peptides, polypeptides, and proteins, and that factor H or biologically active fragments thereof encompasses all species and strain variations.

As used herein, the term "biologically active" fragment of factor H refers to any portion of a factor H protein having some or all the complement inhibitory activity of the full-length factor H protein, and includes, but is not limited to, factor H fragments comprising SCRs 1-4, SCRs 1-5, SCRs 1-8, SCRs 1-18, SCRs 19-20, or any homolog of a naturally-occurring factor H or fragment thereof, as described in detail below. In certain embodiments, the biologically active fragment of factor H has one or more of the following properties: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

In one aspect, there is provided a soluble composition comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) FH; wherein the CR2 portion contains at least one amino acid substitution. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds EBV gp350. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds IFNα. In some embodiments, the CR2 portion selectively binds IFNα. In some embodiments, the CR2 portion selectively binds IFNα and also selectively binds EBV gp350. In some embodiments, the CR2 portion selectively binds EBV gp350. As used herein, "selectively binds" means that a construct exhibits enhanced binding to one ligand and/or decreased binding to a different ligand. For example, "selectively binds" can mean: 1) that a construct which has been altered has a binding affinity for a first ligand that is similar to the binding affinity of the unaltered construct for the first ligand whereas the construct that has been altered has a lower affinity for a second ligand than does the unaltered construct, and therefore the altered construct "selectively binds" the first ligand as compared to the binding of the unaltered construct to the two ligands; 2) that a construct which has been altered has increased binding to a first ligand as compared to the binding of the unaltered construct to the first ligand while retaining binding to a second ligand that is similar to the binding of the unaltered construct to the second ligand, and therefore the construct "selectively binds" the first ligand as compared to the binding of the unaltered construct to the two ligands; or 3) that a construct which has been altered has increased binding to a first ligand as compared to the binding of the unaltered construct to the first ligand and also has a lower binding affinity for a second ligand as compared to the binding of the unaltered construct to the second ligand, and therefore the altered construct "selectively binds" the first ligand and not the second ligand as compared to the binding of the unaltered construct to the two ligands. In certain embodiments, the construct is a fusion protein. In certain embodiments, the complement inhibitor portion of the construct comprises full-length human (SEQ ID NO:5) or mouse (SEQ ID NO:8) factor H. In certain embodiments, the complement inhibitor portion of the construct comprises a biologically active fragment of human (SEQ ID NO:5) or mouse (SEQ ID NO:8) factor H. In certain embodiments, the biologically active fragment of human factor H (SEQ ID NO:5) is selected from the group consisting of SCRs 1-4 (amino acids 21-262 of SEQ ID NO:5), SCRs 1-5 of factor H (amino acids 21-320 of SEQ ID NO:5), SCRs 1-8 of factor H (amino acids 21-507 of SEQ ID NO:5), and SCRs 1-18 of factor H (amino acids 21-1104 of SEQ ID NO:5). In certain embodiments, the biologically active fragment of mouse factor H (SEQ ID NO:8) is selected from the group consisting of SCRs 1-4 (amino acids 19-264 of SEQ ID NO:8), SCRs 1-5 of factor H (amino acids 19-322 of SEQ ID NO:8), SCRs 1-8 of factor H (amino acids 19-507 of SEQ ID NO:8), and SCRs 1-18 of factor H (amino acids 19-1109 of SEQ ID NO:8). In certain embodiments, the biologically active fragment of human (SEQ ID NO:5) or mouse (SEQ ID NO:8) factor H comprises (and in certain embodiments consists of or consists essentially of) at least the first four N-terminal SCR domains of factor H, including for example, at least any of the first 5, 6, 7, 8, 9, 10, 11, 12, 13, 14, 15, 16, 17, 18, or more N-terminal SCR domains of factor H.

Complement Activator Proteins

Provided herein are soluble compositions comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement activator portion; wherein the CR2 portion contains at least one amino acid substitution. In certain embodiments, the construct is a fusion protein. A number of endogenous soluble proteins that activate complement have also been identified. These complement activators include, but are not limited to, various immunoglobulin (Ig) proteins, including human Ig isotype $G_1$ (Ig$G_1$), human Ig isotype M (IgM), mouse Ig isotype $G_3$ (Ig$G_3$), and mouse IgM Fc, as well as cobra venom factor (CVF) and biologically-active fragments thereof. The complement activating activity of Ig proteins has been localized to the Fc domain. Therefore biologically-active fragments of complement-activating human and mouse Ig proteins include the Fc domain, such as human Ig$G_1$ Fc domain, human IgM Fc domain, mouse Ig$G_3$ Fc domain, and mouse IgM Fc domain.

Immunoglobulin Proteins

As used herein, the term "antibody" or "immunoglobulin" refers to glycoproteins of the immunoglobulin (Ig) superfamily of proteins. An antibody or immunoglobulin (Ig) molecule is tetrameric, comprising two identical light chain polypeptides and two identical heavy chain polypeptides. The two heavy chains are linked together by disulfide bonds, and each heavy chain is linked to a light chain by a disulfide bond. Each full-length Ig molecule contains at least two binding sites for a specific target or antigen.

The immune system produces several different classes of Ig molecules (isotypes), including IgA, IgD, IgE, IgG, and IgM, each distinguished by the particular class of heavy chain polypeptide present: alpha ($\alpha$) found in IgA, delta ($\delta$) found in IgD, epsilon ($\epsilon$) found in IgE, gamma ($\gamma$) found in IgG, and mu ($\mu$) found in IgM. There are at least five different $\gamma$ heavy chain polypeptides (isotypes) found in IgG. In contrast, there are only light chain polypeptide isotypes, referred to as kappa ($\kappa$) and lambda ($\lambda$) chains. The distinctive characteristics of antibody isotypes are defined by sequences of the constant domains of the heavy chain.

An IgG molecule comprises two light chains (either $\kappa$ or $\lambda$ form) and two heavy chains ($\gamma$ form) bound together by disulfide bonds. The $\kappa$ and $\lambda$ forms of IgG light chain both contain a domain of relatively variable amino acid sequences, called the variable region (variously referred to as a "$V_L$-," "$V_\kappa$-," or "$V_\lambda$-region") and a domain of relatively conserved amino acid sequences, called the constant region ($C_L$-region). Similarly, each IgG heavy chain contains a variable region ($V_H$-region) and one or more conserved regions: a complete IgG heavy chain contains three constant domains ("$C_H1$-," "$C_H2$-," and "$C_H3$-regions") and a hinge region. Within each $V_L$- or $V_H$-region, hypervariable regions, also known as complementarity-determining regions ("CDR"), are interspersed between relatively conserved framework regions ("FR"). Generally, the variable region of a light or heavy chain polypeptide contains four FR and three CDR arranged in the following order along the polypeptide: $NH_2$-FR1-CDR1-FR2-CDR2-FR3-CDR3-FR4-COOH. Together the CDR and FR determine the three-dimensional structure of the IgG binding site and thus, the specific target protein or antigen to which that IgG molecule binds. Each IgG molecule is dimeric, able to bind two antigen molecules. Cleavage of a dimeric IgG with the protease papain produces two identical antigen-binding fragments ("Fab'") and an "Fc" fragment or Fc domain, so named because is readily crystallized.

In some embodiments, the composition comprises a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement activator portion selected from the group consisting of: human Ig isotype $G_1$ (Ig$G_1$), human Ig isotype M (IgM), mouse Ig isotype $G_3$ (Ig$G_3$), mouse IgM Fc, human Ig$G_1$ Fc domain, human IgM Fc domain, mouse Ig$G_3$ Fc domain, and mouse IgM Fc domain, and wherein the CR2 portion contains at least one amino acid substitution. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds EBV gp350. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds IFN$\alpha$. In some embodiments, the CR2 portion selectively binds IFN$\alpha$. In some embodiments, the CR2 portion selectively binds IFN$\alpha$ and also selectively binds EBV gp350. In some embodiments, the CR2 portion selectively binds EBV gp350. As used herein, "selectively binds" means that a construct exhibits enhanced binding to one ligand and/or decreased binding to a different ligand. For example, "selectively binds" can mean: 1) that a construct which has been altered has a binding affinity for a first ligand that is similar to the binding affinity of the unaltered construct for the first ligand whereas the construct that has been altered has a lower affinity for a second ligand than does the unaltered construct, and therefore the altered construct "selectively binds" the first ligand as compared to the binding of the unaltered construct to the two ligands; 2) that a construct which has been altered has increased binding to a first ligand as compared to the binding of the unaltered construct to the first ligand while retaining binding to a second ligand that is similar to the binding of the unaltered construct to the second ligand, and therefore the construct "selectively binds" the first ligand as compared to the binding of the unaltered construct to the two ligands; or 3) that a construct which has been altered has increased binding to a first ligand as compared to the binding of the unaltered construct to the first ligand and also has a lower binding affinity for a second ligand as compared to the binding of the unaltered construct to the second ligand, and therefore the altered construct "selectively binds" the first ligand and not the second ligand as compared to the binding of the unaltered construct to the two ligands. In certain embodiments, the construct is a fusion protein. In certain embodiments, the complement activator portion of the construct comprises an Ig protein or biologically-active fragment thereof. In certain embodiments, the Ig protein or biologically-active fragment thereof comprises human $IgG_1$, human $IgG_1$ Fc domain, human IgM, human IgM Fc domain, mouse $IgG_3$, mouse $IgG_3$ Fc domain, mouse IgM, and mouse IgM Fc domain.

Cobra Venom Factor (CVF)

As used herein, the terms "cobra venom factor," "CVF," and "C3b (Cobra)" refer to the non-toxic, complement-activating component of cobra venom. Like naturally occurring human C3b, CVF (SEQ ID NO:13) forms a complex, or convertase, with complement components Factor B and Factor D. This CVFBbD convertase is capable of activating C3 in a wide variety of species via the alternative complement pathway. CVFBbD convertase is Factor H-resistant and is therefore not blocked through the activity of Factor I or CR1 and can convert nearly 100% of the C3 to C3 and C5 fragments. Levels of iC3b, C3a, SC5b-9, C5a and the Factor B cleavage product Bb are all extremely high in CVF treated sera. The cloning and sequencing of CVF from the monocled cobra (*Naja kaouthia*) was reported in Fritzinger, et al., "Molecular cloning and derived primary structure of cobra venom factor," *Proc. Nat'l Acad. Sci. USA* 91(26): 12775-779 (1994); the sequence was deposited in the GenBank database under Accession Number U09969. Both the Fritzinger et al. reference and the sequence deposited in GenBank under Accession Number U09969 are hereby incorporated herein by reference. The terms "cobra venom factor," "CVF," and "C3b (Cobra)" also refer to hybrid CVF molecules comprising a CVF portion and a complement component 3 (C3) portion, such as those described in Fritzinger et al., "Functional characterization of human C3/cobra venom factor hybrid proteins for therapeutic complement depletion," *Develop. Comp. Immunol.* 33(1): 105-116 (2009), which is incorporated herein by reference. Those hybrids comprise proteins in which the 113 or 315 C-terminal residues of C3 were replaced with corresponding CVF sequences. Both hybrids formed stable convertases that exhibited C3-cleaving activity, although at different rates. Neither convertase cleaved C5. Both convertases showed partial resistance to inactivation by factors H and I, allowing them to deplete complement in human serum.

In one aspect, the composition comprises a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) CVF. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds EBV gp350. In some embodiments, the CR2 portion selectively binds one or more C3 proteolytic fragments selected from the group consisting of C3d, iC3dg, C3dg, and a cell-bound fragment of C3b that binds to the two N-terminal SCR domains of CR2 and also selectively binds IFNα. In some embodiments, the CR2 portion selectively binds IFNα. In some embodiments, the CR2 portion selectively binds IFNα and also selectively binds EBV gp350. In some embodiments, the CR2 portion selectively binds EBV gp350. As used herein, "selectively binds" means that a construct exhibits enhanced binding to one ligand and/or decreased binding to a different ligand. For example, "selectively binds" can mean: 1) that a construct which has been altered has a binding affinity for a first ligand that is similar to the binding affinity of the unaltered construct for the first ligand whereas the construct that has been altered has a lower affinity for a second ligand than does the unaltered construct, and therefore the altered construct "selectively binds" the first ligand as compared to the binding of the unaltered construct to the two ligands; 2) that a construct which has been altered has increased binding to a first ligand as compared to the binding of the unaltered construct to the first ligand while retaining binding to a second ligand that is similar to the binding of the unaltered construct to the second ligand, and therefore the construct "selectively binds" the first ligand as compared to the binding of the unaltered construct to the two ligands; or 3) that a construct which has been altered has increased binding to a first ligand as compared to the binding of the unaltered construct to the first ligand and also has a lower binding affinity for a second ligand as compared to the binding of the unaltered construct to the second ligand, and therefore the altered construct "selectively binds" the first ligand and not the second ligand as compared to the binding of the unaltered construct to the two ligands. In certain embodiments, the construct is a fusion protein.

Compositions of the Invention

Amino Acid Residues in CR2 Involved in Selective Binding to Particular Ligands

Structural analyses of CR2 binding to EBV gp350, IFNα, and C3d described herein (see Example 1) identified a number of CR2 amino acid residues that are important for binding of each of those ligands. While some of those amino acid residues are important for binding of all three ligands, others are important for binding one specific ligand (e.g., EBV gp350, IFNα, or C3d).

For example, residues determined to be important for the CR2-EBV gp350 binding interaction are N11, R13, A22, R28, S32, R36, K41, K57, Y64, K67, Y68, R83, G84 and R89 (see Table 2). Residues determined to be important for the CR2-EBV gp350 binding interaction but not the CR2-C3d or the CR2-IFNα binding interaction are N11, R36, K41, Y64, and K67 (see Table 2). Residues determined to be important for the CR2-IFNα binding interaction are R13, Y16, R28, S42, K48, K50, Y68, R83, G84 and R89 (see Table 2). Residues determined to be important for the CR2-IFNα binding interaction but not the CR2-C3d or CR2-EBV gp350 binding interaction are S42 and K50 (see Table 2). Residues determined to be important for the CR2-C3d binding interaction are I9, R13, Y16, A22, R28, Y29, C31, S32, G33, T34, K48, D56, K57, Y68, S70, R83, G84, R89, H90, D92, S93, A97, T100, N101, S109, and S128 (see Table 2). Residues determined to be important for the CR2-C3d binding interaction but not the CR2-gp350 or the CR2-IFNα binding interaction are I9, Y29, C31, G33, T34, D56, S70, H90, D92, S93, A97, T100, N101, S109, and S128 (see Table 2). The amino acid residues determined to be important for the CR2-C3d binding interaction are likely important for the CR2 binding interaction with other cell surface-bound C3 fragments such as C3dg, and iC3b. Residues determined to be important for the CR2-gp350, the CR2-IFNα, and the CR2-C3d binding interactions are R13, Y16, A22, R28, S32, K48, K57, Y68, R83, G84, and R89. Because these amino acid residues are important for binding interactions between CR2 and more than one of its ligands, mutating amino acid residues at one or more of those positions may also improve the targeting capability of the CR2 portion for C3d and/or other CR2 ligands.

The improved targeting groups described herein, comprising at least one or more mutations in the various amino acid residues important for the binding interactions between CR2 and EBV-gp350, CR2 and IFNα, and/or CR2 and C3d can be used to deliver a complement modulator (e.g., a complement inhibitor or complement activator) to any physiological site (e.g., a site of inflammation) suitable for the use of the CR2 targeting groups described in US Patent Publication No. 2008/0267980 A1, US Patent Publication No. US 2008/0221011 A1, and US Patent Publication No. 2005/0260198 A1, all of which are incorporated herein by reference.

Mutation of CR2 amino acid residues determined to be important for a binding interaction between CR2 and a specific ligand will likely decrease the binding affinity of CR2 for that specific ligand while leaving the binding affinity of CR2 for its other ligands relatively unaffected. For example, mutation of at least one of amino acid residues N11, R36, K41, Y64, and K67 in CR2 (SEQ ID NO:1) will likely reduce the binding affinity of CR2 for EBV gp350 while leaving its binding affinity for C3d and IFNα unchanged. Similarly, mutation of at least one of amino acid residues S42 and K50 will likely reduce the binding affinity of CR2 for IFNα while leaving its binding affinity for C3d and gp350 unchanged. Mutation of at least one of amino acid residues I9, Y29, C31, G33, T34, D56, S70, H90, D92, S93, A97, T100, N101, S109, and S128 will likely reduce the binding affinity of CR2 for C3d while leaving its binding affinity for IFNα and gp350 unchanged.

Provided herein are soluble compositions comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least one amino acid substitution. In certain embodiments, the construct is a fusion protein. In some embodiments the construct selectively binds to one or more C3 proteolytic fragments but does not bind to or has reduced binding affinity for IFNα or EBV gp350. In some embodiments, the construct selectively binds to one or more C3 proteolytic fragments and IFNα but does not bind to or has reduced binding affinity for EBV gp350. In some embodiments the construct selectively binds to one or more C3 proteolytic fragments and EBV gp350 but does not bind to or has reduced binding affinity for IFNα. In some embodiments, the construct selectively binds to IFNα but does not bind to or has reduced binding affinity for one or more C3 proteolytic fragments and EBV gp350. In some embodiments, the construct selectively binds to IFNα and EBV gp350 but does not bind to or has reduced binding affinity for one or more C3 proteolytic fragments. In some embodiments, the construct selectively binds to EBV gp350 but does not bind to or has reduced binding affinity for IFNα and one or more C3 proteolytic fragments.

In certain embodiments, the CR2 portion contains at least one amino acid substitution at an amino acid residue selected from the group consisting of: N11, R36, K41, S42, K50, Y64 and K67. In certain embodiments, the CR2 portion contains at least two amino acid substitutions at an amino acid residue selected from the group consisting of: N11, R36, K41, S42, K50, Y64 and K67. In certain embodiments, the CR2 portion contains at least three amino acid substitutions at an amino acid residue selected from the group consisting of: N11, R36, K41, S42, K50, Y64 and K67. In certain embodiments, the CR2 portion contains at least four amino acid substitutions at an amino acid residue selected from the group consisting of: N11, R36, K41, S42, K50, Y64 and K67. In certain embodiments, the CR2 portion contains at least five amino acid substitutions at an amino acid residue selected from the group consisting of: N11, R36, K41, S42, K50, Y64 and K67. In certain embodiments, the CR2 portion contains at least six amino acid substitutions at an amino acid residue selected from the group consisting of: N11, R36, K41, S42, K50, Y64 and K67. In certain embodiments, the CR2 portion contains at least seven amino acid substitutions at an amino acid residue selected from the group consisting of: N11, R36, K41, S42, K50, Y64 and K67. In any of the above embodiments, the at least one, two, three, four, five, six, or seven amino acid substitutions may be conservative substitutions. In any of the above embodiments, the at least one, two, three, four, five, six, or seven amino acid substitutions may be non-conservative substitutions.

In certain embodiments, the CR2 portion contains at least one amino acid substitution at an amino acid residue selected from the group consisting of: N11, R36, K41, Y64 and K67, and the CR2 portion has decreased binding affinity for EBV gp350. In certain embodiments, the CR2 portion contains at least two amino acid substitutions at an amino acid residue selected from the group consisting of: N11, R36, K41, Y64 and K67, and the CR2 portion has decreased binding affinity for EBV gp350. In certain embodiments, the CR2 portion contains at least three amino acid substitutions at an amino acid residue selected from the group consisting of: N11, R36, K41, Y64 and K67, and the CR2 portion has decreased binding affinity for EBV gp350. In certain embodiments, the CR2 portion contains at least four amino acid substitutions at an amino acid residue selected from the group consisting of: N11, R36, K41, Y64 and K67, and the CR2 portion has decreased binding affinity for EBV gp350. In certain embodiments, the CR2 portion contains at least five amino acid substitutions at an amino acid residue selected from the group consisting of: N11, R36, K41, Y64 and K67, and the CR2 portion has decreased binding affinity for EBV gp350. In any of the above embodiments, the at least one, two, three, four, or five amino acid substitutions may be conservative substitutions. In any of the above embodiments, the at least one, two, three, four, or five amino acid substitutions may be non-conservative substitutions.

In certain embodiments, the CR2 portion contains at least one amino acid substitution at an amino acid residue selected from the group consisting of: S42 and K50, and the CR2 portion has decreased binding affinity for IFNα. In certain embodiments, the CR2 portion contains at least two amino acid substitutions at an amino acid residue selected from the group consisting of: S42 and K50, and the CR2 portion has decreased binding affinity for IFNα. In any of the above embodiments, the at least one or two amino acid substitutions may be conservative substitutions. In any of the above embodiments, the at least one or two amino acid substitutions may be non-conservative substitutions.

In certain embodiments, the CR2 portion comprises a polypeptide that contains some or all of the ligand binding sites of the CR2 protein, and includes, but is not limited to, full-length CR2 proteins (such as human CR2 as shown in SEQ ID NO:1), soluble CR2 proteins (such as a CR2 fragment comprising the extracellular domain of CR2) and other biologically active fragments of CR2, such as a CR2 fragment comprising SCR1-2 (SEQ ID NO:2), or any homolog of a naturally occurring CR2 or fragment thereof, as described in detail below. In certain embodiments, the CR2 portion has one or more of the following properties of CR2: (1) the ability to selectively bind to the C3 proteolytic fragment C3d, (2) the ability to selectively bind to the C3 proteolytic fragment iC3b, (3) the ability to selectively bind to the C3 proteolytic fragment C3dg, (4) the ability to selectively bind to one or more cell-bound fragments of the C3 proteolytic fragment C3b that bind to the two N-terminal SCR domains of CR2, (5) the ability to selectively bind to EBV gp350, and (6) the ability to selectively bind to IFNα.

In certain embodiments, the CR2 portion comprises the first two N-terminal SCR domains of CR2 (amino acids 23 through 146 of SEQ ID NO:2). In certain embodiments, the CR2 portion comprises the first three N-terminal SCR domains of CR2 (amino acids 23 through 212 of SEQ ID NO:1). In certain embodiments, the CR2 portion comprises the first four N-terminal SCR domains of CR2 (amino acids 23 through 271 of SEQ ID NO:1). In certain embodiments, the CR2 portion comprises (and in some embodiments consists of or consists essentially of) at least the first two N-terminal SCR domains of CR2, including for example at least any of the first 3, 4, 5, 6, 7, 8, 9, 10, 11, 12, 13, 14, or 15 SCR domains of CR2.

In certain embodiments, the CR2 portion of the constructs described herein comprises (and in some embodiments consists of or consists essentially of) at least 1, 2, 3, 4, 5, 6, 7, or more amino acid substitutions. In certain embodiments, the amino acid substitutions may be conservative substitutions. In certain embodiments, the amino acid substitutions may be non-conservative substitutions. In certain embodiments, the amino acid substitutions may be a mixture of conservative and non-conservative substitutions.

Compositions for Targeted Delivery of Complement Modulators to Areas of Complement System Activation In some aspects, there is provided a soluble composition capable of targeted delivery of a complement modulator to sites of complement system activation comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least one amino acid substitution that decreases binding affinity of the CR2 portion for EBV gp350. In certain embodiments, the CR2 portion contains at least one amino acid substitution at an amino acid residue selected from the group consisting of: N11, R36, K41, Y64 and K67 and does not bind to, or has decreased binding affinity for, EBV gp350. In certain embodiments, the CR2 portion contains at least two amino acid substitutions at amino acid residues selected from the group consisting of: N11, R36, K41, Y64 and K67 and does not bind to, or has decreased binding affinity for, EBV gp350. In certain embodiments, the CR2 portion contains at least three amino acid substitutions at amino acid residues selected from the group consisting of: N11, R36, K41, Y64 and K67 and does not bind to, or has decreased binding affinity for, EBV gp350. In certain embodiments, the CR2 portion contains at least four amino acid substitutions at amino acid residues selected from the group consisting of: N11, R36, K41, Y64 and K67 and does not bind to, or has decreased binding affinity for, EBV gp350. In certain embodiments, the CR2 portion contains five amino acid substitutions at amino acid residues N11, R36, K41, Y64 and K67 and does not bind to, or has decreased binding affinity for, EBV gp350. In any of the above embodiments, the at least one, two, three, four, or five amino acid substitutions may be conservative substitutions. In any of the above embodiments, the at least one, two, three, four, or five amino acid substitutions may be non-conservative substitutions. In certain embodiments, the CR2 portion contains one or more substitutions in amino acids from the group consisting of: N11A, R36A, K41A, Y64A, and K67A. In certain embodiments, the construct is a fusion protein. In some embodiments, the CR2 portion selectively binds to one or more proteins from the group consisting of: C3d, iC3b, C3dg, one or more cell-bound fragments of C3b that bind to the two N-terminal SCR domains of CR2, CD23, and IFNα. In some embodiments, the construct does not bind to EBV gp350. In other embodiments, the construct has decreased binding affinity to EBV gp350. In some embodiments, the at least one amino acid substitution decreases the binding affinity of the CR2 portion for EBV gp350 by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the complement modulator portion is a complement inhibitor. In some of these embodiments, the complement inhibitor is selected from the group consisting of: MCP, DAF, CD59, Crry, CR1, and FH. In other embodiments, the complement modulator portion is a complement activator. In some of these embodiments, the complement activator is selected from the group consisting of: human Ig isotype $G_1$ (IgG$_1$), human Ig isotype M (IgM), mouse Ig isotype $G_3$ (IgG$_3$), mouse IgM Fc, human IgG$_1$ Fc domain, human IgM Fc domain, mouse IgG$_3$ Fc domain, mouse IgM Fc domain, and CVF.

In some aspects, there is provided a soluble composition capable of targeted delivery of a complement modulator to sites of complement system activation comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least one amino acid substitution that decreases binding affinity of the CR2 portion for IFNα. In certain embodiments, the CR2 portion contains at least one amino acid substitution at an amino acid residue selected from the group consisting of S42 and K50 and does not bind to, or has decreased binding affinity for, IFNα. In certain embodiments, the CR2 portion contains at least two amino acid substitutions at amino acid residues S42 and K50 and does not bind to, or has decreased binding affinity for, IFNα. In any of the above embodiments, the at least one or two amino acid substitutions may be conservative substitutions. In any of the above embodiments, the at least one or two amino acid substitutions may be non-conservative substitutions. In certain embodiments, the CR2 portion contains one or more substitutions in amino acids from the group consisting of: S42A and K50A. In certain embodiments, the construct is a fusion protein. In some embodiments, the CR2 portion selectively binds to one or more proteins from the group consisting of: C3d, iC3b, C3dg, one or more cell-bound fragments of C3b that bind to the two N-terminal SCR domains of CR2, CD23, and EBV gp350. In some embodiments, the construct does not bind to IFNα. In other embodiments, the construct has decreased binding affinity to IFNα. In some embodiments, the at least one amino acid substitution decreases the binding affinity of the CR2 portion for IFNα by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the complement modulator portion is a complement inhibitor. In some of these embodiments, the complement inhibitor is selected from the group consisting of: MCP, DAF, CD59, Crry, CR1, and FH. In other embodiments, the complement modulator portion is a complement activator. In some of these embodiments, the complement activator is selected from the group consisting of: human Ig isotype $G_1$ (IgG$_1$), human Ig isotype M (IgM), mouse Ig isotype $G_3$ (IgG₃), mouse IgM Fc, human IgG₁ Fc domain, human IgM Fc domain, mouse IgG₃ Fc domain, mouse IgM Fc domain, and CVF.

In some aspects, there is provided a soluble composition capable of targeted delivery of a complement modulator to sites of complement system activation comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least two amino acid substitutions that decrease binding affinity of the CR2 portion for EBV gp350 and IFNα. In certain embodiments, the CR2 portion contains at least one amino acid substitution at an amino acid residue selected from the group consisting of: S42 and K50, further contains at least one amino acid substitution at an amino acid residue selected from the group consisting of: N11, R36, K41, Y64 and K67, and does not bind to, or has decreased binding affinity for, EBV gp350 and IFNα. In certain embodiments, the CR2 portion contains at least one amino acid substitution at an amino acid residue selected from the group consisting of: S42 and K50, further contains at least two amino acid substitutions at amino acid residues selected from the group consisting of: N11, R36, K41, Y64 and K67, and does not bind to, or has decreased binding affinity for, EBV gp350 and IFNα. In certain embodiments, the CR2 portion contains at least one amino acid substitution at an amino acid residue selected from the group consisting of: S42 and K50, further contains at least three amino acid substitutions at amino acid residues selected from the group consisting of: N11, R36, K41, Y64 and K67, and does not bind to, or has decreased binding affinity for, EBV gp350 and IFNα. In certain embodiments, the CR2 portion contains at least one amino acid substitution at an amino acid residue selected from the group consisting of: S42 and K50, further contains at least four amino acid substitutions at amino acid residues selected from the group consisting of: N11, R36, K41, Y64 and K67, and does not bind to, or has decreased binding affinity for, EBV gp350 and IFNα. In certain embodiments, the CR2 portion contains at least one amino acid substitution at an amino acid residue selected from the group consisting of: S42 and K50, further contains five amino acid substitutions at amino acid residues N11, R36, K41, Y64 and K67, and does not bind to, or has decreased binding affinity for, EBV gp350 and IFNα. In any of the above embodiments, the at least two amino acid substitutions may be conservative substitutions. In any of the above embodiments, the at least two amino acid substitutions may be non-conservative substitutions. In certain embodiments, the CR2 portion contains one or more substitutions in an amino acid from the group consisting of: N11A, R36A, K41A, Y64A, and K67A and a mutation from the group consisting of S42A and K50A. In certain embodiments, the construct is a fusion protein. In some embodiments, the CR2 portion selectively binds to one or more proteins from the group consisting of: C3d, iC3b, C3dg, one or more cell-bound fragments of C3b that bind to the two N-terminal SCR domains of CR2, and CD23. In some embodiments, the construct does not bind to IFNα and EBV gp350. In other embodiments, the construct has decreased binding affinity to IFNα and EBV gp350. In some embodiments, the at least two amino acid substitutions decrease the binding affinity of the CR2 portion for IFNα and EBV gp350 by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the complement modulator portion is a complement inhibitor. In some of these embodiments, the complement inhibitor is selected from the group consisting of: MCP, DAF, CD59, Crry, CR1, and FH. In other embodiments, the complement modulator portion is a complement activator. In some of these embodiments, the complement activator is selected from the group consisting of: human Ig isotype G₁ (IgG₁), human Ig isotype M (IgM), mouse Ig isotype G₃ (IgG₃), mouse IgM Fc, human IgG₁ Fc domain, human IgM Fc domain, mouse IgG₃ Fc domain, mouse IgM Fc domain, and CVF.

In some aspects, there is provided a soluble composition capable of targeted delivery of a complement modulator to sites of complement system activation comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least three amino acid substitutions that decrease binding affinity of the CR2 portion for EBV gp350 and IFNα. In certain embodiments, the CR2 portion contains amino acid substitutions at amino acid residues S42 and K50, further contains at least one amino acid substitution at an amino acid residue selected from the group consisting of: N11, R36, K41, Y64 and K67, and does not bind to, or has decreased binding affinity for, EBV gp350 and IFNα. In certain embodiments, the CR2 portion contains amino acid substitutions at amino acid residues S42 and K50, further contains at least two amino acid substitutions at amino acid residues selected from the group consisting of: N11, R36, K41, Y64 and K67, and does not bind to, or has decreased binding affinity for, EBV gp350 and IFNα. In certain embodiments, the CR2 portion contains amino acid substitutions at amino acid residues S42 and K50, further contains at least three amino acid substitutions at amino acid residues selected from the group consisting of: N11, R36, K41, Y64 and K67, and does not bind to, or has decreased binding affinity for, EBV gp350 and IFNα. In certain embodiments, the CR2 portion contains amino acid substitutions at amino acid residues S42 and K50, further contains at least four amino acid substitutions at amino acid residues selected from the group consisting of: N11, R36, K41, Y64 and K67, and does not bind to, or has decreased binding affinity for, EBV gp350 and IFNα. In certain embodiments, the CR2 portion contains amino acid substitutions at amino acid residues S42 and K50, further contains five amino acid substitutions at amino acid residues N11, R36, K41, Y64 and K67, and does not bind to, or has decreased binding affinity for, EBV gp350 and IFNα. In any of the above embodiments, the at least three amino acid substitutions may be conservative substitutions. In any of the above embodiments, the at least three amino acid substitutions may be non-conservative substitutions. In certain embodiments, the CR2 portion contains one or more substitutions in an amino acid from the group consisting of: N11A, R36A, K41A, Y64A, and K67A and mutations S42A and K50A. In certain embodiments, the construct is a fusion protein. In some embodiments, the CR2 portion selectively binds to one or more proteins from the group consisting of: C3d, iC3b, C3dg, one or more cell-bound fragments of C3b that bind to the two N-terminal SCR domains of CR2, and CD23. In some embodiments, the construct does not bind to IFNα and EBV gp350. In other embodiments, the construct has decreased binding affinity to IFNα and EBV gp350. In some embodiments, the at least three amino acid substitutions decrease the binding affinity of the CR2 portion for IFNα and EBV gp350 by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the complement modulator portion is a complement inhibitor. In some of these embodiments, the complement inhibitor is selected from the group consisting of: MCP, DAF, CD59, Crry, CR1, and FH. In other embodiments, the complement modulator portion is a complement activator. In some of these embodiments, the complement activator is selected from the group consisting of: human Ig isotype $G_1$ (IgG$_1$), human Ig isotype M (IgM), mouse Ig isotype $G_3$ (IgG$_3$), mouse IgM Fc, human IgG$_1$ Fc domain, human IgM Fc domain, mouse IgG$_3$ Fc domain, mouse IgM Fc domain, and CVF.

Compositions for Targeted Delivery of Complement Modulators to Sites of Epstein Barr Virus infection In some aspects, there is provided a soluble composition capable of targeted delivery of a complement modulator to sites of Epstein Barr Virus infection comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least one amino acid substitution that decreases binding affinity of the CR2 portion for one or more C3 proteolytic fragments. In certain embodiments, the CR2 portion contains at least one amino acid substitution at an amino acid residue selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least two amino acid substitutions at amino acid residues selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least three amino acid substitutions at amino acid residues selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least four amino acid substitutions at amino acid residues selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least five amino acid substitutions at amino acid residues selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least six amino acid substitutions at amino acid residues selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least seven amino acid substitutions at amino acid residues selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least eight amino acid substitutions at amino acid residues selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least nine amino acid substitutions at amino acid residues selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least ten amino acid substitutions at amino acid residues selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least eleven amino acid substitutions at amino acid residues selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least twelve amino acid substitutions at amino acid residues selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least thirteen amino acid substitutions at amino acid residues selected from the group consisting of: 19, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains at least fourteen amino acid substitutions at amino acid residues selected from the group consisting of: I9, Y29, C31, G33, T34, D56, S70, H90, D92, S93, A97, T100, N101, S109, and S128 and does not bind to, or has decreased binding affinity for, one or more C3 proteolytic fragments. In certain embodiments, the CR2 portion contains fifteen amino acid substitutions at amino acid residues I9, Y29, C31, G33, T34, D56, S70, H90, D92, S93, A97, T100, N101, S109, and S128 and does not bind to, or has decreased binding affinity for, one or more C3 proteolytic fragments. In some embodiments, the one or more C3 proteolytic fragments are selected from the group consisting of C3d, iC3b, C3dg, and one or more cell-bound fragments of C3b that bind to the two N-terminal SCR domains of CR2. In any of the above embodiments, the at least one, two, three, four, five, six, seven, eight, nine, ten, eleven, twelve, thirteen, fourteen, or fifteen amino acid substitutions may be conservative substitutions. In any of the above embodiments, the at least one, two, three, four, five, six, seven, eight, nine, ten, eleven, twelve, thirteen, fourteen, or fifteen amino acid substitutions may be nonconservative substitutions. In certain embodiments, the construct is a fusion protein. In some embodiments, the CR2 portion selectively binds to one or more proteins from the group consisting of: CD23, EBV gp350, and IFNα. In some embodiments, the construct does not bind to one or more C3 proteolytic fragments. In other embodiments, the construct has decreased binding affinity to one or more C3 proteolytic fragments. In some embodiments, the at least one amino acid substitution decreases the binding affinity of the CR2 portion for one or more C3 proteolytic fragments by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the complement modulator portion is a complement inhibitor. In some of these embodiments, the complement inhibitor is selected from the group consisting of: MCP, DAF, CD59, Crry, CR1, and FH. In other embodiments, the complement modulator portion is a complement activator. In some of these embodiments, the complement activator is selected from the group consisting of: human Ig isotype $G_1$ (IgG$_1$), human Ig isotype M (IgM), mouse Ig isotype $G_3$ (IgG$_3$), mouse IgM Fc, human IgG$_1$ Fc domain, human IgM Fc domain, mouse IgG$_3$ Fc domain, mouse IgM Fc domain, and CVF.

In some aspects, there is provided a soluble composition capable of targeted delivery of a complement modulator to sites of Epstein Barr Virus infection comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least two amino acid substitutions that decrease binding affinity of the CR2 portion for one or more C3 proteolytic fragments and IFNα. In certain embodiments, the CR2 portion contains at least one amino acid substitution at an amino acid residue selected from the group consisting of: S42 and K50, further contains at least one amino acid substitution at an amino acid residue selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains at least two amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα In certain embodiments, the CR2 portion contains at least one amino acid substitution at an amino acid residue selected from the group consisting of: S42 and K50, further contains at least three amino acid substitutions at amino acid residue selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains at least four amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains at least five amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains at least six amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains at least seven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains at least eight amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains at least nine amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains at least ten amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains at least eleven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains at least twelve amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains at least thirteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains at least fourteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains at least one amino acid substitution at an amino acid residue selected from the group consisting of: S42 and K50, further contains fifteen amino acid substitutions at amino acid residues I9, Y29, C31, G33, T34, D56, S70, H90, D92, S93, A97, T100, N101, S109, and S128, and does not bind to, or has decreased binding affinity for, one or more C3 proteolytic fragments and IFNα. In some embodiments, the one or more C3 proteolytic fragments are selected from the group consisting of C3d, iC3b, C3dg, and one or more cell-bound fragments of C3b that bind to the two N-terminal SCR domains of CR2. In any of the above embodiments, the at least two amino acid substitutions may be conservative substitutions. In any of the above embodiments, the at least two amino acid substitutions may be non-conservative substitutions. In certain embodiments, the CR2 portion contains a substitution of an amino acid from the group consisting of S42A and K50A. In certain embodiments, the construct is a fusion protein. In some embodiments, the CR2 portion selectively binds to one or more proteins from the group consisting of: CD23 and EBV gp350. In some embodiments, the construct does not bind to IFNα and one or more C3 proteolytic fragments. In other embodiments, the construct has decreased binding affinity to IFNα and one or more C3 proteolytic fragments. In some embodiments, the at least two amino acid substitutions decrease the binding affinity of the CR2 portion for IFNα and one or more C3 proteolytic fragments by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the complement modulator portion is a complement inhibitor. In some of these embodiments, the complement inhibitor is selected from the group consisting of: MCP, DAF, CD59, Crry, CR1, and FH. In other embodiments, the complement modulator portion is a complement activator. In some of these embodiments, the complement activator is selected from the group consisting of: human Ig isotype $G_1$ (IgG$_1$), human Ig isotype M (IgM), mouse Ig isotype $G_3$ (IgG$_3$), mouse IgM Fc, human IgG$_1$ Fc domain, human IgM Fc domain, mouse IgG$_3$ Fc domain, mouse IgM Fc domain, and CVF.

In some aspects, there is provided a soluble composition capable of targeted delivery of a complement modulator to sites of complement system activation comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least three amino acid substitutions that decrease binding affinity of the CR2 portion for one or more C3 proteolytic fragments and IFNα. In certain embodiments, the CR2 portion contains amino acid substitutions at amino acid residues S42 and K50, further contains at least one amino acid substitution at an amino acid residue selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least two amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least three amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least four amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least five amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least six amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least seven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least eight amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least nine amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least ten amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least eleven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least twelve amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least thirteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains at least fourteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and IFNα. In certain embodiments, the CR2 portion contains amino acid substitutions at amino acid residues S42 and K50, further contains fifteen amino acid substitutions at amino acid residues I9, Y29, C31, G33, T34, D56, S70, H90, D92, S93, A97, T100, N101, S109, and S128, and does not bind to, or has decreased binding affinity for, one or more C3 proteolytic fragments and IFNα. In some embodiments, the one or more C3 proteolytic fragments are selected from the group consisting of C3d, iC3b, C3dg, and one or more cell-bound fragments of C3b that bind to the two N-terminal SCR domains of CR2. In any of the above embodiments, the at least three amino acid substitutions may be conservative substitutions. In any of the above embodiments, the at least three amino acid substitutions may be non-conservative substitutions. In certain embodiments, the CR2 portion contains substitutions of amino acids S42A and K50A. In certain embodiments, the construct is a fusion protein. In some embodiments, the CR2 portion selectively binds to one or more proteins from the group consisting of: CD23 and EBV gp350. In some embodiments, the construct does not bind to IFNα and one or more C3 proteolytic fragments. In other embodiments, the construct has decreased binding affinity to IFNα and one or more C3 proteolytic fragments. In some embodiments, the at least three amino acid substitutions decreases the binding affinity of the CR2 portion for IFNα and one or more C3 proteolytic fragments by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the complement modulator portion is a complement inhibitor. In some of these embodiments, the complement inhibitor is selected from the group consisting of: MCP, DAF, CD59, Crry, CR1, and FH. In other embodiments, the complement modulator portion is a complement activator. In some of these embodiments, the complement activator is selected from the group consisting of: human Ig isotype $G_1$ (Ig$G_1$), human Ig isotype M (IgM), mouse Ig isotype $G_3$ (Ig$G_3$), mouse IgM Fc, human Ig$G_1$ Fc domain, human IgM Fc domain, mouse Ig$G_3$ Fc domain, mouse IgM Fc domain, and CVF.

Compositions for Targeted Delivery of Complement Modulators to Sites of Interferon Alpha Production In some aspects, there is provided a soluble composition capable of targeted delivery of a complement modulator to sites of IFNα production comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least two amino acid substitutions that decrease binding affinity of the CR2 portion for one or more C3 proteolytic fragments and EBV gp350. In certain embodiments, the CR2 portion contains at least one amino acid substitution at an amino acid residue selected from the group consisting of: N11, R36, K41, Y64 and K67, further contains at least one amino acid substitution at an amino acid residue selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at an amino acid residue selected from the group consisting of: N11, R36, K41, Y64 and K67, further contains at least two amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at amino acid residues selected from the group consisting of: N11, R36, K41, Y64 and K67, further contains at least three amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at an amino acid residue selected from the group consisting of: N11, R36, K41, Y64 and K67, further contains at least four amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at amino acid residues selected from the group consisting of: N11, R36, K41, Y64 and K67, further contains at least five amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at amino acid residues selected from the group consisting of: N11, R36, K41, Y64 and K67, further contains at least six amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at an amino acid residue selected from the group consisting of: N11, R36, K41, Y64 and K67, further contains at least seven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at an amino acid residue selected from the group consisting of: N11, R36, K41, Y64 and K67, further contains at least eight amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at an amino acid residue selected from the group consisting of: N11, R36, K41, Y64 and K67, further contains at least nine amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at an amino acid residue selected from the group consisting of: N11, R36, K41, Y64 and K67, further contains at least ten amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at amino acid residues selected from the group consisting of: N11, R36, K41, Y64 and K67, further contains at least eleven amino acid substitutions at an amino acid residue selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at an amino acid residue selected from the group consisting of: N11, R36, K41, Y64 and K67, further contains at least twelve amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at an amino acid residue selected from the group consisting of: N11, R36, K41, Y64 and K67, further contains at least thirteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at an amino acid residue selected from the group consisting of: N11, R36, K41, Y64 and K67, further contains at least fourteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least one amino acid substitution at an amino acid residue selected from the group consisting of: N11, R36, K41, Y64 and K67, further contains fifteen amino acid substitutions at amino acid residues I9, Y29, C31, G33, T34, D56, S70, H90, D92, S93, A97, T100, N101, S109, and S128, and does not bind to, or has decreased binding affinity for, one or more C3 proteolytic fragments and EBV gp350. In some embodiments, the one or more C3 proteolytic fragments are selected from the group consisting of C3d, iC3b, C3dg, and one or more cell-bound fragments of C3b that bind to the two N-terminal SCR domains of CR2. In any of the above embodiments, the at least two amino acid substitutions may be conservative substitutions. In certain embodiments, the CR2 portion contains one or more substitutions of amino acids from the group consisting of: N11A, R36A, K41A, Y64A, and K67A. In any of the above embodiments, the at least two amino acid substitutions may be non-conservative substitutions. In certain embodiments, the construct is a fusion protein. In some embodiments, the CR2 portion selectively binds to one or more proteins from the group consisting of: CD23 and IFNα. In some embodiments, the construct does not bind to EBV gp350 and one or more C3 proteolytic fragments. In other embodiments, the construct has decreased binding affinity to EBV gp350 and one or more C3 proteolytic fragments. In some embodiments, the at least two amino acid substitutions decreases the binding affinity of the CR2 portion for EBV gp350 and one or more C3 proteolytic fragments by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the complement modulator portion is a complement inhibitor. In some of these embodiments, the complement inhibitor is selected from the group consisting of: MCP, DAF, CD59, Crry, CR1, and FH. In other embodiments, the complement modulator portion is a complement activator. In some of these embodiments, the complement activator is selected from the group consisting of: human Ig isotype $G_1$ (IgG$_1$), human Ig isotype M (IgM), mouse Ig isotype $G_3$ (IgG$_3$), mouse IgM Fc, human IgG$_1$ Fc domain, human IgM Fc domain, mouse IgG$_3$ Fc domain, mouse IgM Fc domain, and CVF.

In some aspects, there is provided a soluble composition capable of targeted delivery of a complement modulator to sites of IFNα production comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least three amino acid substitutions that decrease binding affinity of the CR2 portion for one or more C3 proteolytic fragments and EBV gp350. In certain embodiments, the CR2 portion contains at least two amino acid substitutions at amino acid residues selected from the group consisting of: N11, R36, K41, Y64 and K67, further contains at least one amino acid substitution at an amino acid residue selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at an amino acid residue selected from the group consisting of: N11, R36, K41, Y64 and K67, further contains at least two amino acid substitutions at an amino acid residue selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residues selected from the group consisting of: N11, R36, K41, Y64 and K67, further contains at least three amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residues selected from the group consisting of: N11, R36, K41, Y64 and K67, further contains at least four amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residues selected from the group consisting of: N11, R36, K41, Y64 and K67, further contains at least five amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residues selected from the group consisting of: N11, R36, K41, Y64 and K67, further contains at least six amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residues selected from the group consisting of: N11, R36, K41, Y64 and K67, further contains at least seven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residues selected from the group consisting of: N11, R36, K41, Y64 and K67, further contains at least eight amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residues selected from the group consisting of: N11, R36, K41, Y64 and K67, further contains at least nine amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residues selected from the group consisting of: N11, R36, K41, Y64 and K67, further contains at least ten amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residues selected from the group consisting of: N11, R36, K41, Y64 and K67, further contains at least eleven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residues selected from the group consisting of: N11, R36, K41, Y64 and K67, further contains at least twelve amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residues selected from the group consisting of: N11, R36, K41, Y64 and K67, further contains at least thirteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residues selected from the group consisting of: N11, R36, K41, Y64 and K67, further contains at least fourteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least two amino acid substitutions at amino acid residue selected from the group consisting of: N11, R36, K41, Y64 and K67, further contains fifteen amino acid substitutions at amino acid residues I9, Y29, C31, G33, T34, D56, S70, H90, D92, S93, A97, T100, N101, S109, and S128, and does not bind to, or has decreased binding affinity for, one or more C3 proteolytic fragments and EBV gp350. In some embodiments, the one or more C3 proteolytic fragments are selected from the group consisting of C3d, iC3b, C3dg, and one or more cell-bound fragments of C3b that bind to the two N-terminal SCR domains of CR2. In any of the above embodiments, the at least three amino acid substitutions may be conservative substitutions. In any of the above embodiments, the at least three amino acid substitutions may be non-conservative substitutions. In certain embodiments, the CR2 portion contains one or more substitutions of amino acids from the group consisting of: N11A, R36A, K41A, Y64A, and K67A. In certain embodiments, the construct is a fusion protein. In some embodiments, the CR2 portion selectively binds to one or more proteins from the group consisting of: CD23 and IFNα. In some embodiments, the construct does not bind to EBV gp350 and one or more C3 proteolytic fragments. In other embodiments, the construct has decreased binding affinity to EBV gp350 and one or more C3 proteolytic fragments. In some embodiments, the at least three amino acid substitutions decreases the binding affinity of the CR2 portion for EBV gp350 and one or more C3 proteolytic fragments by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the complement modulator portion is a complement inhibitor. In some of these embodiments, the complement inhibitor is selected from the group consisting of: MCP, DAF, CD59, Crry, CR1, and FH. In other embodiments, the complement modulator portion is a complement activator. In some of these embodiments, the complement activator is selected from the group consisting of: human Ig isotype $G_1$ (IgG$_1$), human Ig isotype M (IgM), mouse Ig isotype $G_3$ (IgG$_3$), mouse IgM Fc, human IgG$_1$ Fc domain, human IgM Fc domain, mouse IgG$_3$ Fc domain, mouse IgM Fc domain, and CVF.

In some aspects, there is provided a soluble composition capable of targeted delivery of a complement modulator to sites of IFNα production comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least four amino acid substitutions that decrease binding affinity of the CR2 portion for one or more C3 proteolytic fragments and EBV gp350. In certain embodiments, the CR2 portion contains at least three amino acid substitutions at amino acid residues selected from the group consisting of: N11, R36, K41, Y64 and K67, further contains at least one amino acid substitution at an amino acid residue selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least two amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least three amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least four amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least five amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least six amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least seven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least eight amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least nine amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least ten amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least eleven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least twelve amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least thirteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains at least fourteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least three amino acid substitutions at amino acid residues selected from the group consisting of: N11, R36, K41, Y64 and K67, further contains fifteen amino acid substitutions at amino acid residues I9, Y29, C31, G33, T34, D56, S70, H90, D92, S93, A97, T100, N101, S109, and S128, and does not bind to, or has decreased binding affinity for, one or more C3 proteolytic fragments and EBV gp350. In some embodiments, the one or more C3 proteolytic fragments are selected from the group consisting of C3d, iC3b, C3dg, and one or more cell-bound fragments of C3b that bind to the two N-terminal SCR domains of CR2. In any of the above embodiments, the at least four amino acid substitutions may be conservative substitutions. In any of the above embodiments, the at least four amino acid substitutions may be non-conservative substitutions. In certain embodiments, the CR2 portion contains one or more substitutions in amino acids from the group consisting of: N11A, R36A, K41A, Y64A, and K67A In certain embodiments, the construct is a fusion protein. In some embodiments, the CR2 portion selectively binds to one or more proteins from the group consisting of: CD23 and IFNα. In some embodiments, the construct does not bind to EBV gp350 and one or more C3 proteolytic fragments. In other embodiments, the construct has decreased binding affinity to EBV gp350 and one or more C3 proteolytic fragments. In some embodiments, the at least four amino acid substitutions decreases the binding affinity of the CR2 portion for EBV gp350 and one or more C3 proteolytic fragments by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the complement modulator portion is a complement inhibitor. In other embodiments, some of these complement inhibitor is selected from the group consisting of: MCP, DAF, CD59, Crry, CR1, and FH. In other embodiments, the complement modulator portion is a complement activator. In some of these embodiments, the complement activator is selected from the group consisting of: human Ig isotype $G_1$ (Ig$G_1$), human Ig isotype M (IgM), mouse Ig isotype $G_3$ (Ig$G_3$), mouse IgM Fc, human Ig$G_1$ Fc domain, human IgM Fc domain, mouse Ig$G_3$ Fc domain, mouse IgM Fc domain, and CVF.

In some aspects, there is provided a soluble composition capable of targeted delivery of a complement modulator to sites of IFNα production comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least five amino acid substitutions that decrease binding affinity of the CR2 portion for one or more C3 proteolytic fragments and EBV gp350. In certain embodiments, the CR2 portion contains at least four amino acid substitutions at amino acid residues selected from the group consisting of: N11, R36, K41, Y64 and K67, further contains at least one amino acid substitution at an amino acid residue selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least two amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least three amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least four amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least five amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least six amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least seven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least eight amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least nine amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least ten amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least eleven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least twelve amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least thirteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains at least fourteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains at least four amino acid substitutions at amino acid residues selected from the group consisting of: N11, R36, K41, Y64 and K67, further contains fifteen amino acid substitutions at amino acid residues I9, Y29, C31, G33, T34, D56, S70, H90, D92, S93, A97, T100, N101, S109, and S128, and does not bind to, or has decreased binding affinity for, one or more C3 proteolytic fragments and EBV gp350. In some embodiments, the one or more C3 proteolytic fragments are selected from the group consisting of C3d, iC3b, C3dg, and one or more cell-bound fragments of C3b that bind to the two N-terminal SCR domains of CR2. In any of the above embodiments, the at least five amino acid substitutions may be conservative substitutions. In any of the above embodiments, the at least five amino acid substitutions may be non-conservative substitutions. In certain embodiments, the CR2 portion contains one or more substitutions of amino acids from the group consisting of: N11A, R36A, K41A, Y64A, and K67A In certain embodiments, the construct is a fusion protein. In some embodiments, the CR2 portion selectively binds to one or more proteins from the group consisting of: CD23 and IFNα. In some embodiments, the construct does not bind to EBV gp350 and one or more C3 proteolytic fragments. In other embodiments, the construct has decreased binding affinity to EBV gp350 and one or more C3 proteolytic fragments. In some embodiments, the at least five amino acid substitutions decreases the binding affinity of the CR2 portion for EBV gp350 and one or more C3 proteolytic fragments by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the complement modulator portion is a complement inhibitor. In some of these embodiments, the complement inhibitor is selected from the group consisting of: MCP, DAF, CD59, Crry, CR1, and FH. In other embodiments, the complement modulator portion is a complement activator. In some of these embodiments, the complement activator is selected from the group consisting of: human Ig isotype $G_1$ (IgG$_1$), human Ig isotype M (IgM), mouse Ig isotype $G_3$ (IgG$_3$), mouse IgM Fc, human IgG$_1$ Fc domain, human IgM Fc domain, mouse IgG$_3$ Fc domain, mouse IgM Fc domain, and CVF.

In some aspects, there is provided a soluble composition capable of targeted delivery of a complement modulator to sites of IFNα production comprising a construct, wherein the construct comprises: (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion; wherein the CR2 portion contains at least six amino acid substitutions that decrease binding affinity of the CR2 portion for one or more C3 proteolytic fragments and EBV gp350. In certain embodiments, the CR2 portion contains five amino acid substitutions at amino acid residues N11, R36, K41, Y64 and K67, further contains at least one amino acid substitution at an amino acid residue selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least two amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least three amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least four amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least five amino acid substitutions at amino acid residues selected from the group consisting of:

I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least six amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least seven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least eight amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least nine amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least ten amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least eleven amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least twelve amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least thirteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains at least fourteen amino acid substitutions at amino acid residues selected from the group consisting of: I9, Y29, C31, G33, T34, D56, S70, H90, D92, S93, A97, T100, N101, S109, and S128, and does not bind to, or has decreased binding affinity for, one or more C3 proteolytic fragments and EBV gp350. In certain embodiments, the CR2 portion contains five amino acid substitutions at amino acid residues N11, R36, K41, Y64 and K67, further contains fifteen amino acid substitutions at amino acid residues I9, Y29, C31, G33, T34, D56, S70, H90, D92, S93, A97, T100, N101, S109, and S128, and does not bind to, or has decreased binding affinity for, one or more C3 proteolytic fragments and EBV gp350. In some embodiments, the one or more C3 proteolytic fragments are selected from the group consisting of C3d, iC3b, C3dg, and one or more cell-bound fragments of C3b that bind to the two N-terminal SCR domains of CR2. In any of the above embodiments, the at least six amino acid substitutions may be conservative substitutions. In any of the above embodiments, the at least six amino acid substitutions may be non-conservative substitutions. In certain embodiments, the CR2 portion contains one or more substitutions of amino acids from the group consisting of: N11A, R36A, K41A, Y64A, and K67A In certain embodiments, the construct is a fusion protein. In some embodiments, the CR2 portion selectively binds to one or more proteins from the group consisting of: CD23 and IFNα. In some embodiments, the construct does not bind to EBV gp350 and one or more C3 proteolytic fragments. In other embodiments, the construct has decreased binding affinity to EBV gp350 and one or more C3 proteolytic fragments. In some embodiments, the at least six amino acid substitutions decreases the binding affinity of the CR2 portion for EBV gp350 and one or more C3 proteolytic fragments by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the complement modulator portion is a complement inhibitor. In some of these embodiments, the complement inhibitor is selected from the group consisting of: MCP, DAF, CD59, Crry, CR1, and FH. In other embodiments, the complement modulator portion is a complement activator. In some of these embodiments, the complement activator is selected from the group consisting of: human Ig isotype $G_1$ (Ig$G_1$), human Ig isotype M (IgM), mouse Ig isotype $G_3$ (Ig$G_3$), mouse IgM Fc, human Ig$G_1$ Fc domain, human IgM Fc domain, mouse Ig$G_3$ Fc domain, mouse IgM Fc domain, and CVF.

Other CR2 Substitutions for Targeted Delivery of Complement Modulators

In any embodiments of any of the compositions described herein, the CR2 portion can further contain at least one, two, three, four, five, six, seven, eight, nine, ten, or eleven additional amino acid substitutions at other positions in the CR2 portion. In certain embodiments, the CR2 portion further contains at least one amino acid substitution selected from the group consisting of: R13, Y16, A22, R28, S32, K48, K57, Y68, R83, G84, and R89. In certain embodiments, the CR2 portion further contains at least two amino acid substitutions selected from the group consisting of: R13, Y16, A22, R28, S32, K48, K57, Y68, R83, G84, and R89. In certain embodiments, the CR2 portion further contains at least three amino acid substitutions selected from the group consisting of: R13, Y16, A22, R28, S32, K48, K57, Y68, R83, G84, and R89. In certain embodiments, the CR2 portion further contains at least four amino acid substitutions selected from the group consisting of: R13, Y16, A22, R28, S32, K48, K57, Y68, R83, G84, and R89. In certain embodiments, the CR2 portion further contains at least five amino acid substitutions selected from the group consisting of: R13, Y16, A22, R28, S32, K48, K57, Y68, R83, G84, and R89. In certain embodiments, the CR2 portion further contains at least six amino acid substitutions selected from the group consisting of: R13, Y16, A22, R28, S32, K48, K57, Y68, R83, G84, and R89. In certain embodiments, the CR2 portion further contains at least seven amino acid substitutions selected from the group consisting of: R13, Y16, A22, R28, S32, K48, K57, Y68, R83, G84, and R89. In certain embodiments, the CR2 portion further contains at least eight amino acid substitutions selected from the group consisting of: R13, Y16, A22, R28, S32, K48, K57, Y68, R83, G84, and R89. In certain embodiments, the CR2 portion further contains at least nine amino acid substitutions selected from the group consisting of: R13, Y16, A22, R28, S32, K48, K57, Y68, R83, G84, and R89. In certain embodiments, the CR2 portion further contains at least ten amino acid substitutions selected from the group consisting of: R13, Y16, A22, R28, S32, K48, K57, Y68, R83, G84, and R89. In certain embodiments, the CR2 portion further contains at least eleven amino acid substitutions selected from the group consisting of: R13, Y16, A22, R28, S32, K48, K57, Y68, R83, G84, and R89. In any of the above embodiments, the at least one, two, three, four, five, six, seven, eight, nine, ten or eleven amino acid substitutions may be conservative substitutions. In any of the above embodiments, the at least one, two, three, four, five, six, seven, eight, nine, ten or eleven amino acid substitutions may be non-conservative substitutions.

Linker Proteins

In any of the embodiments described herein, the construct comprising a CR2 portion or a biologically active fragment thereof and a complement inhibitor portion comprising human CD59, mouse CD59 isoform A, mouse CD59 isoform B, mouse Crry protein, human factor H, mouse factor H, human CR1, human MCP, human DAF or mouse DAF or a biologically active fragment thereof also includes an amino acid linker sequence linking the CR2 portion and the complement inhibitor portion (e.g., human CD59, mouse CD59 isoform A, mouse CD59 isoform B, mouse Crry protein, human factor H, mouse factor H, human CR1, human MCP, human DAF or mouse DAF or a biologically active fragment thereof).

In any of the embodiments described herein, the construct comprising a CR2 portion or a biologically active fragment thereof and a complement activator portion comprising human $IgG_1$, human IgM, mouse $IgG_3$, mouse IgM, or CVF or a biologically-active fragment thereof also includes an amino acid linker sequence linking the CR2 portion and the complement activator portion (e.g., human $IgG_1$, human IgM, mouse $IgG_3$, mouse IgM, or CVF or a biologically active fragment thereof).

Examples of linker sequences are known in the art, and include, for example, $(Gly_4Ser)$, $(Gly_4Ser)_2$, $(Gly_4Ser)_3$, $(Gly_3Ser)_4$, $(SerGly_4)$, $(SerGly_4)_2$, $(SerGly_4)_3$, and $(SerGly_4)_4$. Linking sequences can also comprise "natural" linking sequences found between different domains of complement factors. For example, VSVFPLE (SEQ ID NO:26) or EYFNKYSS (SEQ ID NO:27), the linking sequence between the first two N-terminal short consensus repeat domains of human CR2, can be used. In some embodiments, the linking sequence between the fourth and the fifth N-terminal short consensus repeat domains of human CR2 (EEIF) (SEQ ID NO:28) is used. In some embodiments, the linker sequence comprises at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, or 100 amino acids, inclusive, as well as any numerical value in between these numbers.

Pharmaceutical Compositions

In another aspect, provided herein are pharmaceutical compositions comprising any of the constructs and/or fusion proteins described herein. Pharmaceutical compositions comprising any of the constructs and/or fusion proteins described herein are generally formulated as sterile, substantially isotonic pharmaceutical solutions in full compliance with all Good Manufacturing Practice (GMP) regulations of the U.S. Food and Drug Administration. In certain embodiments, the composition is free of pathogen. For injection, the pharmaceutical compositions can be in the form of liquid solutions, for example in physiologically compatible buffers such as Hank's Balanced Salt Solution, Phosphate-Buffered Saline or Ringer's solution. In addition, the pharmaceutical compositions provided herein can be in solid form and redissolved or resuspended immediately prior to use. Lyophilized compositions are also contemplated.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., fractionated oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

In certain embodiments, the compositions are formulated in accordance with routine procedures as a pharmaceutical composition adapted for injection. In certain embodiments, the pharmaceutical compositions provided herein are formulated for intravenous, intraperitoneal, or intraocular injection. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions may further comprise additional ingredients, for example preservatives, buffers, tonicity agents, antioxidants and stabilizers, nonionic wetting or clarifying agents, viscosity-increasing agents, and the like.

Suitable preservatives for use in a solution include polyquaternium-1, benzalkonium chloride, thimerosal, chlorobutanol, methyl paraben, propyl paraben, phenylethyl alcohol, disodium-EDTA, sorbic acid, benzethonium chloride, and the like. Typically (but not necessarily) such preservatives are employed at a level of from 0.001% to 1.0% by weight.

Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5.

Suitable tonicity agents include dextran 40, dextran 70, dextrose, glycerin, potassium chloride, propylene glycol, sodium chloride, and the like, such that the sodium chloride equivalent of the injectable solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

The pharmaceutical compositions may be suitable for a variety of modes of administration described herein, including for example systemic or localized administration. The pharmaceutical compositions can be in the form of injectable solutions or in a form suitable for oral administration. The pharmaceutical compositions described herein can be packaged in single unit dosages or in multidosage forms. In certain embodiments, the pharmaceutical compositions are suitable for administration to an individual, a vertebrate, a mammal, or a human by any route of administration described herein, including oral administration or intravenous injection.

Methods of the Invention
Methods of Making a Targeted Construct for Complement System Modulation Provided herein are methods for making a construct that selectively binds to one or more ligands of CR2, wherein the method comprises mutating one or more amino acids in a complement receptor 2 (CR2) portion of the construct, and wherein the construct comprises (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion. In certain embodiments, the construct is a fusion protein. In some embodiments the construct selectively binds to one or more C3 proteolytic fragments but does not bind to or has reduced binding affinity for IFNα or EBV gp350. In some embodiments, the construct selectively binds to one or more C3 proteolytic fragments and IFNα but does not bind to or has reduced binding affinity for EBV gp350. In some embodiments the construct selectively binds to one or more C3 proteolytic fragments and EBV gp350 but does not bind to or has reduced binding affinity for IFNα. In some embodiments, the construct selectively binds to IFNα but does not bind to or has reduced binding affinity for one or more C3 proteolytic fragments and EBV gp350. In some embodiments, the construct selectively binds to IFNα and EBV gp350 but does not bind to or has reduced binding affinity for one or more C3 proteolytic fragments. In some embodiments, the construct selectively binds to EBV gp350 but does not bind to or has reduced binding affinity for IFNα and one or more C3 proteolytic fragments.

In one aspect, there is provided a method for making a construct that selectively binds to one or more C3 proteolytic fragments but does not selectively bind to EBV gp350 or IFNα, wherein the method comprises (a) mutating one or more amino acids in a complement receptor 2 (CR2) portion of the construct from the group consisting of: N11, R36, K41, Y64 and K67; and (b) mutating one or more amino acids in a complement receptor 2 (CR2) portion of the construct from the group consisting of: S42 and K50, wherein the construct comprises (i) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (ii) a complement modulator portion. In some embodiments, the one or more mutations in the complement receptor 2 (CR2) portion of the construct are mutations to the amino acid alanine. In some embodiments, the method further comprises mutating one or more amino acids in the complement receptor 2 (CR2) portion of the construct selected from the group consisting of: R13, Y16, A22, R28, S32, K48, K57, Y68, R83, G84, and R89. In some embodiments, the method comprises mutating any of 1, 2, 3, 4, 5, 6, 7, 8, 9, 10, 11, 12, 13, 14, 15, 16, 17, or 18 amino acids in the complement receptor 2 (CR2) portion of the construct.

In one aspect, there is provided a method for making a construct that selectively binds to one or more C3 proteolytic fragments and EBV gp350, but does not selectively bind to IFNα, wherein the method comprises mutating one or more amino acids in a complement receptor 2 (CR2) portion of the construct from the group consisting of: S42 and K50, wherein the construct comprises (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion. In some embodiments, the one or more mutations in the complement receptor 2 (CR2) portion of the construct are mutations to the amino acid alanine. In some embodiments, the method further comprises mutating one or more amino acids in the complement receptor 2 (CR2) portion of the construct selected from the group consisting of: R13, Y16, A22, R28, S32, K48, K57, Y68, R83, G84, and R89. In some embodiments, the method comprises mutating any of 1, 2, 3, 4, 5, 6, 7, 8, 9, 10, 11, 12, or 13 amino acids in the complement receptor 2 (CR2) portion of the construct.

In one aspect, there is provided a method for making a construct that selectively binds to one or more C3 proteolytic fragments and IFNα, but does not selectively bind to EBV gp350, wherein the method comprises mutating one or more amino acids in a complement receptor 2 (CR2) portion of the construct from the group consisting of: N11, R36, K41, Y64 and K67, wherein the construct comprises (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion. In some embodiments, the one or more mutations in the complement receptor 2 (CR2) portion of the construct are mutations to the amino acid alanine. In some embodiments, the method further comprises mutating one or more amino acids in the complement receptor 2 (CR2) portion of the construct selected from the group consisting of: R13, Y16, A22, R28, S32, K48, K57, Y68, R83, G84, and R89. In some embodiments, the method comprises mutating any of 1, 2, 3, 4, 5, 6, 7, 8, 9, 10, 11, 12, 13, 14, 15, or 16 amino acids in the complement receptor 2 (CR2) portion of the construct.

In one aspect, there is provided a method for making a construct that selectively binds to IFNα but does not selectively bind to one or more C3 proteolytic fragments and EBV gp350, wherein the method comprises (a) mutating one or more amino acids in a complement receptor 2 (CR2) portion of the construct from the group consisting of: N11, R36, K41, Y64 and K67; and (b) mutating one or more amino acids in a complement receptor 2 (CR2) portion of the construct from the group consisting of: I9, Y29, C31, G33, T34, D56, S70, H90, D92, S93, A97, T100, N101, S109, and S128, wherein the construct comprises (i) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (ii) a complement modulator portion. In some embodiments, the one or more mutations in the complement receptor 2 (CR2) portion of the construct are mutations to the amino acid alanine. In some embodiments, the method further comprises mutating one or more amino acids in the complement receptor 2 (CR2) portion of the construct selected from the group consisting of: R13, Y16, A22, R28, S32, K48, K57, Y68, R83, G84, and R89. In some embodiments, the method comprises mutating any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 amino acids in the complement receptor 2 (CR2) portion of the construct.

In one aspect, there is provided a method for making a construct that selectively binds to EBV gp350 and IFNα, but does not selectively bind to one or more C3 proteolytic fragments, wherein the method comprises mutating one or more amino acids in a complement receptor 2 (CR2) portion of the construct from the group consisting of: I9, Y29, C31, G33, T34, D56, S70, H90, D92, S93, A97, T100, N101, S109, and S128, wherein the construct comprises (a) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (b) a complement modulator portion. In some embodiments, the one or more mutations in the complement receptor 2 (CR2) portion of the construct are mutations to the amino acid alanine. In some embodiments, the method further comprises mutating one or more amino acids in the complement receptor 2 (CR2) portion of the construct selected from the group consisting of: R13, Y16, A22, R28, S32, K48, K57, Y68, R83, G84, and R89. In some embodiments, the method comprises mutating any of 1, 2, 3, 4, 5, 6, 7, 8, 9, 10, 11, 12, 13, 14, 15, 16, 17, 18, 19, 20, 21, 22, 23, 24, 25, or 26 amino acids in the complement receptor 2 (CR2) portion of the construct.

In one aspect, there is provided a method for making a construct that selectively binds to EBV gp350 but does not selectively bind to one or more C3 proteolytic fragments and IFNα, wherein the method comprises (a) mutating one or more amino acids in a complement receptor 2 (CR2) portion of the construct from the group consisting of: S42 and K50; and (b) mutating one or more amino acids in a complement receptor 2 (CR2) portion of the construct from the group consisting of: I9, Y29, C31, G33, T34, D56, S70, H90, D92, S93, A97, T100, N101, S109, and S128, wherein the construct comprises (i) a complement receptor 2 (CR2) portion comprising a CR2 protein of SEQ ID NO:1 or a biologically active fragment thereof, wherein the CR2 portion contains at least the first two N-terminal SCR domains of the CR2 protein; and (ii) a complement modulator portion. In some embodiments, the one or more mutations in the complement receptor 2 (CR2) portion of the construct are mutations to the amino acid alanine. In some embodiments, the method further comprises mutating one or more amino acids in the complement receptor 2 (CR2) portion of the construct selected from the group consisting of: R13, Y16, A22, R28, S32, K48, K57, Y68, R83, G84, and R89. In some embodiments, the method comprises mutating any of 1, 2, 3, 4, 5, 6, 7, 8, 9, 10, 11, 12, 13, 14, 15, 16, 17, 18, 19, 20, 21, 22, 23, 24, 25, 26, 27, or 28 amino acids in the complement receptor 2 (CR2) portion of the construct.

Methods for Reducing the Binding Affinity for or Altering the Binding Kinetics of the CR2 Portion of the Construct for One or More Ligands In another aspect, provided herein are methods for reducing the binding affinity of the CR2 portion of any of the constructs disclosed herein for one or more CR2 ligands, the method comprising introducing one or more mutations in the amino acid sequence of the CR2 portion of the construct wherein the one or more mutations reduces binding affinity of the CR2 portion of the construct for one or more CR2 ligands.

In certain aspects, there is provided a method for reducing the binding affinity of the CR2 portion of any of the constructs disclosed herein for EBV gp350 and IFNα, the method comprising mutating at least one amino acid residue in the CR2 portion selected from the group consisting of: N11, R36, K41, S42, K50, Y64 and K67. In certain embodiments, the method comprises mutating at least two amino acid residues in the CR2 portion selected from the group consisting of: N11, R36, K41, S42, K50, Y64 and K67. In certain embodiments, the method comprises mutating at least three amino acid residues in the CR2 portion selected from the group consisting of: N11, R36, K41, S42, K50, Y64 and K67. In certain embodiments, the method comprises mutating at least four amino acid residues in the CR2 portion selected from the group consisting of: N11, R36, K41, S42, K50, Y64 and K67. In certain embodiments, the method comprises mutating at least five amino acid residues in the CR2 portion selected from the group consisting of: N11, R36, K41, S42, K50, Y64 and K67. In certain embodiments, the method comprises mutating at least six amino acid residues in the CR2 portion selected from the group consisting of: N11, R36, K41, S42, K50, Y64 and K67. In certain embodiments, the method comprises mutating seven amino acid residues in the CR2 portion selected from the group consisting of: N11, R36, K41, S42, K50, Y64 and K67. In certain embodiments, the at least one, two, three, four, five, six or seven mutations are conservative amino acid substitutions. In certain embodiments, the at least one, two, three, four, five, six or seven mutations are non-conservative amino acid substitutions. In some embodiments, the binding affinity of the construct for EBV gp350 and/or IFNα is reduced by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages.

In certain aspects, there is provided a method for reducing the binding affinity of the CR2 portion of any of the constructs disclosed herein for EBV gp350, the method comprising mutating at least one amino acid residue selected from the group consisting of N11, R36, K41, Y64 and K67. In certain embodiments, the method comprises mutating at least two amino acid residues selected from the group consisting of N11, R36, K41, Y64 and K67. In certain embodiments, the method comprises mutating at least three amino acid residues selected from the group consisting of N11, R36, K41, Y64 and K67. In certain embodiments, the method comprises mutating at least four amino acid residues selected from the group consisting of N11, R36, K41, Y64 and K67. In certain embodiments, the method comprises mutating at least five amino acid residues selected from the group consisting of N11, R36, K41, Y64 and K67. In certain embodiments, the at least one, two, three, four, or five mutations may be conservative amino acid substitutions. In certain embodiments, the at least one, two, three, four, or five mutations may be non-conservative amino acid substitutions. In some embodiments, the binding affinity of the construct for EBV gp350 is reduced by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages.

In certain aspects, there is provided a method for reducing the binding affinity of the CR2 portion of any of the constructs disclosed herein for IFNα, the method comprising mutating at least one amino acid residue selected from the group consisting of S42 and K50. In certain embodiments, the method comprises mutating two amino acid residues selected from the group consisting of S42 and K50. In certain embodiments, the at least one or two mutations may be conservative amino acid substitutions. In certain embodiments, the at least one or two mutations may be non-conservative amino acid substitutions. In some embodiments, the binding affinity of the construct for IFNα is reduced by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages.

In another aspect, the method for reducing the binding affinity of the CR2 portion of any of the constructs disclosed herein for one or more CR2 ligands further comprises mutating at least one, two, three, four, five, six, seven, eight, nine, ten, or eleven amino acids residues at other positions in the CR2 portion. In certain embodiments, the CR2 portion optionally further contains at least one amino acid substitution selected from the group consisting of: R13, Y16, A22, R28, S32, K48, K57, Y68, R83, G84, and R89. In certain embodiments, the CR2 portion optionally further contains at least two amino acid substitutions selected from the group consisting of: R13, Y16, A22, R28, S32, K48, K57, Y68, R83, G84, and R89. In certain embodiments, the CR2 portion optionally further contains at least three amino acid substitutions selected from the group consisting of: R13, Y16, A22, R28, S32, K48, K57, Y68, R83, G84, and R89. In certain embodiments, the CR2 portion optionally further contains at least four amino acid substitutions selected from the group consisting of: R13, Y16, A22, R28, S32, K48, K57, Y68, R83, G84, and R89. In certain embodiments, the CR2 portion optionally further contains at least five amino acid substitutions selected from the group consisting of: R13, Y16, A22, R28, S32, K48, K57, Y68, R83, G84, and R89. In certain embodiments, the CR2 portion optionally further contains at least six amino acid substitutions selected from the group consisting of: R13, Y16, A22, R28, S32, K48, K57, Y68, R83, G84, and R89. In certain embodiments, the CR2 portion optionally further contains at least seven amino acid substitutions selected from the group consisting of: R13, Y16, A22, R28, S32, K48, K57, Y68, R83, G84, and R89. In certain embodiments, the CR2 portion optionally further contains at least eight amino acid substitutions selected from the group consisting of: R13, Y16, A22, R28, S32, K48, K57, Y68, R83, G84, and R89. In certain embodiments, the CR2 portion optionally further contains at least nine amino acid substitutions selected from the group consisting of: R13, Y16, A22, R28, S32, K48, K57, Y68, R83, G84, and R89. In certain embodiments, the CR2 portion optionally further contains at least ten amino acid substitutions selected from the group consisting of: R13, Y16, A22, R28, S32, K48, K57, Y68, R83, G84, and R89. In certain embodiments, the CR2 portion optionally further contains eleven amino acid substitutions selected from the group consisting of: R13, Y16, A22, R28, S32, K48, K57, Y68, R83, G84, and R89. In any of the above embodiments, the at least one, two, three, four, five, six, seven, eight, nine, ten or eleven amino acid substitutions may be conservative substitutions. In any of the above embodiments, the at least one, two, three, four, five, six, seven, eight, nine, ten or eleven amino acid substitutions may be non-conservative substitutions.

In another aspect, provided herein are methods of altering the binding kinetics of the CR2 portion of the construct for C3, C3(H$_2$O) or cell surface-bound C3 proteolytic fragments, such as C3d, C3dg, and iC3b, relative to other CR2 ligands (e.g., EBV gp350 and IFNα). In certain embodiments, the altering improves the binding kinetics of the CR2 portion of the construct for cell surface-bound proteolytic fragments of C3, such as C3d, C3dg, and iC3b, and the method comprises mutating at least one amino acid residue in the CR2 portion of the construct selected from the group consisting of N11, R36, K41, S42, K50, Y64 and K67. In certain embodiments, the altering improves the binding kinetics of the CR2 portion of the construct for cell surface-bound proteolytic fragments of C3, such as C3d, C3dg, and iC3b, and the method comprises mutating at least two amino acid residues in the CR2 portion of the construct selected from the group consisting of N11, R36, K41, S42, K50, Y64 and K67. In certain embodiments, the altering improves the binding kinetics of the CR2 portion of the construct for cell surface-bound proteolytic fragments of C3, such as C3d, C3dg, and iC3b, and the method comprises mutating at least three amino acid residues in the CR2 portion of the construct selected from the group consisting of N11, R36, K41, S42, K50, Y64 and K67. In certain embodiments, the altering improves the binding kinetics of the CR2 portion of the construct for cell surface-bound proteolytic fragments of C3, such as C3d, C3dg, and iC3b, and the method comprises mutating at least four amino acid residues in the CR2 portion of the construct selected from the group consisting of N11, R36, K41, S42, K50, Y64 and K67. In certain embodiments, the altering improves the binding kinetics of the CR2 portion of the construct for cell surface-bound proteolytic fragments of C3, such as C3d, C3dg, and iC3b, and the method comprises mutating at least five amino acid residues in the CR2 portion of the construct selected from the group consisting of N11, R36, K41, S42, K50, Y64 and K67. In certain embodiments, the altering improves the binding kinetics of the CR2 portion of the construct for cell surface-bound proteolytic fragments of C3, such as C3d, C3dg, and iC3b, and the method comprises mutating at least six amino acid residues in the CR2 portion of the construct selected from the group consisting of N11, R36, K41, S42, K50, Y64 and K67. In certain embodiments, the altering improves the binding kinetics of the CR2 portion of the construct for cell surface-bound proteolytic fragments of C3, such as C3d, C3dg, and iC3b, and the method comprises mutating at least seven amino acid residues in the CR2 portion of the construct selected from the group consisting of N11, R36, K41, S42, K50, Y64 and K67. In certain embodiments, the cell surface-bound fragment of C3 is selected from the group consisting of C3d, C3dg, and iC3b. In certain embodiments, the cell surface-bound fragment of C3 is C3d. In certain embodiments, the cell surface-bound fragment of C3 is C3dg. In certain embodiments, the cell surface-bound fragment of C3 is iC3b. In certain embodiments, the at least one, two, three, four, five, six, or seven mutations may be conservative amino acid substitutions. In certain embodiments, the at least one, two, three, four, five, six, or seven mutations may be non-conservative amino acid substitutions. In some embodiments, the altering improves the binding kinetics of the CR2 portion of the construct for cell surface-bound proteolytic fragments of C3, such as C3d, C3dg, and iC3b by any of at least 20%, 25%, 30%, 35%, 40%, 45%, 50%, 55%, 60%, 65%, 70%, 75%, 80%, 85%, 90%, 95%, or 100%.

In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least one amino acid residue selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least two amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least three amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least four amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least five amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least six amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least seven amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least eight amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least nine amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least ten amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least eleven amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least twelve amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least thirteen amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating at least fourteen amino acid residues selected from the group consisting of I9, Y29, C31, G33, T34, D56, S70, H90, D92, S93, A97, T100, N101, S109, and S128. In certain aspects, the altering worsens the binding kinetics of the CR2 portion of the construct for C3, C3(H$_2$O), and/or cell surface-bound C3 proteolytic fragments, such as, but not limited to, C3d, C3dg, and iC3b, and the method comprises mutating fifteen amino acid residues selected from the group consisting of I9, Y29, C31, G33, T34, D56, S70, H90, D92, S93, A97, T100, N101, S109, and S128. In certain embodiments, the at least one, two, three, four, five, six, seven, eight, nine, ten, eleven, twelve, thirteen, fourteen, or fifteen mutations may be conservative amino acid substitutions. In certain embodiments, the at least one, two, three, four, five, six, seven, eight, nine, ten, eleven, twelve, thirteen, fourteen, or fifteen mutations may be non-conservative amino acid substitutions. In some embodiments, the altering worsens the binding kinetics of the CR2 portion of the construct for cell surface-bound proteolytic fragments of C3, such as C3d, C3dg, and iC3b by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages.

Methods of Treating Complement-Associated Diseases or Conditions

Provided herein are methods of treating a complement-associated disease or condition in an individual comprising administering to the individual any of the compositions described herein. As used herein, an "individual" can be a vertebrate, a mammal, or a human. Specifically, as used herein, a "mammal" can be a nonhuman primate, mouse, rat, pig, dog, cat, monkey, cow, or horse. It is understood that administration of the composition to the individual can have the effect of, but is not limited to, reducing the symptoms of the condition, a reduction in the severity of the condition, or the complete ablation of the condition.

Methods of Treatment by Inhibiting Complement Activity

In some aspects, there is provided a method of treating a complement-associated disease or condition in an individual comprising administering to the individual any of the compositions described herein, wherein the complement modulator portion of the composition comprises a complement inhibitor or biologically-active fragment thereof, and wherein the administration of the composition inhibits complement activity. In some embodiments, the composition selectively binds to one or more C3 proteolytic fragments but does not bind to, or has reduced binding affinity for, IFNα and EBV gp350. In some embodiments, the composition selectively binds to one or more C3 proteolytic fragments and EBV gp350 but does not bind to, or has reduced binding affinity for, IFNα. In some embodiments, the composition selectively binds to one or more C3 proteolytic fragments and IFNα but does not bind to, or has reduced binding affinity for, EBV gp350. In some embodiments, the composition selectively binds to IFNα but does not bind to, or has reduced binding affinity for, EBV gp350 and one or more C3 proteolytic fragments. In some embodiments, the composition selectively binds to IFNα and EBV gp350 but does not bind to, or has reduced binding affinity for, one or more C3 proteolytic fragments. In some embodiments, the composition selectively binds to EBV gp350 but does not bind to, or has reduced binding affinity for, one or more C3 proteolytic fragments and IFNα. In some embodiments, the one or more C3 proteolytic fragments are selected from the group consisting of C3d, iC3b, C3dg, and one or more cell-bound fragments of C3b that bind to the two N-terminal SCR domains of CR2.

In some aspects, there is provided a method of treating a complement-associated disease or condition in an individual comprising administering to the individual any of the compositions described herein, wherein the complement modulator portion of the composition comprises a complement inhibitor or biologically-active fragment thereof, wherein the administration of the composition inhibits complement activity; and wherein the complement associated disease or condition is an inflammatory condition. In some embodiments, the complement associated disease or condition can include an inflammatory condition such as, but not limited to, asthma, systemic lupus erythematosus, rheumatoid arthritis, reactive arthritis, spondylarthritis, systemic vasculitis, insulin dependent diabetes mellitus, multiple sclerosis, experimental allergic encephalomyelitis, Sjögren's syndrome, graft versus host disease, inflammatory bowel disease including Crohn's disease, ulcerative colitis, ischemia reperfusion injury, myocardial Infarction, Alzheimer's disease, transplant rejection (allogeneic and xenogeneic), thermal trauma, any immune complex-induced inflammation, glomerulonephritis, myasthenia gravis, cerebral lupus, Guillain-Barré syndrome, vasculitis, systemic sclerosis, anaphylaxis, catheter reactions, atheroma, infertility, thyroiditis, adult respitory distress syndrome (ARDS), post-bypass syndrome, hemodialysis, juvenile rheumatoid, Behçets syndrome, hemolytic anemia, pemphigus, bullous pemphigoid, stroke, atherosclerosis, and scleroderma. In some embodiments, the complement inhibitor is selected from the group consisting of: MCP, DAF, CD59, Crry, CR1, and FH. In some embodiments, the composition selectively binds to one or more C3 proteolytic fragments and EBV gp350 but does not bind to, or has reduced binding affinity for, IFNα. In some embodiments, the composition selectively binds to one or more C3 proteolytic fragments and IFNα but does not bind to, or has reduced binding affinity for, EBV gp350. In some embodiments, the composition selectively binds to IFNα but does not bind to, or has reduced binding affinity for, EBV gp350 and one or more C3 proteolytic fragments. In some embodiments, the composition selectively binds to IFNα and EBV gp350 but does not bind to, or has reduced binding affinity for, one or more C3 proteolytic fragments. In some embodiments, the composition selectively binds to EBV gp350 but does not bind to, or has reduced binding affinity for, one or more C3 proteolytic fragments and IFNα. In some embodiments, the one or more C3 proteolytic fragments are selected from the group consisting of C3d, iC3b, C3dg, and one or more cell-bound fragments of C3b that bind to the two N-terminal SCR domains of CR2.

In some aspects, there is provided a method of treating a complement-associated disease or condition in an individual comprising administering to the individual any of the compositions described herein, wherein the complement modulator portion of the composition comprises a complement inhibitor or biologically-active fragment thereof, wherein the administration of the composition inhibits complement activity, and wherein the complement associated disease or condition is a viral infection. In some embodiments, the viral infection can include, but is not limited to, Influenza virus A, Influenza virus B, Respiratory syncytial virus, Dengue virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Hantavirus. In some aspects, the complement associated disease or condition is a result of the response of an individual to a viral vector. In certain embodiments, the viral vector includes, but is not limited to, adenovirus, vaccinia virus, adeno associated virus, modified vaccinia ancara virus, cytomegalovirus, or any other viral vector known in the art. In some embodiments, the complement inhibitor is selected from the group consisting of: MCP, DAF, CD59, Crry, CR1, and FH. In some embodiments, the composition selectively binds to one or more C3 proteolytic fragments and EBV gp350 but does not bind to, or has reduced binding affinity for, IFNα. In some embodiments, the composition selectively binds to one or more C3 proteolytic fragments and IFNα but does not bind to, or has reduced binding affinity for, EBV gp350. In some embodiments, the composition selectively binds to IFNα but does not bind to, or has reduced binding affinity for, EBV gp350 and one or more C3 proteolytic fragments. In some embodiments, the composition selectively binds to IFNα and EBV gp350 but does not bind to, or has reduced binding affinity for, one or more C3 proteolytic fragments. In some embodiments, the composition selectively binds to EBV gp350 but does not bind to, or has reduced binding affinity for, one or more C3 proteolytic fragments and IFNα.

In some embodiments, the one or more C3 proteolytic fragments are selected from the group consisting of C3d, iC3b, C3dg, and one or more cell-bound fragments of C3b that bind to the two N-terminal SCR domains of CR2. In some embodiments, the CR2 portion of the composition has one or more mutations selected from the group consisting of: I9, Y29, C31, G33, T34, D56, S70, H90, D92, S93, A97, T100, N101, S109, and S128 and does not bind to, or has reduced binding efficiency for, one or more C3 proteolytic fragments. In some embodiments, the CR2 portion of the composition has one or more mutations selected from the group consisting of: N11, R36, K41, Y64 and K67 and does not bind to, or has reduced binding efficiency for, EBV gp350. In some embodiments, the CR2 portion of the composition has one or more mutations selected from the group consisting of: S42A and K50A and does not bind to, or has reduced binding efficiency for, IFNα. In some embodiments, the CR2 portion of the composition has one or more mutations selected from the group consisting of: I9, Y29, C31, G33, T34, D56, S70, H90, D92, S93, A97, T100, N101, S109, S128, N11, R36, K41, Y64 and K67 and does not bind to, or has reduced binding efficiency for, one or more C3 proteolytic fragments and EBV gp350. In some embodiments, the CR2 portion of the composition has one or more mutations selected from the group consisting of: I9, Y29, C31, G33, T34, D56, S70, H90, D92, S93, A97, T100, N101, S109, S128, S42A and K50A and does not bind to, or has reduced binding efficiency for, one or more C3 proteolytic fragments and IFNα. In some embodiments, the CR2 portion of the composition has one or more mutations selected from the group consisting of: N11, R36, K41, Y64 K67, S42A and K50A and does not bind to, or has reduced binding efficiency for, EBV gp350 and IFNα.

In some aspects, there is provided a method of treating a complement-associated disease or condition in an individual comprising administering to the individual any of the compositions described herein, wherein the complement modulator portion of the composition comprises a complement inhibitor or biologically-active fragment thereof, wherein the administration of the composition inhibits complement activity, and wherein the complement associated disease or condition is a fungal infection. It is understood in the art that *Candida* express a CR3-like protein that has similar binding properties as CR2. The *Candida* CR3-like protein appears to be involved in pathogenesis. Therefore, an embodiment of the invention is directed to a method of treating an individual with a fungal infection, wherein the treatment blocks fungal-"CR3" function as well as inhibits complement, comprising administering to a subject any of the compositions described herein, wherein the complement modulator portion of the composition comprises a complement inhibitor or biologically-active fragment thereof. In some embodiments, the complement inhibitor is selected from the group consisting of: MCP, DAF, CD59, Crry, CR1, and FH. In some embodiments, the composition selectively binds to one or more C3 proteolytic fragments and EBV gp350 but does not bind to, or has reduced binding affinity for, IFNα. In some embodiments, the composition selectively binds to one or more C3 proteolytic fragments and IFNα but does not bind to, or has reduced binding affinity for, EBV gp350. In some embodiments, the composition selectively binds to IFNα but does not bind to, or has reduced binding affinity for, EBV gp350 and one or more C3 proteolytic fragments. In some embodiments, the composition selectively binds to IFNα and EBV gp350 but does not bind to, or has reduced binding affinity for, one or more C3 proteolytic fragments. In some embodiments, the composition selectively binds to EBV gp350 but does not bind to, or has reduced binding affinity for, one or more C3 proteolytic fragments and IFNα. In some embodiments, the one or more C3 proteolytic fragments are selected from the group consisting of C3d, iC3b, C3dg, and one or more cell-bound fragments of C3b that bind to the two N-terminal SCR domains of CR2. In some embodiments, the CR2 portion of the composition has one or more mutations selected from the group consisting of: I9, Y29, C31, G33, T34, D56, S70, H90, D92, S93, A97, T100, N101, S109, and S128 and does not bind to, or has reduced binding efficiency for, one or more C3 proteolytic fragments. In some embodiments, the CR2 portion of the composition has one or more mutations selected from the group consisting of: N11, R36, K41, Y64 and K67 and does not bind to, or has reduced binding efficiency for, EBV gp350. In some embodiments, the CR2 portion of the composition has one or more mutations selected from the group consisting of: S42A and K50A and does not bind to, or has reduced binding efficiency for, IFNα. In some embodiments, the CR2 portion of the composition has one or more mutations selected from the group consisting of: I9, Y29, C31, G33, T34, D56, S70, H90, D92, S93, A97, T100, N101, S109, S128, N11, R36, K41, Y64 and K67 and does not bind to, or has reduced binding efficiency for, one or more C3 proteolytic fragments and EBV gp350. In some embodiments, the CR2 portion of the composition has one or more mutations selected from the group consisting of: I9, Y29, C31, G33, T34, D56, S70, H90, D92, S93, A97, T100, N101, S109, S128, S42A and K50A and does not bind to, or has reduced binding efficiency for, one or more C3 proteolytic fragments and IFNα. In some embodiments, the CR2 portion of the composition has one or more mutations selected from the group consisting of: N11, R36, K41, Y64 K67, S42A and K50A and does not bind to, or has reduced binding efficiency for, EBV gp350 and IFNα.

Apoptosis occurring during normal development is non-inflammatory and is involved in induction of immunological tolerance. Although apoptotic cell death can be inflammatory depending on how it is activated and in what cell types (for example, therapeutic agents that ligate Fas are able to induce inflammation), necrotic cell death results in a sustained and powerful inflammatory response mediated by released cell contents and by proinflammatory cytokines released by stimulated phagocytes. Apoptotic cells and vesicles are normally cleared by phagocytes, thus preventing the pro-inflammatory consequences of cell lysis. In this context, it has been shown that apoptotic cells and apoptotic bodies directly fix complement, and that complement can sustain an anti-inflammatory response due to opsonization and enhanced phagocytosis of apoptotic cells.

Inflammation is involved in nonspecific recruitment of immune cells that can influence innate and adaptive immune responses. Modulating complement activation during apoptosis-based tumor therapy to inhibit phagocytic uptake of apoptotic cells/bodies enhances the Inflammatory/innate immune response within the tumor environment. In addition, apoptotic cells can be a source of immunogenic self antigens and uncleared apoptotic bodies can result in auto-immunization. In addition to creating an enhanced immunostimulatory environment, modulating complement at a site in which tumor cells have been induced to undergo apoptosis further augments or triggers specific immunity against a tumor to which the host is normally tolerant.

Accordingly, in some aspects, there is provided a method of enhancing the outcome of an apoptosis-based therapy (e.g., gene therapy with adenovirus expressing Fas ligand) in an individual comprising administering to the individual any of the compositions described herein, wherein the complement modulator portion of the composition comprises a complement inhibitor or biologically-active fragment thereof and wherein the administration of the composition inhibits complement activity. In some embodiments, the complement inhibitor is selected from the group consisting of: MCP, DAF, CD59, Crry, CR1, and FH. In some embodiments, the composition selectively binds to one or more C3 proteolytic fragments and EBV gp350 but does not bind to, or has reduced binding affinity for, IFNα. In some embodiments, the composition selectively binds to one or more C3 proteolytic fragments and IFNα but does not bind to, or has reduced binding affinity for, EBV gp350. In some embodiments, the composition selectively binds to IFNα but does not bind to, or has reduced binding affinity for, EBV gp350 and one or more C3 proteolytic fragments. In some embodiments, the composition selectively binds to IFNα and EBV gp350 but does not bind to, or has reduced binding affinity for, one or more C3 proteolytic fragments. In some embodiments, the composition selectively binds to EBV gp350 but does not bind to, or has reduced binding affinity for, one or more C3 proteolytic fragments and IFNα. In some embodiments, the one or more C3 proteolytic fragments are selected from the group consisting of C3d, iC3b, C3dg, and one or more cell-bound fragments of C3b that bind to the two N-terminal SCR domains of CR2. In some embodiments, the CR2 portion of the composition has one or more mutations selected from the group consisting of: I9, Y29, C31, G33, T34, D56, S70, H90, D92, S93, A97, T100, N101, S109, and S128 and does not bind to, or has reduced binding efficiency for, one or more C3 proteolytic fragments. In some embodiments, the CR2 portion of the composition has one or more mutations selected from the group consisting of: N11, R36, K41, Y64 and K67 and does not bind to, or has reduced binding efficiency for, EBV gp350. In some embodiments, the CR2 portion of the composition has one or more mutations selected from the group consisting of: S42A and K50A and does not bind to, or has reduced binding efficiency for, IFNα. In some embodiments, the CR2 portion of the composition has one or more mutations selected from the group consisting of: I9, Y29, C31, G33, T34, D56, S70, H90, D92, S93, A97, T100, N101, S109, S128, N11, R36, K41, Y64 and K67 and does not bind to, or has reduced binding efficiency for, one or more C3 proteolytic fragments and EBV gp350. In some embodiments, the CR2 portion of the composition has one or more mutations selected from the group consisting of: I9, Y29, C31, G33, T34, D56, S70, H90, D92, S93, A97, T100, N101, S109, S128, S42A and K50A and does not bind to, or has reduced binding efficiency for, one or more C3 proteolytic fragments and IFNα. In some embodiments, the CR2 portion of the composition has one or more mutations selected from the group consisting of: N11, R36, K41, Y64 K67, S42A and K50A and does not bind to, or has reduced binding efficiency for, EBV gp350 and IFNα.

Methods of Treatment by Enhancing Complement Activity

In some aspects, there is provided a method of treating a complement-associated disease or condition in an individual comprising administering to the individual any of the compositions described herein, wherein the complement modulator portion of the composition comprises a complement activator or biologically-active fragment thereof, and wherein the administration of the composition enhances complement activity. In some embodiments, enhancing complement activity can have the effect of, but is not limited to, reducing the symptoms of the condition, a reduction in the severity of the condition, or the complete ablation of the condition. In some embodiments, the composition selectively binds to one or more C3 proteolytic fragments and EBV gp350 but does not bind to, or has reduced binding affinity for, IFNα. In some embodiments, the composition selectively binds to one or more C3 proteolytic fragments and IFNα but does not bind to, or has reduced binding affinity for, EBV gp350. In some embodiments, the composition selectively binds to IFNα but does not bind to, or has reduced binding affinity for, EBV gp350 and one or more C3 proteolytic fragments. In some embodiments, the composition selectively binds to IFNα and EBV gp350 but does not bind to, or has reduced binding affinity for, one or more C3 proteolytic fragments. In some embodiments, the composition selectively binds to EBV gp350 but does not bind to, or has reduced binding affinity for, one or more C3 proteolytic fragments and IFNα. In some embodiments, the one or more C3 proteolytic fragments are selected from the group consisting of C3d, iC3b, C3dg, and one or more cell-bound fragments of C3b that bind to the two N-terminal SCR domains of CR2.

In some aspects, there is provided a method of treating a complement-associated disease or condition in an individual comprising administering to the individual any of the compositions described herein, wherein the complement modulator portion of the composition comprises a complement activator or biologically-active fragment thereof, wherein the administration of the composition enhances complement activity, and wherein the complement-associated disease or condition is cancer. A representative but non-limiting list of cancers that the disclosed complement enhancing compositions can be used to treat includes: lymphoma, B cell lymphoma, T cell lymphoma, mycosis fungoides, multiple myeloma, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, urothelial carcinomas, adenocarcinomas, sarcomas, gliomas, high grade gliomas, blastomas, neuroblastomas, plasmacytomas, histiocytomas, adenomas, hypoxic tumors, myelomas, AIDS-related lymphomas or sarcomas, metastatic cancers, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers, testicular cancer, colon and rectal cancers, stomach cancer, prostatic cancer, Waldenstroms disease or pancreatic cancer. In other embodiments, the complement-associated disease or condition is a precancerous condition such as, but not limited to, cervical and anal dysplasias, other dysplasias, severe dysplasias, hyperplasias, atypical hyperplasias, and neoplasias. In certain embodiments, the complement activator is selected from the group consisting of: human Ig isotype $G_1$ (Ig$G_1$), human Ig isotype M (IgM), mouse Ig isotype $G_3$ (Ig$G_3$), mouse IgM Fc, human Ig$G_1$ Fc domain, human IgM Fc domain, mouse Ig$G_3$ Fc domain, mouse IgM Fc domain, and CVF. In some embodiments, the composition selectively binds to one or more C3 proteolytic fragments and EBV gp350 but does not bind to, or has reduced binding affinity for, IFNα. In some embodiments, the composition selectively binds to one or more C3 proteolytic fragments and IFNα but does not bind to, or has reduced binding affinity for, EBV gp350. In some embodiments, the composition selectively binds to IFNα but does not bind to, or has reduced binding affinity for, EBV gp350 and one or more C3 proteolytic fragments. In some embodiments, the composition selectively binds to IFNα and EBV gp350 but does not bind to, or has reduced binding affinity for, one or more C3 proteolytic fragments. In some embodiments, the composition selectively binds to EBV gp350 but does not bind to, or has reduced binding affinity for, one or more C3 proteolytic fragments and IFNα. In some embodiments, the one or more C3 proteolytic fragments are selected from the group consisting of C3d, iC3b, C3dg, and one or more cell-bound fragments of C3b that bind to the two N-terminal SCR domains of CR2. In some embodiments, the CR2 portion of the composition has one or more mutations selected from the group consisting of: I9, Y29, C31, G33, T34, D56, S70, H90, D92, S93, A97, T100, N101, S109, and S128 and does not bind to, or has reduced binding efficiency for, one or more C3 proteolytic fragments. In some embodiments, the CR2 portion of the composition has one or more mutations selected from the group consisting of: N11, R36, K41, Y64 and K67 and does not bind to, or has reduced binding efficiency for, EBV gp350. In some embodiments, the CR2 portion of the composition has one or more mutations selected from the group consisting of: S42A and K50A and does not bind to, or has reduced binding efficiency for, IFNα. In some embodiments, the CR2 portion of the composition has one or more mutations selected from the group consisting of: I9, Y29, C31, G33, T34, D56, S70, H90, D92, S93, A97, T100, N101, S109, S128, N11, R36, K41, Y64 and K67 and does not bind to, or has reduced binding efficiency for, one or more C3 proteolytic fragments and EBV gp350. In some embodiments, the CR2 portion of the composition has one or more mutations selected from the group consisting of: I9, Y29, C31, G33, T34, D56, S70, H90, D92, S93, A97, T100, N101, S109, S128, S42A and K50A and does not bind to, or has reduced binding efficiency for, one or more C3 proteolytic fragments and IFNα. In some embodiments, the CR2 portion of the composition has one or more mutations selected from the group consisting of: N11, R36, K41, Y64 K67, S42A and K50A and does not bind to, or has reduced binding efficiency for, EBV gp350 and IFNα.

In some aspects, there is provided a method of treating a complement-associated disease or condition in an individual comprising administering to the individual any of the compositions described herein, wherein the complement modulator portion of the composition comprises a complement activator or biologically-active fragment thereof, wherein the administration of the composition enhances complement activity, and wherein the complement-associated disease or condition is a viral infection. A representative but non-limiting list of viral infections that the disclosed complement enhancing compositions can be used to treat includes: Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papillomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Human T-cell Leukemia virus type-1, Hantavirus, Rubella virus, Simian Immunodeficiency virus, Human Immunodeficiency virus type-1, and Human Immunodeficiency virus type-2. In certain embodiments, the complement activator is selected from the group consisting of: human Ig isotype $G_1$ ($IgG_1$), human Ig isotype M (IgM), mouse Ig isotype $G_3$ ($IgG_3$), mouse IgM Fc, human $IgG_1$ Fc domain, human IgM Fc domain, mouse $IgG_3$ Fc domain, mouse IgM Fc domain, and CVF. In some embodiments, the composition selectively binds to one or more C3 proteolytic fragments and EBV gp350 but does not bind to, or has reduced binding affinity for, IFNα. In some embodiments, the composition selectively binds to one or more C3 proteolytic fragments and IFNα but does not bind to, or has reduced binding affinity for, EBV gp350. In some embodiments, the composition selectively binds to IFNα but does not bind to, or has reduced binding affinity for, EBV gp350 and one or more C3 proteolytic fragments. In some embodiments, the composition selectively binds to IFNα and EBV gp350 but does not bind to, or has reduced binding affinity for, one or more C3 proteolytic fragments. In some embodiments, the composition selectively binds to EBV gp350 but does not bind to, or has reduced binding affinity for, one or more C3 proteolytic fragments and IFNα. In some embodiments, the one or more C3 proteolytic fragments are selected from the group consisting of C3d, iC3b, C3dg, and one or more cell-bound fragments of C3b that bind to the two N-terminal SCR domains of CR2. In some embodiments, the CR2 portion of the composition has one or more mutations selected from the group consisting of: I9, Y29, C31, G33, T34, D56, S70, H90, D92, S93, A97, T100, N101, S109, and S128 and does not bind to, or has reduced binding efficiency for, one or more C3 proteolytic fragments. In some embodiments, the CR2 portion of the composition has one or more mutations selected from the group consisting of: N11, R36, K41, Y64 and K67 and does not bind to, or has reduced binding efficiency for, EBV gp350. In some embodiments, the CR2 portion of the composition has one or more mutations selected from the group consisting of: S42A and K50A and does not bind to, or has reduced binding efficiency for, IFNα. In some embodiments, the CR2 portion of the composition has one or more mutations selected from the group consisting of: I9, Y29, C31, G33, T34, D56, S70, H90, D92, S93, A97, T100, N101, S109, S128, N11, R36, K41, Y64 and K67 and does not bind to, or has reduced binding efficiency for, one or more C3 proteolytic fragments and EBV gp350. In some embodiments, the CR2 portion of the composition has one or more mutations selected from the group consisting of: I9, Y29, C31, G33, T34, D56, S70, H90, D92, S93, A97, T100, N101, S109, S128, S42A and K50A and does not bind to, or has reduced binding efficiency for, one or more C3 proteolytic fragments and IFNα. In some embodiments, the CR2 portion of the composition has one or more mutations selected from the group consisting of: N11, R36, K41, Y64 K67, S42A and K50A and does not bind to, or has reduced binding efficiency for, EBV gp350 and IFNα.

In some aspects, there is provided a method of treating a complement-associated disease or condition in an individual comprising administering to the individual any of the compositions described herein, wherein the complement modulator portion of the composition comprises a complement activator or biologically-active fragment thereof, wherein the administration of the composition enhances complement activity, and wherein the complement-associated disease or condition is a bacterial infection. A representative but non-limiting list of bacterial infections that the disclosed complement enhancing compositions can be used to treat includes bacterial infection by: *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsial* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neisseria meningitidis, Neisseria gonorrhea, Pseudomonas aeruginosa*, other *Pseudomonas* species, *Haemophilus Influenzae, Haemophilus ducreyi*, other *Hemophilus* species, *Clostridium tetani*, other *Clostridium* species, *Yersinia enterolitica*, and other *Yersinia* species. In certain embodiments, the complement activator is selected from the group consisting of: human Ig isotype $G_1$ ($IgG_1$), human Ig isotype M (IgM), mouse Ig isotype $G_3$ ($IgG_3$), mouse IgM Fc, human $IgG_1$ Fc domain, human IgM Fc domain, mouse $IgG_3$ Fc domain, mouse IgM Fc domain, and CVF. In some embodiments, the composition selectively binds to one or more C3 proteolytic fragments and EBV gp350 but does not bind to, or has reduced binding affinity for, IFNα. In some embodiments, the composition selectively binds to one or more C3 proteolytic fragments and IFNα but does not bind to, or has reduced binding affinity for, EBV gp350. In some embodiments, the composition selectively binds to IFNα but does not bind to, or has reduced binding affinity for, EBV gp350 and one or more C3 proteolytic fragments. In some embodiments, the composition selectively binds to IFNα and EBV gp350 but does not bind to, or has reduced binding affinity for, one or more C3 proteolytic fragments. In some embodiments, the composition selectively binds to EBV gp350 but does not bind to, or has reduced binding affinity for, one or more C3 proteolytic fragments and IFNα. In some embodiments, the one or more C3 proteolytic fragments are selected from the group consisting of C3d, iC3b, C3dg, and one or more cell-bound fragments of C3b that bind to the two N-terminal SCR domains of CR2. In some embodiments, the CR2 portion of the composition has one or more mutations selected from the group consisting of: I9, Y29, C31, G33, T34, D56, S70, H90, D92, S93, A97, T100, N101, S109, and S128 and does not bind to, or has reduced binding efficiency for, one or more C3 proteolytic fragments. In some embodiments, the CR2 portion of the composition has one or more mutations selected from the group consisting of: N11, R36, K41, Y64 and K67 and does not bind to, or has reduced binding efficiency for, EBV gp350. In some embodiments, the CR2 portion of the composition has one or more mutations selected from the group consisting of: S42A and K50A and does not bind to, or has reduced binding efficiency for, IFNα. In some embodiments, the CR2 portion of the composition has one or more mutations selected from the group consisting of: I9, Y29, C31, G33, T34, D56, S70, H90, D92, S93, A97, T100, N101, 5109, 5128, N11, R36, K41, Y64 and K67 and does not bind to, or has reduced binding efficiency for, one or more C3 proteolytic fragments and EBV gp350. In some embodiments, the CR2 portion of the composition has one or more mutations selected from the group consisting of: I9, Y29, C31, G33, T34, D56, S70, H90, D92, S93, A97, T100, N101, 5109, 5128, S42A and K50A and does not bind to, or has reduced binding efficiency for, one or more C3 proteolytic fragments and IFNα. In some embodiments, the CR2 portion of the composition has one or more mutations selected from the group consisting of: N11, R36, K41, Y64 K67, S42A and K50A and does not bind to, or has reduced binding efficiency for, EBV gp350 and IFNα.

In some aspects, there is provided a method of treating a complement-associated disease or condition in an individual comprising administering to the individual any of the compositions described herein, wherein the complement modulator portion of the composition comprises a complement activator or biologically-active fragment thereof, wherein the administration of the composition enhances complement activity, and wherein the complement-associated disease or condition is a parasitic infection. A representative but non-limiting list of parasitic infections that the disclosed complement enhancing compositions can be used to treat includes: *Toxoplasma gondii, Plasmodium falciparum, Plasmodium vivax, Plasmodium malariae*, other *Plasmodium* species., *Trypanosoma brucei, Trypanosoma cruzi, Leishmania major*, other *Leishmania* species, *Schistosoma mansoni*, other *Schistosoma* species, and *Entamoeba histolytica*. In certain embodiments, the complement activator is selected from the group consisting of: human Ig isotype $G_1$ ($IgG_1$), human Ig isotype M (IgM), mouse Ig isotype $G_3$ ($IgG_3$), mouse IgM Fc, human $IgG_1$ Fc domain, human IgM Fc domain, mouse $IgG_3$ Fc domain, mouse IgM Fc domain, and CVF. In some embodiments, the composition selectively binds to one or more C3 proteolytic fragments and EBV gp350 but does not bind to, or has reduced binding affinity for, IFNα. In some embodiments, the composition selectively binds to one or more C3 proteolytic fragments and IFNα but does not bind to, or has reduced binding affinity for, EBV gp350. In some embodiments, the composition selectively binds to IFNα but does not bind to, or has reduced binding affinity for, EBV gp350 and one or more C3 proteolytic fragments. In some embodiments, the composition selectively binds to IFNα and EBV gp350 but does not bind to, or has reduced binding affinity for, one or more C3 proteolytic fragments. In some embodiments, the composition selectively binds to EBV gp350 but does not bind to, or has reduced binding affinity for, one or more C3 proteolytic fragments and IFNα. In some embodiments, the one or more C3 proteolytic fragments are selected from the group consisting of C3d, iC3b, C3dg, and one or more cell-bound fragments of C3b that bind to the two N-terminal SCR domains of CR2. In some embodiments, the CR2 portion of the composition has one or more mutations selected from the group consisting of: I9, Y29, C31, G33, T34, D56, S70, H90, D92, S93, A97, T100, N101, S109, and S128 and does not bind to, or has reduced binding efficiency for, one or more C3 proteolytic fragments. In some embodiments, the CR2 portion of the composition has one or more mutations selected from the group consisting of: N11, R36, K41, Y64 and K67 and does not bind to, or has reduced binding efficiency for, EBV gp350. In some embodiments, the CR2 portion of the composition has one or more mutations selected from the group consisting of: S42A and K50A and does not bind to, or has reduced binding efficiency for, IFNα. In some embodiments, the CR2 portion of the composition has one or more mutations selected from the group consisting of: I9, Y29, C31, G33, T34, D56, S70, H90, D92, S93, A97, T100, N101, S109, S128, N11, R36, K41, Y64 and K67 and does not bind to, or has reduced binding efficiency for, one or more C3 proteolytic fragments and EBV gp350. In some embodiments, the CR2 portion of the composition has one or more mutations selected from the group consisting of: I9, Y29, C31, G33, T34, D56, S70, H90, D92, S93, A97, T100, N101, S109, S128, S42A and K50A and does not bind to, or has reduced binding efficiency for, one or more C3 proteolytic fragments and IFNα. In some embodiments, the CR2 portion of the composition has one or more mutations selected from the group consisting of: N11, R36, K41, Y64 K67, S42A and K50A and does not bind to, or has reduced binding efficiency for, EBV gp350 and IFNα.

In some aspects, there is provided a method of treating a complement-associated disease or condition in an individual comprising administering to the individual any of the compositions described herein, wherein the complement modulator portion of the composition comprises a complement activator or biologically-active fragment thereof, wherein the administration of the composition enhances complement activity, and wherein the complement-associated disease or condition is a fungal infection. A representative but non-limiting list of fungal infections that the disclosed complement enhancing compositions can be used to treat includes: *Candida albicans, Cryptococcus neoformans, Histoplama capsulatum, Aspergillus fumigatus, Coccidiodes immitis, Paracoccidiodes brasiliensis, Blastomyces dermitidis, Pneuomocystis carnii, Penicillium marneffi,* and *Alternaria* alternate. In certain embodiments, the complement activator is selected from the group consisting of: human Ig isotype $G_1$ (IgG$_1$), human Ig isotype M (IgM), mouse Ig isotype $G_3$ (IgG$_3$), mouse IgM Fc, human IgG$_1$ Fc domain, human IgM Fc domain, mouse IgG$_3$ Fc domain, mouse IgM Fc domain, and CVF. In some embodiments, the composition selectively binds to one or more C3 proteolytic fragments and EBV gp350 but does not bind to, or has reduced binding affinity for, IFNα. In some embodiments, the composition selectively binds to one or more C3 proteolytic fragments and IFNα but does not bind to, or has reduced binding affinity for, EBV gp350. In some embodiments, the composition selectively binds to IFNα but does not bind to, or has reduced binding affinity for, EBV gp350 and one or more C3 proteolytic fragments. In some embodiments, the composition selectively binds to IFNα and EBV gp350 but does not bind to, or has reduced binding affinity for, one or more C3 proteolytic fragments. In some embodiments, the composition selectively binds to EBV gp350 but does not bind to, or has reduced binding affinity for, one or more C3 proteolytic fragments and IFNα. In some embodiments, the one or more C3 proteolytic fragments are selected from the group consisting of C3d, iC3b, C3dg, and one or more cell-bound fragments of C3b that bind to the two N-terminal SCR domains of CR2. In some embodiments, the CR2 portion of the composition has one or more mutations selected from the group consisting of: I9, Y29, C31, G33, T34, D56, S70, H90, D92, S93, A97, T100, N101, S109, and S128 and does not bind to, or has reduced binding efficiency for, one or more C3 proteolytic fragments. In some embodiments, the CR2 portion of the composition has one or more mutations selected from the group consisting of: N11, R36, K41, Y64 and K67 and does not bind to, or has reduced binding efficiency for, EBV gp350. In some embodiments, the CR2 portion of the composition has one or more mutations selected from the group consisting of: S42A and K50A and does not bind to, or has reduced binding efficiency for, IFNα. In some embodiments, the CR2 portion of the composition has one or more mutations selected from the group consisting of: I9, Y29, C31, G33, T34, D56, S70, H90, D92, S93, A97, T100, N101, S109, S128, N11, R36, K41, Y64 and K67 and does not bind to, or has reduced binding efficiency for, one or more C3 proteolytic fragments and EBV gp350. In some embodiments, the CR2 portion of the composition has one or more mutations selected from the group consisting of: I9, Y29, C31, G33, T34, D56, S70, H90, D92, S93, A97, T100, N101, S109, S128, S42A and K50A and does not bind to, or has reduced binding efficiency for, one or more C3 proteolytic fragments and IFNα. In some embodiments, the CR2 portion of the composition has one or more mutations selected from the group consisting of: N11, R36, K41, Y64 K67, S42A and K50A and does not bind to, or has reduced binding efficiency for, EBV gp350 and IFNα.

EXAMPLES

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Identification of Amino Acid Residues Important for CR2 Binding Interactions with EBV Gp350 and IFNα

Experimental Methods

Expression and Purification of Recombinant Proteins

Human CR2 SCR1-2 for NMR and isothermal titration calorimetry ("ITC") studies was expressed in *Pichia pastoris* using a BioFlo 110 Fermenter (New Brunswick Scientific, Edison, N.J.) as previously described (46). Briefly, a single colony was grown up in 5 ml *Pichia* basal salt medium containing 1% glycerol (BMG, per liter: 85% phosphoric acid 26.7 ml, calcium sulfate 0.93 g, potassium sulfate 18.2 g, magnesium sulfate-heptahydrate 14.9 g, potassium hydroxide 4.13 g, glycerol 10.0 g, distilled, deionized water to 1 liter) overnight at 30° C. and 250 rpm, expanded to 50 ml BMG (24 hrs) and finally expanded to 300 ml BMG (24 hrs). The inoculation culture was centrifuged at 2500×g 25° C. and resuspended in 30 ml BMG. The 30 ml inoculation culture was used to inoculate 1 L of minimal *Pichia* basal salt medium containing 40 g of glycerol. Dissolved 02 concentration was maintained at 40%, the temperature at 30° C. and the pH at 5.0 using 2 M KOH. Initial feeds were batch glycerol feeds; transition to methanol was eased by a methanol injection before an exponential methanol feed profile was initiated. Methanol induction lasted for two days, after which the culture was centrifuged to remove cellular debris. The supernatant was exchanged into 10 mM formate pH 4.0 before being passed over an SP-Sepharose column (2×5 mL SP HITRAP® columns, GE Biosciences, Pittsburgh, Pa.) followed by a CR2 affinity column, generated in-house by binding GST-C3d to a GSTRAP® column (GE Biosciences, Pittsburgh, Pa.). CR2 was eluted along an increasing linear NaCl gradient, 0-1.0 M in ⅓× Phosphate Buffered Saline (PBS, 1.6 mM $MgCl_2$, 0.9 mM KCl, 0.5 mM $KH_2PO.sub_4$, 45.6 mM NaCl, 2.7 mM $Na_2HPO_4$ pH 7.4). Finally, CR2 SCR1-2 was purified by size exclusion chromatography. Purity and identity of CR2 was monitored via SDS-PAGE, Western blot analysis and mass spectrometry. Both $^{15}N$ and $^{15}N$-$^{13}C$ isotopically labeled proteins were prepared using this strategy. For 15N isotopically labeled CR2 15N-Ammonium sulfate was used. For $^{15}N$-$^{13}C$ isotopically labeled CR2 $^{15}N$-Ammonium sulfate, $^{13}C$-glycerol and $^{13}C$-methanol were used. Isotopically enriched chemicals were purchased from Isotec Inc., Miamisburg, Ohio.

Human CR2 SCR1-2 for ITC studies was generated using the pMAL-P2X expression system (PMAL® maltose protein expression system, New England Biolabs, Ipswich, Mass.) in E. coli as previously described (42, 43). Ampicillin-resistant colonies were used to start overnight cultures that were expanded to 1 L and grown at 37° C. until an $A_{600}$ of 0.3 was obtained. Cultures were induced with 0.3 mM isopropyl-β-D-thiogalactoside (IPTG) at 30° C. overnight before harvesting by centrifugation. Harvested pellets were resuspended in amylose column buffer (20 mM Tris-HCl, pH 7.4, 0.2 M NaCl, 1 mM EDTA) and lysed by sonication. Lysate was clarified by centrifugation and applied to an amylose resin column (New England Biosciences, Ipswich, Mass.). Bound MBP-CR2 SCR1-2 was eluted from the column using amylose column elution buffer (amylose column buffer plus 10 mM maltose). Finally, the MBP-CR2 SCR1-2 was purified by size exclusion chromatography. Purity and identity of MBP-CR2 was monitored via SDS-PAGE and Western blot analysis.

Human C3d for ITC studies was generated using the pGEX expression vector system (GE Healthcare, Piscataway, N.J.) in E. coli as previously described (47). Briefly, ampicillin-resistant colonies were used to start overnight cultures that were expanded to 1 L and grown at 37° C. until an A600 of 0.3 was achieved. Cultures were induced with 0.3 mM IPTG at 30° C. overnight before harvesting by centrifugation. Harvested pellets were resuspended in GST column buffer (50 mM Tris-HCl, pH 8.0, 250 mM NaCl, 1 mM EDTA) and lysed by sonication. Lysate was clarified by centrifugation and applied to a GSTRAP® column (GE Biosciences, Pittsburgh, Pa.). C3d was cleaved from the column by digesting with 50 U of thrombin overnight at 4° C. and subsequently purified by size exclusion chromatography. Purity of C3d was monitored via SDS-PAGE.

Purification of a truncated construct of EBV gp350 comprising residues 1-470 of the wild-type protein for NMR titrations and ITC studies was performed as previously described (46). gp350 was produced by infecting Sf9 insect cells with the gp350-packaged baculovirus particles (pVI-Bac Transfer vector, C-terminal polyhistidine tag) at a multiplicity of infection (MOI) of 3. The baculoviral supernatant was concentrated, buffered with 10 mM Tris-HCl with 10 mM imidazole pH 7.4 and applied to a 5 mL HITRAP® column (GE Biosciences, Pittsburgh, Pa.) and subsequently eluted with a linear imidazole gradient. Purity and identity of gp350 were monitored via SDS-PAGE and Western blot analysis.

Human IFNα for NMR titrations and ITC studies was generated using the pMAL expression vector system (New England Biolabs, Ipswich, Mass.) in E. coli as previously described (48). Ampicillin-resistant colonies were used to start overnight cultures that were expanded to 1 L and grown at 37° C. until an $A_{600}$ of 0.3 was obtained. Cultures were induced with 0.3 mM IPTG at 25° C. overnight before harvesting by centrifugation. Harvested pellets were resuspended in amylose column buffer (20 mM Tris-HCl, pH 7.4, 0.2 M NaCl, 1 mM EDTA) and lysed by sonication. Lysate was clarified by centrifugation and applied to an amylose resin column (New England Biosciences, Ipswich, Mass.). Bound MBP-IFNα was eluted from the column using amylose column elution buffer (amylose column buffer plus 10 mM maltose). After elution the MBP tag was cleaved overnight at 4° C. with Factor Xa (New England Biosciences, Ipswich, Mass.). Finally, IFNα was purified by size exclusion chromatography. Purity and identity of IFNα was monitored via SDS-PAGE and Western blot analysis.

NMR Analysis

NMR experiments were carried out on Varian 600, 800 and 900 MHz magnets housed in the Rocky Mountain Regional NMR facility at the University of Colorado Denver School of Medicine (UCDSOM) campus (600 and 900 MHz) and in the W. M. Keck High Field NMR Facility at the University of Colorado Boulder campus (800 MHz). The uniformly 15N-13C labeled SCR1-2 domains of CR2 in ⅓×PBS were used to sequentially assign the 15N-TROSY-HSQC (49) by using HNCACB (50), CBCA(CO)NH (51) and 15N edited NOESY-HSQC (52) three-dimensional spectra. The NMR data was processed with nm rPipe (53) and analyzed with ccpNMR (54). Chemical shift changes were monitored using ccpNMR by overlaying TROSY-HSQC spectra from free CR2 SCR1-2 and CR2 SCR1-2 with increasing concentrations of either EBV gp350 or IFNα.

Isothermal Titration Calorimetry ("ITC") Analysis

ITC experiments were carried out on a Microcal VP-ITC (GE Healthcare, Piscataway, N.J.) housed in the Biophysics Core facility on the UCDSOM campus. CR2 SCR1-2 in ⅓×PBS was used in titration experiments carried out at 20° C. Each titration experiment consisted of a 5 μl injection followed by 26 injections of 10 μl of graded concentrations of C3d, gp350 or IFNα. Data was analyzed using the software provided by the manufacturer (ORIGIN® graphing software, version 7.0 MicroCal) using either single site or two site binding models (55).

Chemical Shift Analysis

Figure 2:
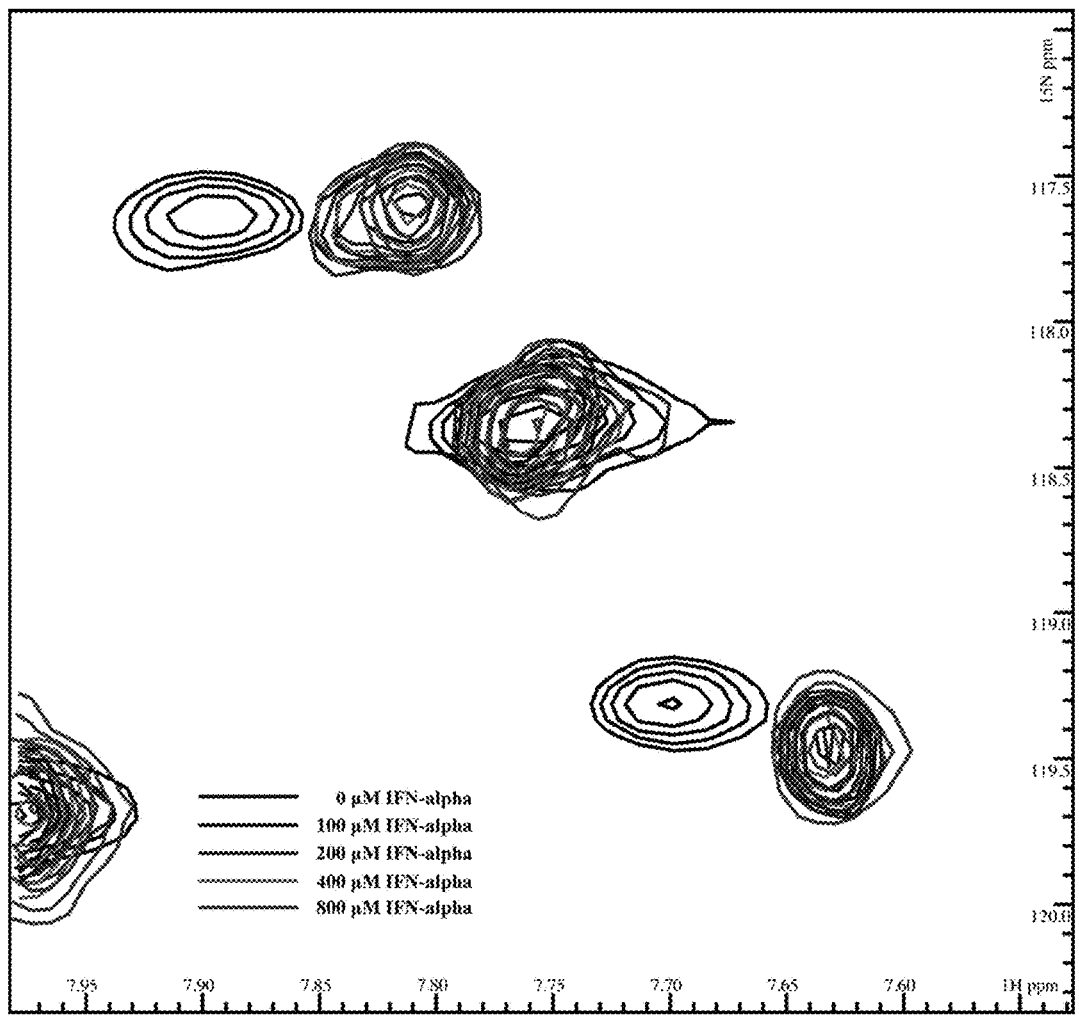
FIG. 2. NMR titration analysis reveals that SCR1 and SCR2 of CR2 are both involved in ligating IFNα. Five superimposed ¹H-¹⁵N TROSY-HSQC spectra of ¹⁵N-labeled CR2SCR1-2 (0.6 mM in ⅓×PBS) collected during titration with increasing amounts of IFNα.
Figure 3:
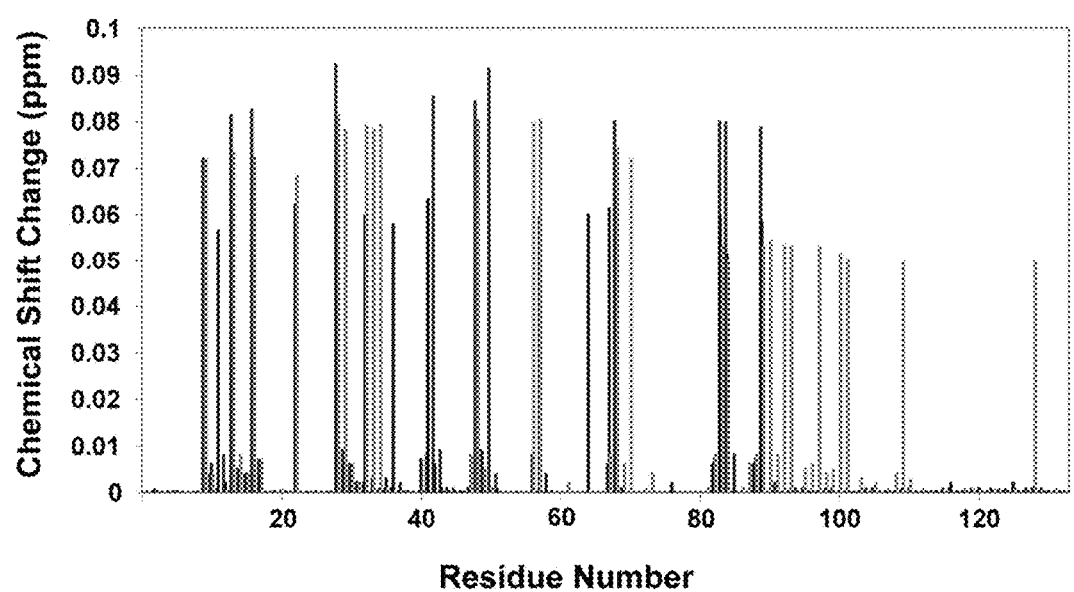
FIG. 3. NMR derived CR2-ligand binding residue comparison. Histogram illustrates chemical shift changes induced in the backbone amides of CR2 SCR1-2 upon binding C3d, IFNα or gp350.
Figure 4A:
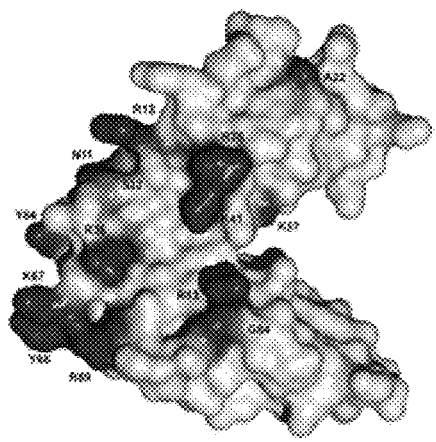
FIGS. 4A-4C. Surface representation of CR2 SCR1-2 x-ray crystal structure in its ligand-bound state (C3d not shown) with NMR-determined ligand binding residues.

Using previously described resonance assignments (48), full-length ligands EBV gp350 and IFNα were titrated into uniformly $^{15}N$-labeled CR2 SCR1-2 samples and the $^{1}H$-$^{15}N$ chemical shifts were monitored (FIGS. 1-3). Titration with EBV gp350 yielded a single mode of binding characterized by the disappearance and reappearance of specific resonances, indicative of a tight binding interaction. The residues on CR2 SCR1-2 exhibiting chemical shift changes with EBV gp350 were N11, R13, A22, R28, S32, R36, K41, K57, Y64, K67, Y68, R83, G84 and R89. Those residues encompass the SCR1, SCR2 and the inter-SCR linker region between SCR1-2 of CR2 (FIGS. 3 and 4A). Chemical shift change magnitudes are shown in FIG. 3. These results suggest that the inter-SCR linker between SCR1-2 and a ridge on SCR1 play the most important role in ligating gp350 to CR2 (FIG. 3). Since this interaction is under slow exchange on the NMR time scale, only an upper limit Kd can be calculated. The Kd was calculated using the minimal observed chemical shift difference between free and bound resonances (about 60 Hz); assuming a diffusion-limited on rate of ~$10^8$ $M^{-1}s^{-1}$, an upper limit to the binding constant was calculated as ~60 μM (Table I).

Figure 4B:
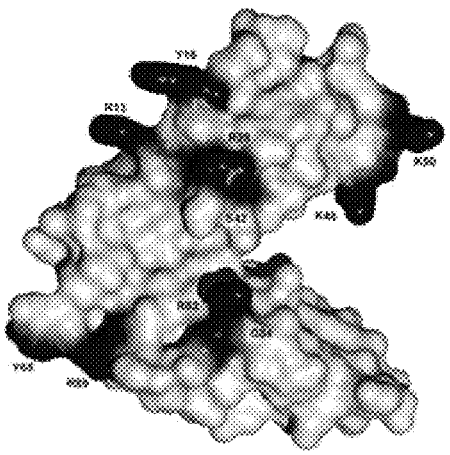

Full length IFNα was also titrated into a uniformly $^{15}$N-labeled CR2 SCR1-2 samples and the $^1$H-$^{15}$N chemical shifts were monitored (FIG. 2). Titration with the cytokine IFNα yielded a single mode of binding similar to that of gp350 ligation and thus a tight interaction. The residues on CR2 SCR1-2 exhibiting chemical shift changes are R13, Y16, R28, S42, K48, K50, Y68, R83, G84 and R89. These residues encompass the SCR1, SCR2 and the inter SCR linker region of CR2 (FIGS. 3 and 4B). Chemical shift change magnitudes are shown in FIG. 3. These results suggest that IFNα binding surface is similar to that of the C3d binding surface (FIG. 3). Similar to the gp350 chemical shift changes, the chemical shift changes for the IFNα suggest a tighter than visible via the NMR time scale; the upper limit Kd was calculated as before to be ~70 μM (Table I).

Figure 4C:
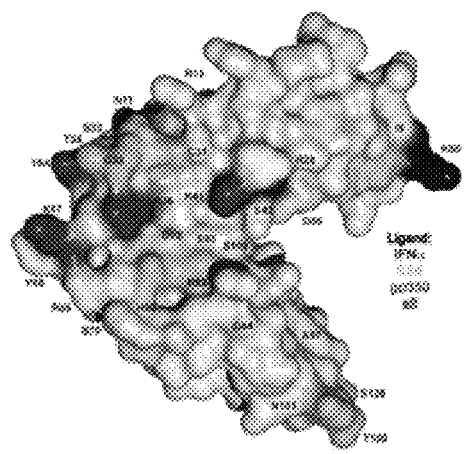

For comparison, unique and shared residues on CR2 required for ligation by C3d, gp350 and IFNα are shown in FIG. 4C. Change in magnitude of chemical shift for each ligation state is shown in FIG. 3.

Results

Chemical Shift Analysis

Using previously described resonance assignments (48), full-length ligands EBV gp350 and IFNα were titrated into uniformly $^{15}$N-labeled CR2 SCR1-2 samples and the $^1$H-$^{15}$N chemical shifts were monitored (FIGS. 1-3). Titration with EBV gp350 yielded a single mode of binding characterized by the disappearance and reappearance of specific resonances, indicative of a tight interaction. The residues on CR2 SCR1-2 exhibiting chemical shift changes are N11, R13, A22, R28, S32, R36, K41, K57, Y64, K67, Y68, R83, G84 and R89. These residues encompass the SCR1, SCR2 and the inter SCR linker region of CR2 (FIGS. 3 and 4A). Chemical shift change magnitudes are shown in FIG. 3. These results suggest that the inter SCR linker and a ridge on SCR1 play the most important role in ligating gp350 to CR2 (FIG. 3). Since this interaction is under slow exchange on the NMR time scale, only an upper limit Kd can be calculated. The Kd was calculated using the minimal observed chemical shift difference between free and bound resonances (about 60 Hz); assuming a diffusion-limited on rate of ~10×8 M−1s−1, an upper limit to the binding constant was calculated as ~60 μM (Table I).

Full length IFNα was also titrated into a uniformly $^{15}$N-labeled CR2 SCR1-2 samples and the $^1$H-$^{15}$N chemical shifts were monitored (FIG. 2). Titration with the cytokine IFNα yielded a single mode of binding similar to that of gp350 ligation and thus a tight interaction. The residues on CR2 SCR1-2 exhibiting chemical shift changes are R13, Y16, R28, S42, K48, K50, Y68, R83, G84 and R89. These residues encompass the SCR1, SCR2 and the inter-SCR linker region between SCR1-2 of CR2 (FIGS. 3 and 4B). Chemical shift change magnitudes are shown in FIG. 3. These results suggest that IFNα binding surface is similar to that of the C3d binding surface (FIG. 3). Similar to the gp350 chemical shift changes, the chemical shift changes for the IFNα suggest a tighter binding interaction than visible via the NMR time scale; the upper limit Kd was calculated as before to be ~70 μM (Table I). For comparison, unique and shared residues on CR2 required for ligation by C3d, gp350 and IFNα are shown in FIG. 4C. Change in magnitude of chemical shift for each ligation state is shown in FIG. 3.

Thermodynamics of CR2-Ligand Interactions

ITC was used to determine binding affinities of CR2-ligand interactions. Consistent with the NMR chemical shift analyses, the interaction between CR2 and C3d was determined to be a two site binding based on the goodness of fit of a two site binding model rather than a single site binding model. The two affinities are 0.13±0.05 μM and 160±20 μM. The interaction between CR2 and gp350 was fit using a single site binding model which yielded an affinity of 0.014±0.009 μM. The interaction between CR2 and IFNα was fit using a single site binding model yielding an affinity of 0.035±0.008 μM. The results of all thermodynamic parameters from NMR and ITC derived affinities are listed in Table 1.

TABLE 1

Table 1. CR2 binding constants from NMR titrations and ITC. Shown are weak and upper limit to tight binding constants for CR2-ligand interactions determined using NMR titrations monitoring chemical shift changes. Also shown are CR2-ligand binding constants determined using ITC. UL, upper limit. ITC, isothermal titration calorimetry.

| CR2 Ligand | NMR Determined $K_d$ (μM) | ITC Determined $K_d$ (μM) |
|---|---|---|
| C3d | Tight, UL 45 | 0.13 ± 0.05 |
|  | Weak 130 ± 60 | 160 ± 20 |
| gp350 | UL, 60 | 0.014 ± 0.009 |
| IFN-α | UL, 70 | 0.036 ± 0.008 |

Discussion

The studies described herein used two approaches to study CR2-ligand interactions with EBV gp350 and IFNα in the fluid phase: (1) NMR spectroscopy experiments in which full-length gp350 or IFNα was titrated into $^{15}$N labeled CR2 SCR1-2 and chemical shifts were monitored; and (2) ITC to further characterize and determine binding constants for each CR2-ligand interaction.

Previous analyses showed that both SCR1 and 2 were needed for the binding of gp350 (1, 12, 20, 56, 57). Furthermore, it was also reported that specific areas of SCR1-2 were important in binding gp350 (20, 58). These areas were between the first and second, the second and third cysteine residues of SCR1, and the second half of SCR2; amino acids included R89 to R96 and T100 to S128 in SCR2 (58). Interactions with the linker was also inferred by the finding that the introduction of a glycosylation site into the linker eliminated gp350, but not C3d binding (20, 31, 57). More recently it has been shown that there are specific interacting amino acids on the surface of CR2 SCR1-2. Mutagenesis studies suggested that residues R13, S15, R28, R36, K41, K56, K67, R83 and R89 are the most important residues in the CR2-gp350 interaction (42, 43). In addition, using HADDOCK, a model of interaction was determined where the linker region between domains one and two of gp350 interacts with the linker between SCR1 and SCR2 of CR2 (43).

However, although there have been suggestions of important regions and more recently amino acids that are important in the interaction between CR2 and gp350, there has been no physical evidence of these interactions occurring. The data described herein now illustrates amino acid residues important for the CR2-gp350 interaction (FIG. 4A). Residues determined to be important to the CR2-gp350 interaction are N11, R13, A22, R28, S32, R36, K41, K57, Y64, K67, Y68, R83, G84 and R89. Since there are multiple interactions within the linker region it is possible to imagine a rearrangement of SCR domains about the linker region upon binding gp350 and thus allowing for all contact points to be met. If that is the case, some of these residues identified herein as important for interaction upon binding might be involved in structural rearrangement upon binding and not intimate amino acid contact sites. Some resonances disappear due to the large size of the ligated complex, approximately 110 kDa, and the resultant increased tumbling time; therefore, alternative labeling techniques are necessary to observe such resonances.

This data appears to confirm that the linker region is important in the CR2-gp350 interaction. The linker interaction has been shown to be important in mutagenesis-derived data as well as in the soft dock model from HADDOCK (43). The linker region between SCR1 and SCR2 is eight amino acids, one of the longest in SCR-containing proteins, and thus is likely to be flexible enough to mediate multiple ligand interactions. Unlike the CR2-C3d interaction, our data suggests that two residues in the linker region, K67 and Y68, are important in the CR2-gp350 interaction. Thus with both a charged residue, K67, and a hydroxyl-containing residue, Y68, it is likely that the interaction with the linker is stronger in the CR2-gp350 interaction than with the CR2-C3d interaction. This information provides a start to defining how CR2 can mediate multiple specific ligand interactions.

As with the CR2-C3d interaction (59, 60), the CR2-gp350 interaction is likely driven largely by electrostatic interactions as is evident by the large number of charged residues among those important in the CR2-gp350 interaction. The majority of these charged residues are found on SCR1, suggesting that this domain plays a more significant role in the CR2-gp350 interaction. Interestingly R83 was also determined to be important in the CR2-gp350, although many other residues around R83 were not shown to exhibit changes in chemical shift during the CR2-C3d interaction. This data, along with the weak interaction found in the CR2-C3d interaction could signify that the R83 interaction is more important in the initial electrostatic attraction of gp350 to CR2 than to significant amino-acid contacts. The charged residues that were identified in this study agree with the HADDOCK model (42, 43). Again, as with the CR2-C3d NMR binding map we have found that there are more residues than just charged residues involved in the CR2-gp350 interaction. Specifically, three hydroxyl-containing amino acids (S32, Y64 and Y68) are important in the CR2-gp350 interaction. These side chain interactions are likely hydrogen bond interactions. This new data suggests that the CR2-gp350 and CR2-C3d binding sites are likely similar which explains why the ligands cross compete, yet there are substantial differences which begin to explain how selective binding occurs.

Figure 5:
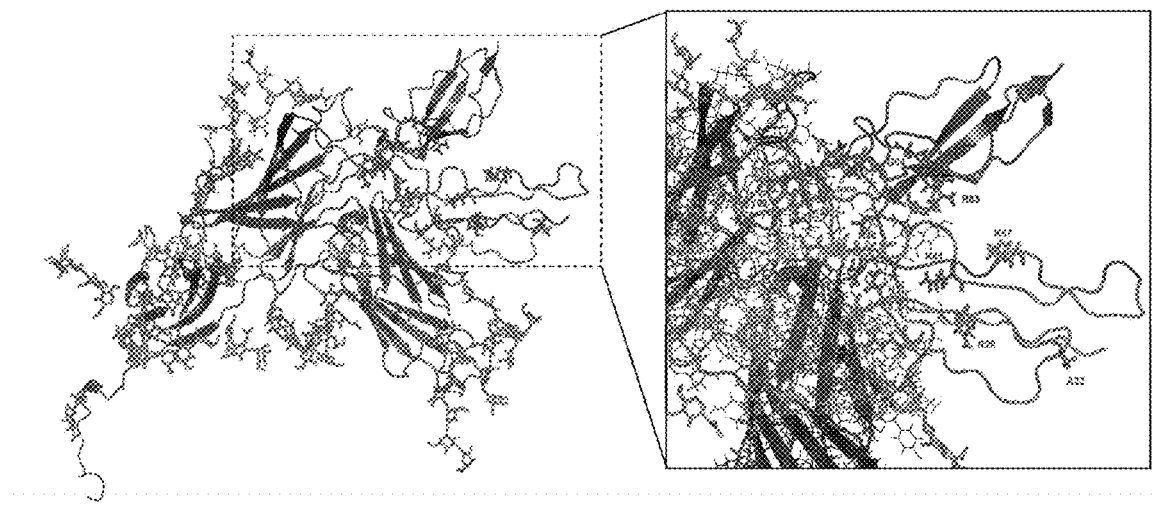
FIG. 5. HADDOCK CR2-gp350 docking model with NMR derived CR2-gp350 ligand binding residues highlighted. Model from Young, et al (43). Black ribbons represent gp350 and light grey represents glycosyl-groups that decorate the surface of gp350. Dark grey ribbons represent CR2 SCR1-2. Inset, magnified view of theoretical side-chain interactions between NMR derived binding residues and gp350 mapped on the docking model of Young, et al.

The HADDOCK model fits well with the NMR determined CR2-gp350 binding residues (FIG. 5). All but two residues, K57 and A22, are found within the hypothetical binding face derived from the HADDOCK model. The A22 chemical shift could likely be due to a slight conformation change in SCR1 upon CR2 binding gp350. Whereas the K57 interaction described by NMR could be used to drive a different and potentially lower energy docking model, as it was not utilized as an active residue in the simulated docking approach of Young, et al (43).

The CR2-IFNα interaction has been characterized in several ways. The first started with investigating sequence similarities between proposed CR2 binding sites on C3d and gp350 (19). To further confirm the potential binding interaction, antibodies raised against peptide sequences of the proposed CR2 binding site on IFNα were found to inhibit the CR2-C3d interaction in cell binding assays. It was also found that IFNα binding to CR2 inhibits CR2-C3d complex formation in cell-binding assays. In addition, it was found that IFNα inhibited the capping of CR2 by gp350, thus acting as an anti-viral inhibitor of early phase infection from EBV (18). More recently a biophysical study has been completed on the thermodynamic properties of CR2-ligand interactions, thus indicating the physical binding of CR2 and IFNα (17). The data presented herein further defines a binding site or binding surface for the CR2-IFNα interaction. Using NMR titration studies, the following amino acids were identified as being involved in the CR2-IFNα interaction—R13, Y16, R28, S42, K48, K50, Y68, R83, G84 and R89.

As with other CR2-ligand interactions, the CR2-IFNα interaction is largely driven by electrostatic interactions. The CR2-IFNα interaction is likely the closest related to the C3d interaction, since the proposed CR2 binding motifs of C3d and IFNα are the closest. In addition, the same linker region residue, Y68, appears to undergo significant perturbations upon addition of either C3d and IFNα, as well as the same overall layout of residues involved in both interactions (FIG. 4C).

Thermodynamic studies of CR2-ligand interactions have yielded slightly differing results (Table 2). As reported previously, the CR2-C3d interaction has been described as either being a two site or a single site binding interaction (17, 48). The ITC data presented herein best fit a two-site model with a weaker Kd of 160 µM and a tighter interaction of 0.13 µM. This Kd is fairly close to the previously determined Kd from a surface plasmon resonance (SPR)-based biophysical study (17). Using ITC, we are now able for the first time to measure in the fluid phase the two separate affinities for the two unique binding events. The CR2-C3d interaction is unique in that all other characterized CR2-ligand interactions fit a simple one to one binding isotherm. In contrast, the current ITC study of the CR2-gp350 interaction best fit a single binding isotherm with a Kd of 0.014 µM, an affinity only slightly tighter than the previously reported Kd of 0.077 µM determined by SPR. The difference in affinities here could be due to the differing experimental conditions of the respective studies. Finally, the ITC data for the CR2-IFNα interaction best fit a single binding isotherm with a Kd of 0.036 µM, an affinity in excellent agreement with the previously reported Kd of 0.042 µM determined by SPR. Again, the difference is likely due to the difference in buffers used as well as differences in each assay, with the ITC experiments using CR2 and IFNα purely in solution, while the SPR studies used CR2 fixed to a solid support. The rank order of binding strength makes sense in that both IFNα and gp350 binding both inhibit C3d binding to CR2, which has been previously reported (17, 18).

TABLE 2

Table 2. Comparison of CR2 ligand binding residues. Shown are residues involved in each CR2-ligand binding interaction. Residues with an asterisk are unique to the respective binding interaction.

| CR2-C3d | CR2-gp350 | CR2-IFN-α |
|---------|-----------|-----------|
| I9*     |           |           |
|         | N11*      |           |
| R13     | R13       |           |
| Y16     |           |           |
| A22     | A22       |           |
| R28     | R28       |           |
| Y29*    |           |           |
| C31*    |           |           |

TABLE 2-continued

Table 2. Comparison of CR2 ligand binding residues. Shown are residues involved in each CR2-ligand binding interaction. Residues with an asterisk are unique to the respective binding interaction.

| CR2-C3d | CR2-gp350 | CR2-IFN-α |
|---|---|---|
| S32 | S32 | |
| G33* | | |
| T34* | | |
| | R36* | |
| | K41* | |
| | | S42* |
| K48 | K48 | |
| | | K50* |
| D56* | | |
| K57 | K57 | |
| | Y64* | |
| | K67* | |
| Y68 | Y68 | Y68 |
| S70* | | |
| R83 | R83 | R83 |
| G84 | G84 | G84 |
| R89 | R89 | R89 |
| H90* | | |
| D92* | | |
| S93* | | |
| A97* | | |
| T100* | | |
| N101* | | |
| S109* | | |
| S128* | | |

REFERENCES

1. Fingeroth, J. D., Clabby, M. L., and Strominger, J. D. (1988) *J. Virol.* 62, 1442-1447.
2. Fujisaku, A., Harley, J. B., Frank, M. B., Gruner, B. A., Frazier, B., and Holers, V. M. (1989) *J. Biol. Chem.* 264, 2118-2125.
3. Moore, M. D., Cooper, N. R., Tack, B. F., and Nemerow, G. R. (1987) *Proc. Nat'l Acad. Sci. USA* 84, 9194-9198.
4. Weis, J. J., Fearon, D. T., Klickstein, L. B., Wong, W. W., Richards, S. A., de Bruyn Kops, A., Smith, J. A., and Weis, J. H. (1986) *Proc. Nat'l Acad. Sci. USA* 83, 5639-5643.
5. Weis, J. J., Toothaker, L. E., Smith, J. A., Weis, J. H., and Fearon, D. T. (1988) *J. Exp. Med.* 167, 1047-1066.
6. Ahearn, J. M., and Fearon, D. T. (1989) *Adv. Immunol.* 46, 183-219.
7. Cooper, N. R., Moore, M. D., and Nemerow, G. R. (1988) *Ann. Rev. Immunol.* 6, 85-113.
8. Holers, V. M. (1995) *Mosby*, 363-391.
9. Tolnay, M., and Tsokos, G. C. (1998) *Clin. Immunol. Immunopathol.* 88, 123-132.
10. Lida, K., Nadler, L., and Nussenzweig, V. (1983) *J. Exp. Med.* 158, 1021-1033.
11. Weis, J. J., Tedder, T. F., and Fearon, D. T. (1984) *Proc. Nat'l Acad. Sci. USA* 81, 881-885.
12. Fingeroth, J. D., Weis, J. J., Tedder, T. F., Strominger, J. L., Biro, P. A., and Fearon, D. T. (1984) *Proc. Nat'l Acad. Sci. USA* 81, 4510-4514.
13. Nemerow, G. R., Houghten, R. A., Moore, M. D., and Cooper, N. R. (1989) *Cell* 56, 369-377.
14. Nemerow, G. R., Wolfert, R., McNaughton, M. E., and Cooper, N. R. (1985) *J. Virol.* 55, 347-351.
15. Aubry, J. P., Pochon, S., Gauchat, J. F., Nueda-Marin, A., Holers, V. M., Graber, P., Siegfried, C., and Bonnefoy, J. Y. (1994) *J. Immunol.* 152, 5806-5813.
16. Aubry, J. P., Pochon, S., Graber, P., Jansen, K. U., and Bonnefoy, J. Y. (1992) *Nature* 358, 505-507.
17. Asokan, R., Hua, J., Young, K. A., Gould, H. J., Hannan, J. P., Kraus, D. M., Szakonyi, G., Grundy, G. J., Chen, X. S., Crow, M. K., and Holers, V. M. (2006) *J. Immunol.* 177, 383-394.
18. Delcayre, A. X., Lotz, M., and Lernhardt, W. (1993) *J. Virol.* 67, 2918-2921.
19. Delcayre, A. X., Salas, F., Mathur, S., Kovats, K., Lotz, M., and Lernhardt, W. (1991) *EMBO J.* 10, 919-926.
20. Martin, D. R., Yuryev, A., Kalli, K. R., Fearon, D. T., and Ahearn, J. M. (1991) *J. Exp. Med.* 174, 1299-1311.
21. Tuveson, D. A., Ahearn, J. M., Matsumoto, A. K., and Fearon, D. T. (1991) *J. Exp. Med.* 173, 1083-1089.
22. Bohnsack, J. F., and Cooper, N. R. (1988) *J. Immunol.* 141, 2569-2576.
23. Carter, R. H., and Fearon, D. T. (1989) *J. Immunol.* 143, 1755-17608.
24. Carter, R. H., and Fearon, D. T. (1992) *Science* 256, 105-107.
25. Carter, R. H., Spycher, M. O., Ng, Y. C., Hoffman, R., and Fearon, D. T. (1988) *J. Immunol.* 141, 457-463.
26. Dempsey, P. W., Allison, M. E., Akkaraju, S., Goodnow, C. C., and Fearon, D. T. (1996) Science 271, 348-350.
27. Luxembourg, A. T., and Cooper, N. R. (1994) *J. Immunol.* 153, 4448-4457.
28. Lyubchenko, T., dal Porto, J., Cambier, J. C., and Holers, V. M. (2005) *J. Immunol.* 174, 3264-3272.
29. Ahearn, J. M., Hayward, S. D., Hickey, J. C., and Fearon, D. T. (1988) *Proc. Nat'l Acad. Sci. USA* 85, 9307-9311.
30. Tanner, J., Weis, J., Fearon, D., Whang, Y., and Kieff, E. (1987) *Cell* 50, 203-213.
31. Lowell, C. A., Klickstein, L. B., Carter, R. H., Mitchell, J. A., Fearon, D. T., and Ahearn, J. M. (1989) *J. Exp. Med.* 170, 1931-1946.
32. Moore, M. D., DiScipio, R. G., Cooper, N. R., and Nemerow, G. R. (1989) *J. Biol. Chem.* 264, 20576-20582.
33. Nemerow, G. R., Mold, C., Schwend, V. K., Tollefson, V., and Cooper, N. R. (1987) *J. Virol* 61, 1416-1420.
34. Mullen, M. M., Haan, K. M., Longnecker, R., and Jardetzky, T. S. (2002) *Mol. Cell.* 9, 375-385.
35. Spriggs, M. K., Armitage, R. J., Comeau, M. R., Strockbine, L., Farrah, T., Macduff, B., Ulrich, D., Alderson, M. R., Mullberg, J., and Cohen, J. I. (1996) *J. Virol.* 70, 5557-5563.
36. Haan, K. M., Lee, S. K., and Longnecker, R. (2001) *Virology* 290, 106-114.
37. Haddad, R. S., and Hutt-Fletcher, L. M. (1989) *J. Virol.* 63, 4998-5005.
38. Molesworth, S. J., Lake, C. M., Borza, C. M., Turk, S. M., and Hutt-Fletcher, L. M. (2000) *J. Virol.* 74, 6324-6332.
39. Baechler, E. C., Batliwalla, F. M., Karypis, G., Gaffney, P. M., Ortmann, W. A., Espe, K. J., Shark, K. B., Grande, W. J., Hughes, K. M., Kapur, V., Gregersen, P. K., and Behrens, T. W. (2003) *Proc. Nat'l Acad. Sci. USA* 100, 2610-2615.
40. Santiago-Raber, M. L., Baccala, R., Haraldsson, K. M., Choubey, D., Stewart, T. A., Kono, D. H., and Theofilopoulos, A. N. (2003) *J. Exp. Med.* 197, 777-788.
41. Takahashi, K., Kozono, Y., Waldschmidt, T. J., Berthiaume, D., Quigg, R. J., Baron, A., and Holers, V. M. (1997) *J. Immunol.* 159, 1557-1569.
42. Young, K. A., Chen, X. S., Holers, V. M., and Hannan, J. P. (2007) *J. Biol. Chem.* 282, 36614-36625.
43. Young, K. A., Herbert, A. P., Barlow, P. N., Holers, V. M., and Hannan, J. P. (2008) *J. Virol.*

44. Dominguez, C., Boelens, R., and Bonvin, A. M. (2003) *J. Am. Chem. Soc.* 125, 1731-1737.
45. Szakonyi, G., Klein, M. G., Hannan, J. P., Young, K. A., Ma, R. Z., Asokan, R., Holers, V. M., and Chen, X. S. (2006) *Nature Struct. Mol. Biol.* 13, 996-1001.
46. Guthridge, J. M., Rakstang, J. K., Young, K. A., Hinshelwood, J., Aslam, M., Robertson, A., Gipson, M. G., Sarrias, M. R., Moore, W. T., Meagher, M., Karp, D., Lambris, J. D., Perkins, S. J., and Holers, V. M. (2001) *Biochemistry* 40, 5931-59419.
47. Hannan, J. P., Young, K. A., Guthridge, J. M., Asokan, R., Szakonyi, G., Chen, X. S., and Holers, V. M. (2005) *J. Mol. Biol.* 346, 845-858.
48. Kovacs, J. M., Hannan, J. P., Eisenmesser, E. Z., and Holers, V. M. (2009) *J. Biol. Chem.* 284, 9513-9520.
49. Pervushin, K., Riek, R., Wider, G., and Wuthrich, K. (1997) *Proc. Nat'l Acad. Sci. USA* 94, 12366-12371.
50. Wittkekind, M. a. L. M. (1993) *J. Magn. Reson.* 101, 201-205.
51. Grzesiek, S. a. A. B. (1992) *J. Magn. Reson.* 96, 432-440.
52. Zuiderweg, E. R., and Fesik, S. W. (1989) *Biochemistry* 28, 2387-2391.
53. Delaglio, F., Grzesiek, S., Vuister, G. W., Zhu, G., Pfeifer, J., and Bax, A. (1995) *J. Biomol. NMR* 6, 277-293.
54. Vranken, W. F., Boucher, W., Stevens, T. J., Fogh, R. H., Pajon, A., Llinas, M., Ulrich, E. L., Markley, J. L., Ionides, J., and Laue, E. D. (2005) *Proteins* 59, 687-696.
55. Wiseman, T., Williston, S., Brandts, J. F., and Lin, L. N. (1989) *Anal. Biochem.* 179, 131-137.
56. Carel, J. C., Myones, B. L., Frazier, B., and Holers, V. M. (1990) *J. Biol. Chem.* 265, 12293-12299.
57. Prota, A. E., Sage, D. R., Stehle, T., and Fingeroth, J. D. (2002) *Proc. Nat'l Acad. Sci. USA* 99, 10641-10646.
58. Molina, H., Brenner, C., Jacobi, S., Gorka, J., Carel, J. C., Kinoshita, T., and Holers, V. M. (1991) *J. Biol. Chem.* 266, 12173-12179.
59. Morikis, D., and Lambris, J. D. (2004) *J. Immunol.* 172, 7537-7547.
60. Zhang, L., Mallik, B., and Morikis, D. (2007) *J. Mol. Biol.* 369, 567-583.

Example 2

Binding Assays

Experimental Methods

Expression and Purification of Recombinant Proteins.

Native human and mutagenized CR2 SCR1-2 for binding studies is expressed in *Pichia pastoris* using a BioFlo 110 Fermenter (New Brunswick Scientific, Edison, N.J.) as previously described (46) and as set forth in Example 1 above. Briefly, a single colony is grown up in 5 ml *Pichia* basal salt medium containing 1% glycerol (BMG, per liter: 85% phosphoric acid 26.7 ml, calcium sulfate 0.93 g, potassium sulfate 18.2 g, magnesium sulfate-7H$_2$O 14.9 g, potassium hydroxide 4.13 g, glycerol 10.0 g, distilled, deionized water to 1 liter) overnight at 30° C. and 250 rpm, expanded to 50 ml BMG (24 hrs) and finally expanded to 300 ml BMG (24 hrs). The inoculation culture is centrifuged at 2500×g 25° C. and resuspended in 30 ml BMG. The 30 ml inoculation culture is used to inoculate 1 L of minimal *Pichia* basal medium containing 40 g of glycerol. Dissolved O$_2$ concentration is maintained at 40%, the temperature at 30° C. and the pH at 5.0 using 2 M KOH. Initial feeds are batch glycerol feeds; transition to methanol is eased by a methanol injection before an exponential methanol feed profile is initiated. Methanol induction lasts for two days, after which the culture is centrifuged to remove cellular debris. The supernatant is exchanged into 10 mM Formate pH 4.0 before being passed over an SP-Sepharose column (2×5 mL SP-HITRAP® columns, GE Biosciences, Pittsburgh, Pa.) followed by a CR2 affinity column, generated in-house by binding GST-C3d to a GSTRAP® column (GE Biosciences, Pittsburgh, Pa.). CR2 is eluted along an increasing linear NaCl gradient, 0-1.0 M in ⅓× Phosphate Buffered Saline (PBS, 1.6 mM MgCl$_2$, 0.9 mM KCl, 0.5 mM KH$_2$PO$_4$, 45.6 mM NaCl, 2.7 mM Na$_2$HPO$_4$ pH 7.4). Finally, native human and mutant CR2 SCR1-2 is purified by size exclusion chromatography. Purity and identity of CR2 is monitored via SDS-PAGE, Western blot analysis and mass spectrometry.

Human C3d for binding studies is generated using the pGEX expression system (GE Healthcare, Piscataway, N.J.) in *E. coli* as previously described (47) and as set forth in Example 1 above. Briefly, ampicillin-resistant colonies are used to start overnight cultures that are expanded to 1 L and grown at 37° C. until an A$_{600}$ of 0.3 is achieved. Cultures are induced with 0.3 mM IPTG at 30° C. overnight before harvesting by centrifugation. Harvested pellets are resuspended in GST column buffer (50 mM Tris-HCl, pH 8.0, 250 mM NaCl, 1 mM EDTA) and lysed by sonication. Lysate is clarified by centrifugation and applied to a GSTRAP® column (GE Biosciences, Pittsburgh, Pa.). C3d is cleaved from the column by digesting with 50 U of thrombin overnight at 4° C. and subsequently purified by size exclusion chromatography. Purity of C3d is monitored via SDS-PAGE.

EBV gp350 is isolated from infected cells in culture by immunoaffinity chromatography using commercially available anti-gp350 antibodies and standard procedures. Human IFNα is purchased from commercial suppliers.

Binding Assays.

Binding of native human CR2 SCR1-2 to EBV gp350, IFNα, and C3d is compared to that of human CR2 SCR1-2 variants containing one or more mutations in amino acids determined to be essential for binding interactions between CR2 and either EBV gp350 or IFNα by enzyme-linked immunosorbent assay (ELISA). Initial binding assays are performed with alanine-containing CR2 variants because it eliminates the side chain beyond the β-carbon of the amino acid without altering the main chain conformation (as glycine or proline sometimes does) or imposing extreme electrostatic or steric effects. The following CR2 SCR1-2 variants are tested for binding to EBV gp350 and to C3d in separate experiments: SCR1-2 N11A, SCR1-2 N11A+R36A, SCR1-2 N11A+R36A+K41A, SCR1-2 N11A+R36A+K41A+Y64A, and SCR1-2 N11A+R36A+K41A+Y64A+K67A. The following CR2 SCR1-2 variants are tested for binding to IFNα and C3d in separate experiments: S42A and S42A+K50A. The effect of the amino acid substitutions on CR2 binding kinetics and other properties (e.g., binding specificity) is assessed by comparing the binding of CR2 SCR1-2 variants to either EBV gp350 or IFNα and C3d to binding of native CR2 SCR1-2 to the same ligands. Alternative conservative or non-conservative amino acid substitutions are tested in subsequent experiments.

Microwell ELISA plates (Corning Life Sciences, New York, N.Y., USA) are coated overnight at 4° C. with an appropriate amount of purified EBV gp350, IFNα, or C3d obtained as described above in 0.1 M NaHCO$_3$, pH 8.6. The coated plates are then washed with 1×PBS three times for one minute each, and then incubated with 200 μl of blocking solution (5 mg/ml bovine serum albumin (BSA) in PBST) at 37° C. for 1 hour. Each well is washed with PBST (80 mM Na$_2$HPO$_4$, 20 mM NaH$_2$PO$_4$, 100 mM NaCl, 0.05%-0.1% (v/v) Tween-20) six times for one minute each. Next, the plates are incubated with increasing concentrations of native human CR2 SCR1-2 and various CR2 SCR1-2 variants in PBS for 1 hour and 30 minutes at 37° C.

After the binding reaction is complete, the plates are again washed with PBST six times for one minute each. Next, the plates are incubated with anti-CR2 primary antibody, washed six times for one minute each with blocking solution, and then incubated with the secondary antibody, horseradish peroxidase-conjugated mouse anti-human IgG specific for Fcγ (Jackson ImmunoResearch Laboratories, Inc.) diluted 1:10,000 in PBST+5 mg/ml BSA, at room temperature for 1 hour. The plates are again washed six times with PBST+5 mg/ml BSA at room temperature, and developed by the addition of 100 μl of 3,3',5,5'-tetramethylbenzidine (TMB) solution, prepared in 50 mM citrate phosphate. After the addition of the TMB solution, the plates are incubated for thirty minutes at room temperature, and then absorbance is measured at 450 nm with an MRX Microplate Reader (Dynex Technologies) according to the manufacturer's instructions. Binding curves are constructed from the raw data, and binding affinities are estimated.

Alternatively, binding affinities are determined more precisely by surface plasmon resonance (SPR) analysis using, for example, a BIACORE® 4000 SPR system (protein binding throughput system, Biacore Life Sciences, GE Healthcare, Piscataway, N.J.) Like the ELISA, microwell plates are coated with either EBV gp350, IFNα, or C3d, and then incubated with increasing concentrations of native human CR2 SCR1-2 or the CR2 SCR1-2 variants. Unlike ELISAs, however, SPR measures binding affinities directly, and does not require use of a detectable label.

The SCR1-2 N11A, SCR1-2 N11A+R36A, SCR1-2 N11A+R36A+K41A, SCR1-2 N11A+R36A+K41A+Y64A, and SCR1-2 N11A+R36A+K41A+Y64A+K67A variants are tested for binding affinity for EBV gp350 and are observed to have progressively less binding affinity for EBV gp350 while maintaining essentially the same binding affinity for C3d as native CR2 SCR1-2. The SCR1-2 S42A and SCR1-2 S42A+K50A variants are tested for binding affinity for IFNα and are observed to have progressively less binding affinity for IFNα while maintaining essentially the same binding affinity for C3d as native CR2 SCR1-2.

SEQUENCES

SEQ ID NO: 1 [complete amino acid sequence of human complement receptor 2 (CR2)]:
MGAAGLLGVFLALVAPGVLGISCGSPPPILNGRISYYSTPIAVGTVIRYSCSGTFRLIGE

KSLLCITKDKVDGTWDKPAPKCEYFNKYSSCPEPIVPGGYKIRGSTPYRHGDSVTFAC

KTNFSMNGNKSVWCQANNMWGPTRLPTCVSVFPLECPALPMIHNGHHTSENVGSIA

PGLSVTYSCESGYLLVGEKIINCLSSGKWSAVPPTCEEARCKSLGRFPNGKVKEPPILR

VGVTANFFCDEGYRLQGPPSSRCVIAGQGVAWTKMPVCEEIFCPSPPPILNGRHIGNS

LANVSYGSIVTYTCDPDPEEGVNFILIGESTLRCTVDSQKTGTWSGPAPRCELSTSAV

QCPHPQILRGRMVSGQKDRYTYNDTVIFACMFGFTLKGSKQIRCNAQGTWEPSAPV

CEKECQAPPNILNGQKEDRHMVRFDPGTSIKYSCNPGYVLVGEESIQCTSEGVWTPP

VPQCKVAACEATGRQLLTKPQHQFVRPDVNSSCGEGYKLSGSVYQECQGTIPWFME

IRLCKEITCPPPPVIYNGAHTGSSLEDFPYGTTVTYTCNPGPERGVEFSLIGESTIRCTSN

DQERGTWSGPAPLCKLSLLAVQCSHVHIANGYKISGKEAPYFYNDTVTFKCYSGFTL

KGSSQIRCKRDNTWDPEIPVCEKGCQPPPGLHHGRHTGGNTVFFVSGMTVDYTCDP

GYLLVGNKSIHCMPSGNWSPSAPRCEETCQHVRQSLQELPAGSRVELVNTSCQDGY

QLTGHAYQMCQDAENGIVVFKKIPLCKVIHCHPPPVIVNGKHTGMMAENFLYGNEVS

YECDQGFYLLGEKNCSAEVILKAWILERAFPQCLRSLCPNPEVKHGYKLNKTHSAYS

HNDIVYVDCNPGFIIVINGSRVIRCHTDNTWVPGVPTCIKKAFIGCPPPPKTPNGNHTGG

NIARFSPGMSILYSCDQGYLVVGEPLLLCTHEGTWSQPAPHCKEVNCSSPADMDGIQ

KGLEPRKMYQYGAVVTLECEDGYMLEGSPQSQCQSDHQWNPPLAVCRSRSLAPVL

CGIAAGLILLTFLIVITLYVISKHRERNYYTDTSQKEAFHLEAREVYSVDPYNPAS

SEQ ID NO: 2 [amino acid sequence of short consensus repeat (SCR) domains 1 and 2 of human CR2]:
ISCGSPPPILNGRISYYSTPIAVGTVIRYSCSGTFRLIGEKSLLCITKDKVDGTWDKPAP

KCEYFNKYSSCPEPIVPGGYKIRGSTPYRHGDSVTFACKTNFSMNGNKSVWCQANN

MWGPTRLPTCVS

| SEQUENCES |
|---|

SEQ ID NO: 3 [amino acid sequence of human CD59 protein]:
MGIQGGSVLFGLLLVLAVFCHSGHSLQCYNCPNPTADCKTAVNCSSDFDACLITKAG

LQVYNKCWKFEHCNFNDVTTRLRENELTYYCCKKDLCNFNEQLENGGTSLSEKTVL

LLVTPFLAAAWSLHP

SEQ ID NO: 4 [amino acid sequence of mouse complement receptor
1-related gene/protein y (Crry)]:
MEVSSRSSEPLDPVWLLVAFGRGGVKLEVLLLFLLPFTLGELRGGLGKHGHTVHREP

AVNRLCADSKRWSGLPVSAQRPFPMGHCPAPSQLPSAKPINLTDESMFPIGTYLLYEC

LPGYIKRQFSITCKQDSTWTSAEDKCIRKQCKTPSDPENGLVHVHTGIQFGSRINYTC

NQGYRLIGSSSAVCVITDQSVDWDTEAPICEWIPCEIPPGIPNGDFFSSTREDFHYGMV

VTYRCNTDARGKALFNLVGEPSLYCTSNDGEIGVWSGPPPQCIELNKCTPPPYVENA

VMLSENRSLFSLRDIVEFRCHPGFIMKGASSVHCQSLNKWEPELPSCFKGVICRLPQE

MSGFQKGLGMKKEYYYGENVTLECEDGYTLEGSSQSQCQSDGSWNPLLAKCVSRSI

SGLIVGIFIGIIVFILVIIVFIVVMILKYKKRNTTDEKYKEVGIHLNYKEDSCVRLQSLLTS

QENSSTTSPARNSLTQEVS

SEQ ID NO: 5 [amino acid sequence of human factor H]:
MRLLAKIICLMLWAICVAEDCNELPPRRNTEILTGSWSDQTYPEGTQAIYKCRPGYRS

LGNVIMVCRKGEWVALNPLRKCQKRPCGHPGDTPFGTFTLTGGNVFEYGVKAVYT

CNEGYQLLGEINYRECDTDGWTNDIPICEVVKCLPVTAPENGKIVSSAMEPDREYHF

GQAVRFVCNSGYKIEGDEEMHCSDDGFWSKEKPKCVEISCKSPDVINGSPISQKIIYK

ENERFQYKCNMGYEYSERGDAVCTESGWRPLPSCEEKSCDNPYIPNGDYSPLRIKHR

TGDEITYQCRNGFYPATRGNTAKCTSTGWIPAPRCTLKPCDYPDIKHGGLYHENMRR

PYFPVAVGKYYSYYCDEHFETPSGSYWDHIHCTQDGWSPAVPCLRKCYFPYLENGY

NQNYGRKFVQGKSIDVACHPGYALPKAQTTVTCMENGWSPTPRCIRVKTCSKSSIDI

ENGFISESQYTYALKEKAKYQCKLGYVTADGETSGSITCGKDGWSAQPTCIKSCDIPV

FMNARTKNDFTWFKLNDTLDYECHDGYESNTGSTTGSIVCGYNGWSDLPICYEREC

ELPKIDVHLVPDRKKDQYKVGEVLKFSCKPGFTIVGPNSVQCYHFGLSPDLPICKEQV

QSCGPPPELLNGNVKEKTKEEYGHSEVVEYYCNPRFLMKGPNKIQCVDGEWTTLPV

CIVEESTCGDIPELEHGWAQLSSPPYYYGDSVEFNCSESFTMIGHRSITCIHGVWTQLP

QCVAIDKLKKCKSSNLIILEEHLKNKKEFDHNSNIRYRCRGKEGWIHTVCINGRWDPE

VNCSMAQIQLCPPPPQIPNSHNMTTTLNYRDGEKVSVLCQENYLIQEGEEITCKDGR

WQSIPLCVEKIPCSQPPQIEHGTINSSRSSQESYAHGTKLSYTCEGGFRISEENETTCYM

GKWSSPPQCEGLPCKSPPEISHGVVAHMSDSYQYGEEVTYKCFEGFGIDGPAIAKCL

GEKWSHPPSCIKTDCLSLPSFENAIPMGEKKDVYKAGEQVTYTCATYYKMDGASNV

TCINSRWTGRPTCRDTSCVNPPTVQNAYIVSRQMSKYPSGERVRYQCRSPYEMFGDE

EVMCLNGNWTEPPQCKDSTGKCGPPPPIDNGDITSFPLSVYAPASSVEYQCQNLYQL

EGNKRITCRNGQWSEPPKCLHPCVISREIMENYNIALRWTAKQKLYSRTGESVEFVC

KRGYRLSSRSHTLRTTCWDGKLEYPTCAKR

| SEQUENCES |
| --- |
| SEQ ID NO: 6 [amino acid sequence of mouse CD59A protein]:<br>MRAQRGLILLLLLLAVFCSTAVSLTCYHCFQPVVSSCNMNSTCSPDQDSCLYAVAG<br><br>MQVYQRCWKQSDCHGEIIMDQLEETKLKFRCCQFNLCNKSDGSLGKTPLLGTSVLV<br><br>AILNLCFLSHL |
| SEQ ID NO: 7 [amino acid sequence of mouse CD59B protein]:<br>MRAQRGLILLLLLLAVFCSTAVSLKCYNCFQFVSSCKINTTCSPNLDSCLYAVAGRQ<br><br>VYQQCWKLSDCNSNYIMSRLDVAGIQSKCCQWGLCNKNLDGLEEPNNAETSSLRKT<br><br>ALLGTSVLVAILKFCF |
| SEQ ID NO: 8 [amino acid sequence of mouse factor H]:<br>MRLSARIIVVLILWTVCAAEDCKGPPPRENSEILSGSWSEQLYPEGTQATYKCRPGYRT<br><br>LGTIVKVCKNGKWVASNPSRICRKKPCGHPGDTPFGSFRLAVGSQFEFGAKVVYTCD<br><br>DGYQLLGEIDYRECGADGWINDIPLCEVVKCLPVTELENGRIVSGAAETDQEYYFGQ<br><br>VVRFECNSGFKIEGHKEIHCSENGLWSNEKPRCVEILCTPPRVENGDGINVKPVYKEN<br><br>ERYHYKCKHGYVPKERGDAVCTGSGWSSQPFCEEKRCSPPYILNGIYTPHRIIHRSDD<br><br>EIRYECNYGFYPVTGSTVSKCTPTGWIPVPRCTLKPCEFPQFKYGRLYYEESLRPNFP<br><br>VSIGNKYSYKCDNGFSPPSGYSWDYLRCTAQGWEPEVPCVRKCVFHYVENGDSAY<br><br>WEKVYVQGQSLKVQCYNGYSLQNGQDTMTCTENGWSPPPKCIRIKTCSASDIHIDN<br><br>GFLSESSSIYALNRETSYRCKQGYVTNTGEISGSITCLQNGWSPQPSCIKSCDMPVFEN<br><br>SITKNTRTWFKLNDKLDYECLVGFENEYKHTKGSITCTYYGWSDTPSCYERECSVPT<br><br>LDRKLVVSPRKEKYRVGDLLEFSCHSGHRVGPDSVQCYHFGWSPGFPTCKGQVASC<br><br>APPLEILNGEINGAKKVEYSHGEVVKYDCKPRFLLKGPNKIQCVDGNWTTLPVCIEEE<br><br>RTCGDIPELEHGSAKCSVPPYHHGDSVEFICEENFTMIGHGSVSCISGKWTQLPKCVA<br><br>TDQLEKCRVLKSTGIEAIKPKLTEFTHNSTMDYKCRDKQEYERSICINGKWDPEPNCT<br><br>SKTSCPPPPQIPNTQVIETTVKYLDGEKLSVLCQDNYLTQDSEEMVCKDGRWQSLPR<br><br>CIEKIPCSQPPTIEHGSINLPRSSEERRDSIESSSHEHGTTFSYVCDDGFRIPEENRITCYM<br><br>GKWSTPPRCVGLPCGPPPSIPLGTVSLELESYQHGEEVTYHCSTGFGIDGPAFIICEGG<br><br>KWSDPPKCIKTDCDVLPTVKNAIIRGKSKKSYRTGEQVTFRCQSPYQMNGSDTVTCV<br><br>NSRWIGQPVCKDNSCVDPPHVPNATIVTRTKNKYLHGDRVRYECNKPLELFGQVEV<br><br>MCENGIVVTEKPKCRDSTGKCGPPPPIDNGDITSLSLPVYEPLSSVEYQCQKYYLLKGK<br><br>KTITCTNGKWSEPPTCLHACVIPENIMESHNIILKWRHTEKIYSHSGEDIEFGCKYGYY<br><br>KARDSPPFRTKCINGTINYPTCV |
| SEQ ID NO: 9 [amino acid sequence of human complement receptor 1 (CR1)]:<br>MGASSPRSPEPVGPPAPGLPFCCGGSLLAVVVLLALPVAWGQCNAPEWLPFARPTNL<br><br>TDEFEFPIGTYLNYECRPGYSGRPFSIICLKNSVWTGAKDRCRRKSCRNPPDPVNGMV<br><br>HVIKGIQFGSQIKYSCTKGYRLIGSSSATCIISGDTVIVVDNETPICDRIPCGLPPTITNGD<br><br>FISTNRENFHYGSVVTYRCNPGSGGRKVFELVGEPSIYCTSNDDQVGIVVSGPAPQCIIP<br><br>NKCTPPNVENGILVSDNRSLFSLNEVVEFRCQPGFVMKGPRRVKCQALNKWEPELPS<br><br>CSRVCQPPPDVLHAERTQRDKDNFSPGQEVFYSCEPGYDLRGAASMRCTPQGDWSP<br><br>AAPTCEVKSCDDFMGQLLNGRVLFPVNLQLGAKVDFVCDEGFQLKGSSASYCVLAG<br><br>MESLWNSSVPVCEQIFCPSPPVIPNGRHTGKPLEVFPFGKAVNYTCDPHPDRGTSFDLI |

| SEQUENCES |
|---|
| GESTIRCTSDPQGNGVWSSPAPRCGILGHCQAPDHFLFAKLKTQTNASDFPIGTSLKY |
| ECRPEYYGRPFSITCLDNLVWSSPKDVCKRKSCKTPPDPVNGMVHVITDIQVGSRINY |
| SCTTGHRLIGHSSAECILSGNAAHWSTKPPICQRIPCGLPPTIANGDFISTNRENFHYGS |
| VVTYRCNPGSGGRKVFELVGEPSIYCTSNDDQVGIVVSGPAPQCIIPNKCTPPNVENGI |
| LVSDNRSLFSLNEVVEFRCQPGFVMKGPRRVKCQALNKWEPELPSCSRVCQPPPDVL |
| HAERTQRDKDNFSPGQEVFYSCEPGYDLRGAASMRCTPQGDWSPAAPTCEVKSCDD |
| FMGQLLNGRVLFPVNLQLGAKVDFVCDEGFQLKGSSASYCVLAGMESLWNSSVPV |
| CEQIFCPSPPVIPNGRHTGKPLEVFPFGKAVNYTCDPHPDRGTSFDLIGESTIRCTSDPQ |
| GNGVWSSPAPRCGILGHCQAPDHFLFAKLKTQTNASDFPIGTSLKYECRPEYYGRPFS |
| ITCLDNLVWSSPKDVCKRKSCKTPPDPVNGMVHVITDIQVGSRINYSCTTGHRLIGHS |
| SAECILSGNTAHWSTKPPICQRIPCGLPPTIANGDFISTNRENFHYGSVVTYRCNLGSR |
| GRKVFELVGEPSIYCTSNDDQVGIVVSGPAPQCIIPNKCTPPNVENGILVSDNRSLFSLN |
| EVVEFRCQPGFVMKGPRRVKCQALNKWEPELPSCSRVCQPPPEILHGEHTPSHQDNF |
| SPGQEVFYSCEPGYDLRGAASLHCTPQGDWSPEAPRCAVKSCDDFLGQLPHGRVLFP |
| LNLQLGAKVSFVCDEGFRLKGSSVSHCVLVGMRSLWNNSVPVCEHIFCPNPPAILNG |
| RHTGTPSGDIPYGKEISYTCDPHPDRGMTFNLIGESTIRCTSDPHGNGVWSSPAPRCEL |
| SVRAGHCKTPEQFPFASPTIPINDFEFPVGTSLNYECRPGYFGKMFSISCLENLVWSSV |
| EDNCRRKSCGPPPEPFNGMVHINTDTQFGSTVNYSCNEGFRLIGSPSTTCLVSGNNVT |
| WDKKAPICEIISCEPPPTISNGDFYSNNRTSFHNGTVVTYQCHTGPDGEQLFELVGERS |
| IYCTSKDDQVGVWSSPPPRCISTNKCTAPEVENAIRVPGNRSFFSLTEIIRFRCQPGFV |
| MVGSHTVQCQTNGRWGPKLPHCSRVCQPPPEILHGEHTLSHQDNFSPGQEVFYSCEP |
| SYDLRGAASLHCTPQGDWSPEAPRCTVKSCDDFLGQLPHGRVLLPLNLQLGAKVSF |
| VCDEGFRLKGRSASHCVLAGMKALWNSSVPVCEQIFCPNPPAILNGRHTGTPFGDIP |
| YGKEISYACDTHPDRGMTFNLIGESSIRCTSDPQGNGVWSSPAPRCELSVPAACPHPP |
| KIQNGHYIGGHVSLYLPGMTISYTCDPGYLLVGKGFIFCTDQGIVVSQLDHYCKEVNC |
| SFPLFMNGISKELEMKKVYHYGDYVTLKCEDGYTLEGSPWSQCQADDRWDPPLAK |
| CTSRAHDALIVGTLSGTIFFILLIIFLSWIILKHRKGNNAHENPKEVAIHLHSQGGSSVH |
| PRTLQTNEENSRVLP |

SEQ ID NO: 10 [amino acid sequence of human membrane cofactor protein (MCP)]:
MEPPGRRECPFPSWRFPGLLLAAMVLLLYSFSDACEEPPTFEAMELIGKPKPYYEIGE

RVDYKCKKGYFYIPPLATHTICDRNHTWLPVSDDACYRETCPYIRDPLNGQAVPANG

TYEFGYQMHFICNEGYYLIGEEILYCELKGSVAIVVSGKPPICEKVLCTPPPKIKNGKHT

FSEVEVFEYLDAVTYSCDPAPGPDPFSLIGESTIYCGDNSVWSRAAPECKVVKCRFPV

VENGKQISGFGKKFYYKATVMFECDKGFYLDGSDTIVCDSNSTWDPPVPKCLKVLPP

SSTKPPALSHSVSTSSTTKSPASSASGPRPTYKPPVSNYPGYPKPEEGILDSLDVWVIA

VIVIAIVVGVAVICVVPYRYLQRRKKKGTYLTDETHREVKFTSL

SEQ ID NO: 11 [amino acid sequence of human decay accelerating factor (DAF/CD55)]:
MTVARPSVPAALPLLGELPRLLLLVLLCLPAVWGDCGLPPDVPNAQPALEGRTSFPE

DTVITYKCEESFVKIPGEKDSVICLKGSQWSDIEEFCNRSCEVPTRLNSASLKQPYITQ

NYFPVGTVVEYECRPGYRREPSLSPKLTCLQNLKWSTAVEFCKKKSCPNPGEIRNGQI

DVPGGILFGATISFSCNTGYKLFGSTSSFCLISGSSVQWSDPLPECREIYCPAPPQIDNGI

IQGERDHYGYRQSVTYACNKGFTMIGEHSIYCTVNNDEGEWSGPPPECRGKSLTSKV

PPTVQKPTTVNVPTTEVSPTSQKTTTKTTTPNAQATRSTPVSRTTKHFHETTPNKGSG

TTSGTTRLLSGHTCFTLTGLLGTLVTMGLLT

SEQ ID NO: 12 [amino acid sequence of mouse decay accelerating factor (DAF/CD55)]:
MIRGRAPRTRPSPPPPLLPLLSLSLLLLSPTVRGDCGPPPDIPNARPILGRHSKFAEQSK

VAYSCNNGFKQVPDKSNIVVCLENGQWSSHETFCEKSCVAPERLSFASLKKEYLNM

NFFPVGTIVEYECRPGFRKQPPLPGKATCLEDLVWSPVAQFCKKKSCPNPKDLDNGH

INIPTGILFGSEIFNSCNPGYRLVGVSSTFCSVTGNTVDWDDEFPVCTEIHCPEPPKINN

GIMRGESDSYTYSQVVTYSCDKGFILVGNASIYCTVSKSDVGQWSSPPPRCIEKSKVP

TKKPTINVPSTGTPSTPQKPTTESVPNPGDQPTPQKPSTVKVSATQHVPVTKTTVRHPI

RTSTDKGEPNTGGDRYIYGHTCLITLTVLHVMLSLIGYLT

SEQ ID NO: 13 [amino acid sequence of CVF from *Naja kaouthia*]:
MERMALYLVAALLIGFPGSSHGALYTLITPAVLRTDTEEQILVEAHGDSTPKQLDIFV

HDFPRKQKTLFQTRVDMNPAGGMLVTPTIEIPAKEVSTDSRQNQYVVVQVTGPQVR

LEKVVLLSYQSSFLFIQTDKGIYTPGSPVLYRVFSMDHNTSKMNKTVIVEFQTPEGILV

SSNSVDLNFFWPYNLPDLVSLGTWRIVAKYEHSPENYTAYFDVRKYVLPSFEVRLQP

SEKFFYIDGNENFHVSITARYLYGEEVEGVAFVLFGVKIDDAKKSIPDSLTRIPIIDGDG

KATLKRDTFRSRFPNLNELVGHTLYASVTVMTESGSDMVVTEQSGIHIVASPYQIHFT

KTPKYFKPGMPYELTVYVTNPDGSPAAHVPVVSEAFHSMGTTLSDGTAKLILNIPLN

AQSLPITVRTNHGDLPRERQATKSMTAIAYQTQGGSGNYLHVAITSTEIKPGDNLPVN

FNVKGNANSLKQIKYFTYLILNKGKIFKVGRQPRRDGQNLVTMNLHITPDLIPSFRFV

AYYQVGNNEIVADSVWVDVKDTCMGTLVVKGDNLIQMPGAAMKIKLEGDPGARV

GLVAVDKAVYVLNDKYKISQAKIVVDTIEKSDFGCTAGSGQNNLGVFEDAGLALTTS

TNLNTKQRSAAKCPQPANRRRRSSVLLLDSNASKAAEFQDQDLRKCCEDVMHENP

MGYTCEKRAKYIQEGDACKAAFLECCRYIKGVRDENQRESELFLARDDNEDGFIADS

DIISRSDFPKSWLWLTKDLTEEPNSQGISSKTMSFYLRDSITTWVVLAVSFTPTKGICV

AEPYEIRVMKVFFIDLQMPYSVVKNEQVEIRAILHNYVNEDIYVRVELLYNPAFCSAS

TKGQRYRQQFPIKALSSRAVPFVIVPLEQGLHDVEIKASVQEALWSDGVRKKLKVVP

EGVQKSIVTIVKLDPRAKGVGGTQLEVIKARKLDDRVPDTEIETKIIIQGDPVAQIIENS

IDGSKLNHLIITPSGCGEQNMIRMAAPVIATYYLDTTEQWETLGINRRTEAVNQIVTG

YAQQMVYKKADHSYAAFTNRASSSWLTAYVVKVFAMAAKMVAGISHEIICGGVR

WLILNRQQPDGAFKENAPVLSGTMQGGIQGAEEEVYLTAFILVALLESKTICNDYVN

SLDSSIKKATNYLLKKYEKLQRPYTTALTAYALAAADQLNDDRVLMAASTGRDHW

EEYNAHTHNIEGTSYALLALLKMKKFDQTGPIVRWLTDQNFYGETYGQTQATVMAF

QALAEYEIQMPTHKDLNLDITIELPDREVPIRYRINYENALLARTVETKLNQDITVTAS

GDGKATMTILTFYNAQLQEKANVCNKFHLNVSVENIHLNAMGAKGALMLKICTRY

| SEQUENCES |
|---|
| LGEVDSTMTIIDISMLTGFLPDAEDLTRLSKGVDRYISRYEVDNNMAQKVAVIIYLNK |
| VSHSEDECLHFKILKHFEVGFIQPGSVKVYSYYNLDEKCTKFYHPDKGTGLLNKICIG |
| NVCRCAGETCSSLNHQERIDVPLQIEKACETNVDYVYKTKLLRIEEQDGNDIYVMDV |
| LEVIKQGTDENPRAKTHQYISQRKCQEALNLKVNDDYLIVVGSRSDLLPTKDKISYIIT |
| KNTWIERWPHEDECQEEEFQKLCDDFAQFSYTLTEFGCPT |
| SEQ ID NO: 14 [amino acid sequence of the human IgG$_1$ heavy chain, C domain]:<br>ASTKGPSVFPLAPSSKSTSGGTAALGCLVKDYFPEPVTVSWNSGALTSGVHTFPAVL |
| QSSGLYSLSSVVTVPSSSLGTQTYICNVNHKPSNTKVDKKVEPKSCDKTHTCPPCPAP |
| ELLGGPSVFLFPPKPKDTLMISRTPEVTCVVVDVSHEDPEVKFNWYVDGVEVHNAKT |
| KPREEQYNSTYRVVSVLTVLHQDWLNGKEYKCKVSNKALPAPIEKTISKAKGQPREP |
| QVYTLPPSRDELTKNQVSLTCLVKGFYPSDIAVEWESNGQPENNYKTTPPVLDSDGS |
| FFLYSKLTVDKSRWQQGNVFSCSVMHEALHNHYTQKSLSLSPGK |
| SEQ ID NO: 15 [amino acid sequence of the human IgG$_1$ light chain, C domain]:<br>TVAAPSVFIFPPSDEQLKSGTASVVCLLNNFYPREAKVQWKVDNALQSGNSQESVTE |
| QDSKDSTYSLSSTLTLSKADYEKHKVYACEVTHQGLSSPVTKSFNRGEC |
| SEQ ID NO: 16 [amino acid sequence of the Fc domain of human IgG$_1$]:<br>EPKSCDKTHTCPPCPAPELLGGPSVFLFPPKPKDTLMISRTPEVTCVVVDVSHEDPEV |
| KFNWYVDGVEVHNAKTKPREEQYNSTYRVVSVLTVLHQDWLNGKEYKCKVSNKA |
| LPAPIEKTISKAKGQPREPQVYTLPPSRDELTKNQVSLTCLVKGFYPSDIAVEWESNG |
| QPENNYKTTPPVLDSDGPFFLYSKLTVDKSRWQQGNVFSCSVMHEALHNHYTQKSL |
| SLSPGK |
| SEQ ID NO: 17 [amino acid sequence of human IgM heavy chain, C domain]:<br>GSASAPTLFPLVSCENSPSDTSSVAVGCLAQDFLPDSITLSWKYKNNSDISSTRGFPSV |
| LRGGKYAATSQVLLPSKDVMQGTDEHVVCKVQHPNGNKEKNVPLPVIAELPPKVSV |
| FVPPRDGFFGNPRKSKLICQATGFSPRQIQVSWLREGKQVGSGVTTDQVQAEAKESG |
| PTTYKVTSTLTIKESDWLGQSMFTCRVDHRGLTFQQNASSMCVPDQDTAIRVFAIPPS |
| FASIFLTKSTKLTCLVTDLTTYDSVTISWTRQNGEAVKTHTNISESHPNATFSAVGEAS |
| ICEDDWNSGERFTCTVTHTDLPSPLKQTISRPKGVALHRPDVYLLPPAREQLNRESA |
| TITCLVTGFSPADVFVQWMQRGQPLSPEKYVTSAPMPEPQAPGRYFAHSILTVSEEE |
| WNTGETYTCVAHEALPNRVTERTVDKSTGKPTLYNVSLVMSDTAGTCY |
| SEQ ID NO: 18 [amino acid sequence of human IgM light chain, C domain]:<br>GSASAPTLFPLVSCENSPSDTSSVAVGCLAQDFLPDSITLSWKYKNNSDISSTRGFPSV |
| LRGGKYAATSQVLLPSKDVMQGTDEHVVCKVQHPNGNKEKNVPLPV |
| SEQ ID NO: 19 [amino acid sequence of the Fc domain of human IgM]:<br>GSASAPTLFPLVSCENSPSDTSSVAVGCLAQDFLPDSITFSWKYKNNSDISSTRGFPSV |
| LRGGKYAATSQVLLPSKDVMQGTDEHVVCKVQHPNGNKEKNVPLPVIAELPPKVSV |
| FVPPRDGFFGNPRSKSKLICQATGFSPRQIQVSWLREGKQVGSGVTTDQVQAEAKES |
| GPTTYKVTSTLTIKESDWLSQSMFTCRVDHRGLTFQQNASSMCVPDQDTAIRVFAIPP |
| SFASIFLTKSTKLTCLVTDLTTYDSVTISWTRQNGEAVKTHTNISESHPNATFSAVGEA |
| SICEDDWNSGERFTCTVTHTDLPSPLKQTISRPKGVALHRPDVYLLPPAREQLNLRES |

```
ATITCLVTGFSPADVFVQWMQRGQPLSPEKYVTSAPMPEPQAPGRYFAHSILTVSEEE

WNTGETYTCVVAHEALPNRVTERTVDKSTGKPTLYNVSLVMSDTAGTCY

SEQ ID NO: 20 [amino acid sequence of mouse IgG3 heavy chain]:
TTTAPSVYPLVPGCSDTSGSSVTLGCLVKGYFPEPVTVKWNYGALSSGVRTVSSVLQ

SGFYSLSSLVTVPSSTWPSQTVICNVAHPASKTELIKRIEPRIPKPSTPPGSSCPPGNILG

GPSVFIFPPKPKDALMISLTPKVTCVVVDVSEDDPDVHVSWFVDNKEVHTAWTQPRE

AQYNSTFRVVSALPIQHQDWMRGKEFKCKVNNKALPAPIERTISKPKGRAQTPQVYT

IPPPREQMSKKKVSLTCLVTNFFSEAISVEWERNGELEQDYKNTPPILDSDGTYFLYS

KLTVDTDSWLQGEIFTCSVVHEALHNHHTQKNLSRSP

SEQ ID NO: 21 [amino acid sequence of mouse IgG3 light chain]:
IVLTQSPAIMSASPGEKVTMTCRASSSVRSSYLHWYQQKPGSSPKLWIYSTSNLASGV

PVRFSGSGSGTSYSLTISSVEAEDAATYYCQQYDSSPSITFGAGTKLELK

SEQ ID NO: 22 [amino acid sequence of mouse IgG3 Fc domain]:
EPRIPKPSTPPGSSCPPGNILGGPSVFIFPPKPKDALMISLTPKVTCVVVDVSEDDPDVH

VSWFVDNKEVHTAWTQPREAQYNSTFRVVSALPIQHQDWMRGKEFKCKVNNKALP

APIERTISKPKGRAQTPQVYTIPPPREQMSKKKVSLTCLVTNFFSEAISVEWERNGELE

QDYKNTPPILDSDGTYFLYSKLTVDTDSWLQGEIFTCSVVHEALHNHHTQKNLSRSP

GK

SEQ ID NO: 23 [amino acid sequence of mouse IgM heavy chain,
C domain]:
SQSFPNVFPLVSCESPLSDKNLVAMGCLARDFLPSTISFTWNYQNNTEVIQGIRTFPTL

RTGGKYLATSQVLLSPKSILEGSDEYLVCKIHYGGKNRDLHVPIPAVAEMNPNVNVF

VPPRDGFSGPAPRKSKLICEATNFTPKPITVSWLKDGKLVESGFTTDPVTIENKGSTPQ

TYKVISTLTISEIDWLNLNVYTCRVDHRGLTFLKNVSSTCAASPSTDILTFTIPPSFADIF

LSKSANLTCLVSNLATYETLNISWASQSGEPLETKIKIMESHPNGTFSAKGVASVCVE

DWNNRKEFVCTVTHRDLPSPQKKFISKPNEVHKHPPAVYLLPPAREQLNLRESATVT

CLVKGFSPADISVQWLQRGQLLPQEKYVTSAPMPEPGAPGFYFTHSILTVTEEEWNS

GETYTCVVGHEALPHLVTERTVDKSTGKPTLYNVSLIMSDTGGTCY

SEQ ID NO: 24 [amino acid sequence of mouse IgM light chain,
C domain]:
SQSFPNVFPLVSCESPLSDKNLVAMGCLARDFLPSTISFTWNYQNNTEVIQGIRTFPTL

RTGGKYLATSQVLLSPKSILEGSDEYLVCKIHYGGKNRDLHVPIP

SEQ ID NO: 25 [amino acid sequence of mouse IgM Fc domain]:
ASPSTDILTFTIPPSFADIFLSKSANLTCLVSNLATYETLNISWASQSGEPLETKIKIMES

HPNGTFSAKGVASVCVEDWNNRKEFVCTVTHRDLPSPQKKFISKPNEVHKHPPAVY

LLPPAREQLNLRESATVTCLVKGFSPADISVQWLQRGQLLPQEKYVTSAPMPEPGAP

GFYFTHSILTVTEEEWNSGETYTCVVGHEALPHLVTERTVDKSTGKPTLYNVSLIMS

DTGGTCY

SEQ ID NO: 26 [linking sequence between the first two N-terminal
short consensus repeat domains of human CR2]:
VSVFPLE SEQ ID NO: 27 [linking sequence between the first two N-terminal
short consensus repeat domains of human CR2]:
EYFNKYSS
```

| SEQUENCES |
| --- |
| SEQ ID NO: 28 [linking sequence between the fourth and the fifth N-terminal short consensus repeat domains of human CR2]: EEIF |

We claim:

1. A soluble composition capable of targeted delivery of a complement modulator to sites of complement system activation comprising a construct, wherein the construct comprises:
   (a) a complement receptor 2 (CR2) portion comprising at least the first two N-terminal short consensus repeat (SCR) domains of CR2; and
   (b) a complement modulator portion;
   wherein the CR2 portion contains an alanine substitution at an amino acid position selected from the group consisting of N11 and Y64 of SEQ ID NO: 2 that decreases binding affinity of the CR2 portion for EBV gp350 relative to a construct in which the CR2 portion has the sequence of SEQ ID NO: 2, or the CR2 portion contains an alanine substitution at an amino acid position selected from the group consisting of S42 and K50 of SEQ ID NO: 2 that decreases binding of the CR2 portion for Interferon-alpha (IFNα) relative to a construct in which the CR2 portion has the sequence of SEQ ID NO: 2.

2. The soluble composition of claim 1, wherein the alanine substitution of the CR2 portion is N11 or Y64 of SEQ ID NO: 2 and the construct exhibits decreased binding affinity for EBV gp350.

3. The soluble composition of claim 1, wherein the construct is a fusion protein comprising a linker between the CR2 portion and the complement modulator portion.

4. The soluble composition of claim 1, wherein the complement modulator portion comprises a complement inhibitor selected from the group consisting of human membrane complement protein (MCP)(SEQ ID NO:10), human decay accelerating factor (DAF)(SEQ ID NO:11), mouse DAF (SEQ ID NO:12), mouse complement receptor 1-related gene/protein y (Crry) (SEQ ID NO:4), human CD59 (SEQ ID NO:3), mouse CD59 isoform A (SEQ ID NO:6), mouse CD59 isoform 8 (SEQ ID NO:7), human complement receptor 1 (CR1) (SEQ ID NO:9), human factor H (SEQ ID NO:5), and mouse factor H (SEQ ID NO:8).

5. The soluble composition of claim 4, wherein the complement inhibitor comprises human MCP (SEQ ID NO:10).

6. The soluble composition of claim 1, wherein the complement modulator portion comprises a complement inhibitor selected from the group consisting of SCR1-4 of human MCP (amino acids 35-285 of SEQ ID NO: 10), SCR1-4 plus a serine/threonine-rich domain of human MCP (amino acids 35-326 of SEQ ID NO: 10), and an extracellular domain of MCP (amino acids 35-343 of SEQ ID NO:10).

7. The soluble composition of claim 4, wherein the complement inhibitor comprises human DAF (SEQ ID NO: 11).

8. The soluble composition of claim 1, wherein the complement modulator portion comprises a complement inhibitor selected from the group consisting of SCR1-4 of human DAF (amino acids 25-285 of SEQ ID NO:11) and SCR1-4 plus a 0-glycosylated serine/threonine-rich domain of human DAF (amino acids 25-353 of SEQ ID NO: 11).

9. The soluble composition of claim 4, wherein the complement inhibitor comprises human CD59 (SEQ ID NO:3).

10. The soluble composition of claim 1, wherein the complement modulator portion comprises a complement inhibitor comprising an extracellular domain of human CD59 lacking its GPI anchor (amino acids 26-101 of SEQ ID NO:3).

11. The soluble composition of claim 4, wherein the complement inhibitor comprises human CR1 (SEQ ID NO:9).

12. The soluble composition of claim 1, wherein the complement modulator portion comprises a complement inhibitor selected from the group consisting of SCR1-3 of human CR1 (amino acids of 42-234 of SEQ ID NO:9), SCR 1-4 of human CR1 (amino acids 42-295 of SEQ ID NO:9), SCR 1-10 of human CR1 (amino acids 42-684 of SEQ ID NO:9), SCR8-10 of human CR1 (amino acids of 491-684 of SEQ ID NO:9), SCR 8-11 of human CR1 (amino acids 491-745 of SEQ ID NO:9), SCR15-17 of human CR1 (amino acids of 941-1134 of SEQ ID NO:9), SCR15-18 of human CR1 (amino acids 941-1195 of SEQ ID NO:9), and SCR22-28 of human CR1 (amino acids 1394-1842 of SEQ ID NO:9).

13. The soluble composition of claim 4, wherein the complement inhibitor comprises human factor H (SEQ ID NO:5).

14. The soluble composition of claim 1, wherein the complement modulator portion comprises a complement inhibitor selected from the group consisting of SCR1-4 of human factor H (amino acids 21-262 of SEQ ID NO:5), SCR1-5 of human factor H (amino acids 21-320 of SEQ ID NO:5), SCR1-8 of human factor H (amino acids 21-507 of SEQ ID NO:5), and SCR1-18 of human factor H (amino acids 21-1104 of SEQ ID NO:5).

15. The soluble composition of claim 4, wherein the complement inhibitor comprises mouse factor H (SEQ ID NO:8).

16. The soluble composition of claim 1, wherein the complement modulator portion comprises a complement inhibitor selected from the group consisting of SCR1-4 of mouse factor H (amino acids 19-264 of SEQ ID NO:8), SCR1-5 of mouse factor H (amino acids 19-322 of SEQ ID NO:8), SCR1-8 of mouse factor H (amino acids 19-507 of SEQ ID NO:8), and SCR1-18 of mouse factor H (amino acids 19-1109 of SEQ ID NO:8).

17. The soluble composition of claim 1, wherein the complement modulator portion comprises a complement activator is selected from the group consisting of human IgG$_1$, human IgG$_1$ Fc domain, human IgM, human IgM Fc domain, mouse IgG$_3$, mouse IgG$_3$ Fc domain, mouse IgM, mouse IgM Fc domain, and cobra venom factor (CVF).

18. A method for making a construct that selectively binds to one or more complement component 3 (C3) proteolytic fragments but does not selectively bind to EBV gp350 or IFNα, wherein the method comprises:
(a) mutating a CR2 portion of the construct to an alanine at a position selected from the group consisting of: N11 and Y64 of SEQ ID NO:2; or
(b) mutating one or more amino acids in a CR2 portion of the construct to an alanine at a position selected from the group consisting of: S42 and K50 of SEQ ID NO:2, wherein the construct comprises:
(i) a CR2 portion comprising at least the first two N-terminal SCR domains of the CR2 protein; and
(ii) a complement modulator portion.

19. The method of claim 18, wherein the method further comprises mutating one or more amino acids in the CR2 portion of the construct at a position selected from the group consisting of: R13, Y16, A22, R28, S32, R36, K41, K48, K57, K67, Y68, R83, G84, and R89 of SEQ ID NO:2.

20. A method of reducing the binding affinity of a construct for EBV-gp350, wherein the construct comprises:
(a) a CR2 portion comprising at least the first two N-terminal SCR domains of CR2; and
(b) a complement modulator portion,
the method comprising mutating an amino acid residue of the CR2 portion selected from the group consisting of N11 and Y64 of SEQ ID NO:2 to alanine.

21. A method of reducing the binding affinity of a construct for IFNα, wherein the construct comprises:
(a) a CR2 portion comprising at least the first two N-terminal short consensus repeat (SCR) domains of CR2; and
(b) a complement modulator portion,
the method comprising mutating an amino acid residue of the CR2 portion selected from the group consisting of S42 and K50 of SEQ ID NO:2 to alanine.

22. The soluble composition of claim 1, wherein the alanine substitution of the CR2 portion is at position S42 or K50 of SEQ ID NO: 2 and the construct exhibits decreased binding affinity for IFNα.

23. The soluble composition of claim 1, wherein the construct exhibits comparable binding affinity for at least one C3 proteolytic fragment selected from the group consisting of C3d, iC3dg, C3dg, and a cell-bound fragment of C3b that binds to CR2 compared to a construct in which the CR2 portion does not contain the at least one amino acid substitution.

24. The soluble composition of claim 1, wherein the construct is a fusion protein without a linker between the CR2 portion and the complement modulator portion.

25. The soluble composition of claim 1, wherein the soluble composition is formulated for intravenous, intraperitoneal, or intraocular injection or oral administration.

26. A method of treating a complement-associated disease or condition in an individual comprising administering the soluble composition of claim 1 to the individual.

27. The method of claim 26, wherein said individual is a human.

28. The soluble composition of claim 1, wherein the alanine substitution of the CR2 portion is at position S42 and K50 of SEQ ID NO: 2 that decreases binding of the CR2 portion for IFNα relative to a construct in which the CR2 portion has the sequence of SEQ ID NO: 2.

* * * * *

UNITED STATES PATENT AND TRADEMARK OFFICE
CERTIFICATE OF CORRECTION

| | |
|---|---|
| PATENT NO. | : 9,650,447 B2 |
| APPLICATION NO. | : 13/697693 |
| DATED | : May 16, 2017 |
| INVENTOR(S) | : James M. Kovacs et al. |

It is certified that error appears in the above-identified patent and that said Letters Patent is hereby corrected as shown below:

Column 165, Line 65, replace "is N11" with --is at position N11--.

Column 166, Line 54, replace "isoform 8" with --isoform B--.

Column 167, Line 8, replace "0-glycosylated" with --O-glycosylated--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*